(12) United States Patent
Deng et al.

(10) Patent No.: US 7,807,672 B2
(45) Date of Patent: Oct. 5, 2010

(54) COMPOUNDS THAT ARE ERK INHIBITORS

(75) Inventors: Yongqi Deng, Newton, MA (US);
Gerald W. Shipps, Jr., Stoneham, MA (US); Alan Cooper, West Caldwell, NJ (US); Yang Nan, Malden, MA (US); Tong Wang, Cambridge, MA (US); M. Arshad Siddiqui, Newton, MA (US); Hugh Zhu, Scotch Plains, NJ (US); Robert Sun, Berkeley Heights, NJ (US); Joseph M. Kelly, Parlin, NJ (US); Ronald Doll, Convent Station, NJ (US); Jagdish Desai, Monroe Township, NJ (US); James J-S Wang, Westfield, NJ (US); Youhao Dong, Cambridge, MA (US); Vincent Madison, Mountain Lakes, NJ (US); Li Xiao, Cranbury, NJ (US); Alan Hruza, Hackettstown, NJ (US); Neng-Yang Shih, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 241 days.

(21) Appl. No.: 11/705,709

(22) Filed: Feb. 13, 2007

(65) Prior Publication Data

US 2007/0232610 A1 Oct. 4, 2007

Related U.S. Application Data

(60) Provisional application No. 60/774,043, filed on Feb. 16, 2006.

(51) Int. Cl.
| | |
|---|---|
| A61K 31/506 | (2006.01) |
| A61K 31/5377 | (2006.01) |
| A61K 31/4025 | (2006.01) |
| A61K 31/496 | (2006.01) |
| C07D 401/06 | (2006.01) |
| C07D 401/12 | (2006.01) |
| C07D 401/14 | (2006.01) |
| C07D 403/12 | (2006.01) |
| C07D 405/12 | (2006.01) |
| C07D 413/12 | (2006.01) |
| C07D 417/06 | (2006.01) |
| C07D 417/12 | (2006.01) |

(52) U.S. Cl. .................. 514/235.5; 514/235.8; 514/248; 514/252.19; 514/254.01; 514/253.09; 514/254.02; 514/254.03; 514/254.05; 514/307; 514/321; 514/326; 514/414; 514/423; 544/121; 544/142; 544/235; 544/335; 544/357; 544/295; 544/366; 544/367; 544/368; 544/369; 544/372; 546/146; 546/199; 546/226; 546/279.1; 548/453

(58) Field of Classification Search ........................ None
See application file for complete search history.

(56) References Cited

U.S. PATENT DOCUMENTS

| | | | |
|---|---|---|---|
| 6,831,175 | B2 | 12/2004 | Li et al. |
| 6,897,231 | B2 | 5/2005 | Bhagwat et al. |
| 7,208,513 | B2 | 4/2007 | Bhagwat et al. |
| 7,211,594 | B2 | 5/2007 | Bhagwat et al. |
| 7,220,771 | B2 | 5/2007 | Bhagwat et al. |
| 7,429,609 | B2 | 9/2008 | Ohi et al. |
| 2002/0103229 | A1 | 8/2002 | Bhagwat et al. |
| 2003/0055068 | A1 | 3/2003 | Bebbington et al. |
| 2004/0127536 | A1 | 7/2004 | Bhagwat et al. |
| 2004/0127538 | A1 | 7/2004 | Oinuma et al. |
| 2005/0009876 | A1 | 1/2005 | Bhagwat et al. |
| 2005/0107386 | A1 | 5/2005 | Narla et al. |
| 2005/0107457 | A1 | 5/2005 | Bhagwat et al. |
| 2007/0060616 | A1 | 3/2007 | Bennett et al. |
| 2007/0149484 | A1 | 6/2007 | Claus et al. |
| 2007/0191604 | A1 | 8/2007 | Cooper et al. |
| 2007/0265333 | A1 | 11/2007 | Fu et al. |
| 2008/0004287 | A1 | 1/2008 | Ma et al. |
| 2008/0007509 | A1 | 1/2008 | Lankhorst et al. |
| 2009/0011284 | A1 | 1/2009 | Wang et al. |
| 2009/0062355 | A1 | 3/2009 | Iizawa et al. |
| 2009/0118284 | A1 | 5/2009 | Cooper et al. |

FOREIGN PATENT DOCUMENTS

| | | |
|---|---|---|
| GB | 2 306 108 A | 4/1997 |
| GB | 2 323 845 A | 7/1998 |
| WO | WO 9745412 A1 | 12/1997 |
| WO | WO 9903498 A1 | 1/1999 |
| WO | WO 9910325 A1 | 3/1999 |

(Continued)

OTHER PUBLICATIONS

PCT International Search Report dated Jul. 9, 2007, for corresponding PCT Application No. PCT/US2007/003665.

*Primary Examiner*—Emily Bernhardt
(74) *Attorney, Agent, or Firm*—Henry C. Jeanette

(57) ABSTRACT

Disclosed are the ERK inhibitors of formula 1.0:

(1.0)

and the pharmaceutically acceptable salts and solvates thereof. Q is a piperidine or piperazine ring that can have a bridge or a fused ring. The piperidine ring can have a double bond in the ring. All other substituents are as defined herein. Also disclosed are methods of treating cancer using the compounds of formula 1.0.

23 Claims, No Drawings

FOREIGN PATENT DOCUMENTS

| | | |
|---|---|---|
| WO | WO 0156557 A2 | 8/2001 |
| WO | WO 0157022 A2 | 8/2001 |
| WO | WO 0168619 A1 | 9/2001 |
| WO | WO 0172721 A2 | 10/2001 |
| WO | WO 02/10137 | 2/2002 |
| WO | WO 0222604 A1 | 3/2002 |
| WO | WO 0222610 A1 | 3/2002 |
| WO | WO 0250065 A2 | 6/2002 |
| WO | WO 02/064586 A2 | 8/2002 |
| WO | WO 02088090 A2 | 11/2002 |
| WO | WO 02088097 A1 | 11/2002 |
| WO | WO 03011854 A1 | 2/2003 |
| WO | WO 03011855 A2 | 2/2003 |
| WO | WO 03035626 A2 | 5/2003 |
| WO | WO 03/091246 A1 | 11/2003 |
| WO | WO 03099212 A2 | 12/2003 |
| WO | WO 2004026867 A2 | 4/2004 |
| WO | WO 2004083203 A1 | 9/2004 |
| WO | WO 2005002673 A1 | 1/2005 |
| WO | WO 2005063258 A1 | 7/2005 |
| WO | WO 2005/100342 A1 | 10/2005 |
| WO | WO 2005100338 A1 | 10/2005 |
| WO | WO 2005/113541 A1 | 12/2005 |
| WO | WO 2005113546 A1 | 12/2005 |
| WO | WO 2006040569 A1 | 4/2006 |
| WO | WO 2006071644 A1 | 7/2006 |
| WO | WO 2006136008 A1 | 12/2006 |
| WO | WO 2007044401 A2 | 4/2007 |
| WO | WO 2007044420 A1 | 4/2007 |
| WO | WO 2008121742 A2 | 10/2008 |
| WO | WO 2008/156739 | 12/2008 |
| WO | WO 2008154241 A1 | 12/2008 |
| WO | WO 2009/105500 | 8/2009 |

COMPOUNDS THAT ARE ERK INHIBITORS

REFERENCE TO RELATED APPLICATION

This Application claims the benefit of U.S. Provisional Application Ser. No. 60/774,043 filed Feb. 16, 2006.

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

This invention provides compounds that inhibit the activity of ERK1 and/or the activity of ERK2.

The compounds of this invention also inhibit the phosphorylation of ERK1 and ERK2.

Thus, this invention provides compounds that are ERK inhibitors (i.e., ERK1 inhibitors and/or ERK2 inhibitors), said compounds being of the formula 1.0:

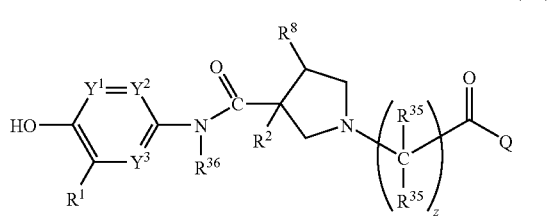

(1.0)

or the pharmaceutically acceptable salts thereof, wherein:

$Y^1$, $Y^2$, and $Y^3$ are each independently selected from the group consisting of: C, N and substituted carbon;

Q is selected from the group consisting of: piperidinyl, piperazinyl, tetrahydropyridinyl (e.g., 1,2,3,6-tetrahydropyridinyl), bridged piperazinyl, bridged piperidinyl, bridged tetrahydropyridinyl, substituted piperidinyl, substituted piperazinyl, substituted tetrahydropyridinyl (e.g., a substituted 1,2,3,6-tetrahydro-pyridinyl), bridged substituted piperazinyl, bridged substituted piperidinyl, and bridged substituted tetrahydropyridinyl;

z is 1 to 3 (and preferably 1); and $R^1$, $R^2$, $R^8$, $R^{35}$ and $R^{36}$ are as defined below.

This invention provides compounds of formula 1.0 (for example, as described in any one of Embodiment Nos. 1 to 90) in pure or isolated form.

This invention also provides a pharmaceutical composition comprising an effective amount of at least one (e.g., 1, 2 or 3, 1 or 2, and usually 1) compound of formula 1.0 (for example, as described in any one of Embodiment Nos. 1 to 90) and a pharmaceutically acceptable carrier.

This invention also provides a pharmaceutical composition comprising an effective amount of at least one (e.g., 1, 2 or 3, 1 or 2, and usually 1) compound of formula 1.0 (for example, as described in any one of Embodiment Nos. 1 to 90) and an effective amount of at least one other (e.g., 1, 2 or 3, 1 or 2, and usually 1) pharmaceutically active ingredient (such as, for example, a chemotherapeutic agent), and a pharmaceutically acceptable carrier.

This invention also provides a method of inhibiting ERK (i.e., inhibiting the activity of ERK) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method of inhibiting ERK1 (i.e., inhibiting the activity of ERK1) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method of inhibiting ERK2 (i.e., inhibiting the activity of ERK2) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method of inhibiting ERK1 and ERK2 (i.e., inhibiting the activity of ERK1 and ERK2) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method of treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90) in combination with at least one (e.g., 1, 2 or 3, 1 or 2, and usually 1) signal transduction inhibitor.

This invention also provides a method of treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90) in combination with at least one (e.g., 1, 2 or 3, 1 or 2, and usually 1) signal transduction inhibitor.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), wherein said cancer is selected from the group consisting of: melanoma, pancreatic cancer, thyroid cancer, colorectal cancer, lung cancer, breast cancer, and ovarian cancer.

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), wherein said cancer is selected from the group consisting of: melanoma, pancreatic cancer, thyroid cancer, colorectal cancer, lung cancer, breast cancer, and ovarian cancer.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

This invention also provides a method for treating melanoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating melanoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating pancreatic cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating pancreatic cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating thyroid cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating thyroid cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating colorectal cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating colorectal cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating lung cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating lung cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating breast cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating breast cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating ovarian cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating ovarian cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides methods of treating breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents).

This invention also provides methods of treating breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents).

This invention also provides methods of treating breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents), and in combination with an effective amount of at least one (e.g., 1, 2 or 3, 1 or 2, or 1) chemotherapeutic agent.

This invention also provides methods of treating breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents), and in combination with an effective amount of at least one (e.g., 1, 2 or 3, 1 or 2, or 1) chemotherapeutic agent.

The methods of treating breast cancer described herein include the treatment of hormone-dependent metastatic and advanced breast cancer, adjuvant therapy for hormone-dependent primary and early breast cancer, the treatment of ductal carcinoma in situ, and the treatment of inflammatory breast cancer in situ.

The methods of treating hormone-dependent breast cancer can also be used to prevent breast cancer in patients having a high risk of developing breast cancer.

Thus, this invention also provides methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents).

This invention also provides methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents).

This invention also provides methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents), and in combination with an effective amount of at least one (e.g., 1, 2 or 3, 1 or 2, or 1) chemotherapeutic agent.

This invention also provides methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90) in combination with hormonal therapies (i.e., antihormonal agents), and in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) a in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of a chemotherapeutic agent wherein said chemotherapeutic agent is temozolomide.

This invention also provides a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of a chemotherapeutic agent, wherein said chemotherapeutic agent is temozolomide.

This invention also provides a method for treating prostate cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating prostate cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating myelodysplastic syndrome in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating myelodysplastic syndrome in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 909), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating acute myelogenous leukemia (AML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating acute myelogenous leukemia (AML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating bladder cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating bladder cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating non-Hodgkin's lymphoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating non-Hodgkin's lymphoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating multiple myeloma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90).

This invention also provides a method for treating multiple myeloma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

This invention also provides a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90).

This invention also provides a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 90), in combination with an effective amount of at least one (e.g., 1, 2 or 3, 1 or 2, or 1) chemotherapeutic agent.

In the methods of this invention the compounds of this invention can be administered concurrently or sequentially (i.e., consecutively) with the chemotherapeutic agents or the signal transduction inhibitor.

The methods of treating cancers described herein can optionally include the administration of an effective amount of radiation (i.e., the methods of treating cancers described herein optionally include the administration of radiation therapy).

DETAILED DESCRIPTION OF THE INVENTION

As described herein, unless otherwise indicated, the use of a drug or compound in a specified period is per treatment cycle. For example, once a day means once per day of each day of the treatment cycle. Twice a day means twice per day each day of the treatment cycle. Once a week means one time per week during the treatment cycle. Once every three weeks means once per three weeks during the treatment cycle.

The following abbreviations have the following meanings unless defined otherwise:
ACN Acetonitrile
AcOH Acetic acid
DAST (diethylamino)sulfur trifluoride
DCC Dicyclohexylcarbodiimide
DCU Dicyclohexylurea
DCM Dichloromethane
DIAD Diisopropylazodicarboxylate
DIEA Diisopropylethylamine
DMAP 4-Dimethylaminopyridine
DME Dimethoxyethane
DMF Dimethylformamide
DMFDMA N,N-Dimethylformamide dimethylacetal
DMSO Dimethyl sulfoxide
DTT Dithiothreitol
EDCl 1-(3-dimethylamino-propyl)-3-ethylcarbodiimide hydrochloride
EtOAc Ethyl acetate
EtOH Ethanol
HATU N,N,N',N'-Tetramethyl-O-(7-Azabenzotriazol-1-yl)Uronium hexafluorophosphate
Hex hexanes
HOBt 1-Hydroxylbenzotriazole
HPLC High pressure liquid chromatography
LCMS Liquid chromatography mass spectrometry
LDA Lithium diisopropylamide
mCPBA meta-Chloroperoxybenzoic acid
MeOH Methanol
MTT (3-[4,5-dimethyl-thiazol-2-yl]-2,5-diphenyltetrazolium bromide, Thiazolyl blue)
NMR Nuclear magnetic resonance
PFP Pentafluorophenol
PMB p-methoxybenzyl
Pyr Pyridine
RT Room temperature
SEMCl 2-(Trimethylsily)ethoxy methyl chloride
TEA Triethylamine
Tr Triphenyl methane
TrCl Triphenyl methane chloride
TFA Trifluoroacetic acid
THF Tetrahydrofuran
TLC Thin layer chromatography
TMS Trimethylsilyl As used herein, unless otherwise specified, the following terms have the following meanings:
"anti-cancer agent" means a drug (medicament or pharmaceutically active ingredient) for treating cancer;

"antineoplastic agent" means a drug (medicament or pharmaceutically active ingredient) for treating cancer (i.e., a chemotherapeutic agent);

"at least one", as used in reference to the number of compounds of this invention means for example 1-6, generally 1-4, more generally 1, 2 or 3, and usually one or two, and more usually one;

"at least one", as used in reference to the number of chemotherapeutic agents used, means for example 1-6, generally 14, more generally 1, 2 or 3, and usually one or two, or one;

"chemotherapeutic agent" means a drug (medicament or pharmaceutically active ingredient) for treating cancer (i.e., and antineeoplastic agent);

"compound" with reference to the antineoplastic agents, includes the agents that are antibodies;

"concurrently" means (1) simultaneously in time (e.g., at the same time); or (2) at different times during the course of a common treatment schedule;

"consecutively" means one following the other;

"different" as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

"effective amount" or "therapeutically effective amount" is meant to describe an amount of compound or a composition of the present invention, or an amount of radiation, effective in treating or inhibiting the diseases or conditions described herein, and thus producing the desired therapeutic, ameliorative, inhibitory or preventative effect; thus, for example, in the methods of treating cancer described herein "effective amount" (or "therapeutically effective amount") means, for example, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; for example, in the treatment of lung cancer (e.g., non small cell lung cancer) a therapeutically effective amount is that amount that alleviates or eliminates cough, shortness of breath and/or pain; also, for example, an effective amount, or a therapeutically effective amount of the ERK inhibitor (i.e., a compound of this invention) is that amount which results in the reduction in ERK (ERK1 and/or ERK2) activity and phosphorylation; the reduction in ERK activity may be determined by the analysis of pharmacodynamic markers such as phosphorylated RSK1,2 and phosphorylated ERK1,2, using techniques well known in the art;

"one or more" has the same meaning as "at least one";

"patient" means an animal, such as a mammal (e.g., a human being, and preferably a human being);

"prodrug" means compounds that are rapidly transformed, for example, by hydrolysis in blood, in vivo to the parent compound, i.e., to the compounds of formula 1.0 or to a salt and/or to a solvate thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes Prodrugs of the novel compounds of this invention;

sequentially-represents (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component; the effective time period is the amount of time given for realization of maximum benefit from the administration of the first component; and "solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

As used herein, unless otherwise specified, the following terms have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl, and the like):

"acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted); the bond to the parent moiety is through the carbonyl; preferred acyls contain a lower alkyl; Non-limiting examples of suitable acyl groups include formyl, acetyl, propanoyl, 2-methylpropanoyl, butanoyl and cyclohexanoyl;

"alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; "lower alkenyl" means an alkenyl group comprising about 2 to about 6 carbon atoms in the chain, and the chain can be straight or branched; the term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl); non-limiting examples of suitable alkenyl groups include ethenyl, propenyl, n-butenyl, 3-methylbut-2-enyl, n-pentenyl, octenyl and decenyl;

"alkoxy" means an alkyl-O— group (i.e., the bond to the parent moiety is through the ether oxygen) in which the alkyl group is unsubstituted or substituted as described below; non-limiting examples of suitable alkoxy groups include methoxy, ethoxy, n-propoxy, isopropoxy, n-butoxy and heptoxy;

"alkoxycarbonyl" means an alkyl-O—CO— group (i.e., the bond to the parent moiety is through the carbonyl) wherein the alkyl group is unsubstituted or substituted as previously defined; non-limiting examples of suitable alkoxycarbonyl groups include methoxycarbonyl and ethoxycarbonyl;

"alkyl" (including the alkyl portions of other moieties, such as trifluoroalkyl and alkyloxy) means an aliphatic hydrocarbon group (chain) that can be straight or branched wherein said group comprises about 1 to about 20 carbon atoms in the chain; preferred alkyl groups comprise about 1 to about 12 carbon atoms in the chain; more preferred alkyl groups comprise about 1 to about 6 carbon atoms in the chain; branched means that one or more lower alkyl groups, such as methyl, ethyl or propyl, are attached to a linear alkyl chain; "lower alkyl" means a group comprising about 1 to about 6 carbon atoms in the chain, and said chain can be straight or branched; the term "substituted alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl); non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl;

"alkylaryl" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryls comprise a lower alkyl group; non-limiting examples of suitable alkylaryl groups include o-tolyl, p-tolyl and xylyl;

"alkylheteroaryl" means an alkyl-heteroaryl- group (i.e., the bond to the parent moiety is through the heteroaryl group) wherein the alkyl is unsubstituted or substituted as defined above and the heteroaryl group is unsubstituted or substituted as defined below;

"alkylsulfinyl" means an alkyl-S(O)— group (i.e., the bond to the parent moiety is through the sulfinyl) wherein the alkyl group is unsubstituted or substituted as previously defined; preferred groups are those in which the alkyl group is lower alkyl;

"alkylsulfonyl" means an alkyl-S(O$_2$)— group (i.e., the bond to the parent moiety is through the sulfonyl) wherein the alkyl group is unsubstituted or substituted as previously defined; preferred groups are those in which the alkyl group is lower alkyl;

"alkylthio" means an alkyl-S— group (i.e., the bond to the parent moiety is through the sulfur) wherein the alkyl group is unsubstituted or substituted as previously described; non-limiting examples of suitable alkylthio groups include methylthio, ethylthio, i-propylthio and heptylthio;

"alkynyl" means an aliphatic hydrocarbon group (chain) comprising at least one carbon to carbon triple bond, wherein the chain can be straight or branched, and wherein the group comprises about 2 to about 15 carbon atoms in the; preferred alkynyl groups comprise about 2 to about 12 carbon atoms in the chain; and more preferably about 2 to about 4 carbon atoms in the chain; Branched means that one or more lower alkyl groups, such as methyl, ethyl or propyl, are attached to a linear alkynyl chain; "lower alkynyl" means an alkynyl group comprising about 2 to about 6 carbon atoms in the chain, and the chain can be straight or branched; non-limiting examples of suitable alkynyl groups include ethynyl, propynyl, 2-butynyl, 3-methylbutynyl, n-pentynyl, and decynyl; the term "substituted alkynyl" means that the alkynyl group is substituted by one or more independently selected, and each substituent is independently selected from the group consisting of alkyl; aryl and cycloalkyl;

"amino means a —NH$_2$ group;

"aralkenyl" (or arylalkenyl) means an aryl-alkenyl- group (i.e., the bond to the parent moiety is through the alkenyl group) wherein the aryl group is unsubstituted or substituted as defined below, and the alkenyl group is unsubstituted or substituted as defined above; preferred aralkenyls contain a lower alkenyl group; non-limiting examples of suitable aralkenyl groups include 2-phenethenyl and 2-naphthylethenyl;

"aralkyl" (or arylalkyl) means an aryl-alkyl- group (i.e., the bond to the parent moiety is through the alkyl group) wherein the aryl is unsubstituted or substituted as defined below and the alkyl is unsubstituted or substituted as defined above; preferred aralkyls comprise a lower alkyl group; non-limiting examples of suitable aralkyl groups include benzyl, 2-phenethyl and naphthalenylmethyl;

"aralkyloxy" (or arylalkyloxy) means an aralkyl-O— group (i.e., the bond to the parent moiety is through the ether oxygen) wherein the aralkyl group is unsubstituted or substituted as previously described; non-limiting examples of suitable aralkyloxy groups include benzyloxy and 1- or 2-naphthalenemethoxy;

"aralkoxycarbonyl" means an aralkyl-O—C(O)— group (i.e., the bond to the parent moiety is through the carbonyl) wherein the aralkyl group is unsubstituted or substituted as previously defined; a non-limiting example of a suitable aralkoxycarbonyl group is benzyloxycarbonyl;

"aralkylthio" means an aralkyl-S— group (i.e., the bond to the parent moiety is through the sulfur) wherein the aralkyl group is unsubstituted or substituted as previously described; a non-limiting example of a suitable aralkylthio group is benzylthio;

"aroyl" means an aryl-C(O)— group (i.e., the bond to the parent moiety is through the carbonyl) wherein the aryl group is unsubstituted or substituted as defined below; non-limiting examples of suitable groups include benzoyl and 1- and 2-naphthoyl;

"aryl" (sometimes abbreviated "ar") means an aromatic monocyclic or multicyclic ring system comprising about 6 to about 14 carbon atoms, preferably about 6 to about 10 carbon atoms; the aryl group can be optionally substituted with one or more independently selected "ring system substituents" (defined below). Non-limiting examples of suitable aryl groups include phenyl and naphthyl;

"arylalkynyl" means an aryl-alkynyl- group (i.e., the bond to the parent moiety is through the alkynyl group) wherein the aryl group is unsubstituted or substituted as defined above, and the alkynyl group is unsubstituted or substituted as defined above;

"arylaminoheteroaryl" means an aryl-amino-heteroaryl group (i.e., the bond to the parent moiety is through the heteroaryl group) wherein the aryl group is unsubstituted or substituted as defined above, the amino group is as defined above (i.e., a —NH— here), and the heteroaryl group is unsubstituted or substituted as defined below;

"arylheteroaryl" means an aryl-heteroaryl group—(i.e., the bond to the parent moiety is through the heteroaryl group) wherein the aryl group is unsubstituted or substituted as defined above, and the heteroaryl group is unsubstituted or substituted as defined below;

"aryloxy" means an aryl-O— group (i.e., the bond to the parent moiety is through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to the parent moiety is through the carbonyl) wherein the aryl group is unsubstituted or substituted as previously defined; non-limiting examples of suitable aryloxycarbonyl groups include phenoxycarbonyl and naphthoxycarbonyl;

"arylsulfinyl" means an aryl-S(O)— group (i.e., the bond to the parent moiety is through the sulfinyl) wherein aryl is unsubstituted or substituted as previously defined;

"arylsulfonyl" means an aryl-S(O$_2$)— group (i.e., the bond to the parent moiety is through the sulfonyl) wherein aryl is unsubstituted or substituted as previously defined;

"arylthio" means an aryl-S— group (i.e., the bond to the parent moiety is through the sulfur) wherein the aryl group is unsubstituted or substituted as previously described; non-limiting examples of suitable arylthio groups include phenylthio and naphthylthio;

"cycloalkenyl" means a non-aromatic mono or multicyclic ring system comprising about 3 to about 10 carbon atoms, preferably about 5 to about 10 carbon atoms that contains at least one carbon-carbon double bond; preferred cycloalkenyl rings contain about 5 to about 7 ring atoms; the cycloalkenyl can be optionally substituted with one or more independently selected "ring system substituents" (defined below); Non-limiting examples of suitable monocyclic cycloalkenyls include cyclopentenyl, cyclohexenyl, cycloheptenyl, and the like; a non-limiting example of a suitable multicyclic cycloalkenyl is norbornylenyl;

"cycloalkyl" means a non-aromatic mono- or multicyclic ring system comprising about 3 to about 7 carbon atoms, preferably about 3 to about 6 carbon atoms; the cycloalkyl can be optionally substituted with one or more independently selected "ring system substituents" (defined below); non-limiting examples of suitable monocyclic cycloalkyls include cyclopropyl, cyclopentyl, cyclohexyl, cycloheptyl and the like; non-limiting examples of suitable multicyclic cycloalkyls include 1-decalin, norbornyl, adamantyl and the like;

"cycloalkylalkyl" means a cycloalkyl-alkyl-group (i.e., the bond to the parent moiety is through the alkyl group) wherein the cycloalkyl moiety is unsubstituted or substituted as defined above, and the alkyl moiety is unsubstituted or substituted as defined above;

"halo" means fluoro, chloro, bromo, or iodo groups; preferred halos are fluoro, chloro or bromo, and more preferred are fluoro and chloro;

"halogen" means fluorine, chlorine, bromine, or iodine; preferred halogens are fluorine, chlorine and bromine;

"haloalkyl" means an alkyl, as defined above, wherein one or more hydrogen atoms on the alkyl is replaced by a halo group, as defined above;

"heteroaralkenyl" means a heteroaryl-alkenyl- group (i.e., the bond to the parent moiety is through the alkenyl group) wherein the heteroaryl group is unsubstituted or substituted as defined below, and the alkenyl group is unsubstituted or substituted as defined above;

"heteroaralkyl" (or heteroarylalkyl) means a heteroaryl-alkyl- group (i.e., the bond to the parent moiety is through the alkyl group) in which the heteroaryl is unsubstituted or substituted as defined below, and the alkyl group is unsubstituted or substituted as defined above; preferred heteroaralkyls comprise an alkyl group that is a lower alkyl group; non-limiting examples of suitable aralkyl groups include pyridylmethyl, 2-(furan-3-yl)ethyl and quinolin-3-ylmethyl;

"heteroaralkylthio" means a heteroaralkyl-S— group wherein the heteroaralkyl group is unsubstituted or substituted as defined above;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryls comprise about 5 to about 6 ring atoms; the "heteroaryl" can be optionally substituted by one or more independently selected "ring system substituents" (defined below); the prefix aza, oxa or thia before the heteroaryl root name means that at least a nitrogen, oxygen or sulfur atom, respectively, is present as a ring atom; a nitrogen atom of a heteroaryl can be optionally oxidized to the corresponding N-oxide; non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like;

"heteroarylalkynyl" (or heteroaralkynyl) means a heteroaryl-alkynyl- group (i.e., the bond to the parent moiety is through the alkynyl group) wherein the heteroaryl group is unsubstituted or substituted as defined above, and the alkynyl group is unsubstituted or substituted as defined above;

"heteroarylaryl" (or heteroararyl) means a heteroaryl-aryl-group (i.e., the bond to the parent moiety is through the aryl group) wherein the heteroaryl group is unsubstituted or substituted as defined above, and the aryl group is unsubstituted or substituted as defined above;

"heteroarylheteroarylaryl" means a heteroaryl-heteroaryl-group (i.e., the bond to the parent moiety is through the last heteroaryl group) wherein each heteroaryl group is independently unsubstituted or substituted as defined above;

"heteroarylsulfinyl" means a heteroaryl-SO— group wherein the heteroaryl group is unsubstituted or substituted as defined above;

"heteroarylsulfonyl" means a heteroaryl-$SO_2$— group wherein the heteroaryl group is unsubstituted or substituted as defined above;

"heteroarylthio" means a heteroaryl-S— group wherein the heteroaryl group is unsubstituted or substituted as defined above;

"heterocyclenyl" (or heterocycloalkenyl) means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system; Preferred heterocyclenyl rings contain about 5 to about 6 ring atoms; the prefix aza, oxa or thia before the heterocyclenyl root name means that at least a nitrogen, oxygen or sulfur atom, respectively, is present as a ring atom; the heterocyclenyl can be optionally substituted by one or more independently selected "Ring system substituents" (defined below); the nitrogen or sulfur atom of the heterocyclenyl can be optionally oxidized to the corresponding N-oxide, S-oxide or S,S-dioxide; non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like; Non-limiting examples of suitable oxaheterocyclenyl groups include 3,4-dihydro-2H-pyran, dihydrofuranyl, fluorodihydrofuranyl, and the like; A non-limiting example of a suitable multicyclic oxaheterocyclenyl group is 7-oxabicyclo[2.2.1]heptenyl; non-limiting examples of suitable monocyclic thiaheterocyclenyl rings include dihydrothiophenyl, dihydrothiopyranyl, and the like;

"heterocycloalkylalkyl" (or heterocyclylalkyl) means a heterocycloalkyl-alkyl-group (i.e., the bond to the parent moiety is through the alkyl group) wherein the heterocycloalkyl group (i.e., the heterocyclyl group) is unsubstituted or substituted as defined below, and the alkyl group is unsubstituted or substituted as defined above;

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyls contain about 5 to about 6 ring atoms; the prefix aza, oxa or thia before the heterocyclyl root name means that at least a nitrogen, oxygen or sulfur atom respectively is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like;

"hydroxyalkyl" means a HO-alkyl- group wherein the alkyl group is substituted or unsubstituted as defined above; preferred hydroxyalkyls comprise a lower alkyl; Non-limiting examples of suitable hydroxyalkyl groups include hydroxymethyl and 2-hydroxyethyl; and "ring system substituent" means a substituent attached to an aromatic or non-aromatic ring system that, for example, replaces an available hydrogen on the ring system; ring system substituents are each independently selected from the group consisting of: alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently selected from the group consisting of: hydrogen, alkyl, aryl, and aralkyl; "Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring; Non-limiting examples include:

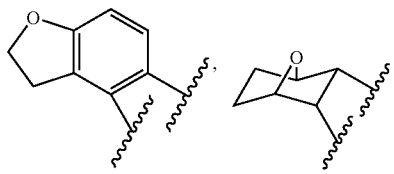

and the like

Lines drawn into a ring mean that the indicated bond may be attached to any of the substitutable ring carbon atoms.

Any carbon or heteroatom with unsatisfied valences in the text, schemes, examples, structural formulae, and any Tables herein is assumed to have the hydrogen atom or atoms to satisfy the valences.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula 1.0 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of formula 1.0, or a pharmaceutically acceptable salt, hydrate or solvate of the compound, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxy-methyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxy-carbonyl)amino) ethyl having from 4 to 10 carbon atoms, 3-phthalidyl, 4-crotonolactonyl, gamma-butyrolacton-4-yl, di-N,N—$(C_1-C_2)$ alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino $(C_2-C_3)$alkyl, and the like.

Similarly, if a compound of formula 1.0 contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyl-oxy)ethyl, 1-methyl-1-(($C_1-C_6$)alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O) $(OH)_2$, $-P(O)(O(C_1-C_6)$alkyl$)_2$ or glycosyl (the radical resulting from the removal of a hydroxyl group of the hemiacetal form of a carbohydrate), and the like.

If a compound of formula 1.0 incorporates an amine functional group, a prodrug can be formed by the replacement of a hydrogen atom in the amine group with a group such as, for example, $R^{70}$-carbonyl, $R^{70}$O-carbonyl, $NR^{70}R^{75}$-carbonyl where $R^{70}$ and $R^{75}$ are each independently $(C_1-C_{10})$alkyl, $(C_3-C_7)$ cycloalkyl, benzyl, or $R^{70}$-carbonyl is a natural α-aminoacyl or natural α-aminoacyl, $-C(OH)C(O)OY^{80}$ wherein $Y^{80}$ is H, $(C_1-C_6)$alkyl or benzyl, $-C(OY^{82})Y^{84}$ wherein $Y^{82}$ is $(C_1-C_4)$ alkyl and $Y^{84}$ is $(C_1-C_6)$alkyl, carboxy $(C_1-C_6)$alkyl, amino$(C_1-C_4)$alkyl or mono-N— or di-N,N-$(C_1-C_6)$alkylaminoalkyl, $-C(Y^{86})Y^{88}$ wherein $Y^{86}$ is H or methyl and $Y^{88}$ is mono-N— or di-N,N-$(C_1-C_6)$alkylamino morpholino, piperidin-1-yl or pyrrolidin-1-yl, and the like.

This invention also includes the compounds of this invention in isolated and purified form.

Polymorphic forms of the compounds of formula 1.0, and of the salts, solvates and prodrugs of the compounds of formula 1.0, are intended to be included in the present invention.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

The compounds of formula 1.0 form salts that are also within the scope of this invention. Reference to a compound of formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula 1.0 may be formed, for example, by reacting a compound of formula 1.0 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of formula 1.0, and salts, solvates and prodrugs thereof, may exist in their tautomeric form (for example, as an amide or imino ether). All such tautomeric forms are contemplated herein as part of the present invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

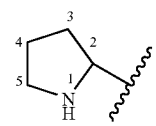

there is no —OH attached directly to carbons marked 2 and 5.

The compounds of formula 1.0 may exist in different tautomeric forms, and all such forms are embraced within the scope of the invention. Also, for example, all keto-enol and imine-enamine forms of the compounds are included in the invention.

Tautomeric forms such as, for example, the moieties:

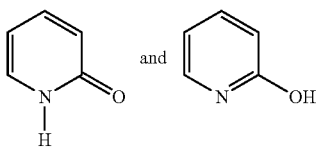

are considered equivalent in certain embodiments of this invention.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^3$, etc.) occurs more than one time in any moiety or in any compound of formula 1.0, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^3C$, $^{14}C$, $^{15}N$, $^{18}O$, $^{17}O$, $^3P$, $^{32}P$, $^{35}S$, $^{18}F$, and $^{36}Cl$, respectively.

Certain isotopically-labelled compounds of formula 1.0 (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of formula 1.0 can generally be prepared by following procedures analogous to those disclosed in the Schemes and/or in the Examples hereinbelow, by substituting an appropriate isotopically labelled reagent for a non-isotopically labelled reagent.

This invention provides compounds of formula 1.0:

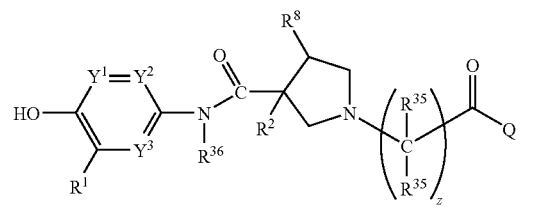

(1.0)

or the pharmaceutically acceptable salts thereof, wherein:

$Y^1$, $Y^2$, and $Y^3$ are each independently selected from the group consisting of: —CH=, —N= and —CR$^9$= (preferably $Y^1$, $Y^2$, and $Y^3$ are each —CH=);

z is 1 to 3 (i.e., 1, 2 or 3, and preferably 1);

Q is a substituent selected from the group consisting of:

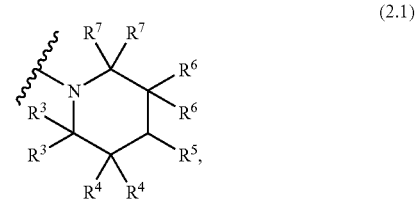

(2.1)

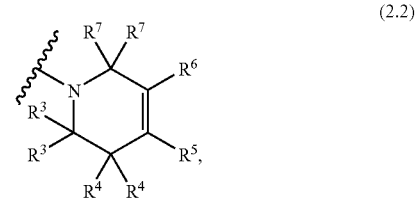

(2.2)

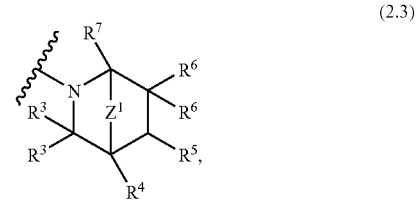

(2.3)

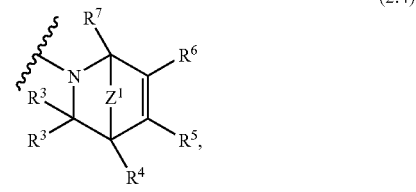

(2.4)

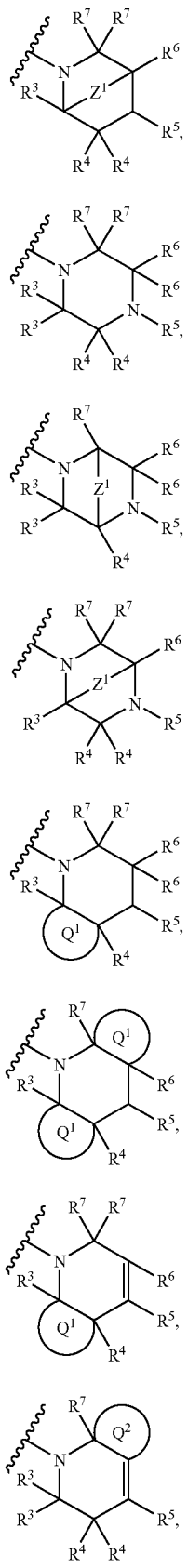

(2.5)
(2.6)
(2.7)
(2.8)
(2.9)
(2.10)
(2.11)
(2.12)

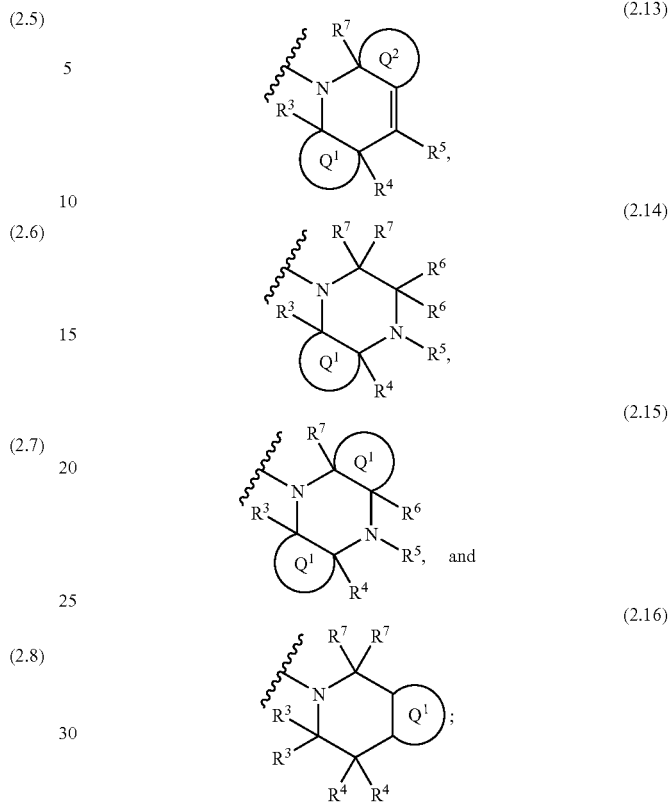

(2.13)
(2.14)
(2.15)
(2.16)

Each $Q^1$ represents a ring independently selected from the group consisting of: cycloalkyl, substituted cycloalkyl, heterocycloalkyl, substituted heterocycloalkyl, aryl, substituted aryl, heteroaryl, and substituted heteroaryl, wherein said substituted rings are substituted with 1 to 3 substituents independently selected from the group consisting of: the $R^{10}$ moieties; provided that when $Q^1$ is aryl, heteroaryl, substituted aryl or substituted heteroaryl then the carbon atoms at the ring junction (i.e., the two carbon atoms common to the fused rings) are not substituted;

$Q^2$ represents a ring selected from the group consisting of: cycloalkyl, substituted cycloalkyl, heterocycloalkyl, and substituted heterocycloalkyl, wherein said substituted rings are substituted with 1 to 3 substituents independently selected from the group consisting of: the $R^{10}$ moieties;

$Z^1$ represents —$(C(R^{24})_2)_w$— wherein each $R^{24}$ is independently selected from the group consisting of: H, alkyl (e.g., $C_1$ to $C_6$ alkyl, for example methyl) and F, and wherein w is 1, 2 or 3, and generally w is 1 or 2, and usually w is 1, and wherein in one example each $R^{24}$ is H, and in another example w is 1, and in another example each $R^{24}$ is H and w is 1, preferably w is 1 and each $R^{24}$ is H (i.e., preferably $Z^1$ is —$CH_2$—);

$Z^2$ is selected from the group consisting of: —$N(R^{44})$—, —O— and —$C(R^{46})_2$— (e.g., $Z^2$ is —NH—, —O— or —$CH_2$—);

m is 1 to 6;
n is 1 to 6;
p is 0 to 6;
t is 0, 1, or 2;
$R^1$ is selected from the group consisting of:
(1) —CN,
(2) —$NO_2$, (3) —OR$^{10}$,
(4) —SR$^{10}$,
(5) —N(R$^{10}$)$_2$,
(6) R$^{10}$,
(7) halo (e.g., Cl, Br, and F),
(8) —CF$_3$;
(9) alkenyl (e.g., —CH=CHCH$_3$);
(10) —C(O)N(R$^{10}$)$_2$ wherein each R$^{10}$ is independently selected, and preferably each R$^{10}$ is independently selected from the group consisting of: (a) H, (b) alkyl (e.g., methyl, butyl, and i-propyl), (c) heteroaryl (e.g., pyridyl), (d) aryl (e.g., phenyl), and (e) cycloalkyl (e.g., cyclopropyl), wherein for example, each R$^{10}$ is selected from the group consisting of: H, methyl, butyl, i-propyl, pyridyl, phenyl and cyclopropyl, wherein, for example, said —C(O)N(R$^{10}$)$_2$ moiety is selected from the group consisting of: —C(O)NH$_2$, —C(O)NH(CH$_3$), —C(O)NH(CH)(CH$_3$)$_2$ (i.e., —C(O)NH(i-propyl)), —C(O)NH(C$_4$H$_9$), —C(O)NH(C$_6$H$_5$) (i.e., —C(O)NH(phenyl)), —C(O)NH(C$_3$H$_5$) (i.e., —C(O)NH(cyclopropyl), and —C(O)NH(C$_5$H$_4$N) (i.e., —C(O)NH(pyridyl), such as

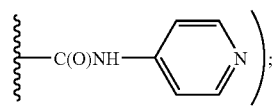

(11) arylalkenyl- (aralkenyl-), for example, aryl(C$_2$ to C$_6$)alkenyl-, such as for example, —CH=CH-phenyl;
R$^2$ is selected from the group consisting of:
(1) H,
(2) —CN,
(3) halo (e.g., F),
(4) alkyl (e.g., C$_1$ to C$_6$ alkyl, such as, for example, methyl, ethyl and propyl, and in another example, methyl and ethyl),
(5) substituted alkyl (e.g., substituted C$_1$ to C6 alkyl, such as, for example, substituted methyl and substituted ethyl) wherein said substituted alkyl is substituted with 1 to 3 substituents (e.g., 1 substituent) selected from the group consisting of: (a) —OH, (b) —O-alkyl (e.g., —O—(C$_1$-C$_3$alkyl), (c) —O-alkyl (e.g., —O—(C$_1$-C$_3$alkyl)) substituted with 1 to 3 F atoms, and (d) —N(R$^{40}$)$_2$ wherein each R$^{40}$ is independently selected from the group consisting of: (i) H, (ii) C$_1$-C$_3$ alkyl (e.g., methyl) and (iii) —CF$_3$, (examples of said substituted alkyl groups described in (5) include but are not limited to —CH$_2$OCH$_3$),
(6) alkynyl (e.g., ethynyl),
(7) alkenyl (e.g., —CH$_2$—CH=CH$_2$),
(8) —(CH$_2$)$_m$R$^{11}$,
(9) —N(R$^{26}$)$_2$,
(10) —OR$^{23}$ (e.g., —OH, —OCH$_3$ and —O-phenyl),
(11) —N(R$^{26}$)C(O)R$^{42}$ wherein in one example R$^{26}$ is H or C$_1$ to C$_6$ alkyl (e.g., methyl) and R$^{42}$ is alkyl (e.g., methyl), and in another example —N(R$^{26}$)C(O)R$^{42}$ is —NHC(O)CH$_3$,
(12) cycloalkyl (e.g., C$_3$ to C$_6$ cycloalkyl, such as, for example, cyclopropyl and cyclohexyl),
(13) cycloalkylalkyl (e.g., C$_3$ to C$_6$ cycloalkyl-(C$_1$ to C$_3$)alkyl-, such as, for example, cyclopropyl-CH$_2$— and cyclohexyl-CH$_2$—), (14)

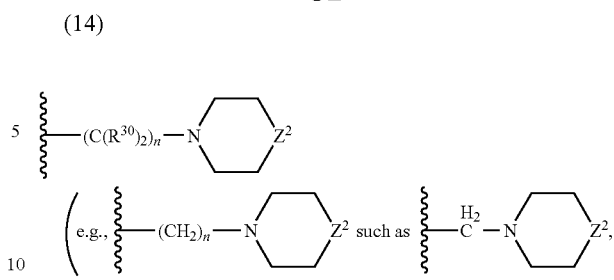

wherein:
(a) in one example said (12) moiety is

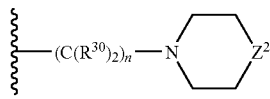

and n is 1,
(b) in another example said (12) moiety is

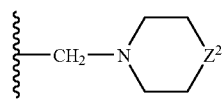

(i.e., n is 1, and each R$^{30}$ is H),
(c) in another example Z$^2$ is —NH— in (a),
(d) in another example Z$^2$ is —NH— in (b),
(e) in another example Z$^2$ is —O— in (a),
(f) in another example Z$^2$ is —O— in (b),
(g) in another example Z$^2$ is —CH$_2$— in (a),
(h) in another example Z$^2$ is —CH$_2$— in (b),
(i) in another example R$^2$ is —(CH$_2$)—R$^1$ and m is 1,
(j) in another example R$^2$ is —N(R$^{26}$)$_2$,
(k) in another example R$^2$ is —N(R$^{26}$)$_2$, and each R$^{26}$ is H (i.e., R$^2$ is —NH$_2$),
(l) in another example R$^2$ is —OR$^{23}$, and
(m) in another example R$^2$ is —OH (i.e., R$^{21}$ is H);
each R$^3$, R$^4$, R$^5$, R$^6$ and R$^7$ is independently selected from the group consisting of:
(1) H,
(2) alkenyl (e.g., —CH$_2$CH=CH$_2$),
(3) substituted alkenyl,
(4) alkyl (e.g., methyl and ethyl),
(5) substituted alkyl,
(6) cycloalkyl (e.g., cyclohexyl),
(7) substituted cycloalkyl,
(8) cycloalkylalkyl-,
(9) substituted cycloalkylalkyl-,
(10) heterocycloalkyl,
(11) substituted heterocycloalkyl,
(12) heterocycloalkylalkyl-,
(13) substituted heterocycloalkylalkyl-,
(14) —C(O)R$^{10}$ wherein in one example R$^{10}$ is selected from the group consisting of: alkyl (e.g., C$_1$ to C$_6$, e.g., methyl), in another example R$^{10}$ is aryl (e.g., phenyl), in another example R$^{10}$ is substituted aryl (e.g., substituted phenyl, such as, for example, fluorophenyl-), in another example R$^{10}$ is heteroaryl (e.g., furanyl), and in another example R$^{10}$ is heterocycloalkyl (e.g., tetrahydrofuranyl-)

(15) arylheteroaryl- (e.g., phenylthiadiazolyl-, and phenylthienyl-),
(16) substituted arylheteroaryl- (e.g., substituted phenylthiadiazolyl-),
(17) heteroarylaryl-, such as, for example, pyrimidinylphenyl-, pyrazinylphenyl-, pyridinylphenyl- (i.e., pyridylphenyl-), furanylphenyl-, thienylphenyl-, thiazolylphenyl-, benzofuranylphenyl-, oxazolylphenyl-, pyrazolylphenyl-, pyrrolylphenyl-, and triazolylphenyl,
(18) substituted heteroarylaryl-, such as, for example, substituted pyrimidinylphenyl-, substituted pyrazinylphenyl-, substituted pyridinylphenyl- (i.e., substituted pyridylphenyl-), substituted furanylphenyl-, substituted thienylphenyl-, substituted thiazolylphenyl-, substituted pyrimidinylphenyl, substituted pyridazinylphenyl, and substituted pyrrolylphenyl-,
(19) aryl (e.g., phenyl and naphthyl),
(20) substituted aryl (e.g., substituted phenyl and substituted naphthyl),
(21) heteroaryl (e.g., thiazolyl, thienyl, pyridyl, pyrimidinyl, bonzoimidazolyl, benzotriazolyl, benzooxazolyl, benzothiazolyl, benzofuranyl, and pyrazinyl),
(22) substituted heteroaryl (e.g., substituted thiazolyl, substituted pyridyl, substituted pyrimidinyl, substituted benzoimidazolyl, and substituted pyrazinyl), examples of substituted heteroaryl groups include, for example bromothiazolyl-, bromopyrimidinyl-, fluoropyrimidinyl-, ethenylpyrimidinyl-, chloropyrazinyl-, cyanobenzoimidazolyl, cyanopyridyl-, nitropyridyl-, methylpyridyl-, $CH_3C(O)$-pyrimidyl-, and N-cyclopropylmethylbenzoimidazolyl-,
(23) heteroarylheteroaryl- (e.g., pyrimidinylpyridyl-, and pyrimidinylthiazolyl-),
(24) substituted heteroarylheteroaryl- (e.g., substituted pyrimidinyl- pyridyl-)
(25) arylaminoheteroaryl- (e.g., phenyl-NH-oxadiazolyl-),
(26) substituted arylaminoheteroaryl- (e.g., substituted phenyl-NH-oxadiazolyl-),
(27) arylalkynyl- (e.g., aryl($C_2$ to $C_4$)alkynyl such as, for example phenylethynyl-),
(28) substituted arylalkynyl- (e.g., substituted aryl($C_2$ to $C_4$)alkynyl-, such as, for example, substituted phenylethynyl-),
(29) heteroarylalkynyl- (e.g., heteroaryl($C_2$ to $C_4$)alkynyl-, such as, for example, pyrimidinylethynyl-),
(30) substituted heteroarylalkynyl- (e.g., substituted heteroaryl($C_2$ to $C_4$)alkynyl-, such as, for example substituted pyrimidinylethynyl-),
(31) —C(O)NHR$^{28}$ (e.g., —C(O)NHCH$_3$),
(32) cycloalkylheteroarylaryl- (e.g., cyclopropylpyrimidylphenyl-).
(33) substituted arylaryl- (e.g., HOCH$_2$-phenyl-phenyl-, Cl-phenyl-phenyl-, F-phenyl-phenyl-, and CH$_3$O-phenyl-phenyl-),
(34) arylalkenylaryl- (e.g., aryl($C_2$-$C_4$)alkenylaryl, such as, for example, phenylethenylphenyl-),
(35) arylaryl- (e.g., phenyl-phenyl-),
(36) substituted arylalkyl- (e.g., Br-phenyl-CH(CH$_3$)—, and 1-phenyl-CH(CH$_3$)—),
(37) arylalkyl- (e.g., benzyl),
(38) —SO$_2$aryl (e.g., —SO$_2$-phenyl),
(39) benzoheteroaryl-C(O)-(substituted heterocycloalkyl)- (e.g., benzopyridazinyl-C(O)-(substituted piperidinyl)-, such as, for example, benzopyridazinyl-C(O)-(methyl substituted piperidinyl)-),
(40) substituted heterocycloalkyl (e.g., N—CH$_3$C(O)-piperidinyl-, N—CH$_3$C(O)-methyl substituted piperidinyl, N-(t-butylC(O)O)-methyl substituted piperidinyl, and N-benzyl-piperidinyl), and
(41) heterocycloalkyl-C(O)-alkyl- (e.g., morpholinyl-C(O)—CH$_2$—),
(42) benzo[1,3]dioxolyl, wherein said R$^3$, R$^4$, R$^5$, R$^6$ and R$^7$ substituted groups (7), (9), (11), (13), (16), (18), (20), (22), (24), (26), (28), (30), (33), (36), (39) and (40), are substituted with 1 to 3 substituents independently selected from the group consisting of: —CH$_2$OH, CN, —OH, —NH$_2$, alkyl (e.g., C$_1$ to C$_6$ alkyl, e.g., methyl, ethyl, and i-propyl), alkenyl (e.g., C$_2$ to C$_6$ alkenyl, such as, for example —CH═CH$_2$), halo (e.g., I, F, Cl and Br, and in one example said halo is selected from the group consisting of: F, Cl and Br, and in another example said halo is F, and in another example said halo is Br, and in another example said halo is Cl), —C(O)—NH—R$^{28}$ (e.g., —C(O)—NH—CH$_3$), —C(O)—NH$_2$, —C(O)OR$^{28}$ (e.g., —C(O)OC$_2$H$_5$), —C(O)R$^{28}$ (e.g., —C(O)CH$_3$), —C(alkyl)═NOH (e.g., —C(CH$_3$)═NOH), —C(alkyl)═NO(alkyl) (e.g., —C(CH$_3$)═NOCH$_3$), alkoxy (e.g., methoxy and t-butoxy), hydroxyl substituted alkyl (e.g., —CH(CH$_3$)OH), dialkylamine wherein each alkyl group is independently selected (e.g., —N(CH$_3$)$_2$), —CF$_3$, —SO$_2$alkyl (e.g., —SO$_2$CH$_3$), and —NHC(O)H, wherein said R$^3$, R$^4$, R$^5$, R$^6$ and R$^7$ substituted groups (3) and (5) are substituted with 1 to 3 substituents independently selected from the group consisting of: —NH$_2$, halo (e.g., F, Cl and Br, and in another example F), —C(O)—NH—R$^{28}$ (e.g., —C(O)—NH—CH$_3$), —C(O)OR$^{28}$ (e.g., —C(O)OC$_2$H$_5$), and —C(O)R$^{28}$ (e.g., —C(O)CH$_3$), and wherein:
in one example said substituted heteroarylaryl (moiety (18) above) is substituted with 1 to 3 substituents independently selected from the group consisting of: —NH$_2$, alkyl (e.g., C$^1$ to C$_6$ alkyl, e.g., methyl), halo (e.g., F, Cl and Br, such as, for example F),
in another example said substituted aryl (moiety (20) above) is substituted with 1 to 3 substituents independently selected from the group consisting of halo (e.g., F, Cl and Br), —C(O)—NH—R$^{28}$ (e.g., —C(O)—NH—CH$_3$), —C(O)OR$^{28}$ (e.g., —C(O)O—C$_2$H$_5$), and —C(O)R$^{28}$ (e.g., —C(O)CH$_3$), and
in another example said substituted heteroaryl (moiety (22) above) is substituted with 1 to 3 substituents selected from the group consisting of: halo (e.g., Br, F, and Cl), alkenyl (e.g., C$_2$ to C$_6$ alkenyl, such as, for example, —CH═CH$_2$);

R$^8$ is selected from the group consisting of: H, —OH, alkyl (e.g., methyl), aryl (e.g., phenyl), —N(R$^{10}$)$_2$ (e.g., —NH$_2$) and —NR$^{10}$C(O)R$^{12}$ (e.g., —NHC(O)CH$_3$);

each R$^9$ is independently selected from the group consisting of: halogen, —CN, —NO$_2$, —OR$^{10}$, —SR$^{10}$, —N(R$^{10}$)$_2$, and R$^{10}$;

each R$^{10}$ is independently selected from the group consisting of: H, alkyl (e.g., i-propyl, t-butyl, and methyl), aryl (e.g., phenyl), arylalkyl, heteroaryl (e.g., pyridyl, such as o-pyridyl, and pyrazolyl), heteroarylalkyl, cycloalkyl (e.g., cyclopropyl), cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said $R^{10}$ substituted alkyl is substituted with 1 to 3 substituents independently selected from the group consisting of: —$NH_2$, —$NHR^{20}$, —$NO_2$, —CN, —$OR^{26}$, halo (e.g., F, Cl and Br, and in another example F), —C(O)—NH—$R^{26}$ (e.g., —C(O)—NH—$CH_3$, i.e., $R^{26}$ is alkyl, such as methyl), —C(O)$OR^{26}$ (e.g., —C(O)$OC_2H_5$, i.e., $R^{26}$ is alkyl, such as ethyl), and —C(O)$R^{26}$ (e.g., —C(O)$CH_3$, i.e., $R^{26}$ is alkyl, such as methyl), and said $R^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —$NH_2$, (2) —$NO_2$, (3) —CN, (4) —OH, (5) —$OR^{20}$, (6) —$OCF_3$, (7) —$CF_3$, (8) —C(O)$R^{38}$ (e.g., $R^{38}$ is H or alkyl (e.g., $C_1$ to $C_6$ alkyl, such as, for example, methyl or ethyl), for example, $R^{38}$ is alkyl (e.g., methyl), thus, an example of —C(O)$R^{38}$ is —C(O)$CH_3$), (9) alkyl (e.g., $C_1$ to $C_6$ alkyl, e.g., methyl, ethyl, and i-propyl), (10) alkenyl (e.g., $C_2$ to $C_6$ alkenyl, such as, for example —CH=$CH_2$), (11) halo (e.g., F, Cl and Br, and in another example F), (12) —C(O)—NH—$R^{26}$(e.g., —C(O)—NH—$CH_3$), (13) —C(O)$OR^{38}$ (e.g., $R^{38}$ is H or alkyl (e.g., $C_1$ to $C_6$ alkyl, such as, for example, methyl or ethyl), for example, $R^{38}$ is alkyl (e.g., methyl or ethyl), thus, for example, —C(O)$OR^3$ is —C(O)$OC_2H_5$), (14) —C(O)—$NR^{32}$—$C(R^{30})_2)_n$—$N(R^8)_2$ (e.g., —C(O)—NH—$(CH_2)_n$—$N(R^{38})_2$) (wherein (a) in one example $R^{32}$ is H, (b) in another example each $R^{30}$ is H, (c) in another example n is 2, (d) in another example each $R^{38}$ is independently selected, (e) in another example each $R^{38}$ is independently selected from the group consisting of: H and alkyl (e.g., methyl), (f) in another example $R^{32}$ is H, each $R^{30}$ is H, and each $R^{38}$ is independently selected, (g) in another example $R^{32}$ is H, each $R^{30}$ is H, and each $R^{38}$ is independently selected from the group consisting of: H and alkyl (e.g., methyl), (15) —$S(O)_tR^{38}$ (wherein in one example t is 2, and in another example $R^{38}$ is alkyl (e.g., methyl), and in another example t is 2 and $R^{38}$ is alkyl (e.g., methyl)), (16) —C(O)—$NR^{32}$—$R^{38}$ (e.g., —C(O)—$NR^{32}$—$R^{38}$) (wherein one example $R^{32}$ is H, in another example $R^{38}$ is alkyl (e.g., propyl), and in another example $R^{32}$ is H and $R^{38}$ is alkyl (e.g., propyl)), (17) —$NR^{32}$—C(O)—$R^{38}$ (e.g., —NH—C(O)—$R^{38}$) (wherein in one example $R^{32}$ is H, in another example $R^{38}$ is alkyl (e.g., methyl), and in another example $R^{32}$ is H and $R^{38}$ is alkyl (e.g., methyl)),

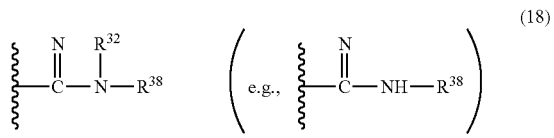

(18)

(wherein in one example $R^{32}$ is H, in another example $R^{38}$ is H, and in another example $R^{32}$ is H and $R^{38}$ is H); and (19) —$NHR^{20}$;

$R^{11}$ is selected from the group consisting of: F, —OH, —CN, —$OR^{10}$, —$NHR^1R^{10}$, —$SR^{10}$ and heteroaryl (e.g., triazolyl, such as, for example,

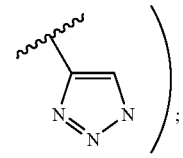

);

$R^{12}$ is selected from the group consisting of: alkyl, aryl, heteroaryl, cycloalkyl, cycloalkylalkyl, heterocycloalkyl and heterocycloalkylalkyl;

$R^{14}$ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;

$R^{15}$ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;

$R^{20}$ represents alkyl (e.g., $C_1$ to $C_6$ alkyl, such as, for example, methyl or ethyl);

$R^{23}$ is selected from the group consisting of: H, alkyl (e.g., $C_1$ to $C_6$ alkyl, such as, for example, methyl and i-propyl), aryl (e.g., phenyl), cycloalkyl (e.g., $C_3$ to $C_6$ cycloalkyl, such as, for example, cyclopropyl and cyclohexyl), and cycloalkylalkyl- (e.g., $C_3$ to $C_6$ cycloalkylalkyl-, such as —$(CH_2)_n$-cycloalkyl, such as —$(CH_2)_n$—($C_3$ to $C_6$)cycloalkyl, wherein each H of each —$(CH_2)_n$— moiety can independently be substituted with an alkyl group (e.g., $C_1$ to $C_6$ alkyl, such as, for example, methyl), and wherein in one example n is 1 and the —$CH_2$— moiety is not substituted, that is, —$CH_2$-cycloalkyl, such as, —$CH_2$-cyclopropyl, is an example of said cycloalkylalkyl-moiety);

each $R^{26}$ is independently selected from the group consisting of: H and alkyl (e.g., $C_1$ to $C_6$ alkyl, such as, for example, methyl and ethyl);

$R^{28}$ is alkyl (e.g., $C_1$ to $C_6$ alkyl, such as, for example, methyl or ethyl);

each $R^{30}$ is independently selected from the group consisting of: H, alkyl (e.g., $C_1$ to $C_6$ alkyl, such as, for example methyl, ethyl and i-propyl), and F, and wherein in one example each $R^{30}$ is H;

each $R^{32}$ is independently selected from the group consisting of: H and alkyl (e.g., $C_1$ to $C_6$ alkyl, such as, for example methyl, ethyl and propyl), and wherein each $R^{32}$ is generally H;

each $R^{35}$ is independently selected from the group consisting of: H and $C_1$ to $C_6$ alkyl (e.g., methyl, ethyl, i-propyl, and propyl), and wherein in one example both $R^{35}$ substituents are the same or different alkyl groups (e.g., both $R^{35}$ groups are the same alkyl group, such as methyl), and in another example one $R^{35}$ group is H and the other $R^{35}$ group is alkyl, such as methyl), and in another example each $R^{35}$ is preferably H;

$R^{36}$ is selected from the group consisting of: H and alkyl (e.g., $C_1$ to $C_6$ alkyl, such as, for example, methyl, ethyl and propyl), and preferably $R^{36}$ is selected from the group consisting of H and methyl, and more preferably $R^{36}$ is H;

each $R^{38}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said $R^{38}$ substituted alkyl is substituted with 1 to 3 substituents independently selected from the group consisting of: —$NH_2$, —$NO_2$, —CN, —$OR^{26}$, halo (e.g., F, Cl and Br, and in another example F), —C(O)—NH—$R^{28}$ (e.g., —C(O)—NH—$CH_3$), —C(O)$OR^{28}$ (e.g., —C(O)$OC_2H_5$), and —C(O)$R^{28}$ (e.g., —C(O)$CH_3$), and said $R^{38}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —$NH_2$, (2) —$NO_2$, (3) —CN, (4) —OH, (5) —$OR^{20}$, (6) —$OCF_3$, (7) —$CF_3$, (8) —C(O)$R^{26}$ (e.g., $R^{26}$ is H or $C_1$ to $C_6$ alkyl, such as, for example, methyl or ethyl, for example, $R^{26}$ is alkyl (e.g., methyl), thus, an example of —C(O)$R^{26}$ is —C(O)$CH_3$), (9) alkyl (e.g., $C_1$ to $C_6$ alkyl, e.g., methyl, ethyl, and i-propyl), (10) alkenyl (e.g., $C_2$ to $C_6$ alkenyl, such as, for example —CH=$CH_2$), (11) halo (e.g., F, Cl and Br, and in another example F), (12) —C(O)—NH—$R^{26}$ (e.g., —C(O)—NH—$CH_3$), (13) —C(O)$OR^{26}$ (e.g., $R^{26}$ is H or e.g., $C_1$ to $C_6$ alkyl, such as, for example, methyl or ethyl, for example, $R^{26}$ is alkyl (e.g., methyl or ethyl), thus, for example, —C(O)$OR^{26}$ is —C(O)$OC_2H_5$); (14) —C(O)—$NR^{32}(C(R^3)_2)_n$—N$(R^{26})_2$ (e.g., —C(O)—NH—$(CH_2)_n$—N$(R^{26})_2$) (wherein (a) in one example $R^{32}$ is H, (b) in another example each $R^{30}$ is H, (c) in another example n is 2, (d) in another example each $R^{26}$ is independently selected, (e) in another example each $R^{26}$ is independently selected from the group consisting of: H and methyl), (f) in another example $R^{32}$ is H, each $R^{30}$ is H, and each $R^{26}$ is independently selected, (g) in another example $R^{32}$ is H, each $R^{30}$ is H, and each $R^{26}$ is independently selected from the group consisting of: H and methyl), (15) —S(O)$_tR^{26}$ (wherein in one example t is 2, and in another example $R^{26}$ is methyl, and in another example t is 2 and $R^{26}$ is methyl), (16) —C(O)N$(R^{32})(R^{26})$ (wherein in one example $R^{32}$ is H, in another example $R^{26}$ is alkyl (e.g., propyl), and in another example $R^{32}$ is H and $R^{26}$ is alkyl (e.g., propyl)), (17) —$NR^{32}$C(O)$R^{26}$ (e.g., —NHC(O)$R^{26}$) (wherein in one example $R^{32}$ is H, in another example $R^{26}$ is alkyl (e.g., methyl), and in another example $R^{32}$ is H and $R^{26}$ is alkyl (e.g., methyl)),

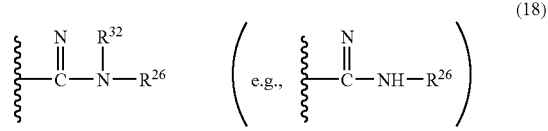

(18)

(wherein in one example $R^{32}$ is H, in another example $R^{26}$ is H, and in another example $R^{32}$ is H and $R^{26}$ is H); and (19) —$NHR^{20}$;

$R^{42}$ is selected from the group consisting of: alkyl (e.g., $C_1$ to $C_6$ alkyl, such as, for example —$CH_3$), aryl (e.g., phenyl), heteroaryl (e.g., thiazolyl and pyridyl), and cycloalkyl (e.g., $C_3$ to $C_6$ cycloalkyl, such as, for example, cyclopropyl);

$R^{44}$ is selected from the group consisting of: H, alkyl (e.g., $C_1$ to $C_6$ alkyl, such as, for example, $C_1$ to $C_3$ alkyl, such as, for example, methyl, ethyl and i-propyl), cycloalkyl (e.g., $C_3$ to $C_6$ cycloalkyl, such as, for example, cyclopropyl and cyclohexyl), and cycloalkylalkyl (e.g., ($C_3$ to $C_6$)alkyl, such as, for example, ($C_3$ to $C_6$)cycloalkyl($C_1$ to $C_3$)alkyl, such as, for example, ($C_3$ to $C_6$)cycloalkyl-methyl-, such as, for example, cyclopropyl-methyl- and cyclohexyl-methyl-), and in one example, $R^{44}$ is H; and Each $R^{46}$ is independently selected from the group consisting of: H, alkyl (e.g., $C_1$ to $C_6$ alkyl, such as, for example, $C_1$ to $C_3$ alkyl, such as, for example, methyl, ethyl and i-propyl), cycloalkyl (e.g., $C_3$ to $C_6$ cycloalkyl, such as, for example, cyclopropyl and cyclohexyl), and cycloalkylalkyl (e.g., ($C_3$ to $C_6$)cycloalkyl($C_1$ to $C_6$)alkyl, such as, for example, ($C_3$ to $C_6$)cycloalkyl($C_1$ to $C_3$)alkyl, such as, for example, ($C_3$ to $C_6$)cycloalkyl-methyl-, such as, for example, cyclopropyl-methyl- and cyclohexyl-methyl-), and in one example, each $R^{46}$ is H.

When $R^1$ is a cycloalkyl group (i.e., $R^1$ is $R^{10}$ wherein $R^{10}$ is cycloalkyl), examples of said cycloalkyl group include, but are limited to, cyclopropyl and cyclobutyl.

When $R^1$ is a heterocycloalkyl group (i.e., $R^1$ is $R^{10}$ wherein $R^{10}$ is heterocycloalkyl), examples of said heterocycloalkyl group include, but are limited to, morpholinyl, pyrrolidinyl, piperidinyl and piperazinyl.

When $R^1$ is a heteroaryl group (i.e., $R^1$ is $R^{10}$ and $R^{10}$ is heteroaryl), examples of said heteroaryl group include, but are not limited to, (a) unsubstituted heteroaryl, (b) heteroaryl substituted with 1 to 3 substituents independently selected from the group consisting of: —C(O)$R^{38}$ (e.g., $R^{38}$ is alkyl such as methyl), —$NHR^{20}$ (e.g., —$NHCH_3$), —$OR^{20}$ (e.g., —$OCH_3$), and halo (e.g., Cl), (c) heteroaryl selected from the group consisting of: pyrrolyl, pyrazolyl, imidazolyl, furanyl, thienyl, thiazolyl, pyridyl, pyridyl N—O, and pyrimidinyl, (d) heteroaryl selected from the group consisting of: pyrrolyl, pyrazolyl, imidazolyl, furanyl, thienyl, thiazolyl, pyridyl, pyridyl N—O, and pyrimidinyl, wherein said heteroaryl is substituted with 1 to 3 substituents independently selected from the group consisting of: —C(O)$R^{38}$ (e.g., $R^{38}$ is alkyl such as methyl), —$NHR^{20}$ (e.g., —$NHCH_3$), —$OR^{20}$ (e.g., —$OCH_3$), and halo (e.g., Cl), and (e) heteroaryl selected from the group consisting of: thienyl substituted with —C(O)$R^{38}$ (such as, for example, thienyl substituted with —C(O)$CH_3$), thiazolyl substituted with —$NHR^{20}$ such as, for example (thazolyl substituted with —$NHCH_3$), pyridyl substituted with halo (such as, for example, pyridyl substituted with —Cl), pyridyl substituted with —$OR^{20}$ (such as, for example, pyridyl substituted with methyl), and pyrimidinyl substituted with —$OR^{20}$ (such as, for example, pyrimidinyl substituted with —$OCH_3$).

When $R^1$ is a heteroarylalkyl group (i.e., $R^1$ is $R^{10}$ and $R^{10}$ is heteroarylalkyl), examples of said heteroarylalkyl group include, but are not limited to, (a) unsubstituted heteroarylalkyl- (b) heteroarylalkyl-substituted with 1 to 3 substituents independently selected from the group consisting of: —C(O)$R^{38}$ (e.g., $R^{38}$ is alkyl such as methyl), —$NHR^{20}$ (e.g., —$NHCH_3$), —$OR^{20}$ (e.g., —$OCH_3$), and halo (e.g., Cl), (c) heteroarylalkyl-selected from the group consisting of: pyrrolylalkyl- (e.g., pyrrolyl$CH_2$—), pyrazolylalkyl- (e.g., pyrazolyl$CH_2$—), imidazolylalkyl- (e.g., imdazolyl-$CH_2$—), furanylalkyl- (e.g., furanyl$CH_2$—), thienylalkyl- (e.g., thienyl$CH_2$—), thiazolylalkyl- (e.g., thiazolyl$CH_2$—), pyridylalkyl- (e.g., pyridyl$CH_2$—), pyridyl N—O alkyl- (e.g., pyridyl(N—O)$CH_2$—), and pyrimidinylalkyl- (e.g., pyrimidinyl$CH_2$—), (d) heteroarylalkyl-selected from the group consisting of: pyrrolylalkyl- (e.g., pyrrolyl$CH_2$—), pyrazolylalkyl- (e.g., pyrazolylCH$_2$—), imidazolylalkyl- (e.g., imdazolylCH$_2$—), furanylalkyl- (e.g., furanylCH$_2$—), thienylalkyl- (e.g., thienylCH$_2$—), thiazolylalkyl- (e.g., thiazolylCH$_2$—), pyridylalkyl- (e.g., pyridylCH$_2$—), pyridyl N—O alkyl- (e.g., pyridyl(N—O)CH$_2$—), and pyrimidinylalkyl- (e.g., pyrimidinylCH$_2$—), wherein said heteroaryl is substituted with 1 to 3 substituents independently selected from the group consisting of: —C(O)R$^{38}$ (e.g., R$^{38}$ is alkyl such as methyl), —NHR$^{20}$ (e.g., —NHCH$_3$), —OR$^{20}$ (e.g., —OCH$_3$), and halo (e.g., Cl), and (e) heteroarylalkyl-selected from the group consisting of: thienylalkyl-substituted with a —C(O)R$^{20}$ group (such as, for example, thienylCH$_2$— substituted with —C(O)CH$_3$), thiazolylalkyl-substituted with —NHR$^{20}$ such as, for example (thazolylCH$_2$-substituted with —NHCH$_3$), pyridylalkyl-substituted with halo (such as, for example, pyridylCH$_2$-substituted with —Cl), pyridylalkyl-substituted with —OR$^{20}$ (such as, for example, pyridylCH$_2$— substituted with methyl), and pyrimidinylalkyl-substituted with —OR$^{20}$ (such as, for example, pyrimidinylCH$_2$— substituted with —OCH$_3$).

When R$^1$ is an aryl group (i.e., R$^1$ is R$^{10}$ and R$^{10}$ is aryl), examples of said aryl group include, but are not limited to, phenyl and naphthyl, and preferably phenyl.

When R$^1$ is an arylalkyl group (i.e., R$^1$ is R$^{10}$ and R$^{10}$ is arylalkyl), examples of said arylalkyl group include, but are not limited to, —(C(R$^{30}$)$_2$)$_n$phenyl (e.g., —(CH$_2$)$_n$phenyl), wherein in one example said arylalkyl- is —(C(R$^{30}$)$_2$)$_n$phenyl wherein n is 1, and in another example said arylalkyl- is —(CH$_2$)$_n$phenyl wherein n is 1 (i.e., said arylalkyl- is benzyl).

When R$^1$ is a substituted arylalkyl group (i.e., R$^1$ is R$^{10}$ and R$^{10}$ is a substituted arylalkyl), examples of said substituted arylalkyl group include, but are not limited to, —(C(R$^3$)$_2$)$_n$substituted phenyl (e.g., —(CH$_2$)$_n$substituted phenyl), wherein in one example said substituted arylalkyl- is —(C(R$^{30}$)$_2$)$_n$ substituted phenyl wherein n is 1, and in another example said substituted arylalkyl- is —(CH$_2$)$_n$substituted phenyl wherein n is 1 (i.e., said substituted arylalkyl- is substituted benzyl), wherein the aryl moiety of said substituted arylalkyl is substituted with 1 to 3 substituents independently selected from the group consisting of: halo (e.g., F, Cl and Br), —CF$_3$, and —OR$^{20}$ (e.g., —OCH$_3$).

In one embodiment the invention R$^1$ is selected from the group consisting of: H, alkyl (e.g., methyl, i-propyl, and t-butyl), cycloalkyl (e.g., cyclopropyl), aryl (e.g., phenyl), substituted aryl (e.g., halo substituted aryl, such as for example, fluorophenyl), halo (e.g., Cl, Br, and F), heteroaryl (e.g., pyridyl and pyrazolyl), —CF$_3$, —C(O)NH$_2$, and —CH$_2$OH.

Those skilled in the art will appreciate that when Q$^1$ is aryl, substituted aryl, heteroaryl or substituted heteroaryl the two carbon atoms common to the two fused rings are not substituted. Thus, there is no R$^3$ and no R$^4$ groups in 2.9 when Q$^1$ is aryl, substituted aryl, heteroaryl or substituted heteroaryl. There is no R$^3$ and no R$^4$ groups in 2.10 when Q$^1$ fused to the R$^3$ and R$^4$ positions is aryl, substituted aryl, heteroaryl or substituted heteroaryl. There is no R$^6$ and no R$^7$ groups in 2.10 when Q$^1$, fused to the R$^6$ and R$^7$ positions is aryl, substituted aryl, heteroaryl or substituted heteroaryl. There is no R$^3$ and no R$^4$ groups in 2.11 when Q$^1$ fused to the R$^3$ and R$^4$ positions is aryl, substituted aryl, heteroaryl or substituted heteroaryl. There is no R$^3$ and no R$^4$ groups in 2.13 when Q$^1$ fused to the R$^3$ and R$^4$ positions is aryl, substituted aryl, heteroaryl or substituted heteroaryl. There is no R$^3$ and no R$^4$ groups in 2.14 when Q$^1$ fused to the R$^3$ and R$^4$ positions is aryl, substituted aryl, heteroaryl or substituted heteroaryl. There is no R$^3$ and no R$^4$ groups in 2.15 when Q$^1$ fused to the R$^3$ and R$^4$ positions is aryl, substituted aryl, heteroaryl or substituted heteroaryl. There is no R$^6$ and no R$^7$ groups in 2.15 when Q$^1$ fused to the R$^3$ and R$^4$ positions is aryl, substituted aryl, heteroaryl or substituted heteroaryl.

In one embodiment of the compounds of formula 1.0, z is 1. Thus, in this embodiment the compounds of formula 1.0 have the formula 1.0A1:

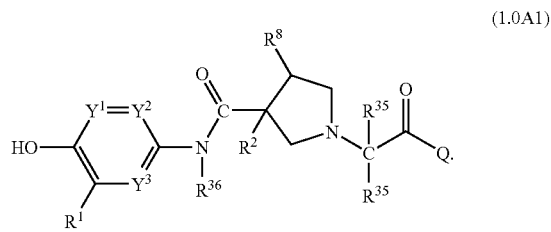

(1.0A1)

In another embodiment of the compounds of formula 1.0, z is 1 and R$^{36}$ is H. Thus, in this embodiment the compounds of formula 1.0 have the formula 1.0A:

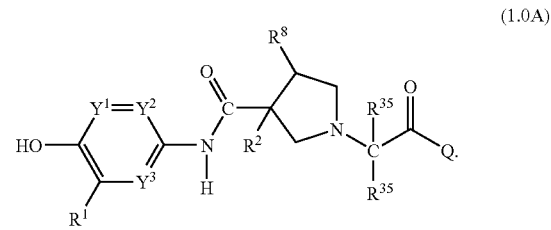

(1.0A)

In another embodiment of the compounds of formula 1.0, z is 1, and each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substituents are H).

In another embodiment of the compounds of formula 1.0, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substituents are H), and R$^{36}$ is selected from the group consisting of: H, methyl, ethyl and propyl.

In another embodiment of the compounds of formula 1.0, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substituents are H), and R$^{36}$ is selected from the group consisting of: H and methyl.

In another embodiment of the compounds of formula 1.0, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substituents are H), and R$^{36}$ is: H.

In another embodiment of the compounds of formula 1.0, each R$^{35}$ is H. Thus, in this embodiment the compounds of formula 1.0 have the formula 1.0B1:

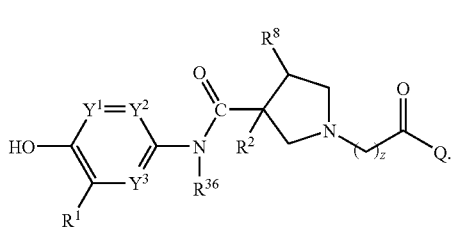
(1.0B1)

In another embodiment of the compounds of formula 1.0, each $R^{35}$ is H and $R^{36}$ is H. Thus, in this embodiment the compounds of formula 1.0 have the formula 1.0B:

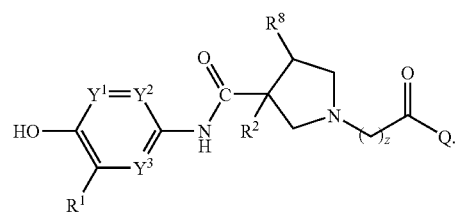
(1.0B)

In another embodiment of the compounds of formula 1.0, z is preferably 1 and each $R^{35}$ is preferably H. Thus, in this embodiment the compounds of formula 1.0 have the formula 1.0C1:

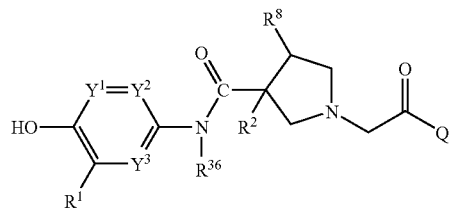
(1.0C1)

In another embodiment of the compounds of formula 1.0, z is preferably 1, each $R^{35}$ is preferably H, and $R^{36}$ is H. Thus, preferably the compounds of formula 1.0 have the formula 1.0C:

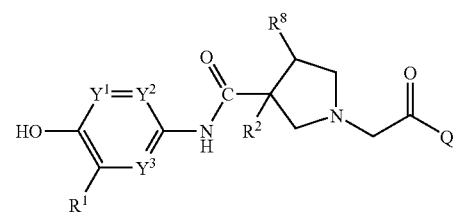
(1.0C)

Another embodiment of this invention is directed to compounds of formula 1.0 having the formula 1.1A:

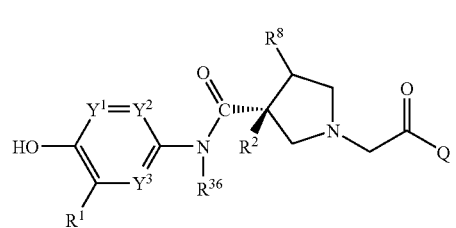
(1.1A)

Another embodiment of this invention is directed to compounds of formula 1.0 having the formula 1.1:

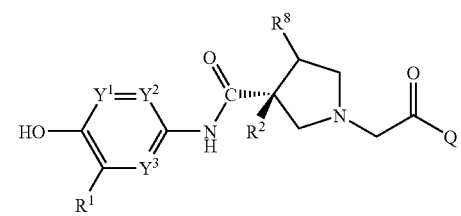
(1.1)

wherein all substituents are as defined for formula 1.0.

Another embodiment of this invention is directed to compounds of formulas 1.0 and 1.1A wherein $Y^1$, $Y^2$, and $Y^3$ are —CH=. Thus, one embodiment of this invention is directed to compounds of formula 1.2A:

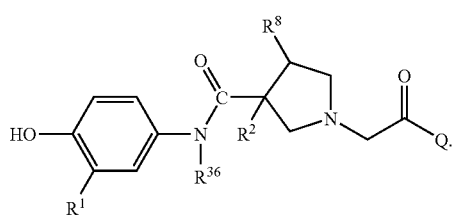
(1.2A)

Another embodiment of this invention is directed to compounds of formulas 1.0 and 1.1 wherein $Y^1$, $Y^2$, and $Y^3$ are —CH=. Thus, one embodiment of this invention is directed to compounds of formula 1.2:

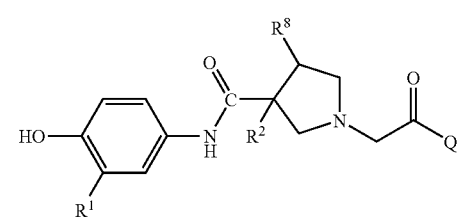
(1.2)

wherein all substituents are as defined for formula 1.0.

Another embodiment of this invention is directed to compounds of formula 1.0 having the formula 1.3A:

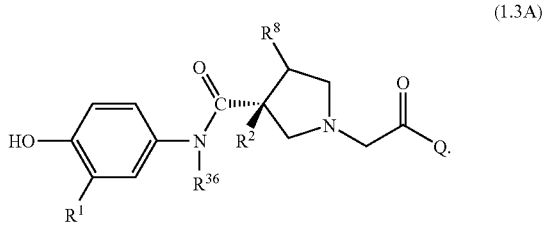

(1.3A)

Another embodiment of this invention is directed to compounds of formula 1.0 having the formula 1.3:

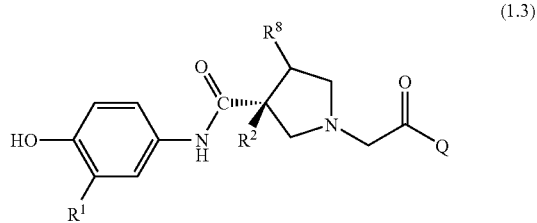

(1.3)

wherein all substituents are as defined for formula 1.0.

Examples of Q include, but are not limited to: moieties 2.1, 2.2, 2.3, 2.4, 2.5, 2.6, 2.7, 2.8, 2.9, 2.10, 2.11, 2.14, or 2.15 wherein each $R^3$, $R^4$, $R^6$, and $R^7$ is independently selected from the group consisting of: H and alkyl (e.g., $C_1$ to $C_6$ alkyl, such as, for example methyl).

Examples of Q also include, but are not limited to: moieties 2.1, 2.2, 2.3, 2.4, 2.5, 2.6, 2.7, 2.8, 2.9, 2.10, 2.11, 2.14, or 2.15 wherein each $R^3$, $R^4$, $R^6$, and $R^7$ is H.

Examples of Q include, but are not limited to: moieties 2.12, 2.13, or 2.16 wherein each $R^3$, $R^4$, and $R^7$ is independently selected from the group consisting of: H and alkyl (e.g., $C_1$ to $C_6$ alkyl, such as, for example methyl).

Examples of Q also include, but are not limited to: moieties 2.12, 2.13, or 2.16 wherein each $R^3$, $R^4$, and $R^7$ is H.

Thus, in one example of Q, Q is moiety 2.1 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.1 wherein each $R^3$, $R^4$, $R^6$, and $R^7$ is independently selected from the group consisting of: H and methyl.

In another example of Q, Q is moiety 2.1 wherein each $R^3$, $R^4$, $R^6$, and $R^7$ is H.

In another example of Q, Q is moiety 2.2 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.2 wherein each $R^3$, $R^4$, $R^6$, and $R^7$ is independently selected from the group consisting of: H and methyl.

In another example of Q, Q is moiety 2.2 wherein each $R^3$, $R^4$, $R^6$, and $R^7$ is H.

In another example of Q, Q is moiety 2.3 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.3 wherein each $R^3$, $R^4$, $R^6$, and $R^7$ is independently selected from the group consisting of: H and methyl.

In another example of Q, Q is moiety 2.3 wherein each $R^3$, $R^4$, $R^6$, and $R^7$ is H.

In another example of Q, Q is moiety 2.4 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.4 wherein each $R^3$, $R^4$, $R^6$, and $R^7$ is independently selected from the group consisting of: H and methyl.

In another example of Q, Q is moiety 2.4 wherein each $R^3$, $R^4$, $R^6$, and $R^7$ is H.

In another example of Q, Q is moiety 2.5 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.5 wherein each $R^3$, $R^4$, $R^6$, and $R^7$ is independently selected from the group consisting of: H and methyl.

In another example of Q, Q is moiety 2.5 wherein each $R^3$, $R^4$, $R^6$, and $R^7$ is H.

In another example of Q, Q is moiety 2.6 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.6 wherein each $R^3$, $R^4$, $R^6$, and $R^7$ is independently selected from the group consisting of: H and methyl.

In another example of Q, Q is moiety 2.7 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.7 wherein each $R^3$, $R^4$, $R^6$, and $R^7$ is independently selected from the group consisting of: H and methyl.

In another example of Q, Q is moiety 2.7 wherein each $R^3 R^4$, $R^6$, and $R^7$ is H.

In another example of Q, Q is moiety 2.8 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.8 wherein each $R^3$, $R^4$, $R^6$, and $R^7$ is independently selected from the group consisting of: H and methyl.

In another example of Q, Q is moiety 2.8 wherein each $R^3$, $R^4$, $R^6$ and $R^7$ is H.

In another example of Q, Q is moiety 2.9 or 2.10 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.9 or 2.10 wherein each $R^3$, $R^4$, $R^6$, and $R^7$ is independently selected from the group consisting of: H and methyl.

In another example of Q, Q is moiety 2.9 or 2.10 wherein each $R^3$, $R^4$, $R^6$, and $R^7$ is H.

In another example of Q, Q is moiety 2.11 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.11 wherein each $R^3$, $R^4$, $R^6$, and $R^7$ is independently selected from the group consisting of: H and methyl.

In another example of Q, Q is moiety 2.11 wherein each $R^3$, $R^4$, $R^6$, and $R^7$ is H.

In another example of Q, Q is moiety 2.12 or 2.13 wherein each $R^3$, $R^4$, and $R^7$ is independently selected from the group consisting of: H and alkyl (e.g., $C_1$ to $C_6$ alkyl, such as, for example methyl).

In another example of Q, Q is moiety 2.12 or 2.13 wherein each $R^3$, $R^4$, and $R^7$ is independently selected from the group consisting of: H and methyl.

In another example of Q, Q is moiety 2.12 or 2.13 wherein each $R^3$, $R^4$, and $R^7$ is H.

In another example of Q, Q is moiety 2.14 or 2.15 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.14 or 2.15 wherein each $R^3$, $R^4$, $R^6$, and $R^7$ is independently selected from the group consisting of: H and methyl.

In another example of Q, Q is moiety 2.14 or 2.15 wherein each $R^3$, $R^4$, $R^6$, and $^7$ is H.

In another example of Q, Q is moiety 2.16 wherein each $R^3$, $R^4$, and $R^7$ is H.

Another example of the Q substituent 2.3 is:

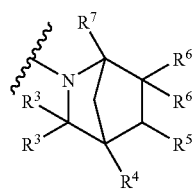

(2.3A)

(i.e., each $R^{24}$ is H and w is 1).

Another example of the Q substituent 2.3 is:

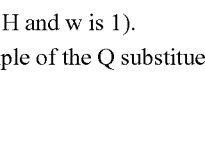

(2.3B)

(i.e., each $R^{24}$ is H and w is 1).

Another example of the Q substituent 2.3 is:

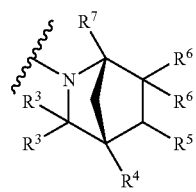

(2.3C)

(i.e., each $R^{24}$ is H and w is 1).

An example of the Q substituent 2.4 is:

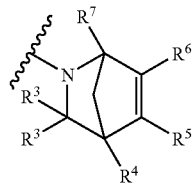

(2.4A)

(i.e., each $R^{24}$ is H and w is 1).

Another example of the Q substituent 2.4 is:

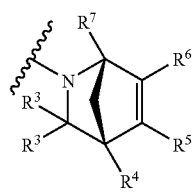

(2.4B)

(i.e., each $R^{24}$ is H and w is 1).

Another example of the Q substituent 2.4 is:

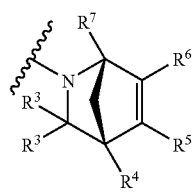

(2.4C)

(i.e., each $R^{24}$ is H and w is 1).

An example of the Q substituent 2.5 is:

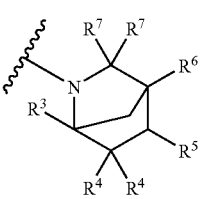

(2.5A)

(i.e., each $R^{24}$ is H and w is 1).

Another example of the Q substituent 2.5 is:

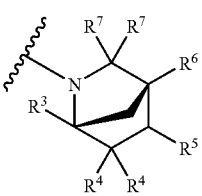

(2.5B)

(i.e., each $R^{24}$ is H and w is 1).

Another example of the Q substituent 2.5 is:

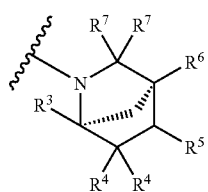

(2.5C)

(i.e., each $R^{24}$ is H and w is 1).

An example of the Q substituent 2.6 is:

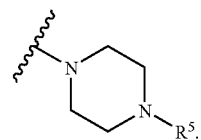

(2.6A)

An example of the Q substituent 2.7 is:

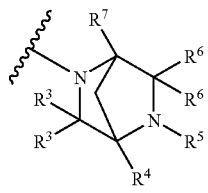

(2.7A)

(i.e., each $R^{24}$ is H and w is 1).

An example of the Q substituent 2.7 is:

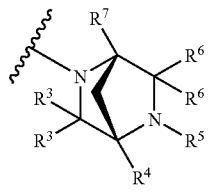

(2.7B)

(i.e., each $R^{24}$ is H and w is 1).

An example of the Q substituent 2.7 is:

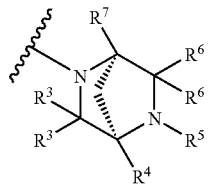

(2.7C)

(i.e., each $R^{24}$ is H and w is 1).

An example of the Q substituent 2.8 is:

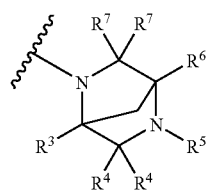

(2.8A)

(i.e., each $R^{24}$ is H and w is 1).

Another example of the Q substituent 2.8 is:

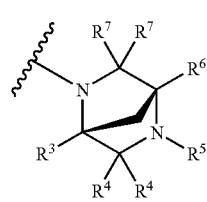

(2.8B)

(i.e., each $R^{24}$ is H and w is 1).

Another example of the Q substituent 2.8 is:

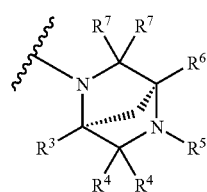

(2.8C)

(i.e., each $R^{24}$ is H and w is 1).

Another example of the Q substituent 2.3 is:

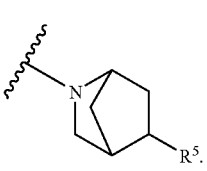

(2.3A1)

Another example of the Q substituent 2.3 is:

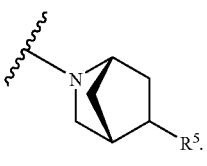

(2.3B1)

Another example of the Q substituent 2.3 is:

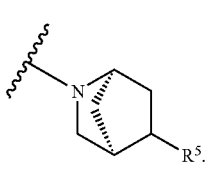
(2.3C1)

Another example of the Q substituent 2.4 is:

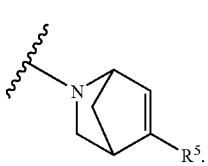
(2.4A1)

Another example of the Q substituent 2.4 is:

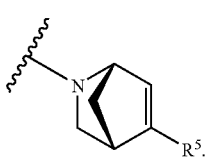
(2.4B1)

Another example of the Q substituent 2.4 is:

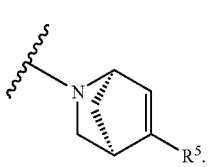
(2.4C1)

Another example of the Q substituent 2.5 is:

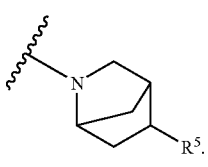
(2.5A1)

Another example of the Q substituent 2.5 is:

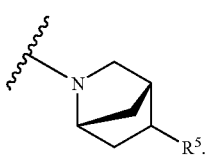
(2.5B1)

Another example of the Q substituent 2.5 is:

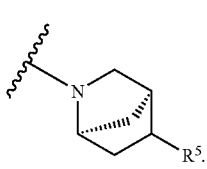
(2.5C1)

Another example of the Q substituent 2.7 is:

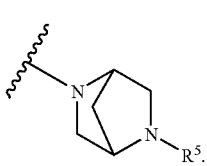
(2.7A1)

Another example of the Q substituent 2.7 is:

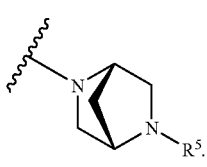
(2.7B1)

Another example of the Q substituent 2.7 is:

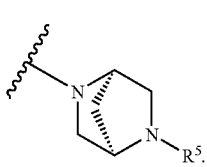
(2.7C1)

Another example of the Q substituent 2.8 is:

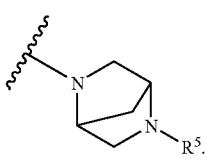
(2.8A1)

Another example of the Q substituent 2.8 is:

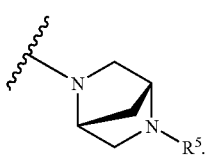
(2.8B1)

Another example of the Q substituent 2.8 is:

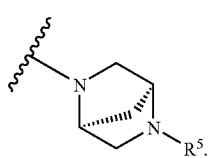
(2.8C1)

Another example of the Q substituent is the piperazine ring:

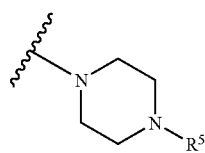

substituted with one or two substituents independently selected from the group consisting of $R^3$ groups, provided that said one or two substituents are not H. In one embodiment said substituents are selected from the group consisting of alkyl groups (e.g., $C_1$ to $C_6$ alkyl, e.g., methyl). In another embodiment there is one substituent on said piperazine ring. In another embodiment there is one substituent on said piperazine ring and said substituent is methyl.

Another example of the Q substituent is the piperazine ring:

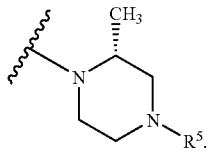

Another example of the Q substituent is the piperidine ring:

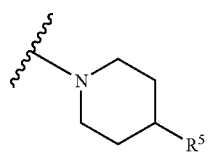

substituted with one or two substituents independently selected from the group consisting of $R^3$ groups, provided that said one or two substituents are not H. In one embodiment said substituents are selected from the group consisting of alkyl groups (e.g., $C_1$ to $C_6$ alkyl, e.g., methyl). In another embodiment there is one substituent on said piperidine ring. In another embodiment there is one substituent on said piperidine ring and said substituent is methyl.

In one example of the Q substituent 2.16

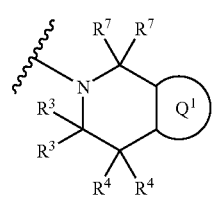
(2.16)

$Q^1$ is heteroaryl.
In another example of the Q substituent 2.16 $Q^1$ is aryl.
Thus, one example of the Q substituent 2.16 is 2.16A:

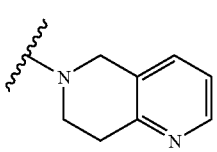
(2.16A)

(i.e., $Q^1$ is pyridyl, and each $R^3$, $R^4$ and $R^7$ is H).
Another example of the Q substituent 2.16 is 2.16B:

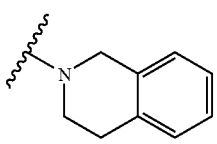
(2.16B)

(i.e., $Q^1$ is phenyl, and each $R^3$, $R^4$ and $R^7$ is H).
When the Q substituent comprises two $Q^1$ rings, each $Q^1$ ring is independently selected. Generally, the $Q^1$ cycloalkyl rings and the $Q^1$ substituted cycloalkyl rings comprise 5 to 7 ring carbons. In general, the heterocycloalkyl $Q^1$ rings and the substituted heterocycloalkyl $Q^1$ rings comprise 5 to 7 ring carbons and comprise 1 to 3 (generally 1 or 2, or generally 1) ring heteroatoms selected from the group consisting of: O, N and S. In general, the heteroaryl $Q^1$ rings and the substituted heteroaryl $Q^1$ rings comprise 5 to 7 ring carbons and comprise 1 to 3 (generally 1 or 2, or generally 1) ring heteroatoms selected from the group consisting of: O, N and S. Examples of the $Q^1$ rings include, but are not limited to: piperidinyl, piperazinyl, pyranyl, pyrrolidinyl, morpholinyl, thiomorpholinyl, pyridyl, pyrimidinyl, pyrrolyl, pyrazolyl, furanyl, thienyl, thiazolyl, imidazolyl, cyclopentyl, cyclohexyl and cycloheptyl. Examples of the $Q^1$ rings also include, but are not limited to: substituted piperidinyl, substituted piperazinyl, substituted pyranyl, substituted pyrrolidinyl, substituted morpholinyl, substituted thiomorpholinyl, substituted pyridyl, substituted pyrimidinyl, substituted pyrrolyl, substituted pyrazolyl, substituted furanyl, substituted thienyl, substituted thiazolyl, substituted imidazolyl, substituted cyclopentyl, substituted cyclohexyl and substituted cycloheptyl wherein said substituted $Q^1$ rings are substituted with 1 to 3 substituents selected from the $R^{10}$ moieties.

Generally, the $Q^2$ cycloalkyl rings and the $Q^2$ substituted cycloalkyl rings comprise 5 to 7 ring carbons. In general, the heterocycloalkyl $Q^2$ rings and the substituted heterocycloalkyl $Q^1$ rings comprise 5 to 7 ring carbons and comprise 1 to 3 (generally 1 or 2, or generally 1) ring heteroatoms selected from the group consisting of: O, N and S.

Examples of the $Q^2$ rings include, but are not limited to: piperidinyl, piperazinyl, pyranyl, pyrrolidinyl, cyclopentyl, cyclohexyl and cycloheptyl. Examples of the $Q^2$ rings also include, but are not limited to: substituted piperidinyl, substituted piperazinyl, substituted pyranyl, substituted pyrrolidinyl, substituted morpholinyl, substituted thiomorpholinyl, substituted cyclopentyl, substituted cyclohexyl and substituted cycloheptyl wherein said substituted $Q^1$ rings are substituted with 1 to 3 substituents selected from the $R^{10}$ moieties.

Examples of $R^1$ for the compounds of this invention (e.g., compounds of formulas 1.0, 1.0A1, 1.0B1, 1.0C1, 1.1, 1.1A, 1.2, 1.2A, 1.3 and 1.3A) include, but are not limited to: methyl, i-propyl, t-butyl, cyclopropyl, o-F-phenyl, m-F-phenyl, p-F-phenyl, Cl, Br, F, phenyl, —$CF_3$, —$C(O)NH_2$, —$CH_2OH$, H, pyridyl (e.g., o-pyridyl), and pyrazolyl (such as, for example,

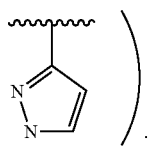

).

Other Examples of $R^1$ for the compounds of this invention (e.g., compounds of formulas 1.0, 1.0A1, 1.0B1, 1.0C1, 1.1, 1.1A, 1.2, 1.2A, 1.3 and 1.3A) include, but are not limited to:

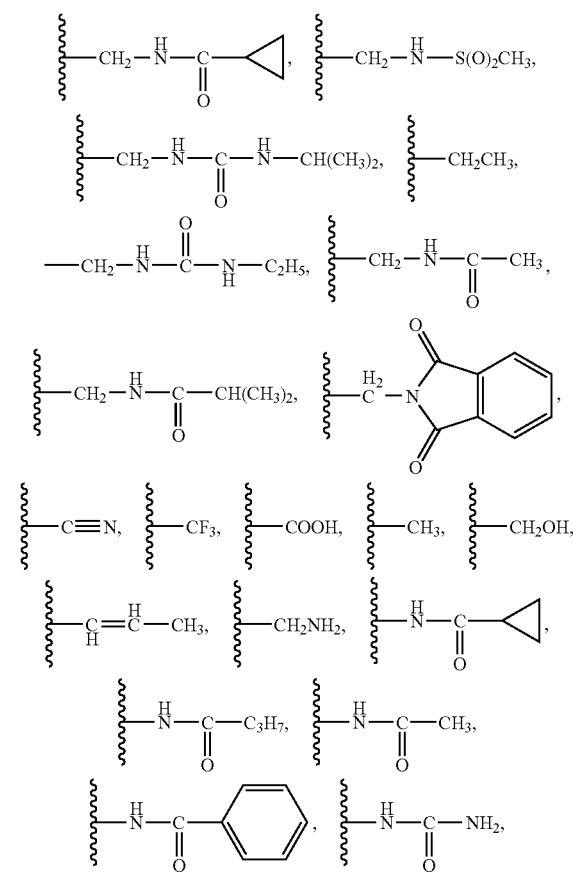

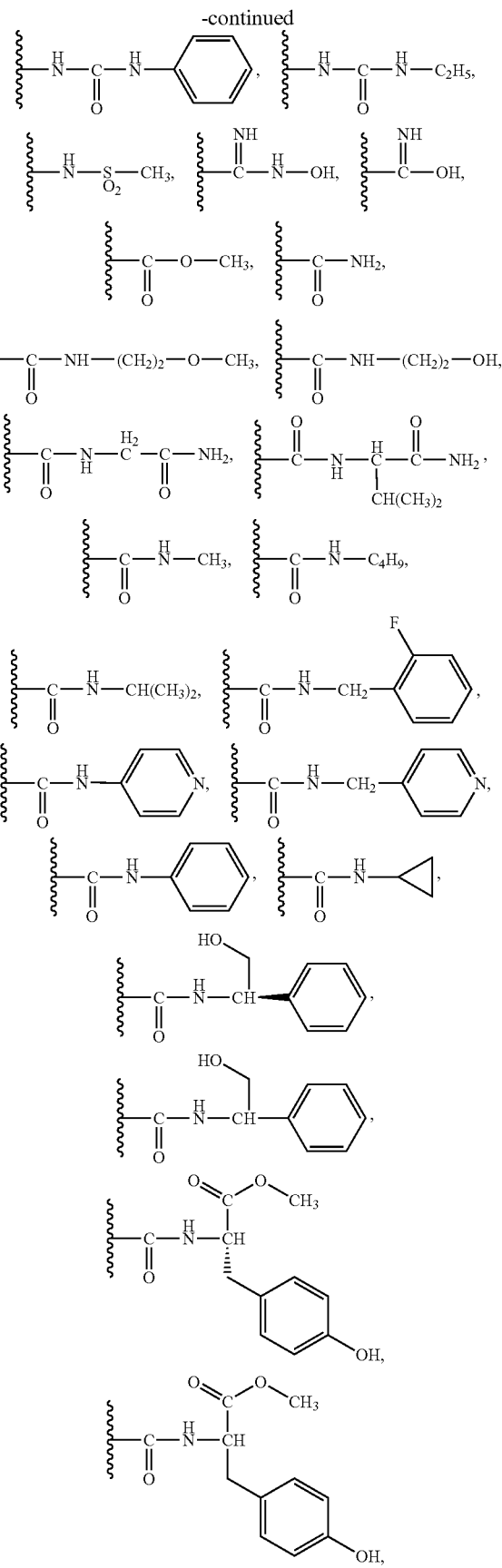

-continued
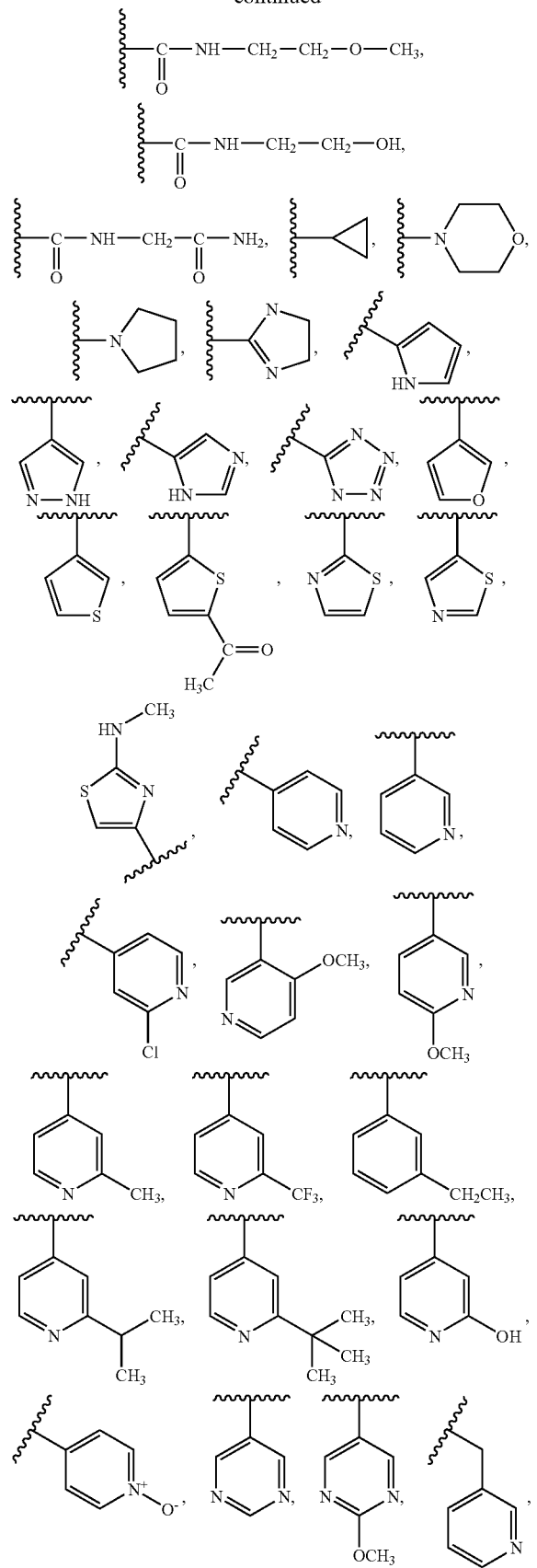
-continued
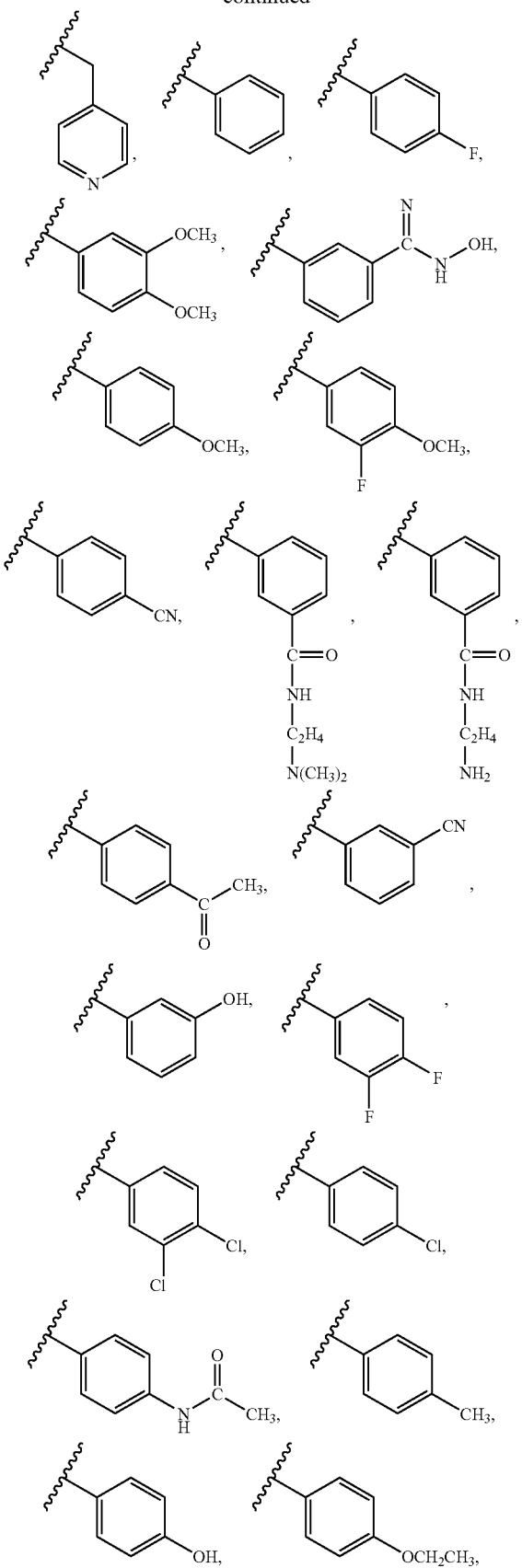

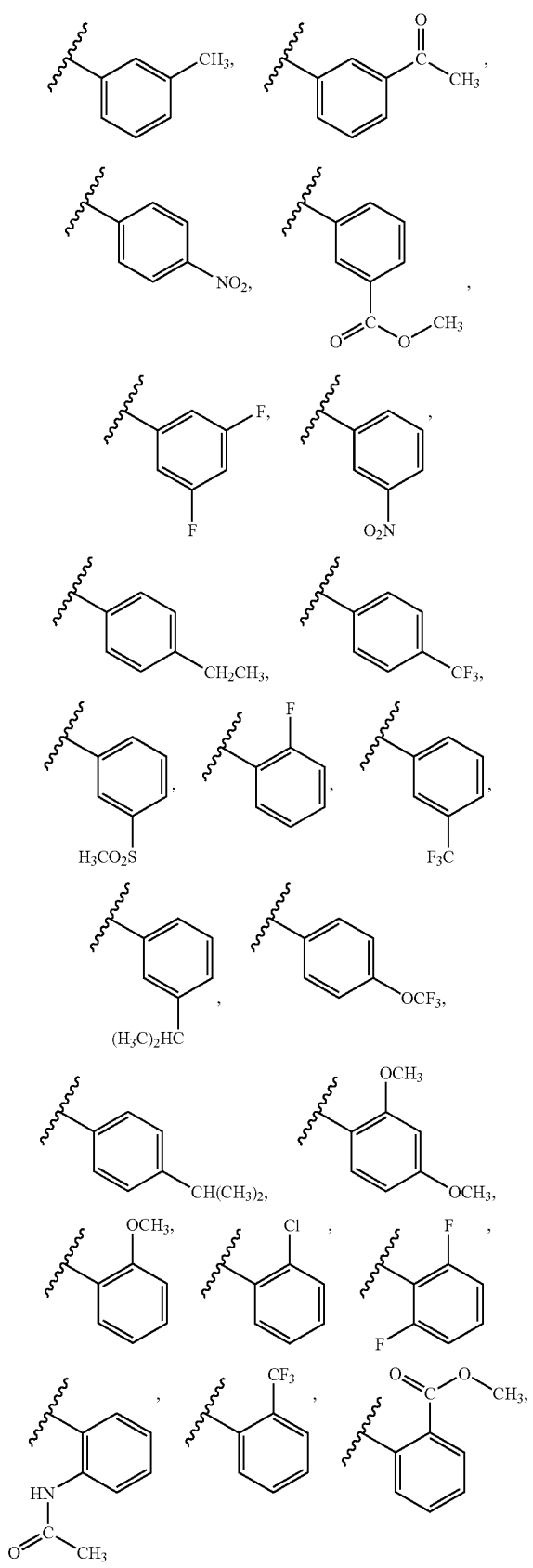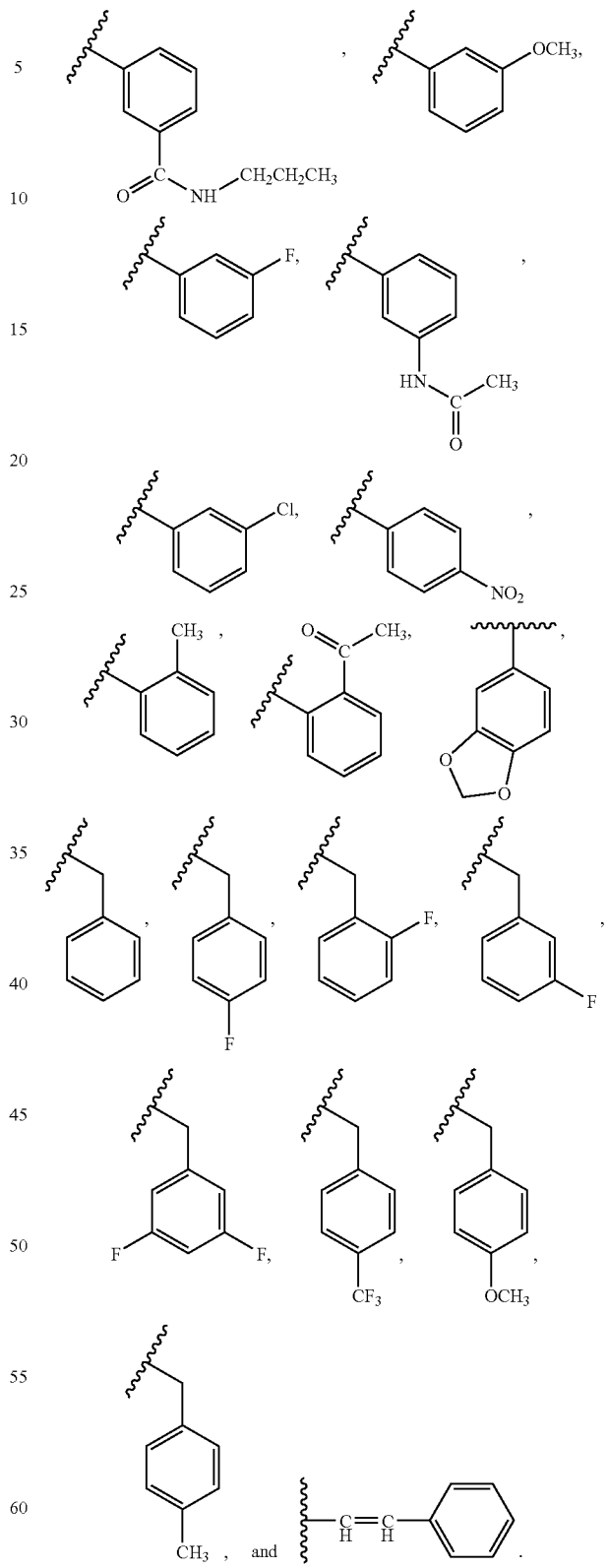
$R^1$, in one embodiment of this invention, is —$CF_3$.
$R^1$, in another embodiment of this invention is substituted aryl, such as,

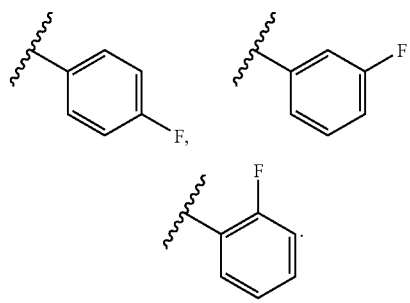

R¹, in another embodiment of this invention, is heteroaryl (e.g., pyridyl, such as

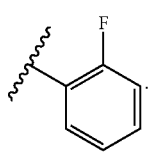

).

R¹, in another embodiment of this invention, is i-propyl.
R¹, in another embodiment of this invention, is t-butyl.
R¹, in another embodiment of this invention, is methyl.
R¹, in another embodiment of this invention, is cyclopropyl.
R¹, in another embodiment of this invention, is i-propyl.
R¹, in another embodiment of this invention, is Cl.
R¹, in another embodiment of this invention, is —CF₃.
R¹, in another embodiment of this invention, is H.
R¹, in another embodiment of this invention, is —CH₂OH.
R¹, in another embodiment of this invention, is —C(O)NH₂.
R¹, in another embodiment of this invention, is pyrazolyl.
R¹, in another embodiment of this invention, is phenyl.

Examples of R⁵ for the compounds of this invention (e.g., compounds of formulas 1.0, 1.0A1, 1.0B1, 1.0C1, 1.1, 1.1A, 1.2, 1.2A, 1.3 and 1.3A) include but are not limited to:

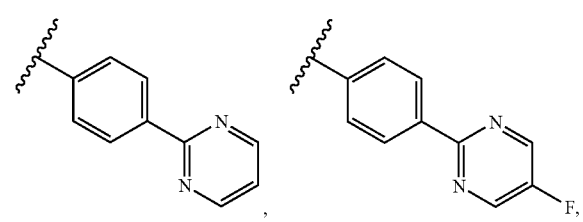

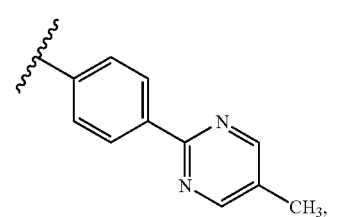

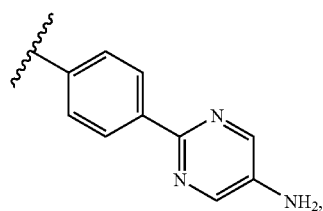

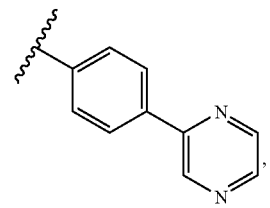

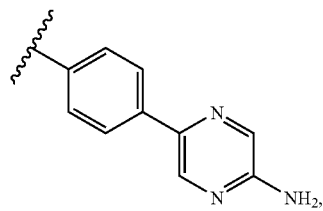

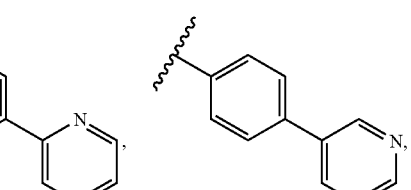

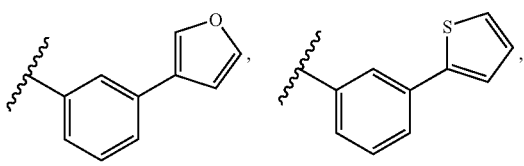

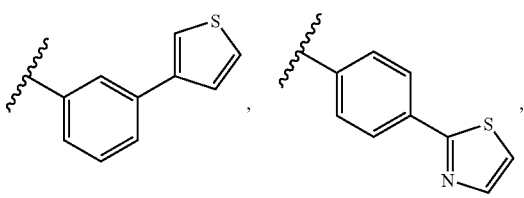

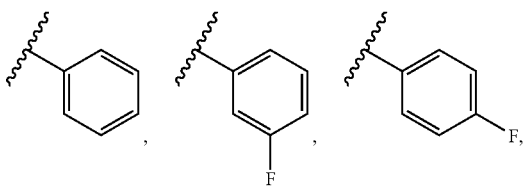

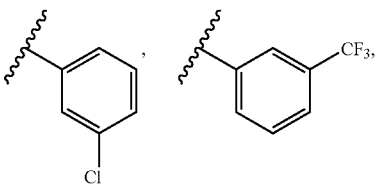

-continued
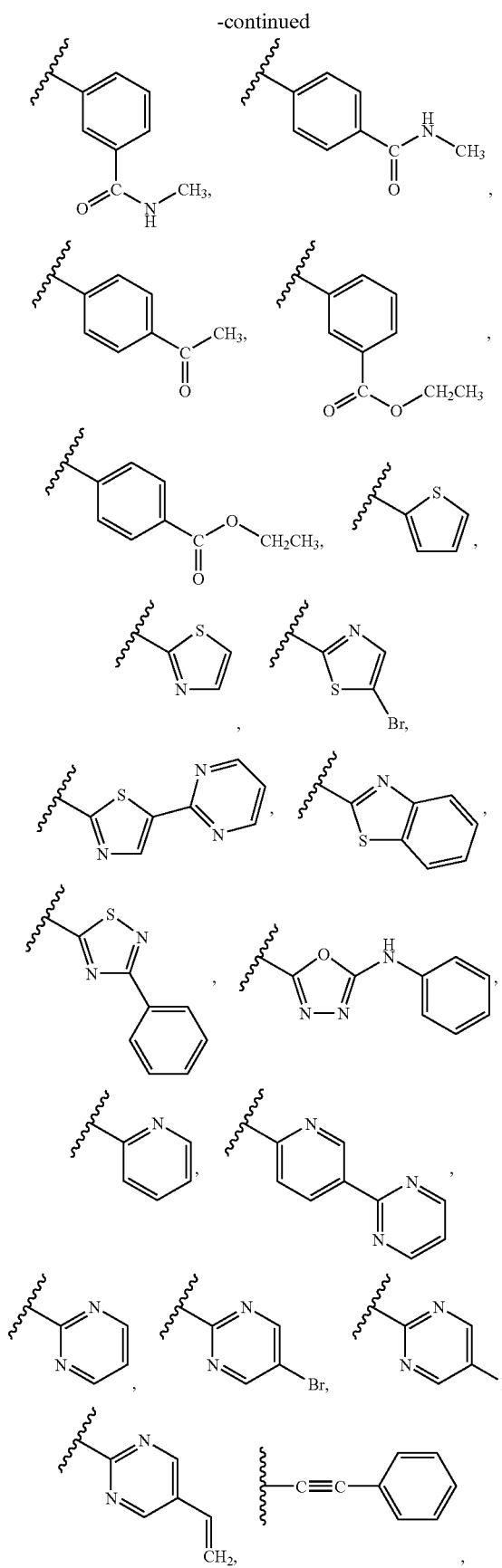
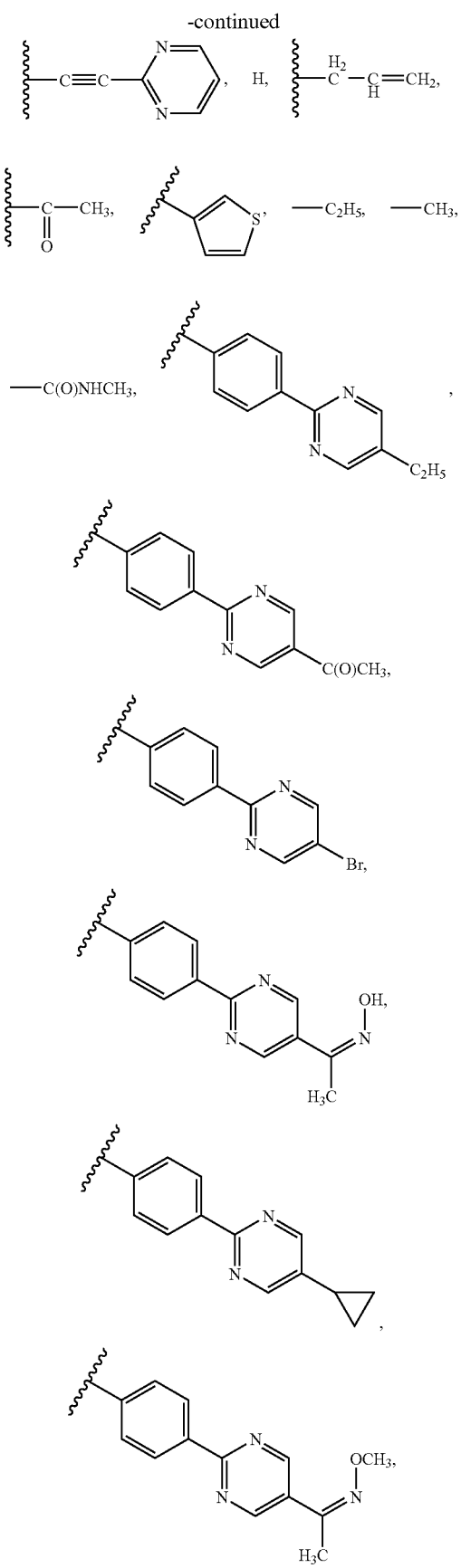

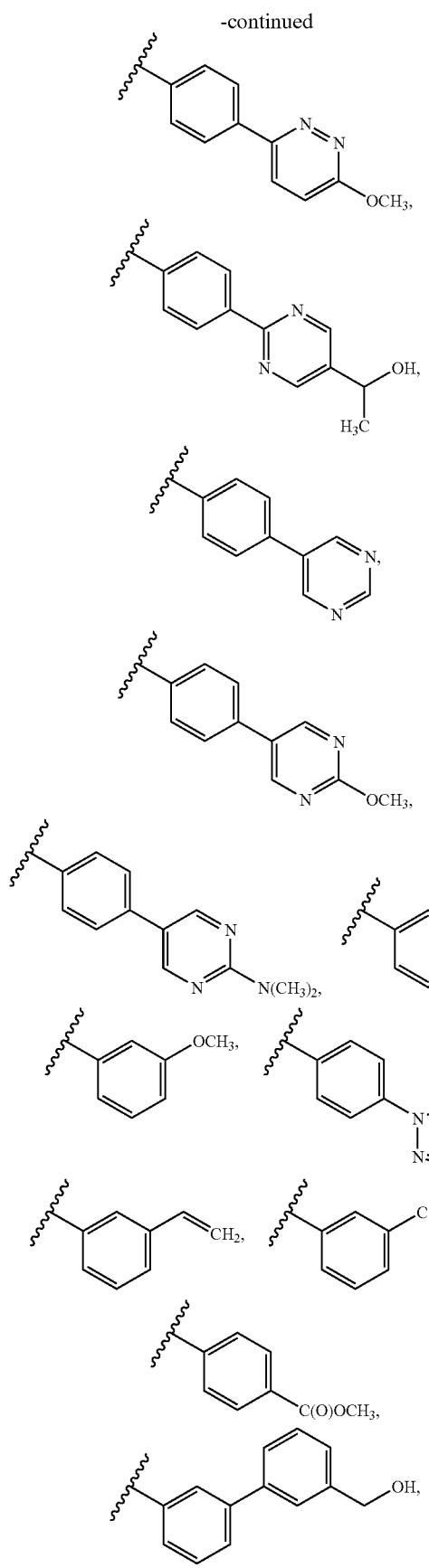
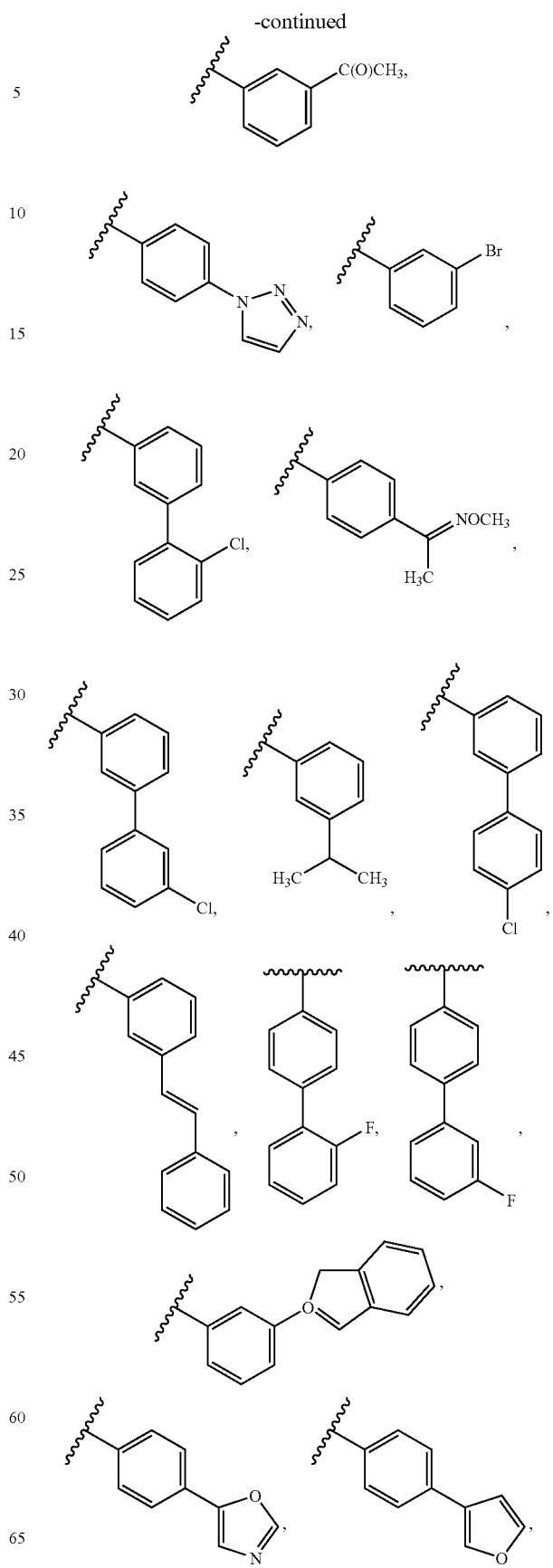

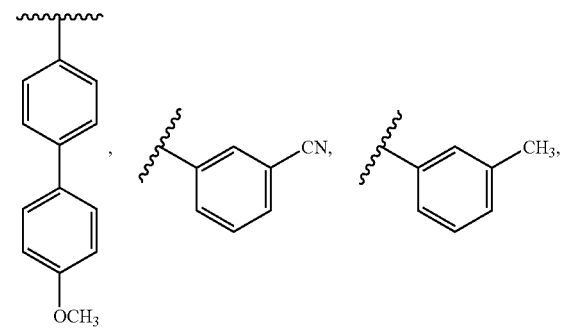
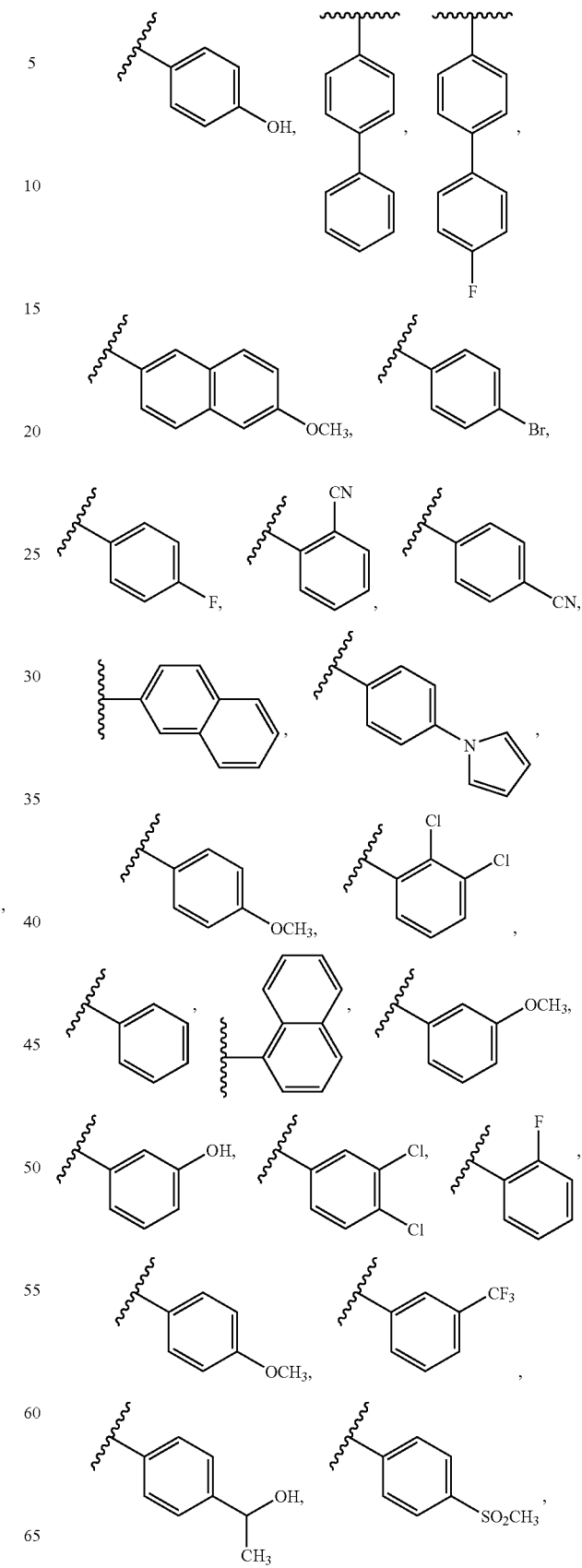

-continued
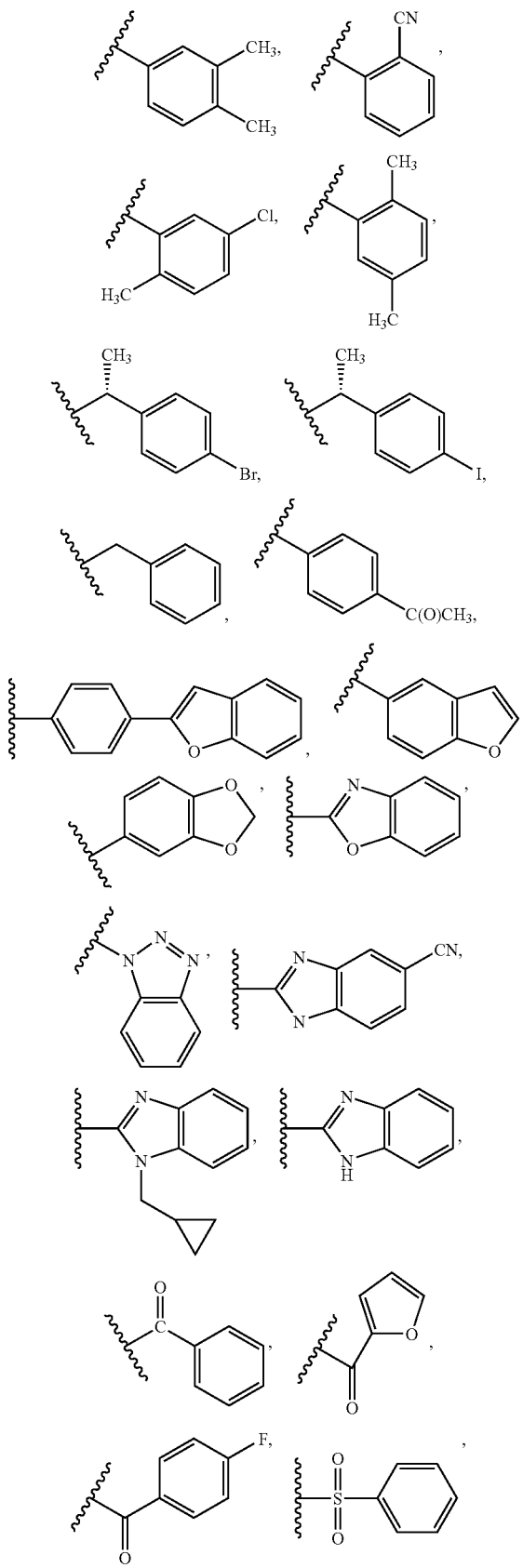
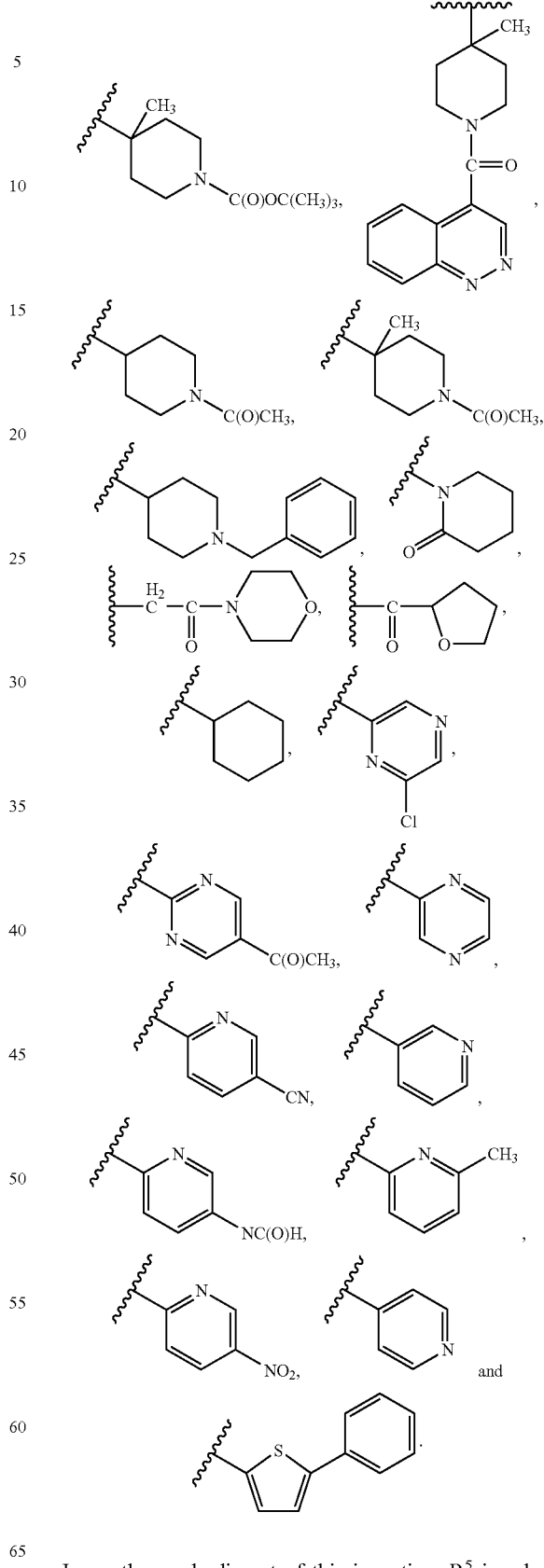
In another embodiment of this invention, $R^5$ is selected from the group consisting of:

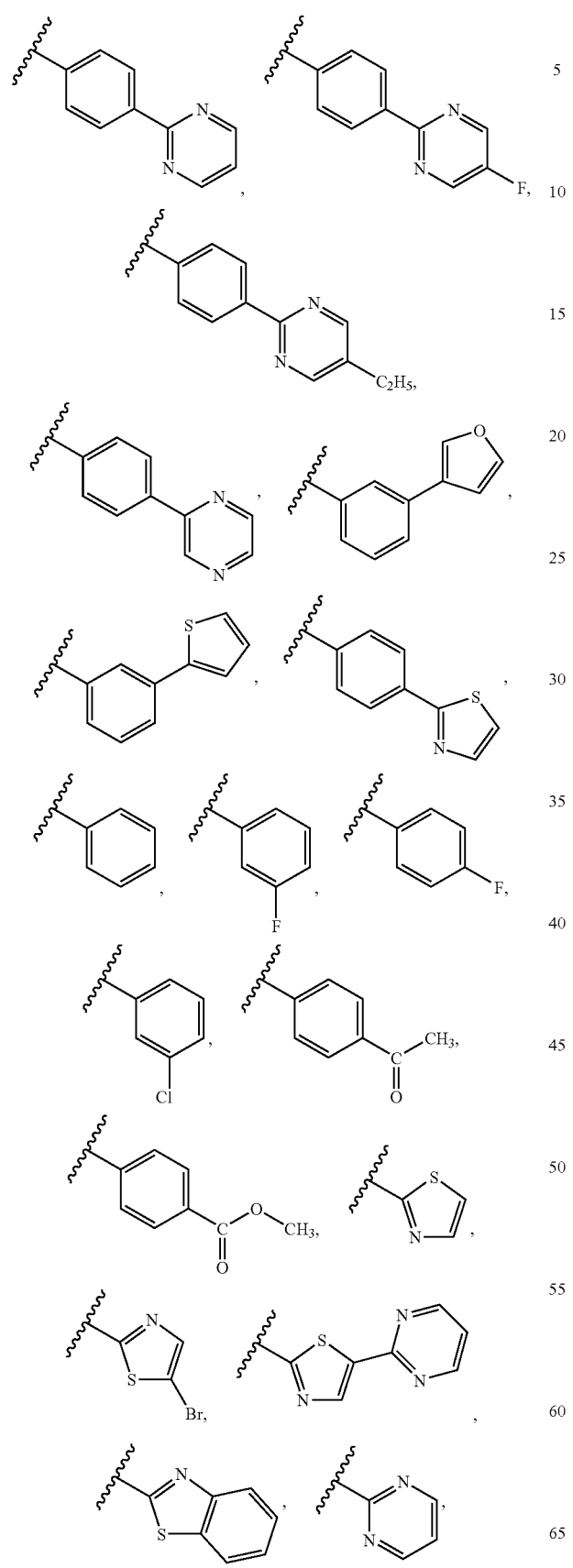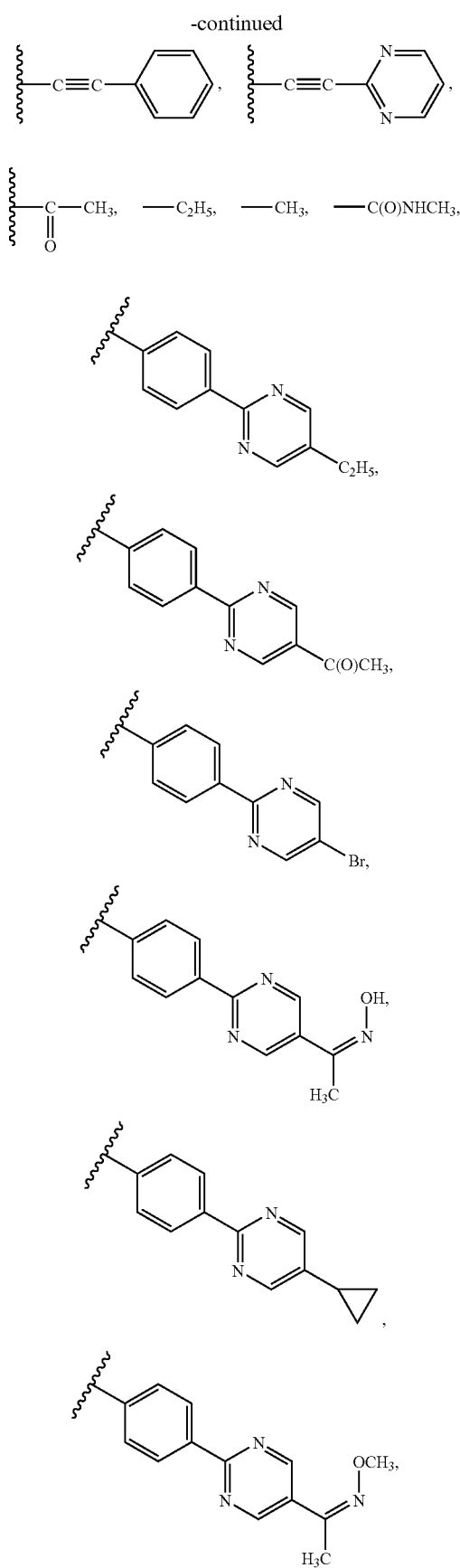

-continued
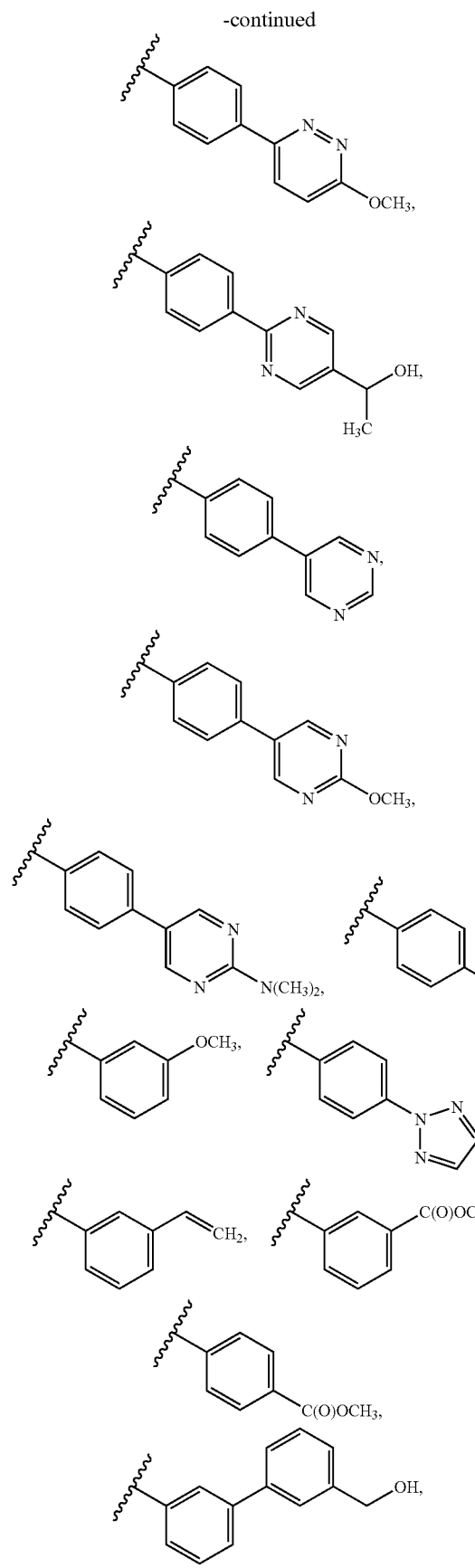
-continued
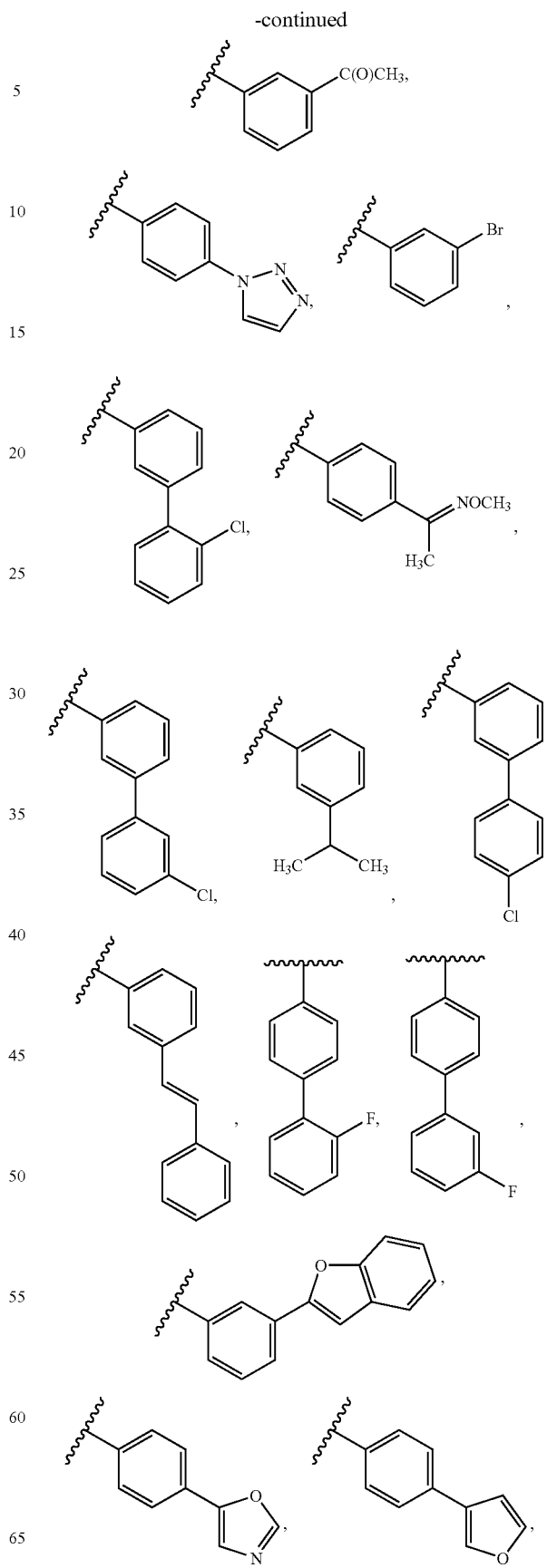

-continued
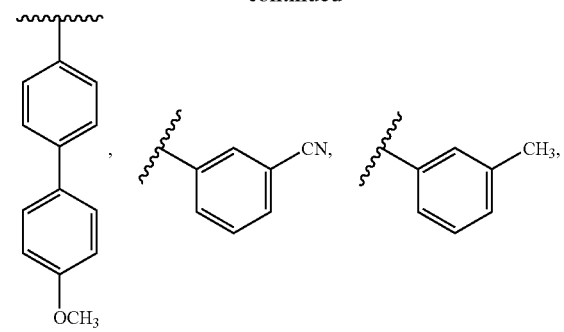
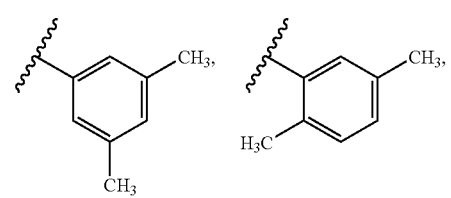
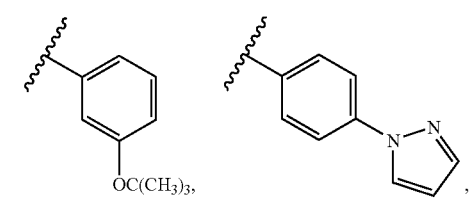
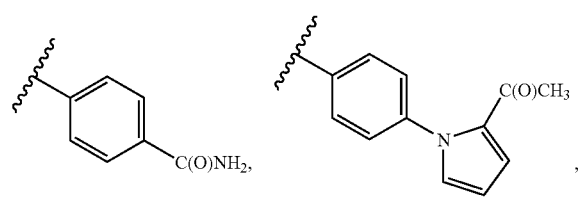
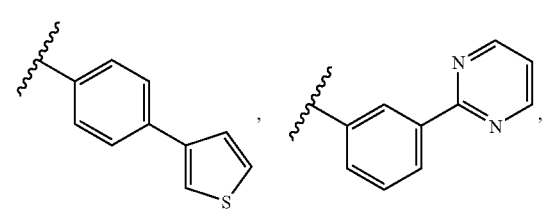
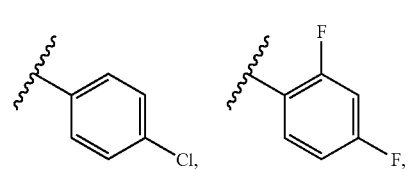
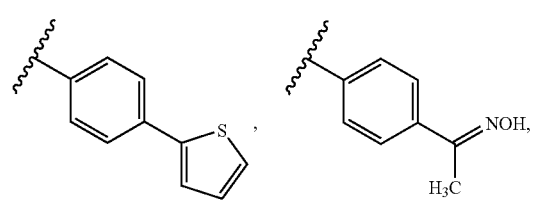
-continued
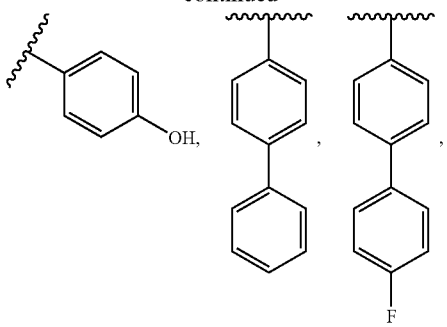
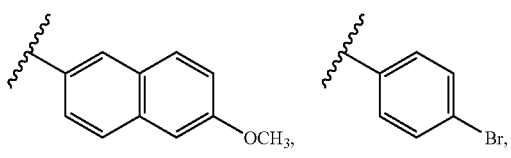
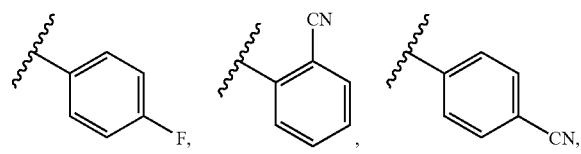
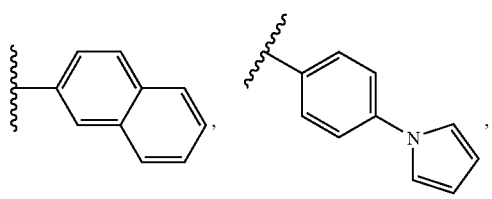
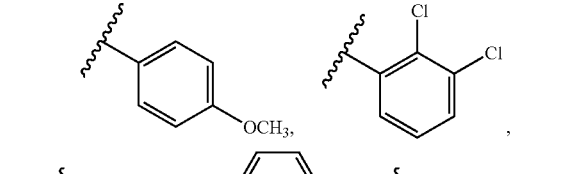
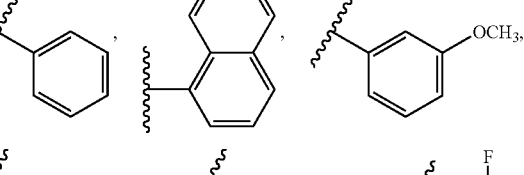
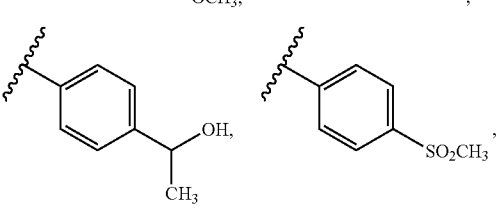

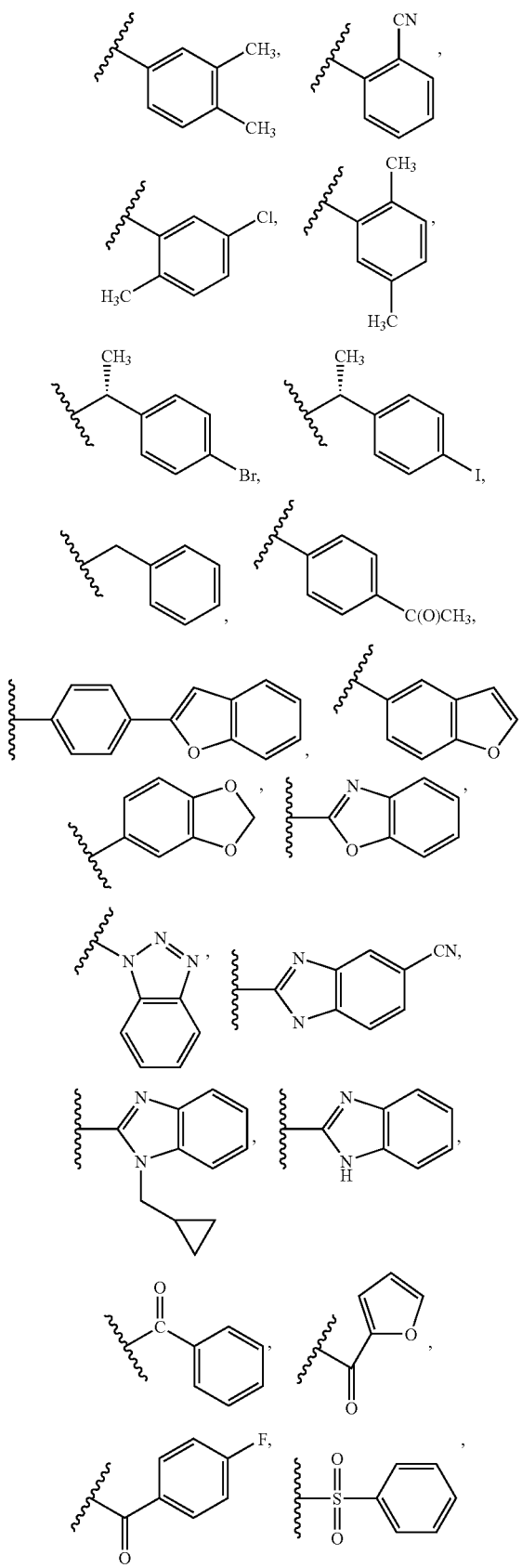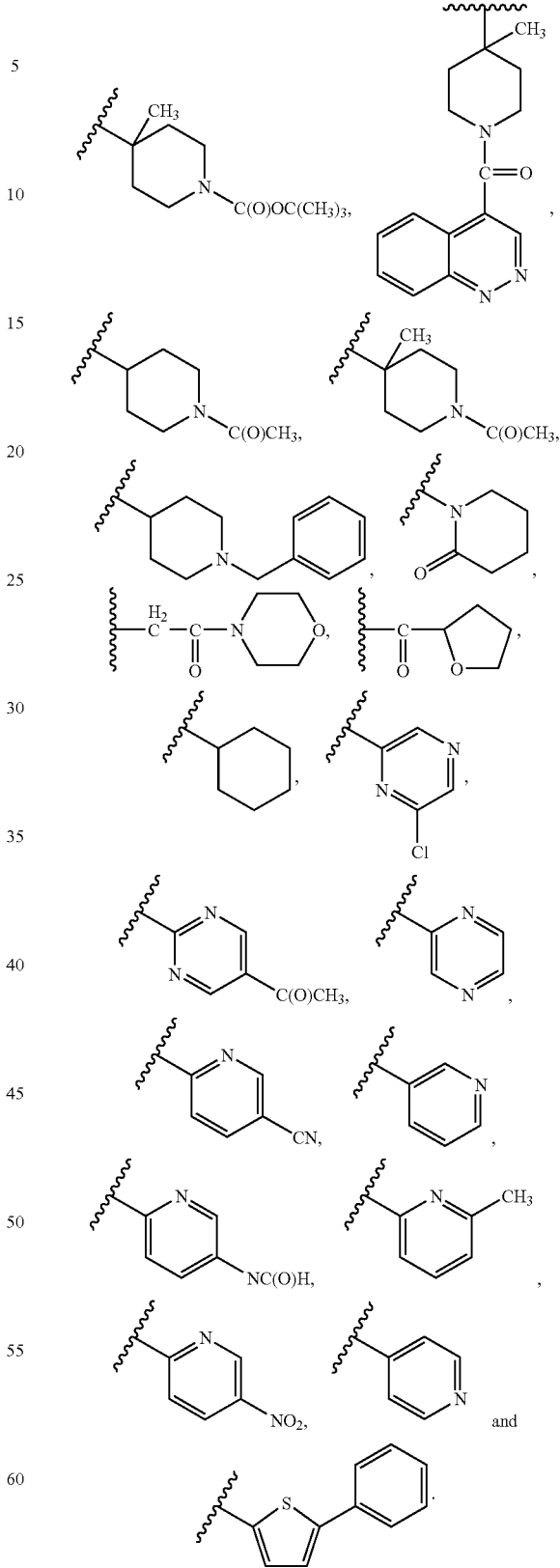
$R^2$, in one embodiment of this invention, is —$(CH_2)_m R^{11}$, wherein $R^{11}$ is —$OR^{10}$.

$R^2$, in another embodiment of this invention, is —$(CH_2)_m$ $R^{11}$ wherein $R^{11}$ is —$OR^{10}$, and $R^{10}$ is H or alkyl.

$R^2$, in another embodiment of this invention, is —$(CH_2)_m$ $R^{11}$, wherein $R^{11}$ is —$OR^{10}$, and $R^{10}$ alkyl (e.g., methyl).

$R^2$, in another embodiment of this invention, is —$(CH_2)_m$ $R^{11}$, wherein m is 1 and $R^{11}$ is —$OR^{10}$.

$R^2$, in another embodiment of this invention, is —$(CH_2)_m$ $R^{11}$, wherein m is 1, $R^{11}$ is —$OR^{10}$, and $R^{10}$ is H or alkyl.

$R^2$, in another embodiment of this invention, is —$(CH_2)_m$ $R^{11}$, wherein m is 1, $R^{11}$ is —$OR^{10}$, and $R^{10}$ alkyl.

$R^2$, in another embodiment of this invention, is —$(CH_2)_m$ $R^{11}$, wherein m is 1, $R^{11}$ is —$OR^{10}$, and $R^{10}$ methyl (i.e., $R^2$ is —$CH_2OCH_3$).

$R^2$, in another embodiment of this invention, is —$OR^{23}$ wherein $R^{23}$ is alkyl, and said alkyl is methyl (i.e., $R^2$ is —$OCH_3$).

$R^2$, in another embodiment of this invention, is alkynyl. An example of an alkynyl group is ethynyl:

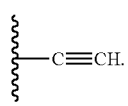

Another example of an alkynyl group is propynyl:

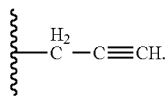

$R^2$, in another embodiment of this invention, is alkenyl. An example of an alkenyl group is —$CH_2$—$CH$=$CH_2$.

In one embodiment, $R^2$ is selected from the group consisting of: ethynyl, —$OCH_3$, and —$CH_2OCH_3$.

In another embodiment, $R^2$ is selected from the group consisting of: H, ethyl, —$CH_2OH$, —$CH_2OCH_3$, —$CH_2F$, —$CF_3$, —$CH_2NH_2$, —$CH_2$—$C$=$CH_2$, —$NH_2$, and —$CH_3$.

Additional examples of the $R^2$—$(CH_2)_m R^{11}$ group include, but are not limited to —$CH_2OH$, —$CH_2CN$, —$CH_2OC_2H_5$, —$(CH_2)_3OCH_3$, —$CH_2F$ and —$CH_2$-triazolyl, such as,

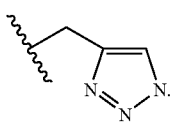

$R^3$, in one embodiment of this invention, is independently selected from the group consisting of: H and alkyl.

$R^3$, in another embodiment of this invention, is independently selected from the group consisting of: H and methyl.

$R^3$, in another embodiment of this invention, is H.

$R^4$, in one embodiment of this invention, $R^4$H.

$R^4$, in another embodiment of this invention, is selected from the group consisting of: H and alkyl.

$R^4$, in another embodiment of this invention, is selected from the group consisting of: H and methyl.

$R^6$, in one embodiment of this invention, is $R^6$H.

$R^7$, in one embodiment of this invention, is independently selected from the group consisting of: H and alkyl.

$R^7$, in another embodiment of this invention, is independently selected from the group consisting of: H and methyl.

$R^7$, in one embodiment of this invention, is H.

$R^8$, in one embodiment of this invention, is H.

$Y^1$, in one embodiment of this invention, is carbon.

$Y^2$, in one embodiment of this invention, is carbon.

$Y^2$ in one embodiment of this invention, is carbon.

$Y^3$ in one embodiment of this invention, is carbon.

$Y^1$, $Y^2$ and $Y^3$, in one embodiment of this invention, are carbon.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16, and each $R^3$, $R^4$, and $R^7$ is independently selected from the group consisting of: H and methyl.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16A, and each $R^3$, $R^4$, and $R^7$ is independently selected from the group consisting of: H and methyl.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16B, and each $R^3$, $R^4$, and $R^7$ is independently selected from the group consisting of: H and methyl.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16, and each $R^3$, $R^4$, and $R^7$ is H.

One embodiment of this invention is directed to a compound of formula 1.0, preferably a compound of formula 1.0C and more preferably a compound of formula 1.0C, (e.g., 1.1, 1.1A, 1.2, 1.2A, 1.3 or 1.3A) wherein substituent Q is 2.16A, and each $R^3$, $R^4$, and $R^7$ is H.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16B, and each $R^3$, $R^4$, and $R^7$ is H.

The compounds of this invention inhibit the activity of ERK1 and ERK2 Thus, this invention further provides a method of inhibiting ERK in mammals, especially humans, by the administration of an effective amount (e.g., a therapeutically effective amount) of one or more (e.g., one) compounds of this invention. The administration of the compounds of this invention to patients, to inhibit ERK1 and/or ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention.

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

In any of the methods of treating cancer described herein, unless stated otherwise, the methods can optionally include the administration of an effective amount of radiation therapy. For radiation therapy, γ-radiation is preferred.

Examples of cancers which may be treated by the methods of this invention include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas, such as glioma blastoma multiforme), (O) cancers of mesenchymal origin (e.g., fibrosarcomas and rhabdomyosarcomas), (P) sarcomas, (Q) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

Chemotherapeutic agents (antineoplastic agent) include but are not limited to: microtubule affecting agents, alkylating agents, antimetabolites, natural products and their derivatives, hormones and steroids (including synthetic analogs), and synthetics.

Examples of alkylating agents (including nitrogen mustards, ethylenimine derivatives, alkyl sulfonates, nitrosoureas and triazenes) include: Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Examples of antimetabolites (including folic acid antagonists, pyrimidine analogs, purine analogs and adenosine deaminase inhibitors) include: Methotrexate, 5-Fluorouracil, Floxuridine, Cytarabine, 6-Mercaptopurine, 6-Thioguanine, Fludarabine phosphate, Pentostatine, and Gemcitabine.

Examples of natural products and their derivatives (including vinca alkaloids, antitumor antibiotics, enzymes, lymphokines and epipodophyllotoxins) include: Vinblastine, Vincristine, Vindesine, Bleomycin, Dactinomycin, Daunorubicin, Doxorubicin, Epirubicin, Idarubicin, Paclitaxel (paclitaxel is a microtubule affecting agent and is commercially available as Taxol®), Paclitaxel derivatives (e.g. taxotere), Mithramycin, Deoxyco-formycin, Mitomycin-C, L-Asparaginase, Interferons (especially IFN-a), Etoposide, and Teniposide.

Examples of hormones and steroids (including synthetic analogs) include: 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex.

Examples of synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Examples of other chemotherapeutics include: Navelbene, CPT-11, Anastrazole, Letrazole, Capecitabinbe, Reloxafine, and Droloxafine.

A microtubule affecting agent (e.g., paclitaxel, a paclitaxel derivative or a paclitaxel-like compound), as used herein, is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents, useful in the methods of this invention, are well known to those skilled in the art and include, but are not limited to: Allocolchicine (NSC 406042), Halichondrin B (NSC 609395), Colchicine (NSC 757), Colchicine derivatives (e.g., NSC 33410), Dolastatin 10 (NSC 376128), Maytansine (NSC 153858), Rhizoxin (NSC 332598), Paclitaxel (Taxol®, NSC 125973), Paclitaxel derivatives (e.g., Taxotere, NSC 608832), Thiocolchicine (NSC 361792), Trityl Cysteine (NSC 83265), Vinblastine Sulfate (NSC 49842), Vincristine Sulfate (NSC 67574), Epothilone A, Epothilone, Discodermolide (see Service, (1996) Science, 274:2009), Estramustine, Nocodazole, MAP4, and the like. Examples of such agents are described in, for example, Bulinski (1997) J. Cell Sci. 110:3055-3064, Panda (1997) Proc. Natl. Acad. Sci. USA 94:10560-10564, Muhlradt (1997) Cancer Res. 57:3344-3346, Nicolaou (1997) Nature 387:268-272, Vasquez (1997) Mol. Biol. Cell. 8:973-985, and Panda (1996) J. Biol. Chem. 271:29807-29812.

Chemotherapeutic agents with paclitaxel-like activity include, but are not limited to, paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Thus, in the methods of this invention wherein at least one chemotherapeutic agent is used, examples of said chemotherapeutic agents include those selected from the group consisting of: microtubule affecting agents, alkylating agents, antimetabolites, natural products and their derivatives, hormones and steroids (including synthetic analogs), and synthetics.

In the methods of this invention wherein at least one chemotherapeutic agent is used, examples of said chemotherapeutic agents also include: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

In the methods of this invention wherein at least one chemotherapeutic agent is used, examples of such chemotherapeutic agents include:

(1) taxanes such as paclitaxel (TAXOL®) and/or docetaxel (Taxotere®);

(2) platinum coordinator compounds, such as, for example, carboplatin, cisplatin and oxaliplatin (e.g. Eloxatin);

(3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), C11033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-C11 (ImClone Systems), DC 101 (a KDR VEGF Receptor 2 from ImClone Systems);

(6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals);

(7) estrogen receptor antagonists or selective estrogen receptor modulators
(SERMs), such as tamoxifen, idoxifene, raloxifene, trans-2,3-dihydroraloxifene, levormeloxifene, droloxifene, MDL 103,323, and acolbifene (Schering Corp.);

(8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda);

(9) epothilones such as BMS-247550 (Bristol-Myers Squibb), and EP0906 (Novartis Pharmaceuticals);

(10) topoisomerase inhibitors such as topotecan (Glaxo SmithKline), and Camptosar (Pharmacia);

(11) vinca alkaloids, such as, navelbine (Anvar and Fabre, France), vincristine and vinblastine;

(12) antibodies that are inhibitors of αVβ3 integrins, such as, LM-609 (see, Clinical Cancer Research, Vol. 6, page 3056-3061, August 2000, the disclosure of which is incorporated herein by reference thereto);

(13) folate antagonists, such as Methotrexate (MTX), and Premetrexed (Alimta);

(14) ribonucleotide reductase inhibitors, such as Hydroxyurea (HU);

(15) anthracyclines, such as Daunorubicin, Doxorubicin (Adriamycin), and Idarubicin;

(16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma);

(17) thalidomide (or related imid);

(18) Bcr/abl kinase inhibitors, such as, for example Gleevec (STI-571), AMN-17, ON012380, SU11248 (Sunitinib) and BMS-354825

(19) MEK1 and/or MEK2 inhibitors, such as PD0325901 and Arry-142886 (AZD6244);

(20) IGF-1 and IGF-2 inhibitors that are small molecules, such as, for example, NVP-AEW541;

(21) small molecule inhibitors of RAF and BRAF kinases, such as, for example, BAY 43-9006 (Sorafenib);

(22) small molecule inhibitors of cell cycle dependent kinases such as CDK1, CDK2, CDK4 and CDK6, such as, for example, CYC202, BMS387032, and Flavopiridol;

(23) alkylating agents, such as, for example, Temodar® brand of temozolomide;

(24) farnesyl protein transferase inhibitors, such as, for example:

(a) Sarasar® brand of Ionifarnib (i.e., 4-[2-[4-(3,10-dibromo-8-chloro-6,11-dihydro-5H-benzo[5,6]cyclohepta[1,2-b]byridin-11-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto), (b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S. Pat. No. 5,968,952 issued Oct. 19, 1999, the disclosures of each being incorporated herein by reference thereto), and (c) Bristol-Myers Squibb 214662:

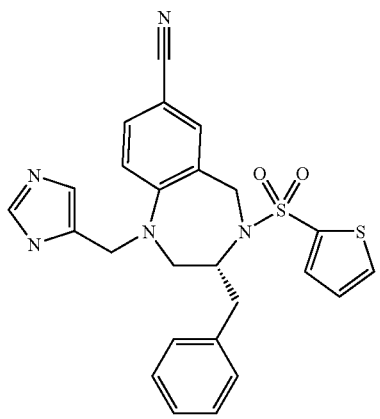

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin®) (trastuzumab).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

For example, the compound of formula 1.0 (e.g., a pharmaceutical composition comprising the compound of formula 1.0); can be administered orally (e.g., as a capsule), and the chemotherapeutic agents can be administered intravenously, usually as an IV solution. The use of a pharmaceutical composition comprising more than one drug is within the scope of this invention.

The compound of formula 1.0 and the chemotherapeutic agents are administered in therapeutically effective dosages to obtain clinically acceptable results, e.g., reduction or elimination of symptoms or of the tumor. Thus, the compound of formula 1.0 and chemotherapeutic agents can be administered concurrently or consecutively in a treatment protocol.

The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The compounds of this invention can be administered orally, preferably as a solid dosage form, and in one embodiment as a capsule, and while the total therapeutically effective daily dose can be administered in one to four, or one to two divided doses per day, generally, the therapeutically effective dose is given once or twice a day, and in one embodiment twice a day. The compounds of this invention can be administered in an amount of about 50 to about 400 mg once per day, and can be administered in an amount of about 50 to about 300 mg once per day. The compounds of this invention are generally administered in an amount of about 50 to about 350 mg twice a day, usually 50 mg to about 200 mg twice a day, and in one embodiment about 75 mg to about 125 mg administered twice a day, and in another embodiment about 100 mg administered twice a day.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m 2/day every 3 to 4 weeks; (I) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m$^2$ IV weekly over 4-8 weeks for 6 months; (aa) for the alkylating agent temozolomide 75 mg/m$^2$ to 250 mg/m$^2$, for example, 150 mg/m$^2$, or for example, 200 mg/m$^2$, such as 200 mg/m$^2$ for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be continuously dosed or used until relapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

The FPT inhibitor Sarasar® (brand of Ionifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®), for example, can be administered once per week in an amount of about 50 to about 100 mg/m$^2$ and in another example about 60 to about 80 mg/m$^2$. In another example Paclitaxel (e.g., Taxol®) can be administered once every three weeks in an amount of about 150 to about 250 mg/m$^2$ and in another example about 175 to about 225 mg/m$^2$.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Other embodiments of this invention are described below. The embodiments have been numbered for the purpose of making it easier to refer to the embodiments. The term "in any one of Embodiment Nos." or the term "of any of Embodiment Nos.", as used below, means that the particular embodiment using that term is intended to cover any one of the embodiments referred to as if any one of the referred to embodiments had been individually described. "Nos." is an abbreviation for Numbers.

Embodiment No. 1 is directed to a compound of formula 1.0, preferably a compound of formula 1.0C, wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15 and 2.16 (e.g., 2.16A or 2.16B).

Embodiment No. 2 is directed to a compound of formula 1.1 wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15, and 2.16 (e.g., 2.16A or 2.16B).

Embodiment No. 3 is directed to a compound of formula 1.2 wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15 and 2.16 (e.g., 2.16A or 2.16B).

Embodiment No. 4 is directed to a compound of formula 1.3 wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15 and 2.16 (e.g., 2.16A or 2.16B).

Embodiment No. 5 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.1.

Embodiment No. 6 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.2.

Embodiment No. 7 is directed to a compound of formula 1.0 (e.g., 1.1, 1.1A, 1.2, 1.2A, 1.3 or 1.3A) wherein substituent Q is 2.3 (e.g., 2.3A, 2.3B or 2.3C).

Embodiment No. 8 is directed to a compound of formula 1.0, preferably a compound of formula 1.0C, (e.g., 1.1, 1.1A, 1.2, 1.2A, 1.3 or 1.3A) wherein substituent Q is 2.4 (e.g., 2.4A, 2.4B or 2.4C).

Embodiment No. 9 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.5 (e.g., 2.5A, 2.5B or 2.5C).

Embodiment No. 10 is directed to any of compounds of formulas to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.6 (e.g., 2.6A).

Embodiment No. 11 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.7.

Embodiment No. 12 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.8.

Embodiment No. 13 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.9.

Embodiment No. 14 is directed to a compound of formula 1.0, preferably a compound of formula 1.0C and more preferably a compound of formula 1.0C, (e.g., 1.1, 1.1A, 1.2, 1.2A, 1.3 or 1.3A) wherein substituent Q is 2.10.

Embodiment No. 15 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.11.

Embodiment No. 16 is directed to a compound of formula 1.0, preferably a compound of formula 1.0C and more preferably a compound of formula 1.0C, (e.g., 1.1, 1.1A, 1.2, 1.2A, 1.3 or 1.3A) wherein substituent Q is 2.12.

Embodiment No. 17 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.13.

Embodiment No. 18 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.14.

Embodiment No. 19 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.15.

Embodiment No. 20 is directed to a compound of formula 1.3 wherein substituent Q is 2.1.

Embodiment No. 21 is directed to a compound of formula 1.3 wherein substituent Q is 2.2.

Embodiment No. 22 is directed to a compound of formula 1.3 wherein substituent Q is 2.3.

Embodiment No. 23 is directed to a compound of formula 1.3 wherein substituent Q is 2.6.

Embodiment No. 24 is directed to a compound of formula 1.3 wherein substituent Q is 2.6A.

Embodiment No. 25 is directed to a compound of formula 1.3 wherein substituent Q is 2.7A.

Embodiment No. 26 is directed to a compound of formula 1.3 wherein substituent Q is 2.7B.

Embodiment No. 27 is directed to a compound of formula 1.3 wherein substituent Q is 2.7C.

Embodiment No. 28 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein each $R^3$, $R^4$, $R^6$, and $R^7$ is independently selected from the group consisting of: H and alkyl.

Embodiment No. 29 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein each $R^3$, $R^4$, $R^6$, and $R^7$ is independently selected from the group consisting of: H and methyl.

Embodiment No. 30 is directed to a compound of formula 1.0, preferably a compound of formula 1.0C and more preferably a compound of formula 1.0C, (e.g., 1.1, 1.1A, 1.2, 1.2A, 1.3 or 1.3A) wherein each $R^3$, $R^4$, $R^6$, and $R^7$ is H.

Embodiment No. 31 is directed to a compound of formula 1.0, preferably a compound of formula 1.0C and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C.

Embodiment No. 32 is directed to a compound of formula 1.0, preferably a compound of formula 1.0C and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C, and each $R^3$, $R^4$, $R^6$, and $R^7$ is independently selected from the group consisting of: H and alkyl.

Embodiment No. 33 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C, and each $R^3$, $R^4$, $R^6$, and $R^7$ is independently selected from the group consisting of: H and methyl.

Embodiment No. 34 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C, and each $R^3$, $R^4$, $R^6$, and $R^7$ is H.

Embodiment No. 35 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 36 is directed to a compound of formula 1.0, preferably a compound of formula 1.0C and more preferably a compound of formula 1.0C, (e.g., 1.1, 1.1A, 1.2, 1.2A, 1.3 or 1.3A) wherein substituent Q is selected from the group consisting of: moieties 2.2, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 37 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.3A, 2.3B, 2.3C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 38 is directed to a compound of formula 1.2 or 1.3 wherein each $R^3$, $R^4$, $R^6$, and $R^7$ is independently selected from the group consisting of: H and alkyl.

Embodiment No. 39 is directed to a compound of formula 1.2 or 1.3 wherein each $R^3$, $R^4$, $R^6$, and $R^7$ is independently selected from the group consisting of: H and methyl.

Embodiment No. 40 is directed to a compound of formula 1.2 or 1.3 wherein each $R^3$, $R^4$, $R^6$, and $R^7$ is H.

Embodiment No. 41 is directed to a compound of formula 1.2 or 1.3 wherein substituent Q is selected from the group consisting of: moieties 2.1, 2.2, 2.3A, 2.3B and 2.3C.

Embodiment No. 42 is directed to a compound of formula 1.2 or 1.3 wherein substituent Q is selected from the group consisting of: moieties 2.1, 2.2, 2.3A, 2.3B and 2.3C, and each $R^3$, $R^4$, $R^6$, and $R^7$ is independently selected from the group consisting of: H and alkyl.

Embodiment No. 43 is directed to a compound of formula 1.2 or 1.3 wherein substituent Q is selected from the group consisting of: moieties 2.1, 2.2, 2.3A, 2.3B and 2.3C, and each $R^3$, $R^4$, $R^6$, and $R^7$ is independently selected from the group consisting of: H and methyl.

Embodiment No. 44 is directed to a compound of formula 1.2 or 1.3 wherein substituent Q is selected from the group consisting of: moieties 2.1, 2.2, 2.3A, 2.3B and 2.3C, and each $R^3$, $R^4$, $R^6$, and $R^7$ is H.

Embodiment No. 45 is directed to a compound of formula 1.2 or 1.3 wherein substituent Q is selected from the group consisting of: moiety 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 46 is directed to a compound of formula 1.2 or 1.3 wherein substituent Q is selected from the group consisting of: moiety 2.2, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 47 is directed to a compound of formula 1.2 or 1.3 wherein substituent Q is selected from the group consisting of: moieties 2.3A, 2.3B and 2.3C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 48 is directed to a compound of formula 1.3 wherein each $R^3$, $R^4$, $R^6$, and $R^7$ is independently selected from the group consisting of: H and alkyl.

Embodiment No. 49 is directed to a compound of formula 1.3 wherein each $R^3$, $R^4$, $R^6$, and $R^7$ is independently selected from the group consisting of: H and methyl.

Embodiment No. 50 is directed to a compound of formula 1.3 wherein each $R^3$, $R^4$, $R^6$, and $R^7$ is H.

Embodiment No. 51 is directed to a compound of formula 1.3 wherein substituent Q is selected from the group consisting of: moieties 2.1, 2.2, 2.3A, 2.3B and 2.3C.

Embodiment No. 52 is directed to a compound of formula 1.3 wherein substituent Q is selected from the group consisting of: moieties 2.1, 2.2, 2.3A, 2.3B and 2.3C, and each $R^3$, $R^4$, $R^6$, and $R^7$ is independently selected from the group consisting of: H and alkyl.

Embodiment No. 53 is directed to a compound of formula 1.3 wherein substituent Q is selected from the group consisting of: moieties 2.1, 2.2, 2.3A, 2.3B and 2.3C, and each $R^3$, $R^4$, $R^6$, and $R^7$ is independently selected from the group consisting of: H and methyl.

Embodiment No. 54 is directed to a compound of formula 1.3 wherein substituent Q is selected from the group consisting of: moieties 2.1, 2.2, 2.3A, 2.3B and 2.3C, and each $R^3$, $R^4$, $R^6$, and $R^7$ is H.

Embodiment No. 55 is directed to a compound of formula 1.3 wherein substituent Q is selected from the group consisting of: moiety 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 56 is directed to a compound of formula 1.3 wherein substituent Q is selected from the group consisting of: moiety 2.2, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 57 is directed to a compound of formula 1.3 wherein substituent Q is selected from the group consisting of: moieties 2.3A1, 2.3B and 2.3C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 58 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C.

Embodiment No. 59 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C, and each $R^3$, $R^4$, $R^6$, and $R^7$ is independently selected from the group consisting of: H and alkyl.

Embodiment No. 60 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C, and each $R^3$, $R^4$, $R^6$, and $R^7$ is independently selected from the group consisting of: H and methyl.

Embodiment No. 61 is directed to a compound of formula 1.0, preferably a compound of formula 1.0C and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C, and each $R^3$, $R^4$, $R^6$, and $R^7$ is H.

Embodiment No. 62 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.6, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 63 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.7A, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 64 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.7B and 2.7C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^1$, $R^6$, and $R^7$ is H.

Embodiment No. 65 is directed to a compound of formula 1.2 or 1.3 wherein substituent Q is selected from the group consisting of: moieties 2.6, 2.7A, 2.7B and 2.7C.

Embodiment No. 66 is directed to a compound of formula 1.2 or 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and alkyl.

Embodiment No. 67 is directed to a compound of formula 1.2 or 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and methyl.

Embodiment No. 68 is directed to a compound of formula 1.2 or 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H.

Embodiment No. 69 is directed to a compound of formula 1.2 or 1.3 wherein substituent Q is selected from the group consisting of: moiety 2.6, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 70 is directed to a compound of formula 1.2 or 1.3 wherein substituent Q is selected from the group consisting of: moiety 2.7A, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 71 is directed to a compound of formula 1.2 or 1.3 wherein substituent Q is selected from the group consisting of: moieties 2.7A and 2.7B, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 72 is directed to a compound of formula 1.3 wherein substituent Q is selected from the group consisting of: moieties 2.6, 2.7A, 2.7B and 2.7C.

Embodiment No. 73 is directed to a compound of formula 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and alkyl.

Embodiment No. 74 is directed to a compound of formula 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and methyl.

Embodiment No. 75 is directed to a compound of formula 1.3 wherein substituent Q is selected from the group consisting of: moieties 2.6, 2.7A, 2.7B and 2.7C, and each $R^3$, $R^4$, $R^6$, and $R^7$ is H.

Embodiment No. 76 is directed to a compound of formula 1.3 wherein substituent Q is selected from the group consisting of: moiety 2.6, and: (1) each $R^3$, $R^4$, $R^6$, and $R^7$ is independently selected from the group consisting of: H and alkyl, or (2) each $R^3$, $R^6$, and $R^7$ is independently selected from the group consisting of: H and methyl, or (3) each $R^3$, $R^4$, $R^6$, and $R^7$ is H.

Embodiment No. 77 is directed to a compound of formula 1.3 wherein substituent Q is selected from the group consisting of: moiety 2.7A, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 78 is directed to a compound of formula 1.3 wherein substituent Q is selected from the group consisting of: moieties 2.7B and 2.7C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 79 is directed to a compound of any one of Embodiment Nos. 1 to 78, wherein $R^1$ is selected from the group consisting of: i-propyl, t-butyl, methyl, cyclopropyl, Cl, —$CF_3$, H, —$CH_2OH$, —$C(O)NH_2$, pyrazolyl, phenyl, pyridyl, o-F-phenyl, m-F-phenyl and p-F-phenyl Embodiment No. 80 is directed to a compound of any one of Embodiment Nos. 1 to 79 wherein $R^5$ is selected from the group consisting of:
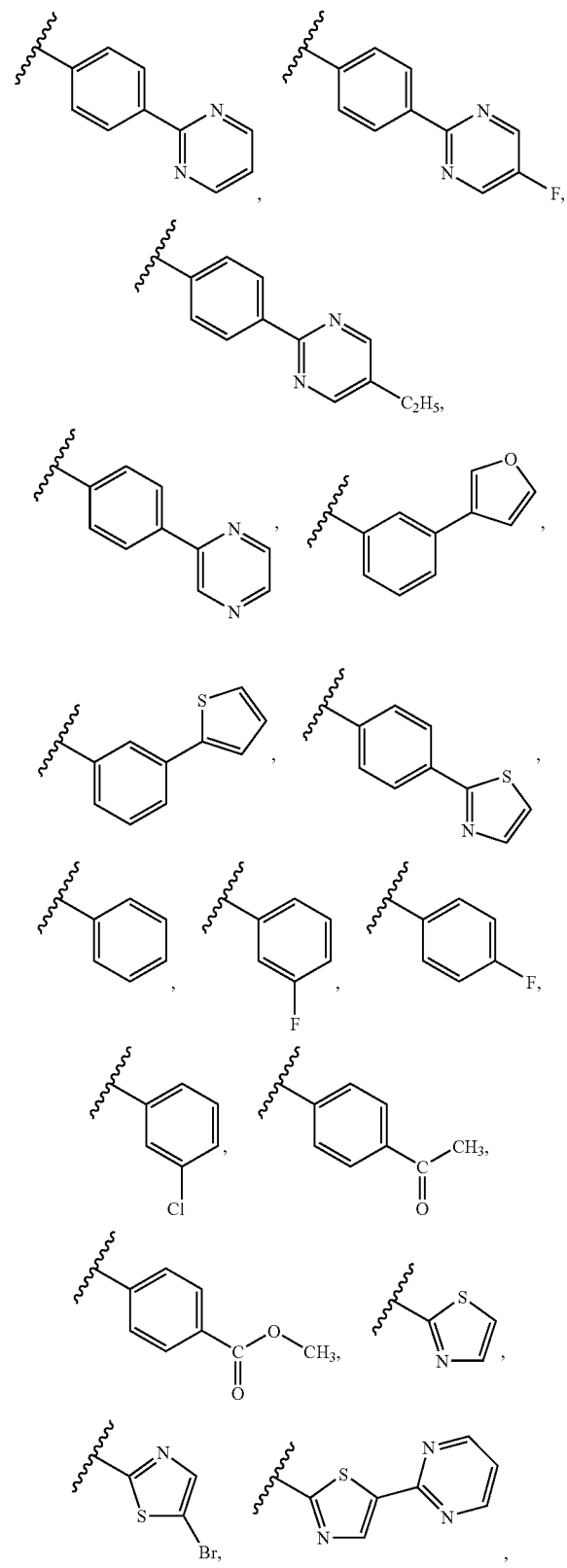
-continued
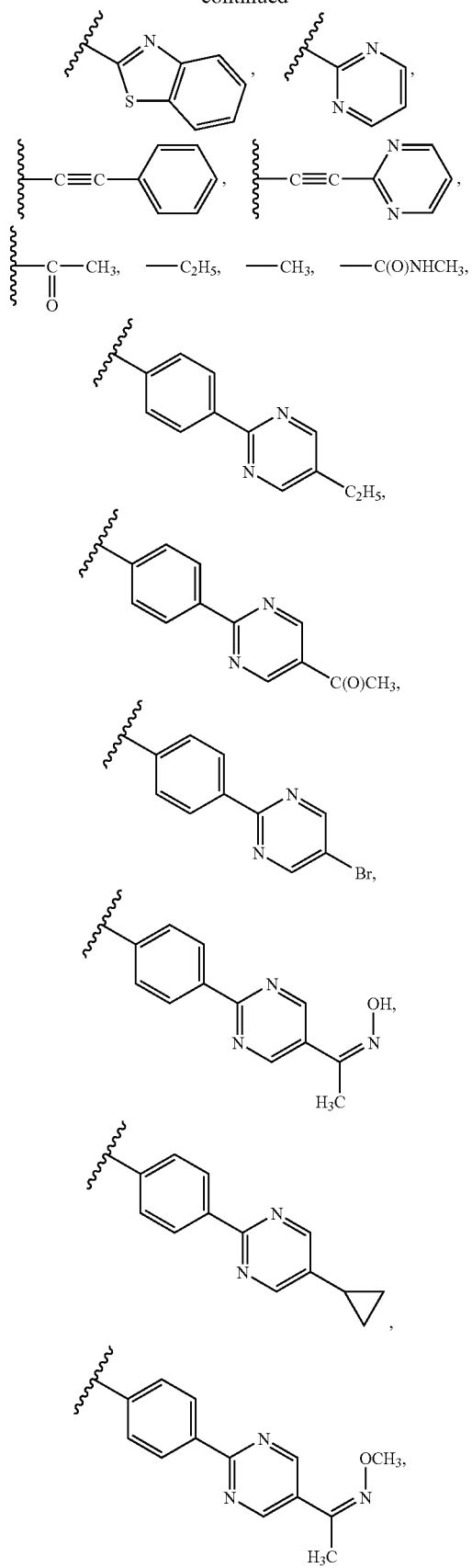

-continued
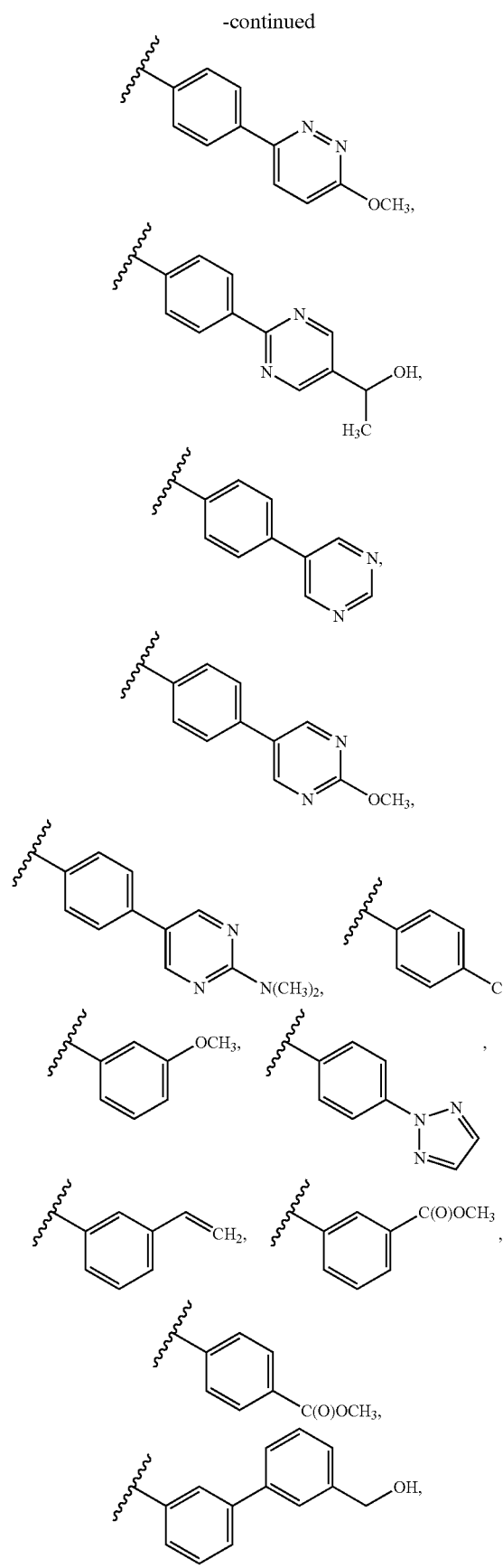
-continued
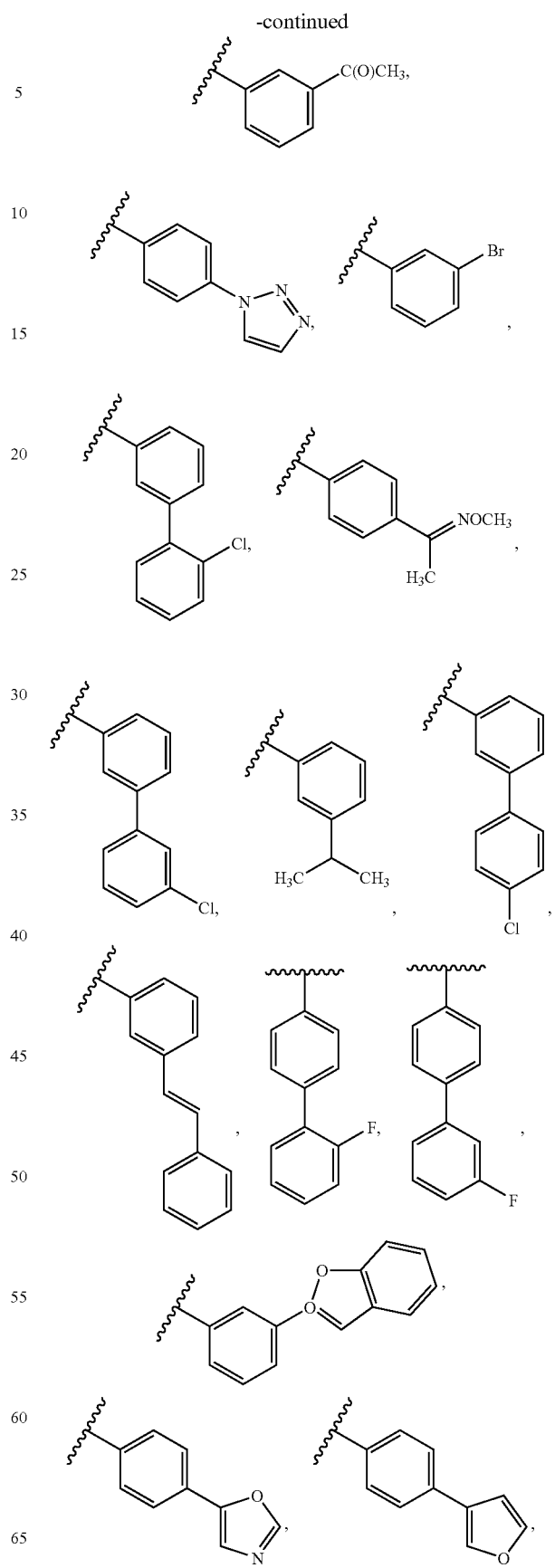

-continued
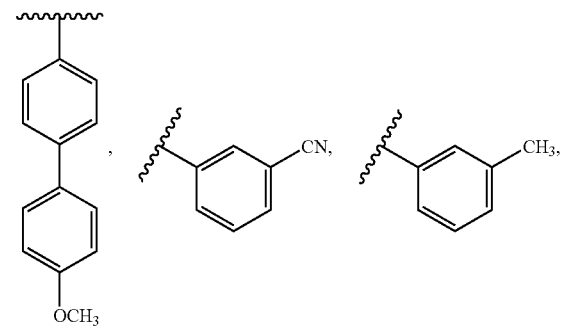
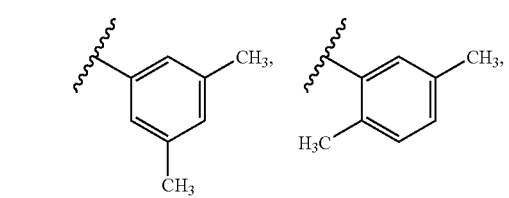
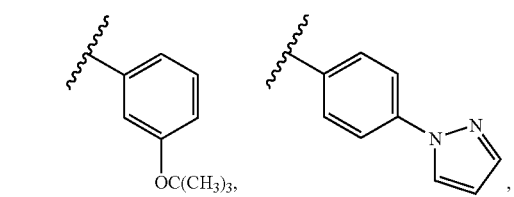
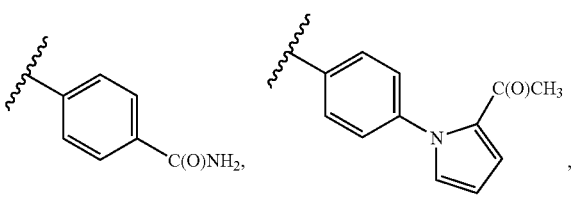
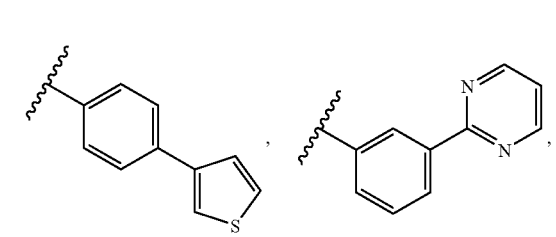
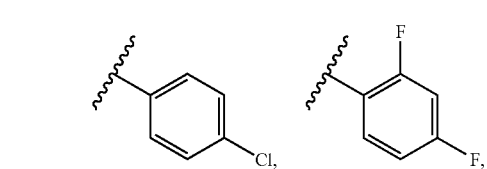
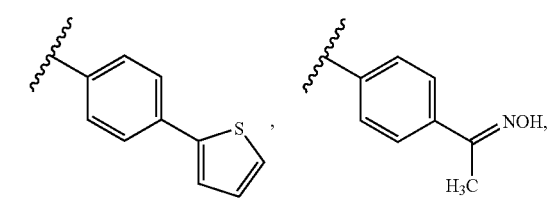
-continued
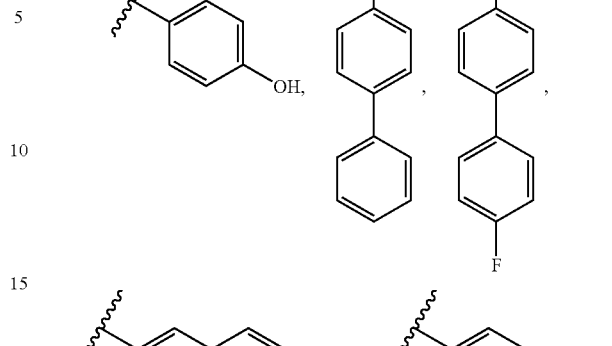
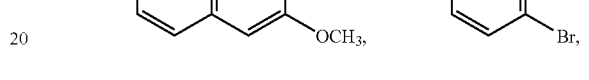
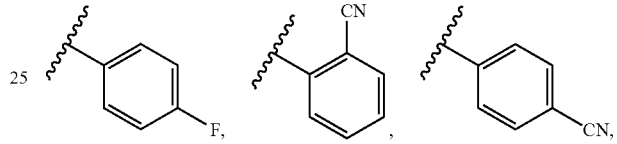
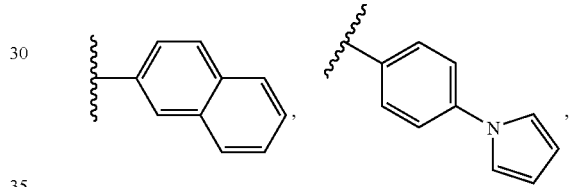
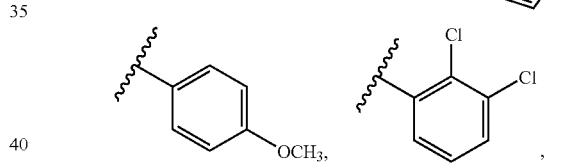
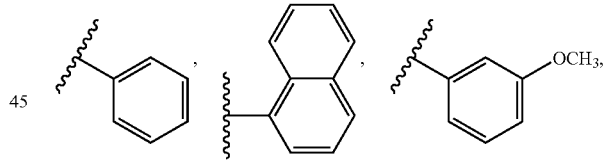
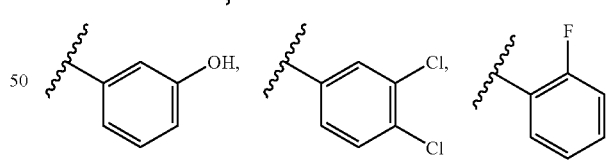
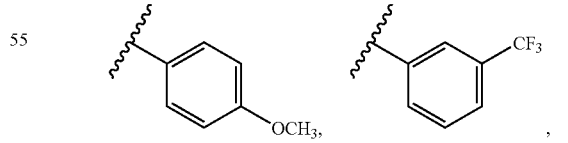
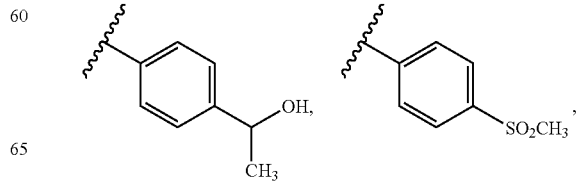

-continued
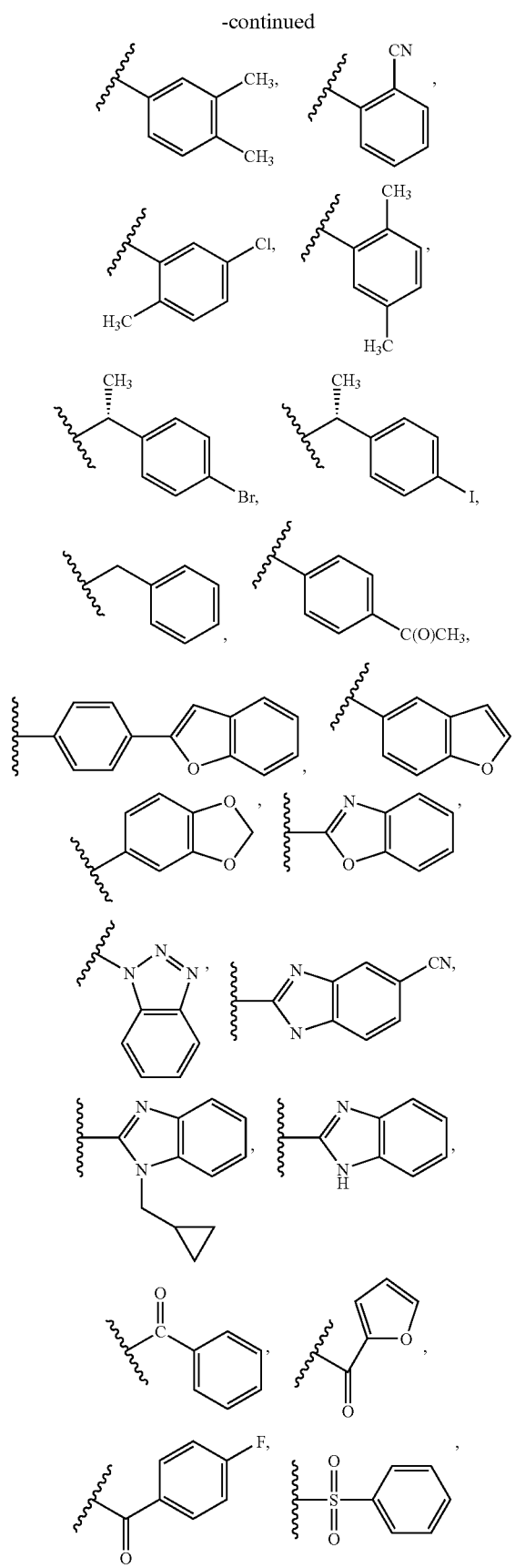
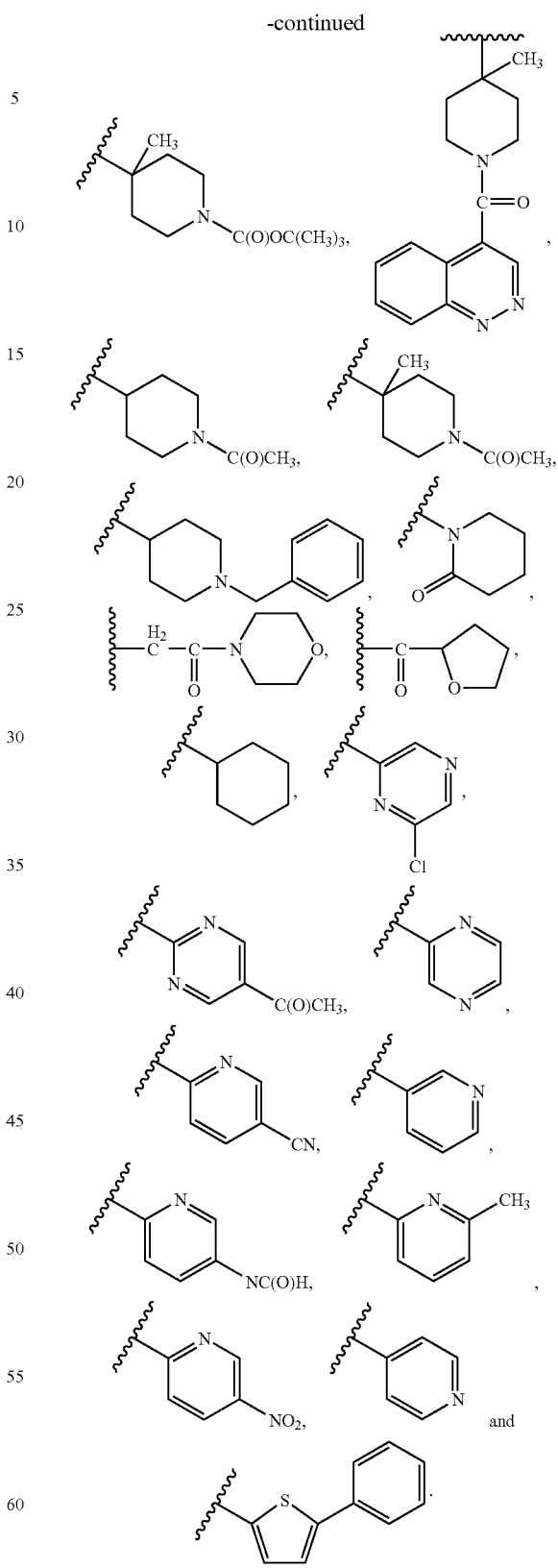
Embodiment No. 81 is directed to a compound of any one of Embodiment Nos. 1 to 78 wherein $R^1$ is selected from the group consisting of the $R^1$ groups in Embodiment No. 79, and wherein R⁵ is selected from the group consisting of the R⁵ groups in Embodiment No. 80

Embodiment No. 82 is directed to a compound of any one of Embodiment Nos. 1 to 81 wherein R² is selected from the group consisting of H, ethyl, —CH₂OH, —CH₂OCH₃, —CH₂F, —CF₃, —CH₂NH₂, —CH₂—C≡CH₂, —NH₂, and —CH₃.

Embodiment No. 83 is directed to a compound of any one of Embodiment Nos. 1 to 81 wherein R² is H.

Embodiment No. 84 is directed to a compound selected from the group consisting of the final compounds of Examples 1-107, 109-110, 112-156, 158-163, 166-170, 172-179, 183-192, 194, and 196 to 228.

Embodiment No. 85 is directed to a compound selected from the group consisting of the final compounds of Examples 1-10, 12-14, 18-65, 67-76, 78-98, 100-102, 104-105, 107, 110, 112-114, 117-128, 130-131, 133, 134-136, 138, 140, 141, 144, 147, 148, 170, 183, 188, 189, 196-223, and 225-228.

Embodiment No. 86 is directed to a compound selected from the group consisting of the final compounds of Examples 1-10, 14, 18-65, 67, 72-75, 78-80, 82-84, 86-95, 97, 101, 102, 104, 107, 110, 117-131, 133-136, 138, 140, 141, 144, 170, 183, 188, 189, 196-223, 225, and 228.

Embodiment No. 87 is directed to a compound selected from the group consisting of the final compounds of Examples 1, 19, 20, 23, 25, 119, 196, 197, and 212.

Embodiment No. 88 is directed to a compound selected from the group consisting of the final compounds of Examples 1, 19, 20, 23, 25, 119, 196, 197, and 212.

Embodiment No. 89 is directed to the compound of Example 25.

Embodiment No. 90 is directed to a compound of any one of Embodiment Nos. 1 to 89 in pure and isolated form.

Embodiment No. 91 is directed to a pharmaceutical composition comprising an effective amount of at least one compound (e.g., 1, 2 or 3, or 1 or 2, or 1, and usually 1) of formula 1.0, preferably a compound of formula 1.0C, and a pharmaceutically acceptable carrier.

Embodiment No. 92 is directed to a pharmaceutical composition comprising an effective amount of a compound of formula 1.0, preferably a compound of formula 1.0C, and a pharmaceutically acceptable carrier.

Embodiment No. 93 is directed to a pharmaceutical composition comprising an effective amount of at least one compound (e.g., 1, 2 or 3, or 1 or 2, or 1, and usually 1) of formula 1.1, and a pharmaceutically acceptable carrier.

Embodiment No. 94 is directed to a pharmaceutical composition comprising an effective amount of a compound of formula 1.1 and a pharmaceutically acceptable carrier.

Embodiment No. 95 is directed to a pharmaceutical composition comprising an effective amount of at least one compound (e.g., 1, 2 or 3, or 1 or 2, or 1, and usually 1) of formula 1.2, and a pharmaceutically acceptable carrier.

Embodiment No. 96 is directed to a pharmaceutical composition comprising an effective amount of a compound of formula 1.2 and a pharmaceutically acceptable carrier.

Embodiment No. 97 is directed to a pharmaceutical composition comprising an effective amount of at least one compound (e.g., 1, 2 or 3, or 1 or 2, or 1, and usually 1) of formula 1.3, and a pharmaceutically acceptable carrier.

Embodiment No. 98 is directed to a pharmaceutical composition comprising an effective amount of a compound of formula 1.3 and a pharmaceutically acceptable carrier.

Embodiment No. 99 is directed to a pharmaceutical composition comprising an effective amount of at least one compound (e.g., 1, 2 or 3, or 1 or 2, or 1, and usually 1) of any one of Embodiment Nos. 1 to 89 and a pharmaceutically acceptable carrier.

Embodiment No. 100 is directed to a pharmaceutical composition comprising an effective amount of a compound of any one of Embodiment Nos. 1 to 89 and a pharmaceutically acceptable carrier.

Embodiment No. 101 is directed to a pharmaceutical composition comprising an effective amount of at least one compound (e.g., 1, 2 or 3, or 1 or 2, or 1, and usually 1) of Embodiment No. 90 and a pharmaceutically acceptable carrier.

Embodiment No. 102 is directed to a pharmaceutical composition comprising an effective amount of one compound of Embodiment No. 90 and a pharmaceutically acceptable carrier.

Embodiment No. 103 is directed to a pharmaceutical composition of any one of Embodiment Nos. 91 to 102 further comprising an effective amount of at least one (e.g., 1, 2 or 3, or 1 or 2, or 1, and usually 1) other active pharmaceutically active ingredient.

Embodiment No. 104 is directed to a pharmaceutical composition of any one of Embodiment Nos. 91 to 102 further comprising an effective amount of another (i.e., one other) pharmaceutically active ingredient.

Embodiment No. 105 is directed to a pharmaceutical composition of any one of Embodiment Nos. 91 to 102 further comprising an effective amount of at least one (e.g., 1, 2 or 3, or 1 or 2, or 1, and usually 1) chemotherapeutic agent.

Embodiment No. 106 is directed to a pharmaceutical composition of any one of Embodiment Nos. 91 to 102 further comprising an effective amount of a chemotherapeutic agent.

Embodiment No. 107 is directed to a method of treating cancer in a patient in need of such treatment, said method comprising administering to said patient an effective amount of at least one (1, 2 or 3, or 1 or 2, or 1, and usually 1) compound of formula 1.0 (preferably formula 1.0C).

Embodiment No. 108 is directed to a method of treating cancer in a patient in need of such treatment, said method comprising administering to said patient an effective amount of one compound of formula 1.0 (preferably formula 1.0C).

Embodiment No. 109 is directed to a method of treating cancer in a patient in need of such treatment, said method comprising administering to said patient an effective amount of at least one (1, 2 or 3, or 1 or 2, or 1, and usually 1) compound of formula 1.1.

Embodiment No. 110 is directed to a method of treating cancer in a patient in need of such treatment, said method comprising administering to said patient an effective amount of one compound of formula 1.1.

Embodiment No. 111 is directed to a method of treating cancer in a patient in need of such treatment, said method comprising administering to said patient an effective amount of at least one (1, 2 or 3, or 1 or 2, or 1, and usually 1) compound of formula 1.2.

Embodiment No. 112 is directed to a method of treating cancer in a patient in need of such treatment, said method comprising administering to said patient an effective amount of one compound of formula 1.2.

Embodiment No. 113 is directed to a method of treating cancer in a patient in need of such treatment, said method comprising administering to said patient an effective amount of at least one (1, 2 or 3, or 1 or 2, or 1, and usually 1) compound of formula 1.3.

Embodiment No. 114 is directed to a method of treating cancer in a patient in need of such treatment, said method comprising administering to said patient an effective amount of one compound of formula 1.3.

Embodiment No. 115 is directed to a method of treating cancer in a patient in need of such treatment, said method comprising administering to said patient an effective amount of at least one (1, 2 or 3, or 1 or 2, or 1, and usually 1) compound of any one of Embodiment Nos. 1 to 85.

Embodiment No. 116 is directed to a method of treating cancer in a patient in need of such treatment, said method comprising administering to said patient an effective amount of a compound of any one of Embodiment Nos. 1 to 90.

Embodiment No. 117 is directed to a method of treating cancer in any one of Embodiment Nos. 107 to 116 further comprising the administration of an effective amount of at least one (1, 2 or 3, or 1 or 2, or 1, and usually 1) chemotherapeutic agent.

Embodiment No. 118 is directed to a method of treating cancer in any one of Embodiment Nos. 107 to 116 further comprising the administration of an effective amount of a chemotherapeutic agent.

Embodiment No. 119 is directed to a method of treating cancer in a patient in need of such treatment comprising administering to said patient an effective amount of a pharmaceutical composition of any one of Embodiment Nos. 91 to 106.

Embodiment No. 120 is directed to a method of treating cancer in a patient in need of such treatment comprising administering to said patient an effective amount of a pharmaceutical composition of any one of Embodiment Nos. 91 to 102.

Embodiment No. 121 is directed to a method of treating cancer in a patient in need of such treatment comprising administering to said patient an effective amount of a pharmaceutical composition of any one of Embodiment Nos. 91 to 102, in combination with an effective amount of at least one (1, 2 or 3, or 1 or 2, or 1, and usually 1) chemotherapeutic agent Embodiment No. 122 is directed to a method of treating cancer in a patient in need of such treatment comprising administering to said patient an effective amount of a pharmaceutical composition of any one of Embodiment Nos. 91 to 102, in combination with an effective amount of one chemotherapeutic agent.

Embodiment No. 123 is directed to a method of treating cancer of any one of Embodiment Nos. 117, 118, 121 and 122 wherein the chemotherapeutic agent is selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

Embodiment No. 124 is directed to a method of treating cancer of any one of Embodiment Nos. 117, 118, 121 and 122 wherein the chemotherapeutic agent is selected from the group consisting of: paclitaxel, docetaxel, carboplatin, cisplatin, navelbine, gemcitabine, and Herceptin.

Embodiment No. 125 is directed to a method of treating cancer of any one of Embodiment Nos. 117, 118, 121 and 122 wherein the chemotherapeutic agent is selected from the group consisting of: Cyclophasphamide, 5-Fluorouracil, Temozolomide, Vincristine, Cisplatin, Carboplatin, and Gemcitabine.

Embodiment No. 126 is directed to a method of treating cancer of any one of Embodiment Nos. 117, 118, 121 and 122 wherein the chemotherapeutic agent is selected from the group consisting of: Gemcitabine, Cisplatin and Carboplatin.

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0 (for example, as described in any one of Embodiment Nos. 1 to 90), and therapeutically effective amounts of at least one (e.g., 1, 2 or 3, or 1 or 2, or 2, or 1) chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of $\alpha V\beta 3$ integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0 (for example, as described in any one of Embodiment Nos. 1 to 90), and therapeutically effective amounts of at least two (e.g., 2 or 3, or 2, and usually 2) different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of $\alpha V\beta 3$ integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said method comprising administering to said patient therapeutically effective amounts at least one (e.g., 1, 2 or 3, or 1 or 2, or 1, and usually 1) compound of formula 1.0 (for example, as described in any one of Embodiment Nos. 1 to 90), and an antineoplastic agent selected from the group consisting of: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with this above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic myeloid leukemia (CML)) in a patient in need of such treatment, said method comprising administering to said patient therapeutically effective amounts at least one (e.g., 1, 2 or 3, or 1 or 2, or 1, and usually 1) compound of formula 1.0 (for example, as described in any one of Embodiment Nos. 1 to 90), and: (1) Gleevec and interferon to treat CML; (2) Gleevec and pegylated interferon to treat CML; (3) Gleevec to treat CML; (4) an anti-tumor nucleoside derivative (e.g., Ara-C) to treat AML; or (5) an anti-tumor nucleoside derivative (e.g., Ara-C) in combination with an anthracycline to treat AML.

This invention also provides a method of treating non-Hodgkin's lymphoma in a patient in need of such treatment, said method comprising administering therapeutically effective amounts at least one (e.g., 1, 2 or 3, or 1 or 2, or 1, and usually 1) compound of formula 1.0 (for example, as described in any one of Embodiment Nos. 1 to 90) and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment, said method comprising administering to said patient therapeutically effective amounts of at least one (e.g., 1, 2 or 3, or 1 or 2, or 1, and usually 1) compound of formula 1.0 (for example, as described in any one of Embodiment Nos. 1 to 90) and: (1) a proteosome inhibitor (e.g., PS-341 from Millenium); or (2) Thalidomide (or related imid).

This invention also provides a method of treating cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) at least one (e.g., 1, 2 or 3, or 1 or 2, or 2, or 1) antineoplastic agent selected from the group consisting of: (1) taxanes, (2) platinum coordinator compounds, (3) anti-tumor nucleoside derivatives, (4) topoisomerase inhibitors, and (5) vinca alkaloids.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) carboplatin, and (c) paclitaxel.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) cisplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) carboplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) Carboplatin, and (c) Docetaxel.

This invention also provides a method of treating cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) an antineoplastic agent selected from the group consisting of: (1) EGF inhibitors that are antibodies, (2) EGF inhibitors that are small molecules, (3) VEGF inhibitors that are antibodies, (4) VEGF kinase inhibitors that are small molecules. This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) at least one (e.g., 1, 2 or 3, or 1 or 2, or 2, or 1) antineoplastic agent selected from the group consisting of: (1) taxanes, and (2) platinum coordinator compounds.

This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) at least one (e.g., 1, 2 or 3, or 1 or 2, or 2, or 1) antineoplastic agent selected from the group consisting of: (1) taxanes, (2) platinum coordinator compounds, and (3) anti-tumor nucleoside derivatives (e.g., 5-Fluorouracil). This invention also provides a method of treating CML in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) Gleevec, and (c) interferon (e.g., Intron-A).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) Gleevec; and (c) pegylated interferon (e.g., Peg-Intron, and Pegasys).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90) and (b) Gleevec.

This invention also provides a method of treating CMML in a patient in need of such treatment, said method comprising administering to said patient therapeutically effective amounts of at least one (e.g., 1, 2 or 3, or 1 or 2, or 1, and usually 1) compound of formula 1.0 (for example, as described in any one of Embodiment Nos. 1 to 90).

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) an anti-tumor nucleoside derivative (e.g., Cytarabine (i.e., Ara-C)).

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) an anti-tumor nucleoside derivative (e.g., Cytarabine (i.e., Ara-C)), and (c) an anthracycline.

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) Rituximab (Rituxan).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), (b) Rituximab (Rituxan), and (c) an anti-tumor nucleoside derivative (e.g., Fludarabine (i.e., F-ara-A).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) Genasense (antisense to BCL-2).

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 105), and (b) a proteosome inhibitor (e.g., PS-341 (Millenium)).

This invention also provides a method of treating multiple myeloma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) Thalidomide or related imid.

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 90), and (b) Thalidomide.

This invention is also directed to the methods of treating cancer described herein, particularly those described above, wherein in addition to the administration of the compound of formula 1.0 (for example, as described in any one of Embodiment Nos. 1 to 90) and antineoplastic agents, radiation therapy is also administered prior to, during, or after the treatment cycle.

This invention also provides a method for treating cancer (e.g., lung cancer, prostate cancer and myeloid leukemias) in a patient in need of such treatment, said method comprising administering to said patient (1) an effective amount of at least one (e.g., 1, 2 or 3, or 1 or 2, or 1, and usually 1) compound of formula 1.0 (for example, as described in any one of Embodiment Nos. 1 to 90), in combination with (2) at least one (e.g., 1, 2 or 3, or 1 or 2, or 2, or 1) antineoplastic agent, microtubule affecting agent and/or radiation therapy.

This invention also provides a method of treating cancer in a patient in need of such treatment, said method comprising administering to said patient an effective amount of at least one (e.g., 1, 2 or 3, or 1 or 2, or 1, and usually 1) compound of formula 1.0 (for example, as described in any one of Embodiment Nos. 1 to 90) in combination with an effective amount of at least one (e.g., 1, 2 or 3, or 1 or 2, or 1, and usually 1) signal transduction inhibitor.

Thus, in one example (e.g., treating non small cell lung cancer): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Carboplatin is administered once per week in an amount to provide an AUC of about 2 to about 3.

In another example (e.g., treating non small cell lung cancer): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and yet in another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Cisplatin is administered once per week in an amount of about 20 to about 40 mg/m$^2$.

In another example (e.g., treating non small cell lung cancer): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Carboplatin is administered once per week in an amount to provide an AUC of about 2 to about 3.

In another example (e.g., treating non small cell lung cancer): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Cisplatin is administered once per week in an amount of about 20 to about 40 mg/m$^2$.

In another example (e.g., treating non small cell lung cancer): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, (2) Paclitaxel (e.g., Taxol®) is administered once every three weeks in an amount of about 150 to about 250 mg/m$^2$, and in another example about 175 to about 225 mg/m$^2$, and in yet another example 175 mg/m$^2$, and (3) Carboplatin is administered once every three weeks in an amount to provide an AUC of about 5 to about 8, and in another example 6.

In another example of treating non small cell lung cancer: (1) the compound of formula 1.0 (for example, as described in any one of Embodiment Nos. 1 to 90) is administered in an amount of 100 mg administered twice a day, (2) Paclitaxel (e.g., Taxol®) is administered once every three weeks in an amount of 175 mg/m$^2$, and (3) Carboplatin is administered once every three weeks in an amount to provide an AUC of 6.

In another example (e.g., treating non small cell lung cancer): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, (2) Paclitaxel (e.g., Taxol®) is administered once every three weeks in an amount of about 150 to about 250 mg/m$^2$, and in another example about 175 to about 225 mg/m$^2$, and (3) Cisplatin is administered once every three weeks in an amount of about 60 to about 100 mg/m.

In another example (e.g., treating non small cell lung cancer): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 50 to about 100 mg/m$^2$, and (3) Carboplatin is administered once every three weeks in an amount to provide an AUC of about 5 to about 8.

In another example (e.g., treating non small cell lung cancer): (1) the compound of formula 1.0 (for example, as described in any one of Embodiment Nos. 1 to 90) is administered in an amount of about 50 mg to about 200 mg twice a day, in another example about 75 mg to about 125 mg administered twice a day, and in yet another example about 100 mg administered twice a day, (2) Docetaxel (e.g., Taxotere® is administered once every three weeks in an amount of about 50 to about 100 mg/m$^2$, and (3) Cisplatin is administered once every three weeks in an amount of about 60 to about 100 mg/m$^2$.

In another example for treating non small cell lung cancer using the compounds of formula 1.0, Docetaxel and Carboplatin: (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®. is administered once every three weeks in an amount of about 75 mg/m$^2$, and (3) Carboplatin is administered once every three weeks in an amount to provide an AUC of about 6.

In another example of the treatments of non-small cell lung cancer described above the Docetaxel (e.g., Taxotere® and Cisplatin, the Docetaxel (e.g., Taxotere®) and Carboplatin, the Paclitaxel (e.g., Taxol®) and Carboplatin, or the Paclitaxel (e.g., Taxol® and Cisplatin are administered on the same day.

In another example (e.g., CML): (1) the compound of formula 1.0 (for example, as described in any one of Embodiment Nos. 1 to 90) is administered in an amount of about 100 mg to about 200 mg administered twice a day, (2) Gleevec is administered in an amount of about 400 to about 800 mg/day orally, and (3) interferon (Intron-A) is administered in an amount of about 5 to about 20 million IU three times per week.

In another example (e.g., CML): (1) the compound of formula 1.0 (for example, as described in any one of Embodiment Nos. 1 to 90) is administered in an amount of about 100 mg to about 200 mg administered twice a day, (2) Gleevec is administered in an amount of about 400 to about 800 mg/day orally, and (3) pegylated interferon (Peg-Intron or Pegasys) is administered in an amount of about 3 to about 6 micrograms/kg/day.

In another example (e.g., non-Hodgkin's lymphoma): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, and (2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, and (2) the proteosome inhibitor (e.g., PS-341—Millenium) is administered in an amount of about 1.5 mg/m$^2$ twice weekly for two consecutive weeks with a one week rest period.

In another example (e.g., multiple myeloma): (1) the compound of formula 1.0 (for example, as described in any one of Embodiment Nos. 1 to 90) is administered in an amount of about 50 mg to about 200 mg twice a day, and in another example about 75 mg to about 125 mg administered twice a day, and in yet another example about 100 mg administered twice a day, and (2) the Thalidomide (or related imid) is administered orally in an amount of about 200 to about 800 mg/day, with dosing being continuous until relapse or toxicity.

In one embodiment of the methods of treating cancer of this invention, the chemotherapeutic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

In another embodiment of the methods of treating cancer of this invention, the chemotherapeutic agents are selected from the group consisting of: paclitaxel, docetaxel, carboplatin, cisplatin, navelbine, gemcitabine, and Herceptin.

Thus, one embodiment of this invention is directed to a method of treating cancer comprising administering to a patient in need of such treatment therapeutically effective amounts of the compound of formula 1.0 (for example, as described in any one of Embodiment Nos. 1 to 90), a taxane, and a platinum coordination compound.

Another embodiment of this invention is directed to a method of treating cancer comprising administering to a patient in need of such treatment therapeutically effective amounts of the compound of formula 1.0 (for example, as described in any one of Embodiment Nos. 1 to 90), a taxane, and a platinum coordination compound, wherein said compound of formula 1.0 is administered every day, said taxane is administered once per week per cycle, and said platinum coordinator compound is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0 (for example, as described in any one of Embodiment Nos. 1 to 90), a taxane, and a platinum coordination compound, wherein said compound of formula 1.0 is administered every day, said taxane is administered once every three weeks per cycle, and said platinum coordinator compound is administered once every three weeks per cycle. In another embodiment the treatment is for one to three weeks per cycle.

Another embodiment of this invention is directed to a method of treating cancer comprising administering to a patient in need of such treatment therapeutically effective amounts of the compound of formula 1.0 (for example, as described in any one of Embodiment Nos. 1 to 90), paclitaxel, and carboplatin. In another embodiment, said compound of formula 1.0 is administered every day, said paclitaxel is administered once per week per cycle, and said carboplatin is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0 (for example, as described in any one of Embodiment Nos. 1 to 90), paclitaxel, and carboplatin. In another embodiment, said compound of formula 1.0 is administered every day, said paclitaxel is administered once every three weeks per cycle, and said carboplatin is administered once every three weeks per cycle. In another embodiment the treatment is for one to three weeks per cycle.

Another embodiment of this invention is directed to a method for treating non small cell lung cancer in a patient in need of such treatment comprising administering daily a therapeutically effective amount of the compound of formula 1.0 (for example, as described in any one of Embodiment Nos. 1 to 90), administering a therapeutically effective amount of carboplatin once a week per cycle, and administering a therapeutically effective amount of paclitaxel once a week per cycle, wherein the treatment is given for one to four weeks per cycle. In another embodiment said compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering daily a therapeutically effective amount of a compound of formula 1.0 (for example, as described in any one of Embodiment Nos. 1 to 90), administering a therapeutically effective amount of carboplatin once every three weeks per cycle, and administering a therapeutically effective amount of paclitaxel once every three weeks per cycle, wherein the treatment is given for one to three weeks. In another embodiment compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering about 50 to about 200 mg of a compound of formula 1.0 (for example, as described in any one of Embodiment Nos. 1 to 90) twice a day, administering carboplatin once per week per cycle in an amount to provide an AUC of about 2 to about 8 (and in another embodiment about 2 to about 3), and administering once per week per cycle about 60 to about 300 mg/m$^2$ (and in another embodiment about 50 to 100 mg/m$^2$, and in yet another embodiment about 60 to about 80 mg/m$^2$) of paclitaxel, wherein the treatment is given for one to four weeks per cycle. In another embodiment said compound of formula 1.0 is administered in amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

In another embodiment, this invention is directed to a method for treating non small cell lung cancer in a patient in need of such treatment comprising administering about 50 to about 200 mg of a compound of formula 1.0 (for example, as described in any one of Embodiment Nos. 1 to 90) twice a day, administering carboplatin once every three weeks per cycle in an amount to provide an AUC of about 2 to about 8 (in another embodiment about 5 to about 8, and in another embodiment 6), and administering once every three weeks per cycle about 150 to about 250 mg/m$^2$ (and in another embodiment about 175 to about 225 mg/m$^2$, and in another embodiment 175 mg/m$^2$) of paclitaxel, wherein the treatment is given for one to three weeks. In another embodiment said compound of formula 1.0 is administered in an amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

Other embodiments of this invention are directed to methods of treating cancer as described in the above embodiments (i.e., the embodiments directed to treating cancer and to treating non small cell lung cancer with a taxane and platinum coordinator compound) except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In another embodiment of the methods of this invention cisplatin is used in amounts of about 30 to about 100 mg/m$^2$. In the another embodiment of the methods of this invention docetaxel is used in amounts of about 30 to about 100 mg/m$^2$.

In another embodiment this invention is directed to a method of treating cancer comprising administering to a patient in need of such treatment therapeutically effective amounts of a compound of formula 1.0 (for example, as described in any one of Embodiment Nos. 1 to 90), a taxane, and an EGF inhibitor that is an antibody. In another embodiment the taxane used is paclitaxel, and the EGF inhibitor is a HER2 antibody (in one embodiment Herceptin) or Cetuximab, and in another embodiment Herceptin is used. The length of treatment, and the amounts and administration of said compound of formula 1.0 and the taxane are as described in the embodiments above. The EGF inhibitor that is an antibody is administered once a week per cycle, and in another embodiment is administered on the same day as the taxane, and in another embodiment is administered consecutively with the taxane. For example, Herceptin is administered in a loading dose of about 3 to about 5 mg/m$^2$ (in another embodiment about 4 mg/m$^2$), and then is administered in a maintenance dose of about 2 mg/m$^2$ once per week per cycle for the remainder of the treatment cycle (usually the cycle is 1 to 4 weeks). In one embodiment the cancer treated is breast cancer.

In another embodiment this invention is directed to a method of treating cancer comprising administering to a patient in need of such treatment therapeutically effective amounts of: (1) a compound of formula 1.0 (for example, as described in any one of Embodiment Nos. 1 to 90), (2) a taxane, and (3) an antineoplastic agent selected from the group consisting of: (a) an EGF inhibitor that is a small molecule, (b) a VEGF inhibitor that is an antibody, and (c) a VEGF kinase inhibitor that is a small molecule. In another embodiment, the taxane paclitaxel or docetaxel is used. In another embodiment the antineoplastic agent is selected from the group consisting of: tarceva, Iressa, bevacizumab, SU5416, SU6688 and BAY 43-9006. The length of treatment, and the amounts and administration of said compound of formula 1.0 and the taxane are as described in the embodiments above. The VEGF kinase inhibitor that is an antibody is usually given once per week per cycle. The EGF and VEGF inhibitors that are small molecules are usually given daily per cycle. In another embodiment, the VEGF inhibitor that is an antibody is given on the same day as the taxane, and in another embodiment is administered concurrently with the taxane. In another embodiment, when the EGF inhibitor that is a small molecule or the VEGF inhibitor that is a small molecule is administered on the same day as the taxane, the administration is concurrently with the taxane. The EGF or VEGF kinase inhibitor is generally administered in an amount of about 10 to about 500 mg/m$^2$.

In another embodiment this invention is directed to a method of treating cancer comprising administering to a patient in need of such treatment therapeutically effective amounts of a compound of formula 1.0 (for example, as described in any one of Embodiment Nos. 1 to 90), an anti-tumor nucleoside derivative, and a platinum coordination compound.

Another embodiment of this invention is directed to a method of treating cancer comprising administering to a patient in need of such treatment therapeutically effective amounts of a compound of formula 1.0 (for example, as described in any one of Embodiment Nos. 1 to 90), an anti-tumor nucleoside derivative, and a platinum coordination compound, wherein said compound of formula 1.0 is administered every day, said anti-tumor nucleoside derivative is administered once per week per cycle, and said platinum coordinator compound is administered once per week per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 90), an anti-tumor nucleoside derivative, and a platinum coordination compound, wherein said compound of formula 1.0 is administered every day, said an anti-tumor nucleoside derivative is administered once per week per cycle, and said platinum coordinator compound is administered once every three weeks per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 90), gemcitabine, and cisplatin. In another embodiment, said compound of formula 1.0 is administered every day, said gemcitabine is administered once per week per cycle, and said cisplatin is administered once per week per cycle. In one embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 90), gemcitabine, and cisplatin. In another embodiment, said compound of formula 1.0 is administered every day, said gemcitabine is administered once per week per cycle, and said cisplatin is administered once every three weeks per cycle. In another embodiment the treatment is for one to seven weeks.

Another embodiment of this invention is directed to a method of treating cancer comprising administering to a patient in need of such treatment therapeutically effective amounts of a compound of formula 1.0 (for example, as described in any one of Embodiment Nos. 1 to 90), gemcitabine, and carboplatin. In another embodiment said compound of formula 1.0 is administered every day, said gemcitabine is administered once per week per cycle, and said carboplatin is administered once per week per cycle. In another embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 90), gemcitabine, and carboplatin. In another embodiment said compound of formula 1.0 is administered every day, said gemcitabine is administered once per week per cycle, and said carboplatin is administered once every three weeks per cycle. In another embodiment the treatment is for one to seven weeks per cycle.

In the above embodiments using gemcitabine, the compound of formula 1.0 (for example, as described in any one of Embodiment Nos. 1 to 90) and the platinum coordinator compound are administered as described above for the embodiments using taxanes. Gemcitabine is administered in an amount of about 500 to about 1250 mg/m$^2$. In one embodiment the gemcitabine is administered on the same day as the platinum coordinator compound, and in another embodiment consecutively with the platinum coordinator compound, and in another embodiment the gemcitabine is administered after the platinum coordinator compound.

Another embodiment of this invention is directed to a method of treating cancer in a patient in need of such treatment comprising administering to said patient a compound of formula 1.0 (for example, as described in any one of Embodiment Nos. 1 to 90) and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The compound of formula 1.0 is administered in the same manner as described above for the other embodiments of this invention. The small molecule antineoplastic agents are usually administered daily, and the antibody antineoplastic agents are usually administered once per week per cycle. In one embodiment the antineoplastic agents are selected from the group consisting of: Herceptin, Cetuximab, Tarceva, Iressa, bevacizumab, IMC-1C11, SU5416, SU6688 and BAY 43-9006.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of a compound of formula 1.0 (for example, as described in any one of Embodiment Nos. 1 to 90) and antineoplastic agents in the embodiments described above. Radiation is administered according to techniques and protocols well know to those skilled in the art.

Another embodiment of this invention is directed to a pharmaceutical composition comprising at least two different chemotherapeutic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 (for example, as described in any one of Embodiment Nos. 1 to 90)) and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 (for example, as described in any one of Embodiment Nos. 1 to 90) and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

Other embodiments of this invention are directed to the use of a combination of at least one (e.g., one) compound of formula 1.0 (for example, as described in any one of Embodiment Nos. 1 to 90) and drugs for the treatment of breast cancer, i.e., this invention is directed to a combination therapy for the treatment of breast cancer. Those skilled in the art will appreciate that the compounds of formula 1.0 and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormone-dependent breast cancer) in a patient in need of such treatment comprising administering to said patient a therapeutically effective amount of at least one (e.g., one) compound of formula 1.0 (for example, as described in any one of Embodiment Nos. 1 to 90) and a therapeutically effective amount of at least one antihormonal agent selected from the group consisting of: (a) aromatase inhibitors, (b) antiestrogens, and (c) LHRH analogues; and said treatment optionally including the administration of at least one chemotherapeutic agent.

The compound of formula 1.0 is preferably administered orally, and in one embodiment is administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and at least one antihormonal agent selected from the group consisting of: (a) aromatase inhibitors, (b) antiestrogens, and (c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and at least one antihormonal agent selected from the group consisting of: (a) aromatase inhibitors, (b) antiestrogens, and (c) LHRH analogues.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and at least one antihormonal agent selected from the group consisting of: (a) aromatase inhibitors, and (b) antiestrogens.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), at least one antihormonal agent selected from the group consisting of: (a) aromatase inhibitors and (b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and at least one aromatase inhibitor.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide; and administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); and (2) at least one antihormonal agent selected from the group consisting of: (a) aromatase inhibitors that are selected from the group consisting of Anastrozole, Letrozole, Exemestane, Fadrozole and Formestane, and (b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); and (2) at least one aromatase inhibitor selected from the group consisting of Anastrozole, Letrozole, Exemestane, Fadrozole and Formestane.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); (2) at least one aromatase inhibitor that is selected from the group consisting of Anastrozole, Letrozole, Exemestane, Fadrozole and Formestane; and (3) administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); (2) at least one aromatase inhibitor; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); (2) at least one antiestrogen; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); (2) at least one aromatase inhibitor that is selected from the group consisting of Anastrozole, Letrozole, Exemestane, Fadrozole and Formestane; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 90); (2) at least one antiestrogen that is selected from the group consisting of: Tamoxifen, Fulvestrant, Raloxifene, and Acolbifene; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Letrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Formestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Goserelin.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90) and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Anastrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Letrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Exemestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fadrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Formestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Anastrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Letrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Exemestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fadrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Formestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fadrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin and Letrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Goserelin and Formestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide and Letrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 90), Leuprolide and Formestane.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90) and Anastrozole.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90) and Letrozole.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90) and Exemestane.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90) and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90) and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90), Anastrozole, and Fulvestrant.

Another embodiment of this invention is directed to the treatment or prevention of breast cancer in a patient in need of such treatment, said treatment comprising the administration of a therapeutically effective amount of at least one compound of formula I (e.g., one), Letrozole, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90), Exemestane, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90), Anastrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90), Letrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 90), Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment or prevention of Breast Cancer wherein the method is directed to the treatment of breast cancer.

The compound of formula 1.0 (for example, as described in any one of Embodiment Nos. 1 to 90), antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, 57$^{th}$ Edition, 2003, published by Thomas PDR at Montvale, N.J. 07645-1742, the disclosure of which is incorporated herein by reference thereto.

In general, in the embodiments directed to the methods of treating Breast Cancer: (1) the compound of formula 1.0 (for example, as described in any one of Embodiment Nos. 1 to 90) can be administered daily (e.g., once per day, and in one embodiment twice a day), (2) the aromatase inhibitors can be administered in accordance with the known protocol for the aromatase inhibitor used (e.g., once per day), (3) the antiestrogens can be administered in accordance with the known protocol for the antiestrogen used (e.g., from once a day to once a month), (4) the LHRH analogue can be administered in accordance with the known protocol for the LHRH analogue used (e.g., once a month to once every three months), and (5) the chemotherapeutic agent can be administered in accordance with the known protocol for the chemotherapeutic agent used (e.g., from once a day to once a week).

Radiation therapy, if administered in the above treatments for breast cancer, is generally administered according to known protocols before administration of the compound of formula 1.0 (for example, as described in any one of Embodiment Nos. 1 to 90), antihormonal agents and optional chemotherapeutic agents.

Treatment according to the methods of treating breast cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for breast cancer can be changed to a discontinuous treatment schedule if, in the judgment of the skilled clinician, the patient would benefit from a discontinuous treatment schedule with one or more of the administered drugs. For example, the compound of formula 1.0 (for example, as described in any one of Embodiment Nos. 1 to 90) can be given using a discontinuous treatment schedule while the remaining drugs used in the treatment are given as described herein. An example of a discontinuous treatment protocol for the compound of formula 1.0 (for example, as described in any one of Embodiment Nos. 1 to 90) is a repeating cycle of three weeks with the compound of formula 1.0 followed by one week without the compound of formula 1.0.

After a complete response is achieved with the breast cancer treatment, maintenance therapy with the compound of formula 1.0 (for example, as described in any one of Embodiment Nos. 1 to 90) can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of breast cancer described above, the compound of formula 1.0 (for example, as described in any one of Embodiment Nos. 1 to 90) is administered continuously in a total daily dose of about 100 mg to about 600 mg. Usually this amount is administered in divided doses, and in one embodiment this amount is administered twice a day. In one embodiment the compound of formula 1.0 (for example, as described in any one of Embodiment Nos. 1 to 90) is dosed twice a day in an amount of about 50 mg to about 300 mg per dose. In another embodiment the compound of formula 1.0 (for example, as described in any one of Embodiment Nos. 1 to 90) is dosed twice a day in an amount of about 100 mg to about 200 mg per dose. Examples include the compound of formula 1.0 (for example, as described in any one of Embodiment Nos. 1 to 90) being dosed twice a day at 100 mg per dose. Examples also include the compound of formula 1.0 (for example, as described in any one of Embodiment Nos. 1 to 90) being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose.

Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 50 mg to about 300 mg per dose wherein each dose is administered twice a day, and (2) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 100 to 200 mg per dose, wherein each dose is administered twice a day, and (2) Anastrozole in an amount of about 1.0 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 50 mg to about 300 mg per dose wherein each dose is administered twice a day, and (2) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 100 to 200 mg per dose, wherein each dose is administered twice a day, and (2) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 50 mg to about 300 mg per dose wherein each dose is administered twice a day, and (2) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 100 to 200 mg per dose, wherein each dose is administered twice a day, and (2) Exemestane in an amount of about 25 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 50 mg to about 300 mg per dose wherein each dose is administered twice a day, and (2) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) orally in an amount of about 100 to 200 mg per dose, wherein each dose is administered twice a day, and (2) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 50 mg to about 300 mg per dose wherein each dose is administered twice a day, and (2) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 100 to 200 mg per dose, wherein each dose is administered twice a day, and (2) Tamoxifen p.o. in an amount of about 20 mg per dose wherein each dose is given once a day.

In other embodiments of the invention breast cancer is treated in a patient in need of such treatment wherein said treatment comprises the administration of the compound of formula 1.0 (for example, as described in any one of Embodiment Nos. 1 to 90), one of the aromatase inhibitors (e.g., Anastrozole, Letrozole, or Exemestane, and in one embodiment Anastrozole), and one of the antiestrogens (e.g., Fulvestrant or Tamoxifen), wherein the compound of formula 1.0, aromatase inhibitor and antiestrogen are administered in the dosages described above.

Thus, for example in another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o in an amount of about 100 to 200 mg per dose, wherein each dose is administered twice a day, (2) Anastrozole p.o. in an amount of about 1.0 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 50 mg to about 300 mg per dose wherein each dose is administered twice a day, (2) Letrozole p.o in an amount of about 1.0 to about 10 mg per dose wherein each dose is given once a day, and (3) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 100 to 200 mg per dose, wherein each dose is administered twice a day, (2) Letrozole p.o. in an amount of about 2.5 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 50 mg to about 300 mg per dose wherein each dose is administered twice a day, (2) Exemestane p.o. in an amount of about 10 to about 50 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 100 to 200 mg per dose, wherein each dose is administered twice a day, (2) Exemestane p.o. in an amount of about 25 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 100 to 200 mg per dose, wherein each dose is administered twice a day, (2) Anastrozole p.o. in an amount of about 1.0 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 50 mg to about 300 mg per dose wherein each dose is administered twice a day, (2) Letrozole p.o. in an amount of about 1.0 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 100 to 200 mg per dose, wherein each dose is administered twice a day, (2) Letrozole p.o. in an amount of about 2.5 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 50 mg to about 300 mg per dose wherein each dose is administered twice a day, (2) Exemestane p.o. in an amount of about 10 to about 50 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 90) p.o. in an amount of about 100 to 200 mg per dose, wherein each dose is administered twice a day, (2) Exemestane p.o. in an amount of about 25 mg per dose wherein each dose is given once a day, and (3) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compound of formula 1.0 (for example, as described in any one of Embodiment Nos. 1 to 90) is dosed twice a day in an amount of about 100 mg per dose.

Other embodiments of the treatment of Breast Cancer are directed to the methods of treating Breast Cancer described above wherein the compound of formula 1.0 (for example, as described in any one of Embodiment Nos. 1 to 90) is dosed twice a day in an amount of about 200 mg per dose.

Other embodiments of the treatment of Breast Cancer are directed to the methods of treating Breast Cancer described above wherein a chemotherapeutic agent is administered in addition to the compound of formula 1.0 (for example, as described in any one of Embodiment Nos. 1 to 90) and antihormonal agent (or antihormonal agents). In these embodiments the dosage ranges of the compound of formula 1.0 and antihormonal agents are as those described above in the combination therapies, or those described above for the individual compound of formula I and antihormonal agents, and the dosages of the chemotherapeutic agents are those described above for the individual chemotherapeutic agent. The dosages for the chemotherapeutic agents are well known in the art.

Other embodiments of this invention are directed to pharmaceutical compositions comprising the compound of formula 1.0 (for example, as described in any one of Embodiment Nos. 1 to 90) and at least one antihormonal agent and a pharmaceutically acceptable carrier.

Other embodiments of this invention are directed to pharmaceutical compositions comprising the compound of formula 1.0 (for example, as described in any one of Embodiment Nos. 1 to 90), at least one antihormonal agent, at least one chemotherapeutic agent, and a pharmaceutically acceptable carrier.

Other embodiments of this invention are directed to pharmaceutical compositions comprising the compound of formula 1.0 (for example, as described in any one of Embodiment Nos. 1 to 107), at least one chemotherapeutic agent, and a pharmaceutically acceptable carrier.

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the compound of formula 1.0, a taxane, and a platinum coordination compound, includes within its scope a method of treating cancer comprising administering to a patient in need of such treatment therapeutically effective amounts of a pharmaceutical composition comprising the compound of formula 1.0, a pharmaceutical composition comprising a taxane, and a pharmaceutical composition comprising a platinum coordination compound.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula 1.0 and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgment of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of an chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Compounds of this invention are exemplified in the following examples, which should not be construed as limiting the scope of the disclosure. Alternative mechanistic pathways and analogous structures within the scope of the invention may be apparent to those skilled in the art.

The LCMS conditions are: (1) column: C-18 reverse phase, 5 um, 4.6×50 mm, (2) MS:PE Sciex API-150EX, and (3) HPLC: Shimadzu LC-10 ADvp, 1 ml/min, linear gradient 10% acetonitirle in water to 95% acetonitrile in water, both contain 0.05% TFA Scheme 1
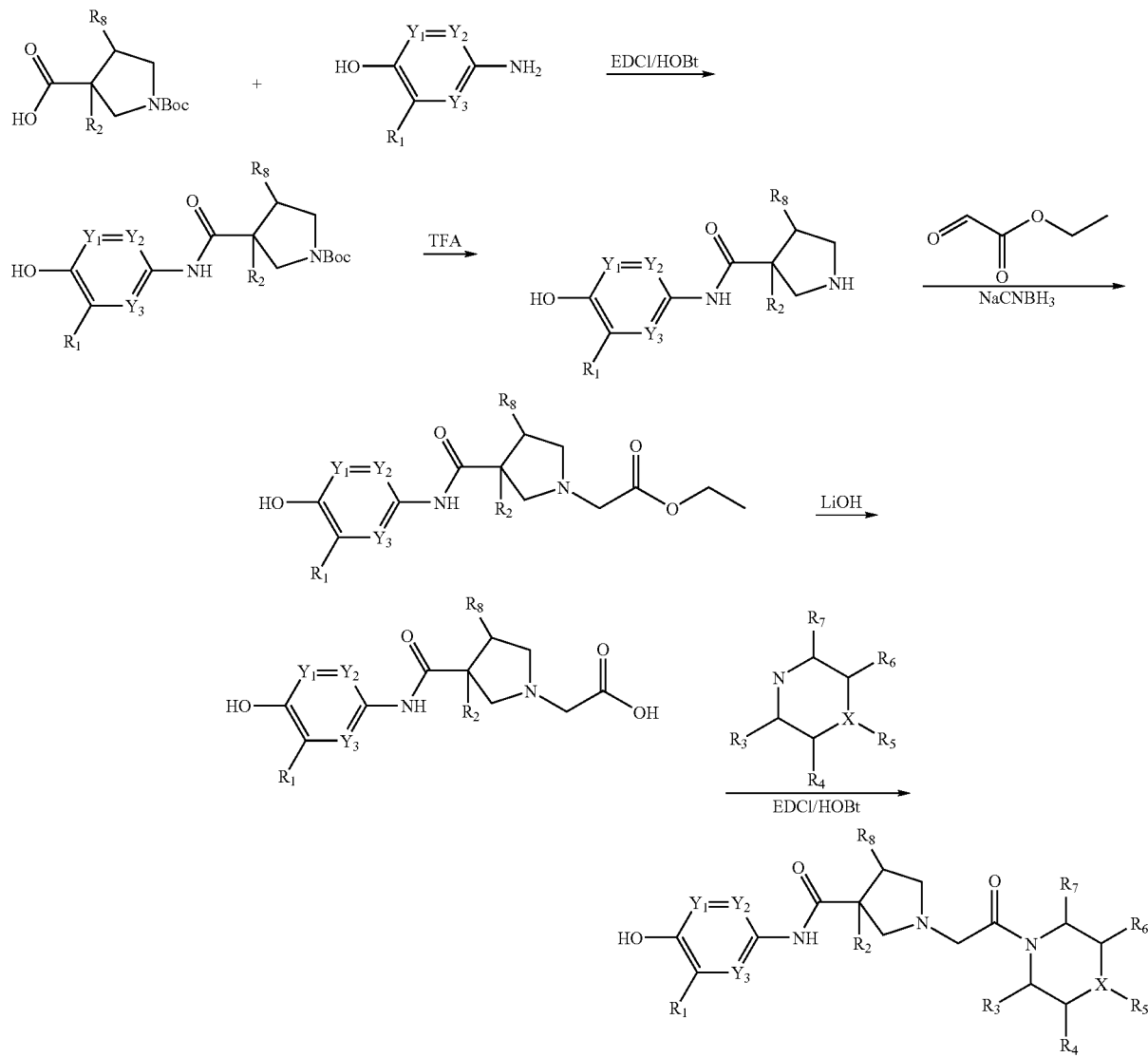
Scheme 2
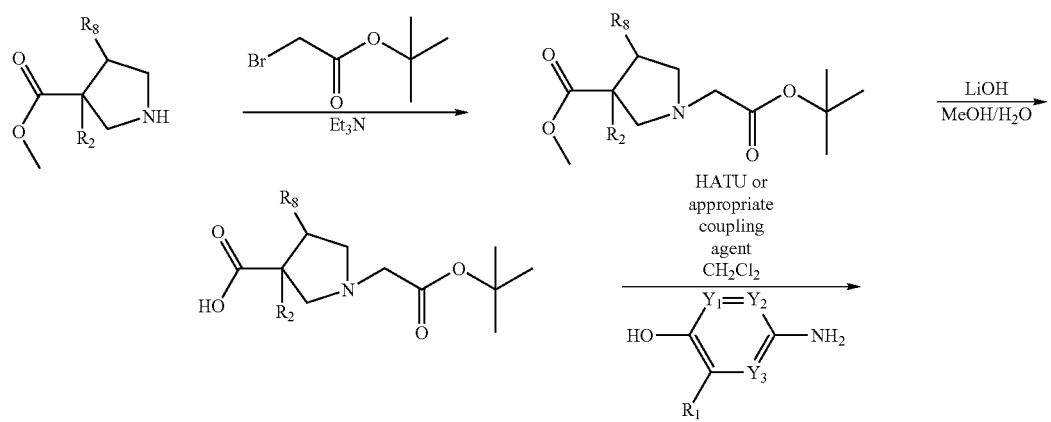

-continued
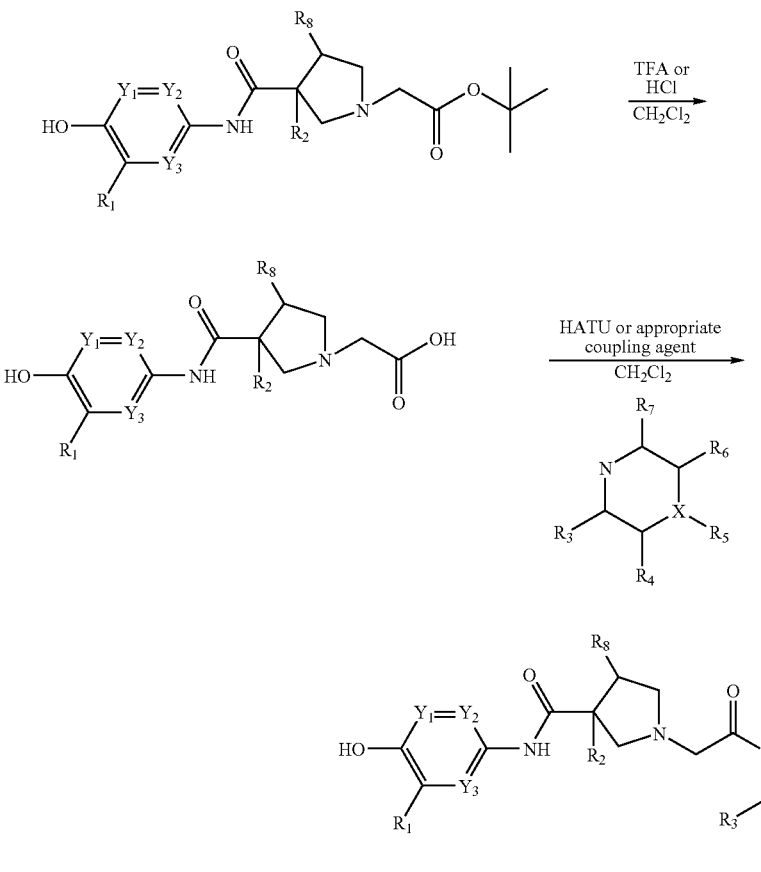
Scheme 3
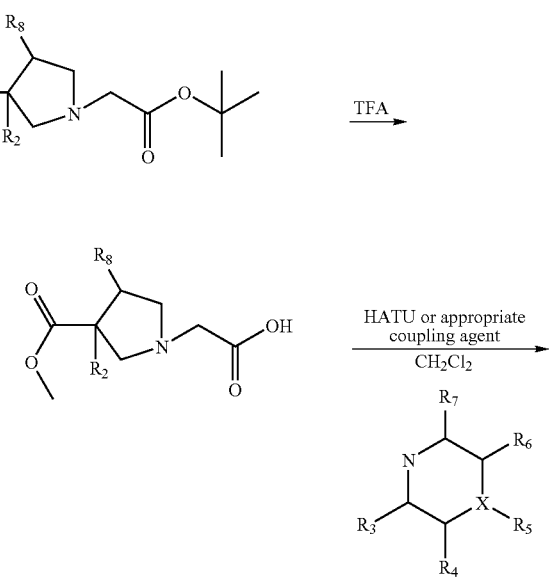

-continued

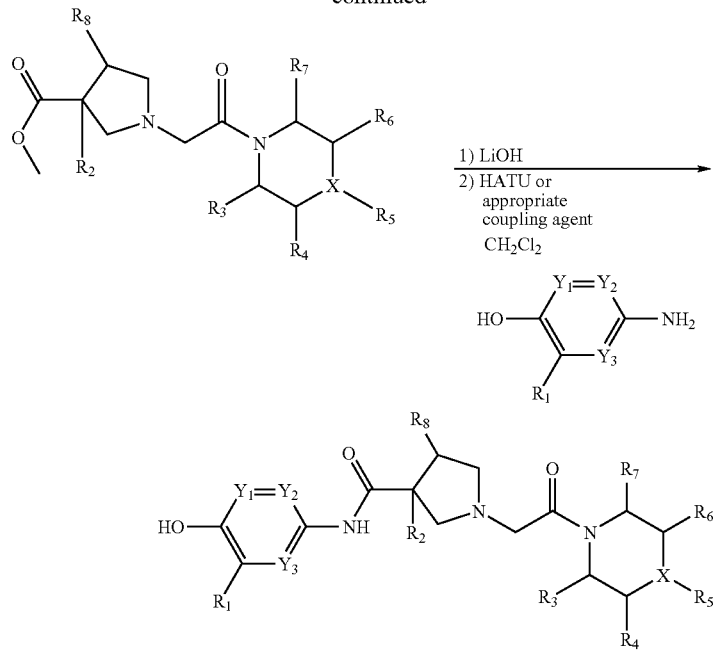

Scheme 4

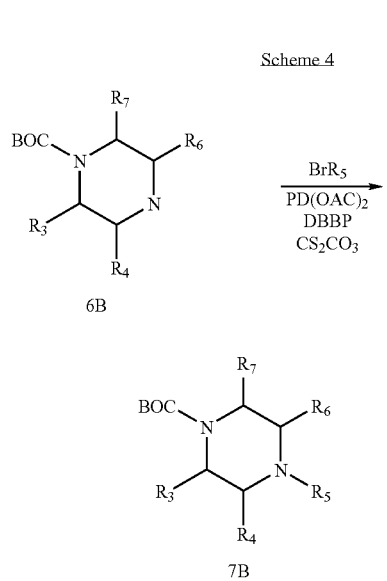

The R[5] substituted piperazine is prepared by Buchwald type coupling of the piperazine 6B with an aryl bromide in the presence of palladium to obtain the piperazine 7B. The BOC group is removed using acidic conditions (e.g., TFA) to give piperazine 7C.

Scheme 5

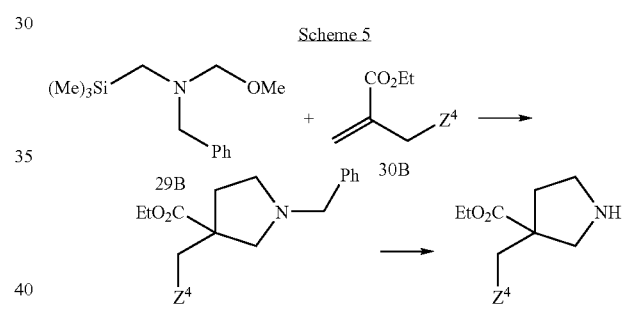

(Bioorganic & Medicinal Chemistry Letters, 8, 15 (1998) pages 1953 to 1958)

The appropriately substituted pyrrolidine 32B can be obtained by reacting 29B with the appropriately substituted compound 30B in the presence of trifluoroacetic acid to obtain 31B. Compound 31B can then be deprotected under hydrogenation conditions (Pd/C, $H_2$) to obtain 32B.

Alternative Process For Scheme 5

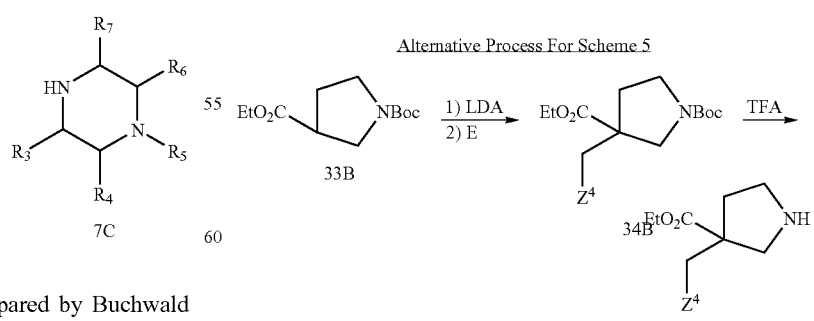

(E = electrophile)

Alternatively, 32B can be obtained by reaction 33B with LDA followed by the addition of a suitable electrophile such as allylbromide, as in example 127, to obtain 34B. Treatment of 34B with trifluoroacetic acid yields 32B.

colboronate 34B to obtain 35B. The ring double bond can then be hydrogenated to obtain 36B followed by removal of the Boc protecting group under trifluoroacetic acid condi-

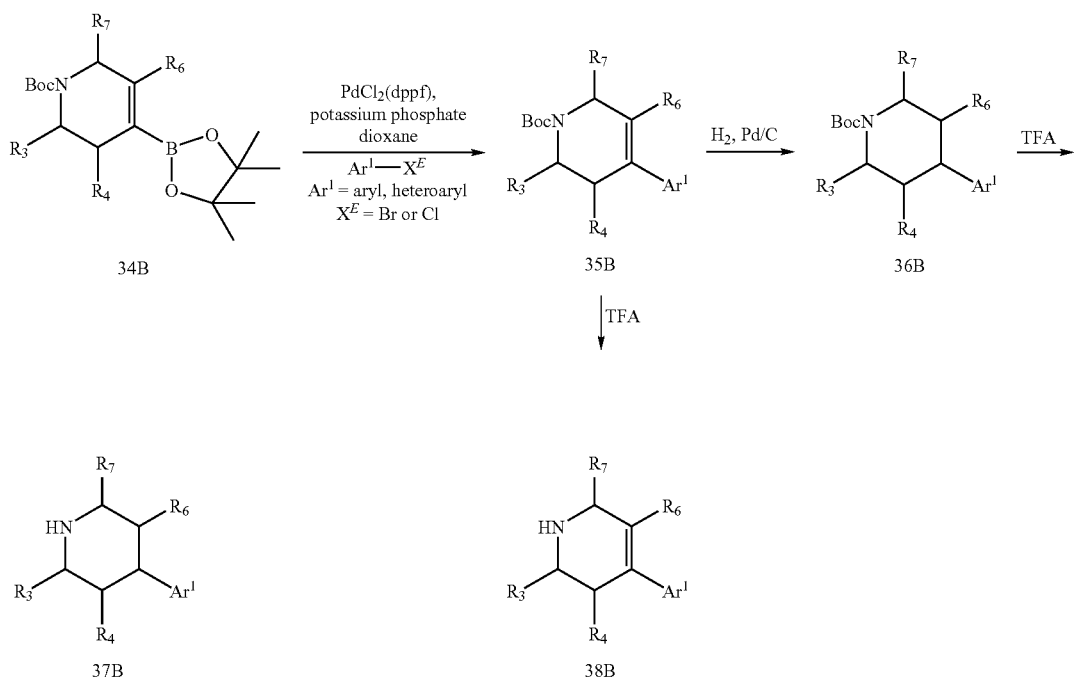

Aryl or heteroaryl substituted piperidines can be prepared by Suzuki coupling of an aryl or heteroaryl halide with the pinitions. Alternatively the double bond can be retained and the Boc group removed to give 38B.

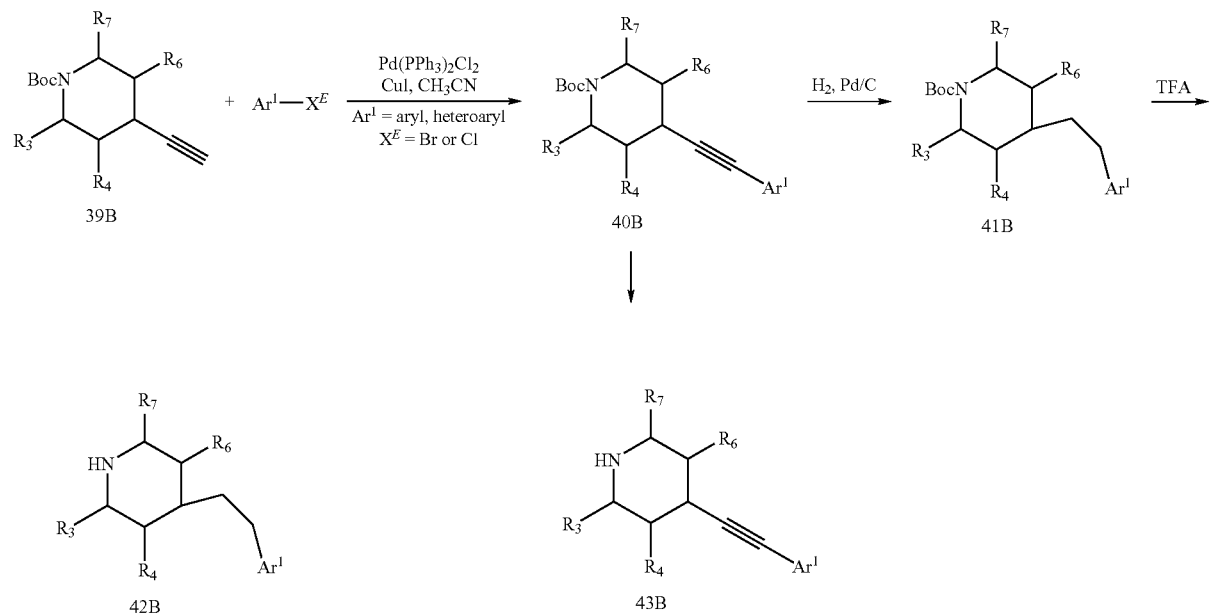

Similarly aryl or heteroaryl substituted piperizines with a 2 carbon spacer can be prepared as shown in Scheme 12 by coupling an aryl or heteroaryl halide with an acetylene derivative 39B that can be prepared according to procedures known in the art to obtain 40B. 40B can then be reduced to 41 B followed by removal of the Boc protecting group under trifluoroacetic acid conditions. Alternatively the Boc protecting group from 40B can be removed under trifluoroacetic acid conditions to give 43B.

PREPARATIVE EXAMPLE 1

Preparation of 4-Amino-2-trifluoromethyl-phenol

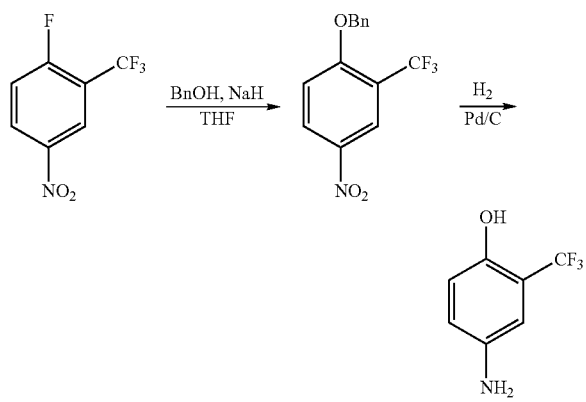

To a solution of 2-fluoro-5-nitrobenzotrifluoride (500 mg, 2.48 mmol) and benzyl alcohol (267 mg, 2.48 mmol) in THF was added sodium hydride (95.1 mg, 2.48 mmol) at 0° C. The reaction was followed by TLC and quenched with saturated ammonium chloride solution after 0.5 h. The mixture was extracted with dichloromethane three times. The combined organic layer was dried over sodium sulfate and concentrated. The residue was triturated with 2.5 mL of hexanes and ethyl acetate (7:1) and a yellow precipitate was collected by filtration to give 1-benzyloxy-4-nitro-2-trifluoromethylbenzene (580 mg, 79%).

To the suspension of 1-benzyloxy-4-nitro-2-trifluoromethylbenzene (575 mg, 1.96 mmol) in methanol was added catalytic amount of 5% palladium on carbon under a hydrogen atmosphere. The mixture was stirred for 4 hrs and filter through celite. The filtrate was concentrated to afford 4-amino-2-trifluoromethylphenol (311 mg, 90%).

PREPARATIVE EXAMPLE 2

Preparation of 4-Amino-2-Bromo-phenol

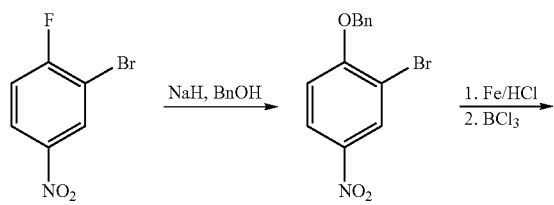

-continued

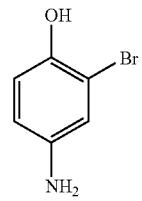

1-Benzyloxy-2-bromo-4-nitrobenzene was prepared from 2-bromo-1-fluoro-4-nitrobenzene using the same procedure described in Scheme 1.

To a solution of 1-benzyloxy-2-bromo-4-nitrobenzene (50 mg, 0.16 mmol) in ethanol (5 mL) and H₂O (0.5 mL) was added iron (134 mg, 2.43 mmol) and one drop of concentrated HCl. The mixture was refluxed for 6 hrs and filtrated. The filtrate was diluted with ethyl acetate, washed with saturated sodium bicarbonated solution, dried over sodium sulfate and concentrated to afford crude 4-amino-1-benzyloxy-2-bromobenzene.

To a solution of 4-amino-1-benzyloxy-2-bromobenzene in 2 mL of dichloromethane at −78 C was added boron trichloride (0.4 mL, 1 M in DCM) dropwise. The reaction was quenched with water at 0 C, concentrated and dried under vacuum to afford 4-amino-2-bromo-1-hydroxybenzene (17 mg, 56% two steps)

PREPARATIVE EXAMPLE 3

Preparation of 5-Amino-biphenyl-2-ol

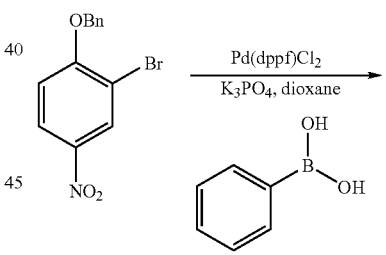

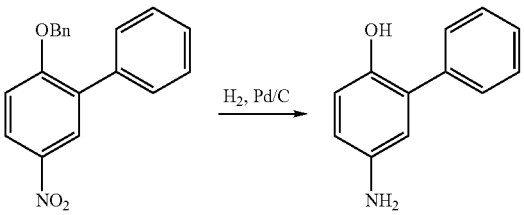

To a mixture of 1-benzyloxy-2-bromo-4-nitrobenzene (100 mg, 0.33 mmol), Pd(dppf)Cl2.DCM (12 mg, 0.016 mmol), phenylboronic acid (48 mg, 0.39 mmol) and potassium phosphate (207 mg, 0.98 mmol) was added dioxane under an argon atmosphere. The mixture was stirred overnight at 80 C and filtered. The filtrate was concentrated and purified by flash chromatography (5:1 hexanes/ethyl acetate) to give 2-benzyloxy-5-nitro-biphenyl (81 mg).

PREPARATIVE EXAMPLE 4

Preparation of 5-Amino-aryl(heteroaryl)-phenols

To a solution of 2-benzyloxy-5-nitro-biphenyl (81 mg, 0.27 mmol)) in 5 mL of methanol was added catalytic amount of 5% palladium on carbon under H2. The mixture was stirred under H2 for 3 hrs and filtered through celite. The filtrate was concentrated to give 2-hydroxy-5-nitro-biphenyl (38 mg).

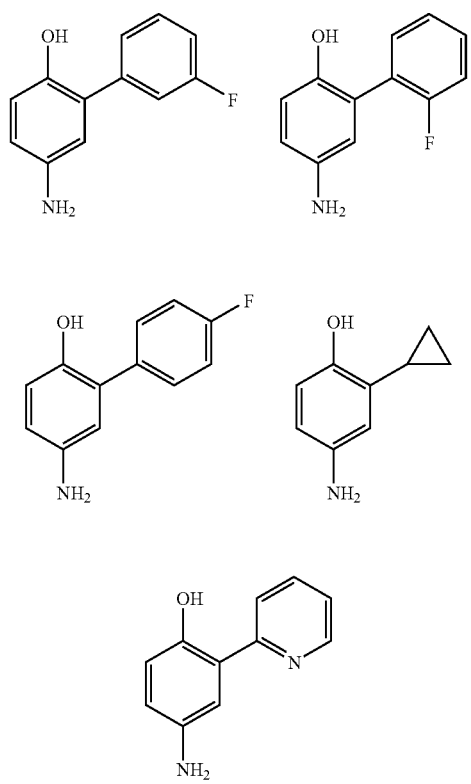

The building blocks were prepared via same methods described in the above scheme to prepare 5-Amino-biphenyl-2-ol

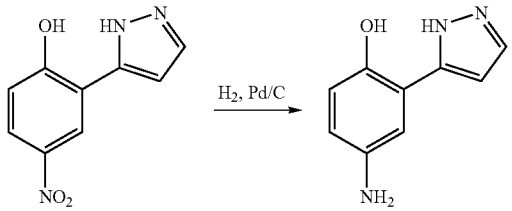

4-Amino-2-(2H-pyrazol-3-yl)phenol was prepared by the procedure described in the preparation of 5-Amino-aryl(heteroaryl)-phenols

PREPARATIVE EXAMPLE 5

Preparation of 4-Amino-2-isopropyl-phenol

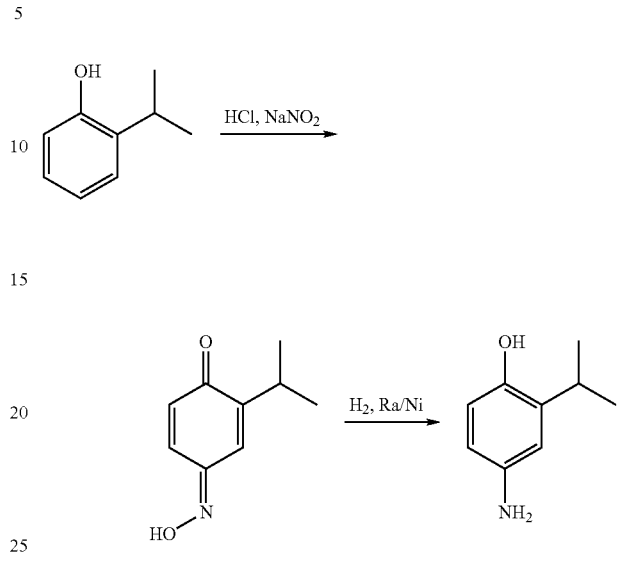

To a solution of 2-isopropylphenol (2.7 g, 0.02 mol) in 15 mL of 95% ethanol and 15 mL of concentrated hydrochloric acid at −5 C was added sodium nitrite (2.1 g, 0.03 mmol) portionwise. The resulting mixture was stirred at 0 C for 5 hr, poured in 125 mL of cold water and filtered. The brown solid washed with water, taken up in concentrated sodium carbonate solution and filtered. The filtrate was acidified with concentrated hydrochloric acid to pH ca. 2. The oil separated soon solidified and the solid was collected by filtration and washed with water to 2-isopropyl-[1,4]benzoquinone 4-oxime (1.2 g, 41%)

To a solution of 2-isopropyl-[1,4]benzoquinone 4-oxime (1.1 g, 6.7 mmol) in methanol was added catalytic amount of Ra/Ni complex. The reaction was stirred under 50 psi H2 atmosphere for 5 hrs and filtered through celite. The filtrate was concentrated to give 4-amino-2-isopropyl-phenol (762 mg, 76%)

PREPARATIVE EXAMPLE 6

Preparation of 4-amino-2-t-butylphenol 4-amino-2-t-butylphenol was prepared by the procedure described in the preparation of 4-Amino-2-isopropyl-phenol substituting 2-tert. butylphenol for 2-isopropylphenol.

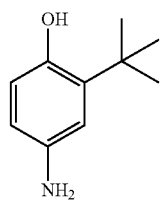

PREPARATIVE EXAMPLE 7

Preparation of 4-(4-Bromo-phenyl)-piperazine-1-carboxylic acid tert-butyl ester

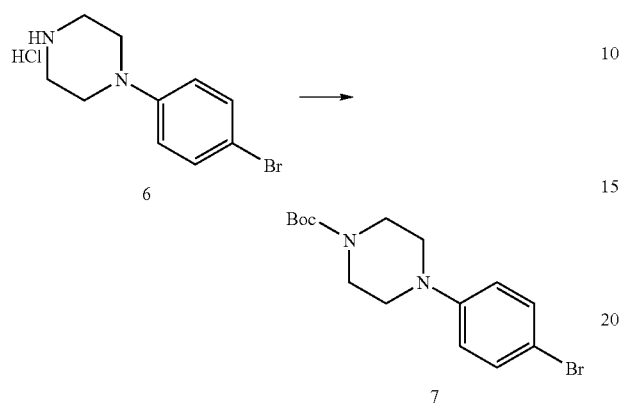

1-(4-Bromo-phenyl)-piperazine hydrochloride (9 gm, 38 mmol) was dissolved in 250 ml of dichloromethane and 9 ml of triethylamine added. Di-tert.butyldicarbonate (8.34 gm, 39 mmol) was added and the reaction mixture stirred for 1 hr. The reaction mixture washed with a solution of saturated sodium bicarbonate (100 ml), the organic layer separated, dried over magnesium sulfate and evaporated to obtain 10.19 gm of crystalline product.

PREPARATIVE EXAMPLE 8

Preparation of 4-(4-boronic acid-phenyl)-piperazine-1-carboxylic acid tert-butyl ester

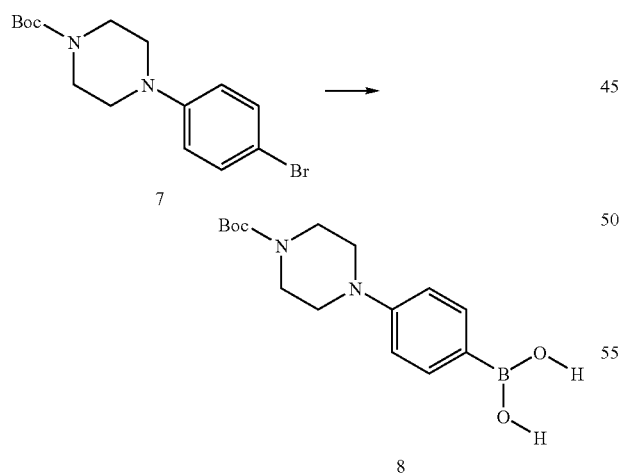

4-(4-Bromo-phenyl)-piperazine-1-carboxylic acid tert-butyl ester (10.19 gm, 30 mmol) was dissolved in 26 ml of tetrahydrofuran. The mixture was cooled to −78 C under a dry nitrogen atmosphere. A 2.5 N solution nButyl lithium in hexanes (26 ml, 65 mmol) was added dropwise and stirred for 30 min. Triisopropylborate (14.68 ml, 63.6 mmol) was added over 10 min. and the reaction mixture let warm to ambient temperature gradually. The reaction mixture was stirred for 18 hrs. A saturated solution of Ammonium chloride (75 ml) was added and the reaction mixture stirred for 5 min. 85% o-Phosphoric acid (7.27 gm) was added and the reaction mixture stirred for 1 hr. The reaction mixture was extracted with ethylacetate three times, dried over magnesium sulfate, filtered and evaporated. The crude product was chromatographed on a silica column to obtain 5.74 gm of title product.

PREPARATIVE EXAMPLE 9

Preparation of 4-(4-Pyrimidin-2-yl-phenyl)-piperazine-1-carboxylic acid tert-butyl ester

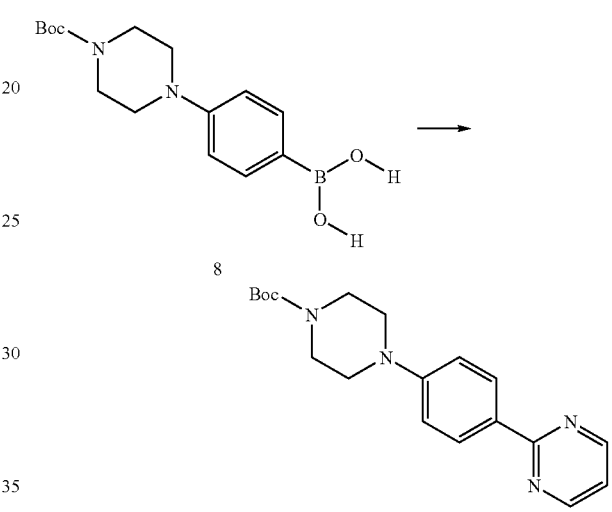

4-(4-boronic acid-phenyl)-piperazine-1-carboxylic acid tert-butyl ester (5.93 gm, 19.3 mmol) was dissolved in 50 ml of a 50% mixture of N,N-dimethylformamide/water. K2CO3 (16 gm) was added and the mixture de-gassed and purged with nitrogen. Pd (dppf)$_2$Cl2 (1.57 gm) and 2-chloropyrimidine (2.72 gm) was added and the reaction mixture stirred at 80 C. After 8 hours the product was extracted into ethylacetate, dried over magnesium sulfate, filtered and evaporated. The crude product was chromatographed on silica gel to obtain 5.03 gm (76.6%) of title product.

PREPARATIVE EXAMPLE 10

Preparation of 2-(4-piperazin-1-yl-phenyl)-pyrimidine

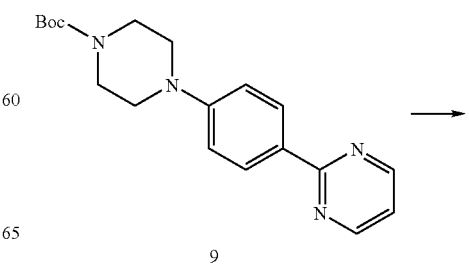

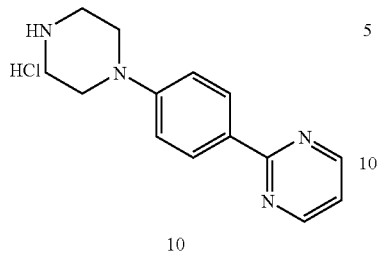
4-(4-Pyrimidin-2-yl-phenyl)-piperazine-1-carboxylic acid tert-butyl ester 5.03 gm was dissolved in 25 ml dichloromethane and 10 ml of 4N HCl dioxane added. After stirring for 2 hrs, the mixture was then evaporated to obtain the title product.
In a similar manner the following piperazine derivatives were prepared:
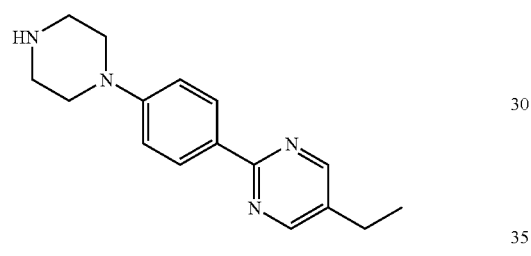
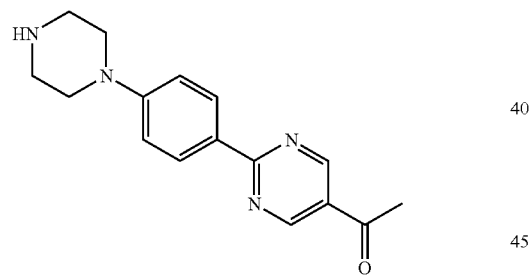
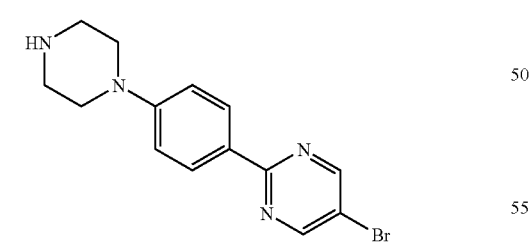
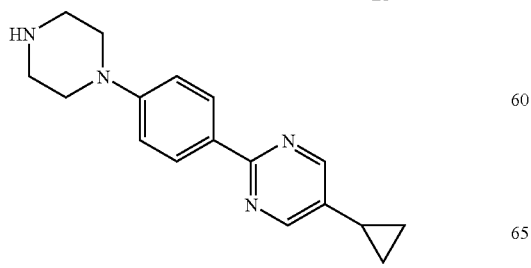
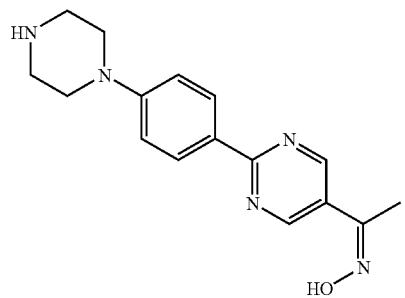
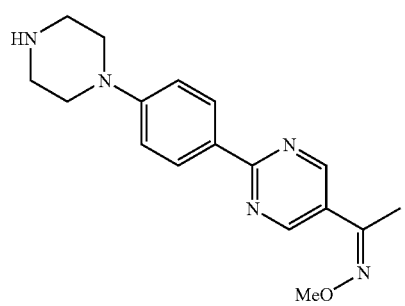
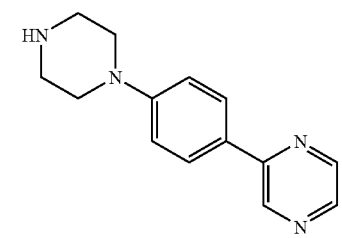
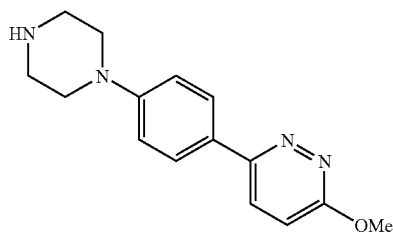
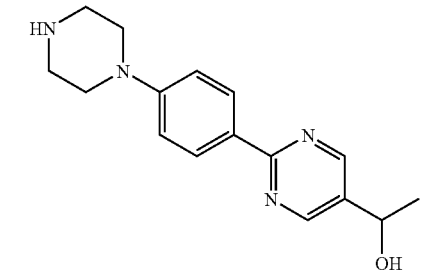
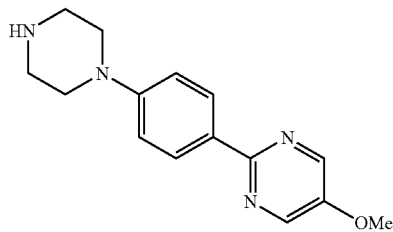

PREPARATIVE EXAMPLE 11

Preparation of
4-(3-Bromo-phenyl)-piperazine-1-carboxylic acid
tert-butyl ester

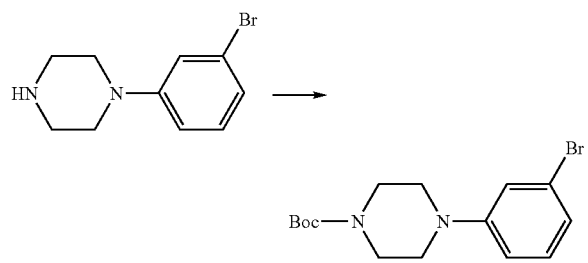

To a solution of 4-(3-bromo-phenyl)-piperidine (2.8 g, 12 mmol), triethylamine (2.4 g, 24 mmol) and DMAP (150 mg, 1.2 mmol) in acetonitrile (15 ml) was added di-tert-butyl dicarbonate. The resulted reaction mixture was stirred at RT for 3 hours. Then water (20 mL) was added and the formed slurry was stirred for 30 min. The formed product was collected by filtration and washed with water. After dry in air, 3.8 g product was obtained (95% yield).

PREPARATIVE EXAMPLE 12

Preparation of
1-(3-Thiophen-2-yl-phenyl)-piperazine

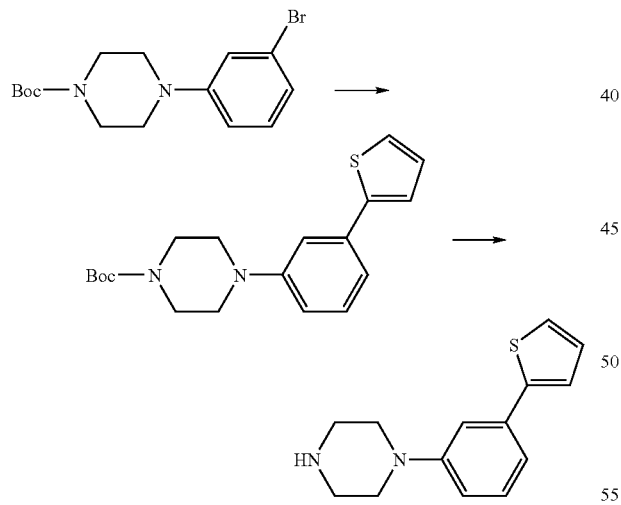

A mixture containing 2-Thiopheneboronic acid (56 mg, 0.44 mmol), 4-(3-Bromo-phenyl)-piperazine-1-carboxylic acid tert-butyl ester (100 mg, 0.29 mmol), Pd (dppf)$_2$Cl$_2$ (12 mg, 0.015 mmol) and K$_2$PO$_4$ (184 mg) in dioxane was degassed with Ar and the reaction mixture stirred at 80 C. After 8 hours the product was filter through celite and the solvent was evaporated.

To the crude product obtained in the previous step, was added 90% TFA (1 mL) and the reaction mixture was stirred at ambient temperature for 1 hour. The excess TFA was removed under vacuum and the residue was purified using prep-HPLC to give desired product (45 mg, 62% yield for two steps) as TFA salt.

Through this method, the following analogues were prepared:

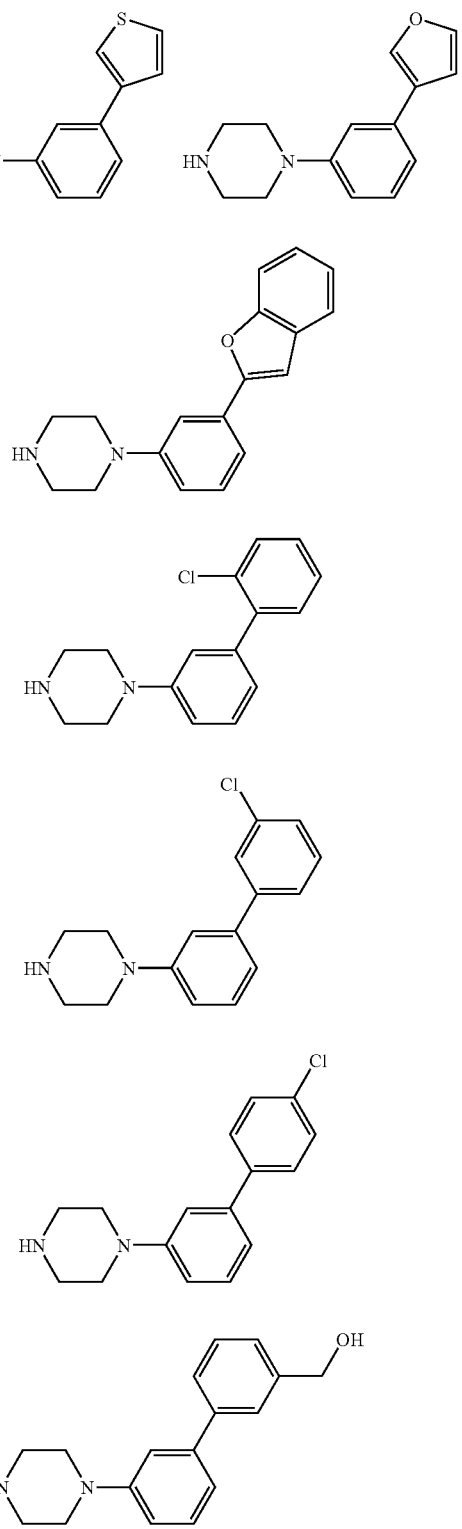

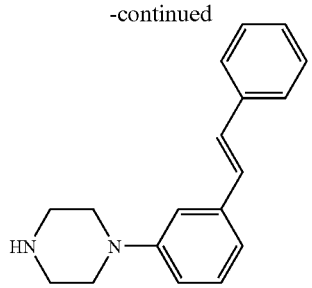

PREPARATIVE EXAMPLE 13

Preparation of 3-piperazin-1-yl-benzoic acid methyl ester

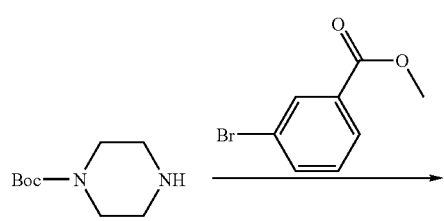

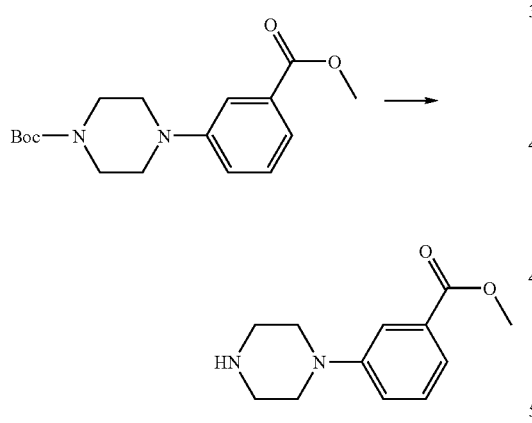

To a mixture containing piperazine-1-carboxylic acid tert-butyl ester (400 mg, 2.16 mmol), 3-bromo-benzoic acid methyl ester (547 mg, 2.56 mmol), Pd(AcO) (32 mg, 0.14 mmol), 2-(di-t-butylphosphino)biphenyl (80 mg, 0.28 mmol) and sodium t-butoxide (400 mg, 4 mmol) in toluene (20 mL) was degassed with Ar. The reaction mixture was heated at 50 C for overnight. At the end of reaction, ethyl acetate was added and the mixture was filter through celite. After removal of solvent, TFA was added to the residue. The reaction mixture was stirred at ambient temperature for 1 hour. The excess TFA was removed under vacuum and the residue was purified using prep-HPLC to give desired product (250 mg, 37% yield for two steps) as TFA salt.

Through this method, the following analogues were prepared:

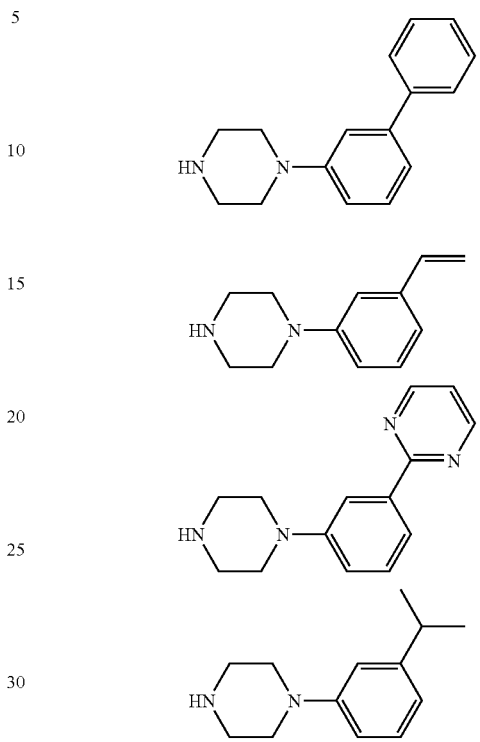

PREPARATIVE EXAMPLE 14

Preparation of 1-(4-Furan-2-yl-phenyl)-piperazine

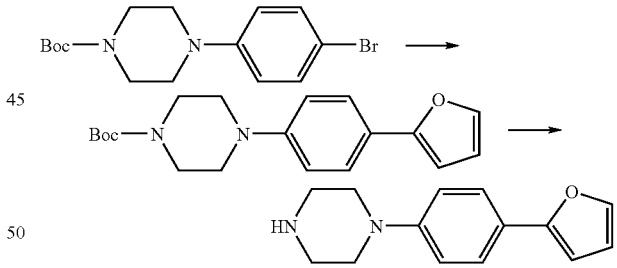

A mixture containing 2-furanboronic acid (49 mg, 0.44 mmol), 4-(4-Bromo-phenyl)-piperazine-1-carboxylic acid tert-butyl ester (100 mg, 0.29 mmol), Pd (dppf)$_2$Cl$_2$ (12 mg, 0.015 mmol) and K$_2$PO$_4$ (184 mg) in dioxane was degassed with Ar and the reaction mixture stirred at 80 C. After 8 hours the product was filter through celite and the solvent was evaporated.

To the crude product obtained in the previous step, was added 90% TFA (1 mL) and the reaction mixture was stirred at ambient temperature for 1 hour. The excess TFA was removed under vacuum and the residue was purified using prep-HPLC to give desired product (40 mg, 60% yield for two steps) as TFA salt.

Through this method, the following analogues were prepared:

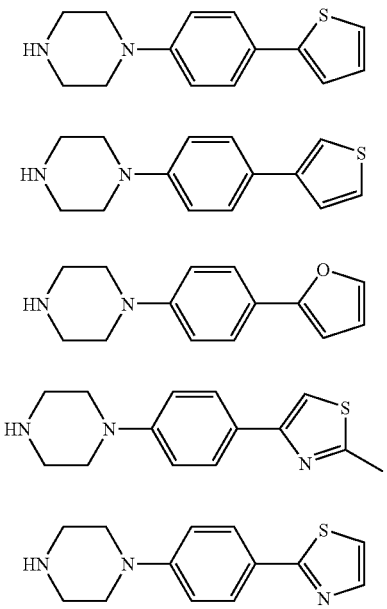

PREPARATIVE EXAMPLE 15

Preparation of 2-(3-Fluoro-phenyl)-2,5-diaza-bicyclo[2.2.1]heptane

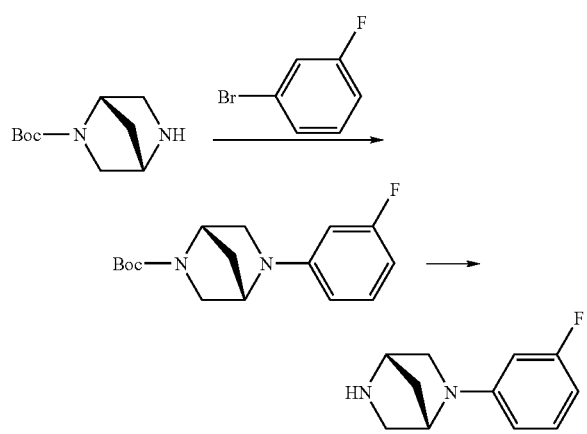

To a mixture containing 2,5-Diaza-bicyclo[2.2.1]heptane-2-carboxylic acid tert-butyl ester (100 mg, 0.5 mmol), 3-fluoro-phenylbromide (103.8 mg, 0.6 mmol), Pd(AcO) (8 mg, 0.03 mmol), 2-(di-t-butylphosphino)biphenyl (20 mg, 0.07 mmol) and sodium t-butoxide (100 mg, 1 mmol) in toluene (3 mL) was degassed with Ar. The reaction mixture was heated at 50 C for overnight. At the end of reaction, ethyl acetate was added and the mixture was filter through celite. After removal of solvent, TFA was added to the residue. The reaction mixture was stirred at ambient temperature for 1 hour. The excess TFA was removed under vacuum and the residue was purified using prep-HPLC to give desired product (60 mg, 41% yield for two steps) as TFA salt.

PREPARATIVE EXAMPLE 16

Preparation of 2-(6-Bromo-pyridin-3-yl)-pyrimidine

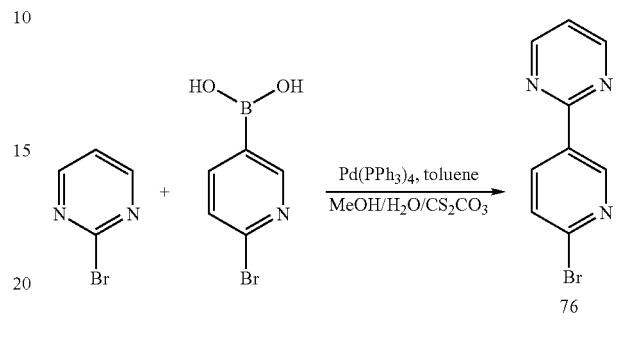

A mixture of 2-bromopyridine (0.43 g, 2.70 mmol), 2-bromopyridine-5-boronic acid (0.55 g, 2.72 mmol), tetrakis(triphenylphosphine)palladium(0) (300 mg, 0.259 mmol), cesium carbonate (1.15 g, 3.03 mmol) was stirred in MeOH/toluene/water (15 ml, 1/1/1) at reflux temperature overnight. The reaction was cooled to room temperature and diluted with EtOAc (200 ml) and water (50 ml). The organic layer was separated, dried over $MgSO_4$, filtered and solvent evaporated yielding a residue which was purified on silica gel eluting with 25% v/vEtOAc/hexanes yielding product 76 as white solid. (0.55 g, 5%) ESMS (MH, 236).

PREPARATIVE EXAMPLE 17

Preparation of 5-(4-Bromo-phenyl)-pyrimidin-2-ylamine

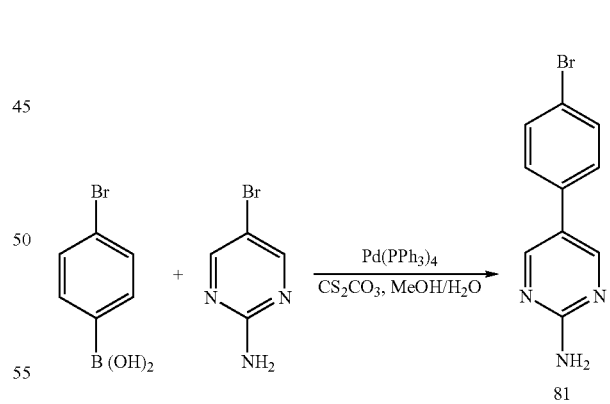

A mixture of 5-bromo-pyrimidin-2-ylamine (0.8 g, 4.59 mmol), 4-bromophenyl boronic acid (1 g, 4.97 mmol), tetrakis(triphenylphosphine)palladium(0) (300 mg, 0.259 mmol), cesium carbonate (1.15 g, 3.03 mmol) was stirred in MeOH/$H_2O$ (20 ml, 1/1) at reflux temperature overnight. The reaction was cooled to room temperature and diluted with EtOAc (200 ml) and water (50 ml). The organic layer was separated, dried over $MgSO_4$, filtered and solvent evaporated yielding a residue which was purified on silica gel eluting with 85% v/vEtOAc/hexanes yielding product 81 as white solid. (0.7 g, 63%). ESMS (MH, 250).

PREPARATIVE EXAMPLE 18

Preparation of 5-(4-piperazin-1-yl-phenyl)-pyrimidin-2-ylamine

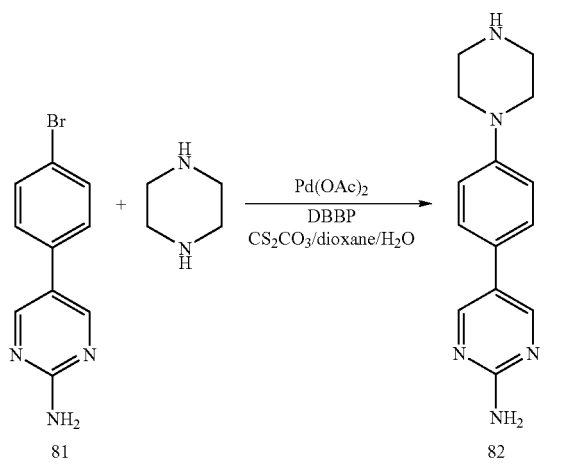

A mixture of 5-(4-bromo-phenyl)-pyrimidin-2-ylamine (100 mg, 0.401 mmol), palladium acetate (20 mg, 0.089 mmol), cesium carbonate (200 mg, 0.62 mmol), piperazine (100 mg, 1.16 mmol) and 2-di-t-butylphosphino)-biphenyl (50 mg, 0.167 mmol) was stirred in dioxane:water (10 ml, v/v 5:1) at reflux temperature for 4 hours. The reaction was cooled, diluted with MeCl$_2$ (100 ml) and H$_2$O (50 ml). The organic layer was separated, dried (MgSO$_4$), filtered and solvent evaporated. The residue was purified by chromatography eluting with 100% EtOAc then with 10% v/v MeOH/EtOAc/NH$_4$OH yielding product 82 as a white solid. (70 mg. 68%) ESMS (MH, 256).

PREPARATIVE EXAMPLE 19

Step 1

Preparation of (S,S)-5-[4-(4,4,5,5-Tetramethyl-[1,3,2]dioxaborolan-2-yl)-phenyl]-2,5-diaza-bicyclo[2.2.1]heptane-2-carboxylic acid tert-butyl ester

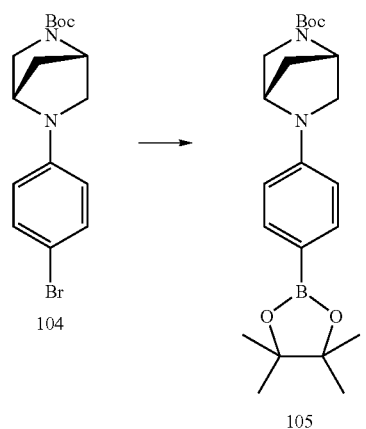

A mixture of (S,S)-5-(4-Bromo-phenyl)-2,5-diaza-bicyclo[2.2.1]heptane-2-carboxylic acid tert-butyl ester (4.0 g, 11.3 mmol), Bis(pinacolato)diboron (4.0 g, 15.7 mmol), KOAc (3.2 g) and Cl$_2$Pd(dppf)CH$_2$Cl$_2$ (800 mg) in 40 mL dioxane was evacuated and recharged with N$_2$ several times. The reaction mixture was then heated to 85° C. overnight. After cooling down to rt, 150 mL ethyl acetate and 30 mL water was added. The mixture was filtered through a pad of Celite and washed with additional ethyl acetate. The separated organic layer was dried (MgSO$_4$) and concentrated. The crude was purified on silica gel column eluting with 30% to 50% ethyl acetate/hexanes to yield the title compound as a white solid (3.3 g). MS (401, MH)

Step 2

Preparation of (S,S)-5-[4-(5-Fluoro-pyrimidin-2-yl)-phenyl]-2,5-diaza-bicyclo[2.2.1]-heptane-2-carboxylic acid tert-butyl ester

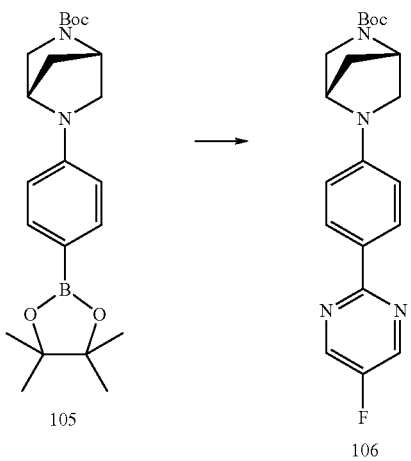

A mixed DMF/H$_2$O (5 mL/5 mL) solution of (S,S)-5-[4-(4,4,5,5-Tetramethyl-[1,3,2]dioxaborolan-2-yl)-phenyl]-2,5-diaza-bicyclo[2.2.1]heptane-2-carboxylic acid tert-butyl ester (800 mg, 2 mmol), 2-chloro-5-fluoro-pyrimidine (340 mg, 2.6 mmol), K$_2$CO$_3$ (552 mg, 4 mmol) and Cl$_2$Pd(dppf)CH$_2$Cl$_2$ (160 mg) was evacuated and recharged with N$_2$ several times. The reaction was heated at 70° C. over 18 hrs. After cooling down to rt, 40 mL ethyl acetate and 10 mL water was added. The mixture was filtered through a pad of Celite and washed with additional ethyl acetate. The separated organic layer was dried (MgSO$_4$) and concentrated. The crude was purified on silica gel column eluting with 50% ethyl acetate/hexanes to yield the title compound (420 mg) as a light yellow solid.

In a similar manner, 106a:

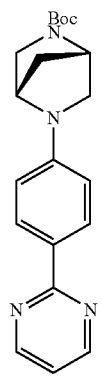

106a was prepared by substituting 2-chloropyrimidine for 2-chloro-5-fluoro-pyrimidine

PREPARATIVE EXAMPLE 20

Preparation of 4-[4-(5-Fluoro-pyrimidin-2-yl)-phenyl]-piperazine-1-carboxylic acid tert-butyl ester

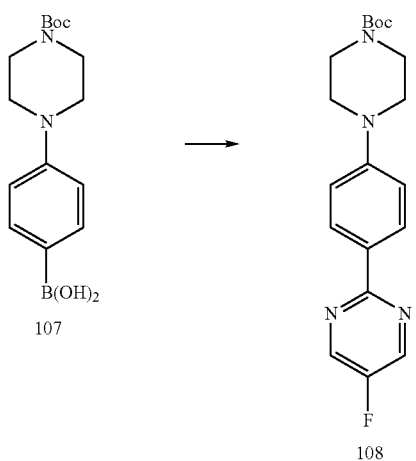

107 → 108

4-[4-(5-Fluoro-pyrimidin-2-yl)-phenyl]-piperazine-1-carboxylic acid tert-butyl ester was prepared similarly as the above substituting (S,S)-5-[4-(4,4,5,5-tetra-methyl[1,3,2]dioxaborolan-2-yl)-phenyl]-2,5-diaza-bicyclo[2.2.1]heptane-2-carboxylic acid tert-butyl ester with 4-[4-(tert-Butoxycarbony)piperazin-1-yl]phenylboronic acid (C. Chen et. al. J. Org. Chem. 2003, 68, 2633).

PREPARATIVE EXAMPLE 21

Preparation of (S,S)-5-(5-Vinyl-pyrimidin-2-yl)-2,5-diaza-bicyclo[2.2.1]heptane-2-carboxylic acid tert-butyl ester

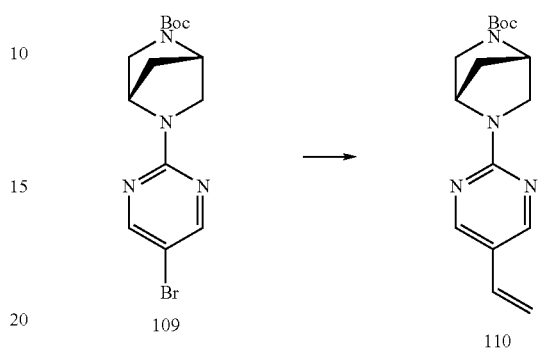

109 → 110

(S,S)-5-(5-Bromo-pyrimidin-2-yl)-2,5-diaza-bicyclo[2.2.1]heptane-2-carboxylic acid tert-butyl ester (177 mg, 0.5 mmol), tributyl vinyl tin (634 mg, 2 mmol) and $Cl_2Pd(dppf)$ $CH_2Cl_2$ (60 mg) was mixed in DMF (3 mL). The mixture was heated at 90° C. over 3 days. The cooled down reaction was participate between ethyl acetate (50 mL) and $H_2O$ (10 mL). The organic layer washed with $H_2O$ (10 mL), brine (10 mL), dried ($MgSO_4$) and filtered. The conc. filtrate was purified on silica gel column eluting with 33% to 50% ethyl acetate/hexanes to yield the title compound as a white solid (54 mg). MS (303, MH).

PREPARATIVE EXAMPLE 21A

Step 1

Preparation of 4-(5-Pyrimidin-2-yl-thiazol-2-yl)-piperazine-1-carboxylic acid tert-butyl ester

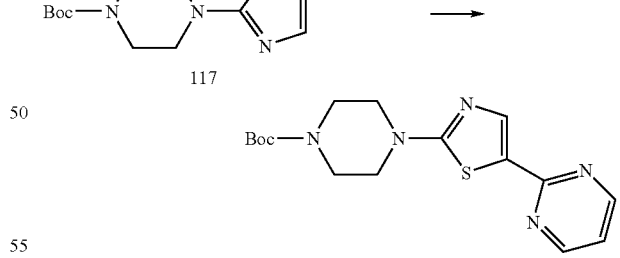

117 → 118

A round bottom flask containing 4-(5-bromo-thiazol-2-yl)-piperazine-1-carboxylic acid tert-butyl ester (100 mg, 0.29 mmol), 2-tributylstannanyl-pyrimidine (130 mg, 0.36 mmol), cesium fluoride (85 mg, 0.56 mmol) and palladium di-tert-butylphosphine was degassed three times with Ar. Dioxane was added and the formed reaction mixture was stirred at 90° C. overnight under Ar. Then the reaction mixture was filter through celite and the solvent was removed under vacuum and crude product was used directly in the next step.

Step 2

Preparation of
2-(2-piperazin-1-yl-thiazol-5-yl)-pyrimidine

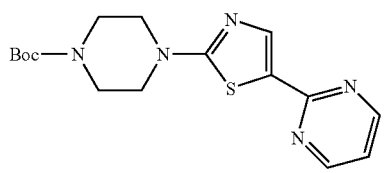

118

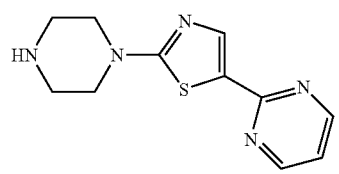

119

To the crude product obtained in the previous step, was added 90% TFA (1 mL) and the reaction mixture was stirred at ambient temperature for 1 hour. The excess TFA was removed under vacuum and the residue was purified using prep-HPLC to give desired product (45 mg, 44% yield for two steps) as TFA salt.

PREPARATIVE EXAMPLE 22

Step 1

Preparation of
4-(4-Bromo-phenyl)-piperidine-1-carboxylic acid tert-butyl ester

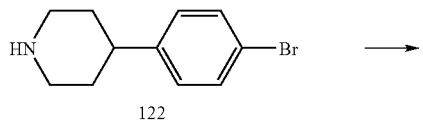

122

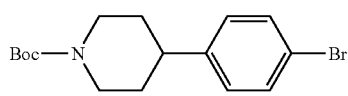

123

To a solution of 4-(4-bromo-phenyl)-piperidine (2.8 g, 12 mmol), triethylamine (2.4 g, 24 mmol) and DMAP (150 mg, 1.2 mmol) in acetonitrile (15 ml) was added di-tert-butyl dicarbonate. The resulted reaction mixture was stirred at RT for 3 hours.

Then water (20 mL) was added and the formed slurry was stirred for 30 min. The formed product was collected by filtration and washed with water. After dry in air, 3.8 g product was obtained (95% yield).

Step 2

Preparation of 4-(4-Pyrimidin-2-yl-phenyl)-piperidine-1-carboxylic acid tert-buyl ester

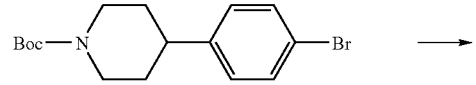

123

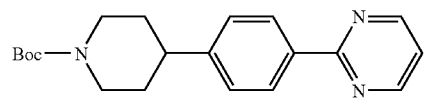

124

A mixture containing 4-(4-bromo-phenyl)-piperidine-1-carboxylic acid tert-butyl ester (100 mg, 0.29 mmol), 2-tributylstannanyl-pyrimidine (130 mg, 0.36 mmol), cesium fluoride (85 mg, 0.56 mmol) and palladium di-tert-butylphosphine was degassed three times with Ar. Dioxane was added and the formed reaction mixture was stirred at 90° C. overnight under Ar. Then the reaction mixture was filter through celite and the solvent was removed under vacuum and crude product was used directly in the next step.

Step 3

Preparation of
2-(4-Piperidin-4-yl-phenyl)-pyrimidine

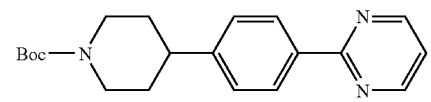

124

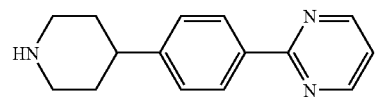

125

To the crude product obtained in the previous step, was added 90% TFA (1 mL) and the reaction mixture was stirred at ambient temperature for 1 hour. The excess TFA was removed under vacuum and the residue was purified using prep-HPLC to give desired product (38 mg, 37% yield for two steps) as TFA salt.

PREPARATIVE EXAMPLE 23

Step 1

Preparation of 4-methyl-benzenesulfonyl azide

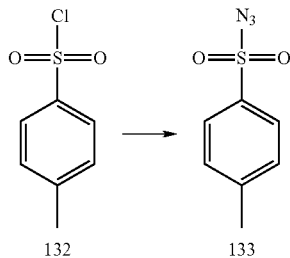

132

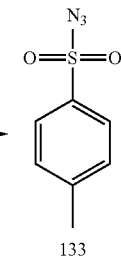

133

To a solution of tosyl chloride (4 g, 21 mmols) in acetone (60 ml) was added at 0-5 C a solution of sodium azide (1.37 g, 21 mmols) and the resulting solution was stirred at that temperature for 2 hours. Acetone was removed and the aqueous mixture was extracted with ether three times. The combined extracts were dried over MgSO₄. Evaporation of solvents provided tosyl azide (4 g, 97%). (*Eur. J. Org. Chem.* 2003, 821-832.)

Step 2

Preparation of (1-diazo-2-oxo-propyl)-phosphonic acid dimethyl ester

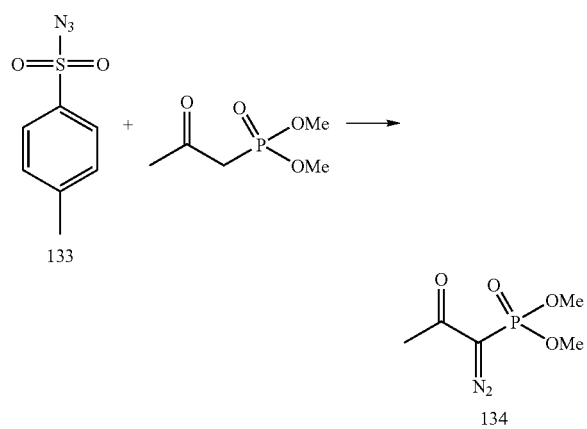

To a suspension of NaH (60% in mineral oil, 0.83 g, 20.8 mmols) in THF (50 ml) was added dropwise at 0 C (2-oxo-propyl)-phosphonic acid dimethyl ester (3.1 g, 18.7 mmols) in THF (50 ml), and the solution was stirred at 0 C for one hour. Tosyl azide (4 g, 20 mmols) was added in one portion, stirred at 0 C for 10 minutes, filtered through Celite and concentrated. The residue was purified by column chromatography on silica gel using ethyl acetate to yield the title compound (2.9 g, 81%) as oil. (*Eur. J. Org. Chem.* 2003, 821-832.)

Step 3

Preparation of 4-ethynyl-piperidine-1-carboxylic acid tert-butyl ester

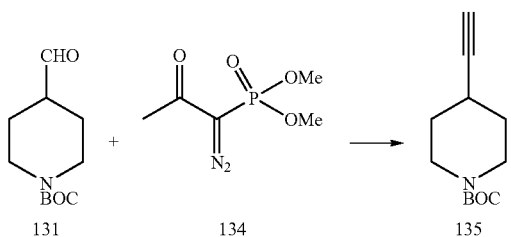

At 0 C., to a stirred mixture of 4-formyl-piperidine-1-carboxylic acid tert-butyl ester (358 mg, 1.68 mmols) and potassium carbonate (464 mg, 3.36 mmols) in methanol (16 ml) was added dropwise a solution of (1-diazo-2-oxo-propyl)-phosphonic acid dimethyl ester (323 mg, 1.68 mmols) in methanol (2 ml). The resulting mixture was stirred at room temperature overnight, filtered and concentrated. The residue was chromatographed on silica gel using a solution of ethyl acetate in hexanes (1:5) to provide the title compound (308 mg, 88%) as colorless crystals. LCMS m/e (154, M–t-Bu+2H). (*J. Am. Chem. Soc.* 2003, 125, 3714.)

Step 4

Preparation of 4-phenylethynyl-piperidine-1-carboxylic acid tert-butyl ester

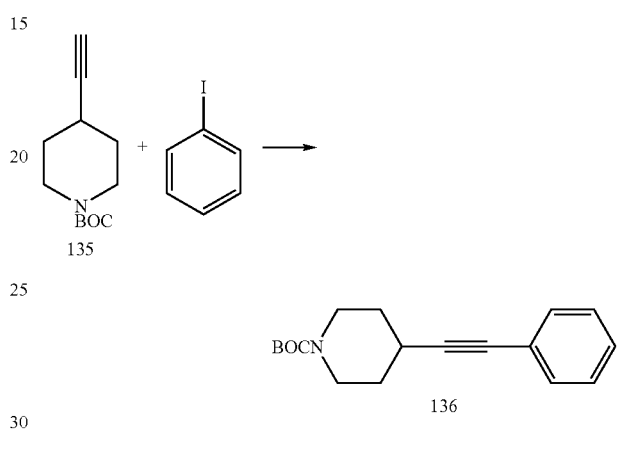

Iodobenzene (135 µl, 1.2 mmols), 4-ethynyl-piperidine-1-carboxylic acid tert-butyl ester (209 mg, 1 mmols) and triethylamine (167 µl, 1.2 mmols) were dissolved in acetonitrile (6 ml). Dichlorobis(triphenylphosphine)palladium(II) (35 mg, 0.05 mmols) and CuI (10 mg, 0.05 mmols) were added, and reaction mixture was stirred at room temperature overnight and continued to stir at 50 C. for two more hours before partitioning between ethyl acetate and water. Organic layer was isolated, washed with 1 N HCl, brine and dried (MgSO₄). Solvents were removed and residue was purified by column chromatography on silica gel using solutions of ethyl acetate in hexanes (1:4; 1:2) to yield the title compound (74 mg). LCMS m/e (230, M–t-Bu+2H)

Step 5

Preparation of 4-phenylethynyl-piperidine

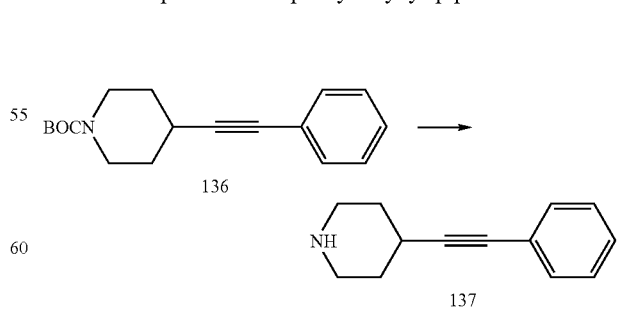

4-Phenylethynyl-piperidine-1-carboxylic acid tert-butyl ester was treated with TFA for 10 minutes and concentrated, lyophilized to provide the title product.

PREPARATIVE EXAMPLE 24

Step 1

Preparation of
4-pyrimidin-2-ylethynyl-piperidine-1-carboxylic
acid tert-butyl ester

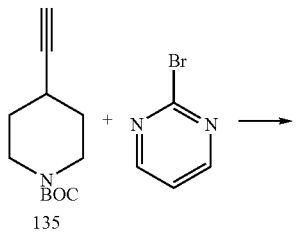

135

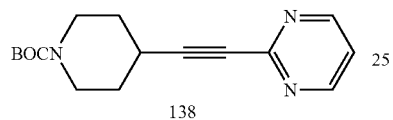

138

To a suspension of 2-bromopyrimidine (175 mg, 1.1 mmols), dichlorobis(triphenylphosphine)palladium(II) (35 mg, 0.05 mmols) and CuI (10 mg, 0.05 mmols) was added a solution of 4-ethynyl-piperidine-1-carboxylic acid tert-butyl ester (209 mg, 1 mmol). The mixture was stirred overnight, filtered through Celite, concentrated. The residue was partitioned between ethyl acetate and water, organic layer was isolated, dried (MgSO$_4$), and concentrated. The residue was chromatographed on silica gel eluting with ethyl acetate in hexanes (1:1) to give un-reacted 2-bromopyrimidine (130 mg), then the title compound (23 mg). LCMS m/e (288, M+H).

Step 2

Preparation of 2-piperidin-4-ylethynyl-pyrimidine

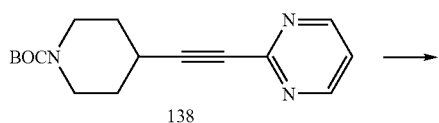

138

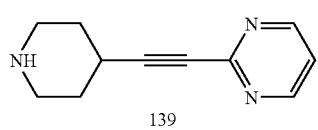

139

4-Pyrimidin-2-ylethynyl-piperidine-1-carboxylic acid tert-butyl ester was treated with TFA for 10 minutes and concentrated, lyophilized to provide the title product.

PREPARATIVE EXAMPLE 25

Preparation of
4-(4-iodophenyl)-piperazine-1-carboxylic acid
tert-butyl ester

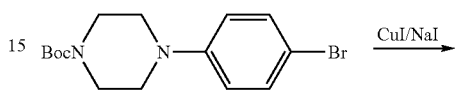

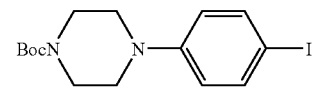

4-(4-Bromo-phenyl)-piperazine-1-carboxylic acid tert-butyl ester (3.2 g, 9.4 mmol), CuI (0.18 g, 0.95 mmol), NaI (2.81 g, 19 mmol) and N,N'-Dimethyl-ethane-1,2-diamine (0.2 mL, 1.88 mmol) were mixed in 10 mL Toluene in a pressure vessel. The vessel was heated at 110° C. for 72 hrs. After cooling, the insoluble was filtered off and washed with toluene several times. The filtrate was concentrated to give a white solid (3.5 g) as the title compound. M+H 388.

PREPARATIVE EXAMPLE 26

Preparation of 4-(4-Imidazol-1-yl-phenyl)-piperazine-1-carboxylic acid tert-butyl ester

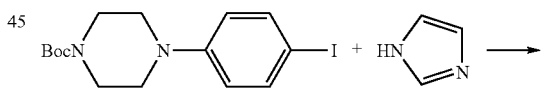

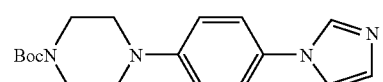

4-(4-Iodo-phenyl)-piperazine-1-carboxylic acid tert-butyl ester (0.194 g, 0.5 mmol), CuI (0.01 g), Cs$_2$CO$_3$ (0.326 g, 1.0 mmol), [1,10]Phenanthroline (0.027 g, 0.15 mmol) and imidazole (0.034 g, 0.5 mmol) were mixed in 3 mL dry DMF in a pressure vessel. The vessel was heated at 110° C. overnight. After cooling to rt, the insoluble was filtered and washed with CH$_2$Cl$_2$. The filtrate was concentrated and the crude was purified with prep TLC (7.5% MeOH-2M NH3/CH$_2$Cl$_2$) to yield the title compound (0.077 g). M+H 328.

PREPARATIVE EXAMPLE 27

Preparation of 4-(4'-Fluoro-biphenyl-4-yl)-piperazine-1-carboxylic acid tert-butyl ester

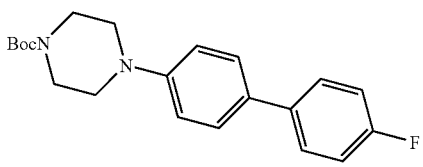

4-(4-Bromo-phenyl)-piperazine-1-carboxylic acid tert-butyl ester (0.171 g, 0.5 mmol), Na$_2$CO$_3$ (0.16 g, 1.5 mmol), 4-fluoro phenyl boronic acid (0.21 g, 1.5 mmol) and (PPh$_3$)$_2$PdCl$_2$ (0.035 g, 0.05 mmol) were mixed in a mixture of THF/H$_2$O (4:1, 7.5 mL) and heated at 70° C. overnight. After cooling to rt, the reaction mixture was partitioned between 50 mL ethyl acetate and 25 mL sat. NaCl solution. The separated organic layer washed with brine (10 mL), dried (MgSO$_4$) and concentrated. The crude was purified with prep TLC (15% ethyl acetate in hexanes) to give a solid (0.071 g). M+H 356.

PREPARATIVE EXAMPLE 28

Preparation of 4-(4-Pyrimidin-2-yl-phenylamino)-piperidine-1-carboxylic acid tert-butyl ester

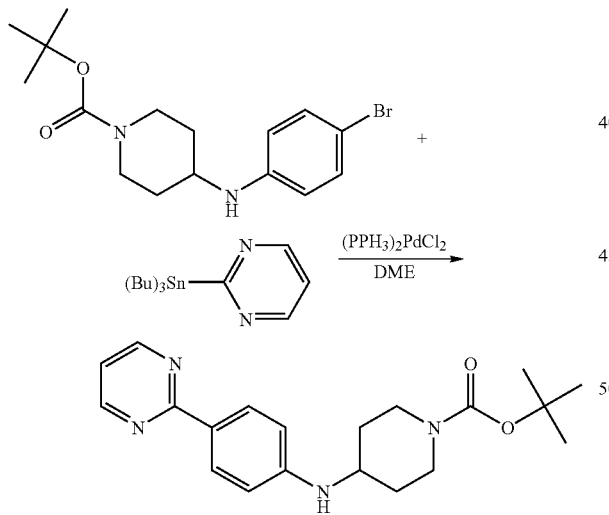

A solution of 4-(4-Bromo-phenylamino)-piperidine-1-carboxylic acid tert-butyl ester (355 mg; 1.002 mmol); 2-tributylstannanyl-pyrimidine (1.1 g; 2.98 mmol); triphenylphosphine palladium dichloride (35 mg, 0.049 mmol) was stirred in DME (4 ml) at 100° C. overnight. Reaction mixture was cooled to room temperature, diluted with EtOAc (100 ml) and water (50 ml). Separated organic layer, washed with brine, dried over Na$_2$SO$_4$, then chromatographed on silica gel eluting with 70% v/v EtOAc/Hexanes yielding product at solid (110 mg; 31%)

Partial $^1$H NMR (400 MHz, CDCl$_3$)σ 8.60 (d, 2H) 8.20(d, 2H) 7.0(m, 1H) 6.60 (d, 2H)

PREPARATIVE EXAMPLE 29

Preparation of piperidin-4-yl-(4-pyrimidin-2-yl-phenyl)-amine hydrochloride

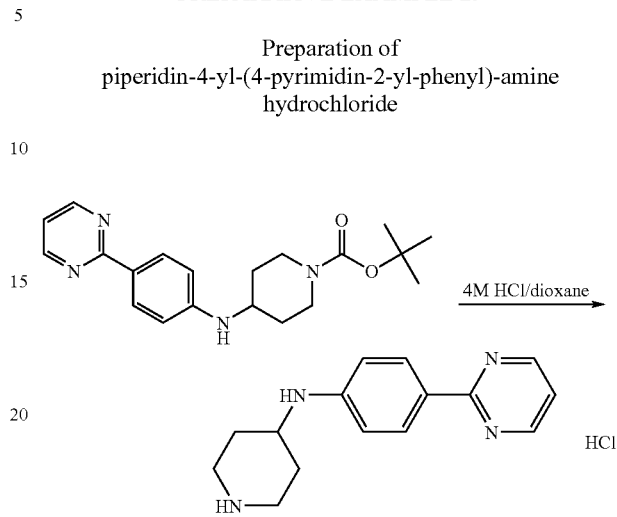

Stirred 4-(4-Pyrimidin-2-yl-phenylamino)-piperidine-1-carboxylic acid tert-butyl ester (110 mg, 0.310 mmol) in 4M HCl (20 ml) at room temperature for 1 hour. Solvent was evaporated yielding desired product piperidin-4-yl-(4-pyrimidin-2-yl-phenyl)-amine, hydrochloride (114 mg).

Partial $^1$H NMR (400 MHz, CDCl$_3$)σ 9.0 (d, 2H) 8.20(d, 2H) 7.60(m, 1H) 6.90 (d, 2H).

PREPARATIVE EXAMPLE 30

Preparation of 4-(5-Nitro-pyridin-2-yl)-piperazine-1-carboxylic acid tert-butyl ester

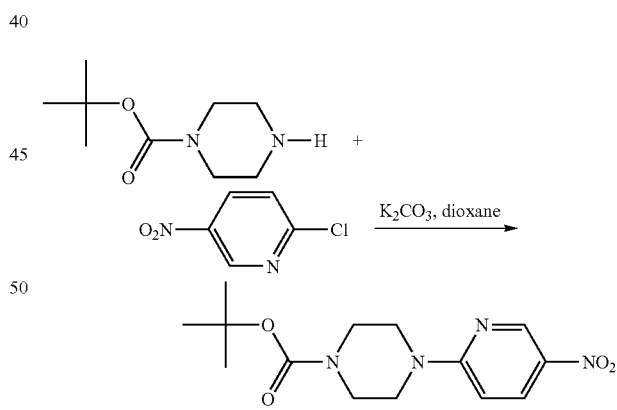

Potassium carbonate (1.7 g, 12.31 mmol) was added to a solution of 2-Chloro-5-nitropyridine (1.33 g, 8.38 mmol) and piperazine-1-carboxylic acid tert-butyl ester (1.57 g, 8.42 mmol) in dioxane (10 ml) then stirred at reflux for 4 hours. The reaction was cooled, and solvent evaporated. The residue was extracted with MeCl$_2$ (100 ml) washed with H$_2$O (50 ml), separated organic layer washed with brine (50 ml) dried over MgSO$_4$, filtered and solvent evaporated yielding a residue which chromatographed on silica gel eluting with 10% v/v EtOAc/hexanes yielding desired product as a pale yellow solid (2.3 g, 88%)

Partial ¹H NMR (400 MHz, CDCl₃)σ 9.0 (s, 1H) 8.20(d, 1H) 6.50 (d, 1H).

PREPARATIVE EXAMPLE 31

Preparation of 1-(5-nitro-pyridin-2-yl)-piperazine

Added 4M HCl/dioxane (15 ml) to a solution of 4-(5-Nitro-pyridin-2-yl)-piperazine-1-carboxylic acid tert-butyl ester (2.3 g, 7.46 mmol) in MeCl₂ (20 ml) at room temperature. Reaction was stirred for 3 hours and solvent was evaporated yielding the product as hydrochloride salt 1-(5-Nitro-pyridin-2-yl)-piperazine hydrochloride 8 (2.2 g)

MS (ESMS, MH, 209)

PREPARATIVE EXAMPLE 32

Preparation of 4-Piperidin-4-yl-benzamide

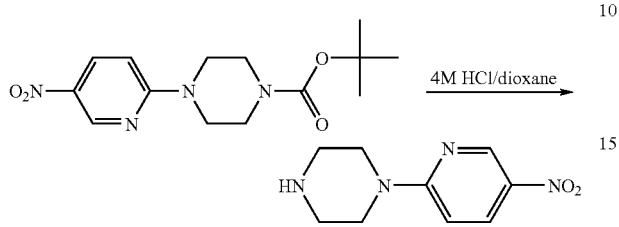

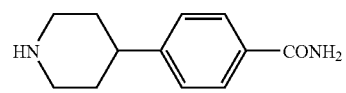

Commercially Available

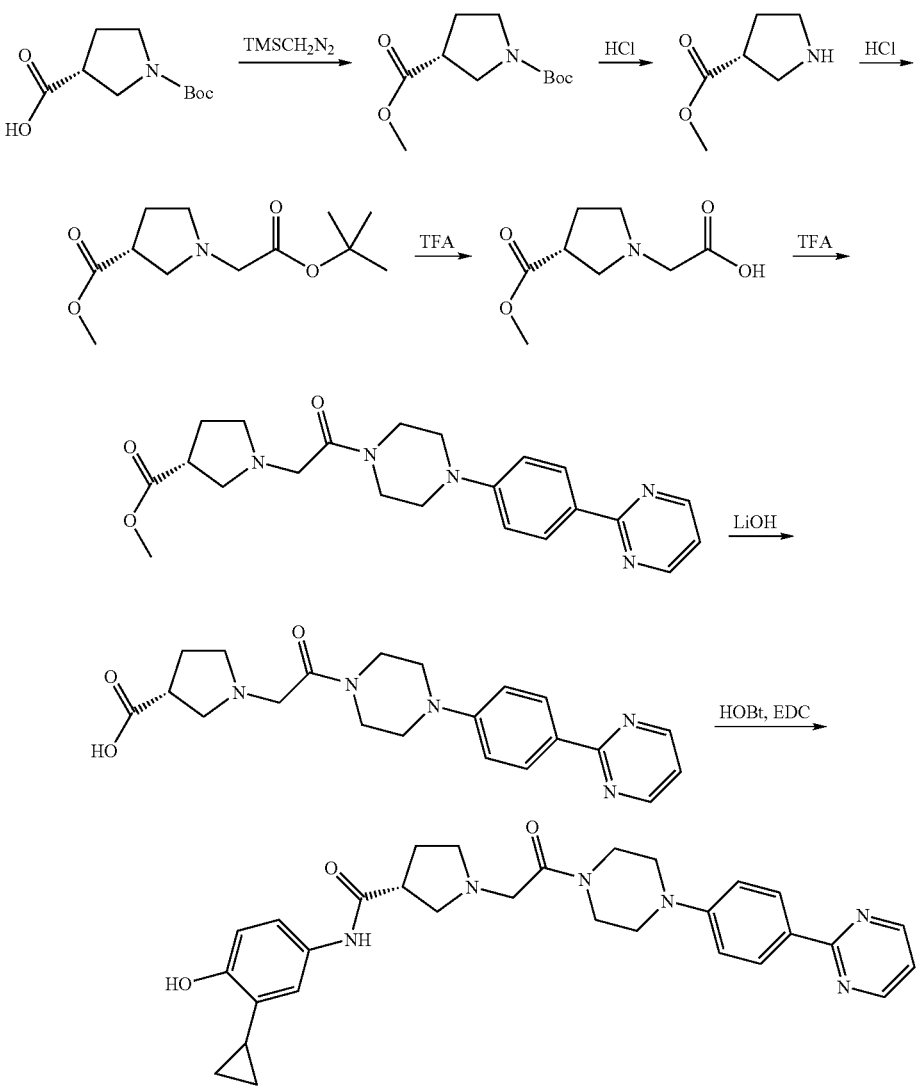

PREPARATIVE EXAMPLE 33

Preparation of Pyrrolidine-3-carboxylic acid methyl ester

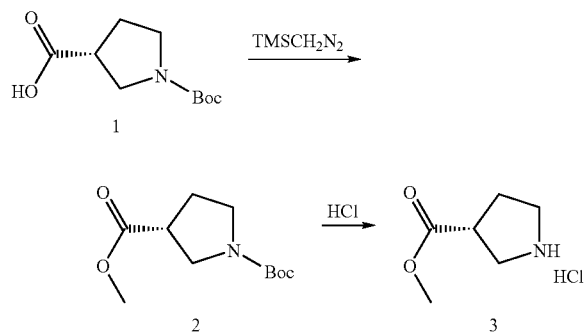

R-pyrrolidine-1,3-dicarboxylic acid 1-tert-butyl ester (2.15 gm, 10 mmol) was dissolved in 12 ml of toluene and 3.5 ml of methanol. Trimethylsilyldiazomethane 2N solution in hexanes (6.56 ml, 13.12 mmol) was added dropwise and the reaction mixture stirred for 2 hours. The mixture was evaporated to obtain 2.1 gm of an oil. The oil was dissolved in dichloromethane (15 ml) and 5 ml of 4N hydrochloric acid in dioxane added. The reaction mixture was stirred for 1 hr and evaporated to give an oil that crystallizes to give 1.68 gm of title product.

PREPARATIVE EXAMPLE 34

Preparation of 1-tert-Butoxycarbonylmethyl-pyrrolidine-3-carboxylic acid methyl ester

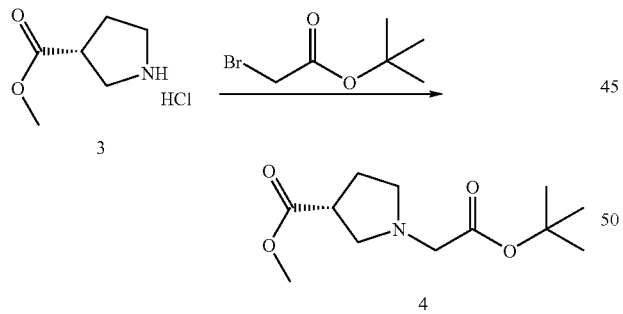

R-pyrrolidine-3-carboxylic acid methyl ester (1.5 gm, 9.1 mmol) was dissolved in N,N-dimethylformamide (45 ml). Diisopropylethylamine (5.7 ml, 31 ml) was added followed by cesium carbonate (4.35 gm, 13.3 mmol). Tert. butylbromoacetate (1.5 ml, 10 mmol) was added dropwise and the reaction mixture stirred for 1 hr. Brine was added to the reaction mixture which was then extracted with ethylacetate three times. The ethylacetate extracts were dried over magnesium sulfate, filtered and evaporated to obtain crude title product. The crude product was chromatographed to obtain 2.15 gm, 97% of title product.

PREPARATIVE EXAMPLE 35

Preparation of 1-Carboxymethyl-pyrrolidine-3-carboxylic acid methyl ester

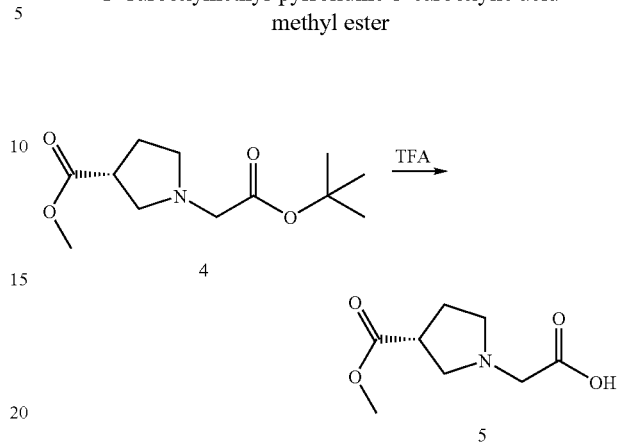

R-1-tert-Butoxycarbonylmethyl-pyrrolidine-3-carboxylic acid methyl ester (2.15 gm, 8.8 mmol) was dissolved in 20 ml of 50% trifluoroacetic acid/dichloromethane and stirred for 2 hrs. The reaction mixture was evaporated to oil and exchanged with hydrochloric acid by dissolving in 20 ml of dichloromethane and adding 10 ml of 1 N HCl in ether to obtain 3.35 gm of a gummy solid.

PREPARATIVE EXAMPLE 36

Preparation of 1-{2-Oxo-2-[4-(4-pyrimidin-2-yl-phenyl)-piperazin-1-yl]-ethyl}-pyrrolidine-3-carboxylic acid methyl ester

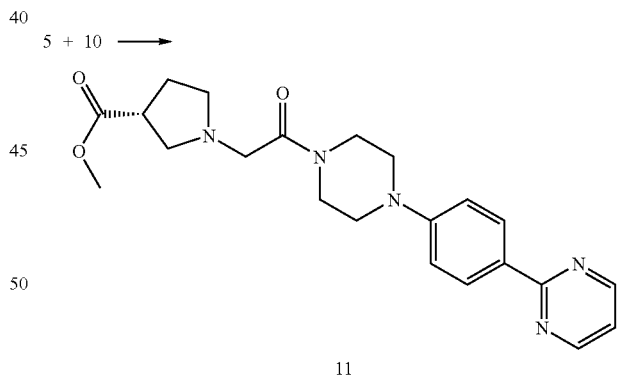

2-(4-piperazin-1-yl-phenyl)-pyrimidine (compound 10 from Step 7, 14.7 mmol) and 1-Carboxymethyl-pyrrolidine-3-carboxylic acid methyl ester (compound 5 from Step 3, 17.6 mmol) were dissolved in 72 ml of DMF. Triethylamine (8 ml, 57 mmol), 1-hydroxybenztriazole (2.29 gm) and 1-(3-dimethylaminopropyl)-3-ethylcarbodiimide hydrochloride (EDCl) (3.43 gm, 18 mmol) were added and the reaction mixture stirred for 24 hrs. After washing with brine, extracting with dichloromethane, and drying over magnesium sulfate, the mixture was evaporated and chromatographed on silica gel to obtain 5.0 gm of title product.

PREPARATIVE EXAMPLE 37

Preparation of 1-{2-Oxo-2-[4-(4-pyrimidin-2-yl-phenyl)-piperazin-1-yl]-ethyl}-pyrrolidine-3-carboxylic acid

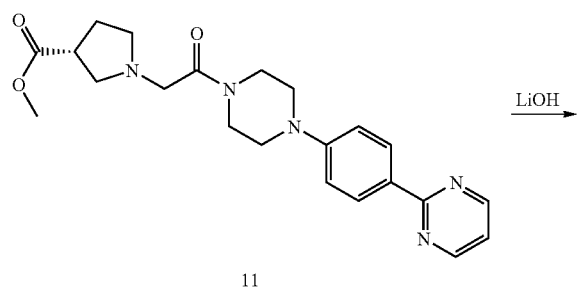

11

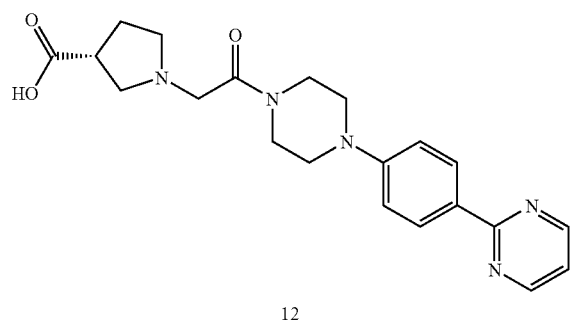

12

1-{2-Oxo-2-[4-(4-pyrimidin-2-yl-phenyl)-piperazin-1-yl]-ethyl}-pyrrolidine-3-carboxylic acid methyl ester (compound 11 from Step 8, 3.3 gm, 8.06 mmol) was dissolved in methanol and 10 ml of 1 N lithium hydroxide added. The reaction mixture was stirred for 18 hrs. 10 ml of 1 N HCl was added to the reaction mixture and evaporated to a white solid (3.94 gm)

PREPARATIVE EXAMPLE 38

Preparation of 1-{2-Oxo-2-[4-(4-pyrimidin-2-yl-phenyl)-piperazin-1-yl]-ethyl}-pyrrolidine-3-carboxylic acid (3-cyclopropyl-4-hydroxy-phenyl)-amide

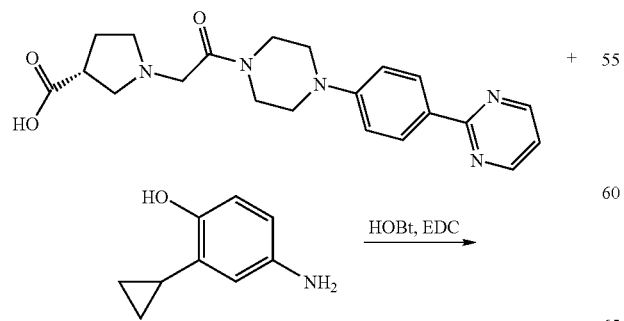

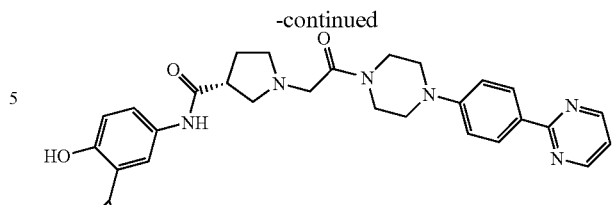

To a solution of 1-{2-oxo-2-[4-(4-pyrimidin-2-yl-phenyl)-piperazin-1-yl]-ethyl}-pyrrolidine-3-carboxylic acid (40 mg, 0.10 mmol) and 4-amino-2-cyclopropyl-phenol (22 mg, 0.15 mmol) in 1.5 mL of DMF was added DIEA (26 uL, 0.15 mL) followed by HATU (57 mg, 0.15 mmol). The reaction was stirred at room temperature for 2 h and purified by chromatography to afford 17 (23 mg), MS found 527.2 (M+H)

SCHEME 9

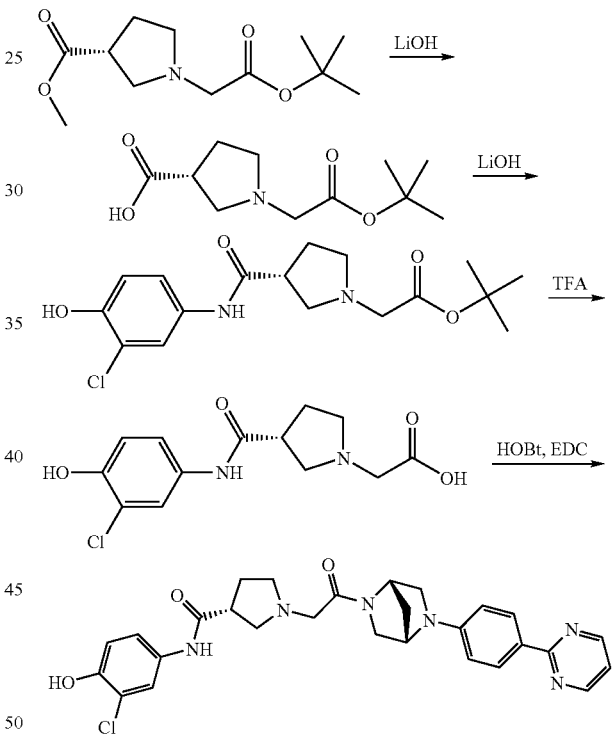

PREPARATIVE EXAMPLE 39

Preparation of 1-tert-Butoxycarbonylmethyl-pyrrolidine-3-carboxylic acid, Lithium Salt

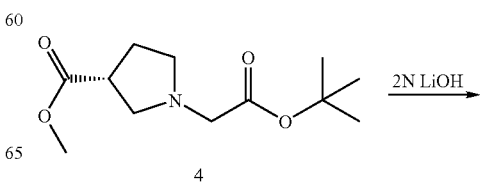

4

-continued

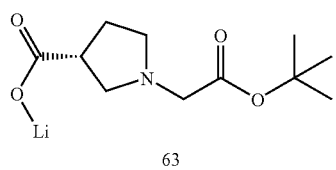

63

1-tert-Butoxycarbonylmethyl-pyrrolidine-3-carboxylic acid methyl ester 4 (see Example 1 Step 2) (0.753 g, 3.098 mmol) was dissolved in MeOH/THF (10 ml; 1/1) and 2N Lithium hydroxide (1.5 ml; 3 mmol) was added. The resultant solution was stirred for 2 hours, and solvent was evaporated yielding title compound 63 as a white solid (0.71 g, 100%). Mass Spec ES (230, M+H).

PREPARATIVE EXAMPLE 40

Preparation of [3-(3-Chloro-4-hydroxy-phenylcarbamoyl)-pyrrolidin-1-yl]-acetic acid tert-butyl ester

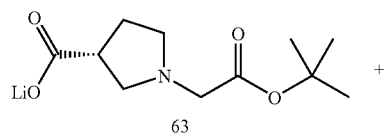
63

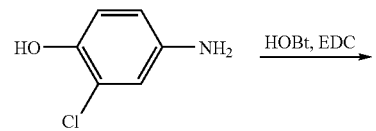

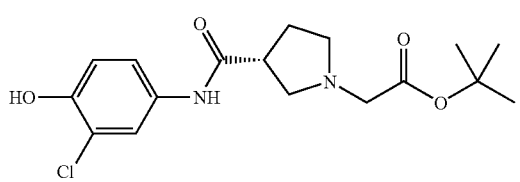

To a mixture of 1-tert-Butoxycarbonylmethyl-pyrrolidine-3-carboxylic acid, Lithium salt (0.5 g, 2.12 mmol) and HOBt (0.45 g, 3.3 mmol) in DMF (10 ml) at 0° C. was added EDCl (630 mg, 3.3 mmol). The formed reaction mixture was stirred at 0° C. for 0.5 hour and then 4-amino-2-chloro-phenol was added. After stirred at RT for overnight, the reaction mixture was added to ice-water (50 g) and the formed precipitated was collected by filtration, washed with sodium bicarbonate and HCl (0.1 N). After drying in air, the crude product (720 mg) was used directly in the next step. Mass Spec ES (355.2, M+H)

PREPARATIVE EXAMPLE 41

Preparation of [3-(3-Chloro-4-hydroxy-phenylcarbamoyl)-pyrrolidin-1-yl]-acetic acid

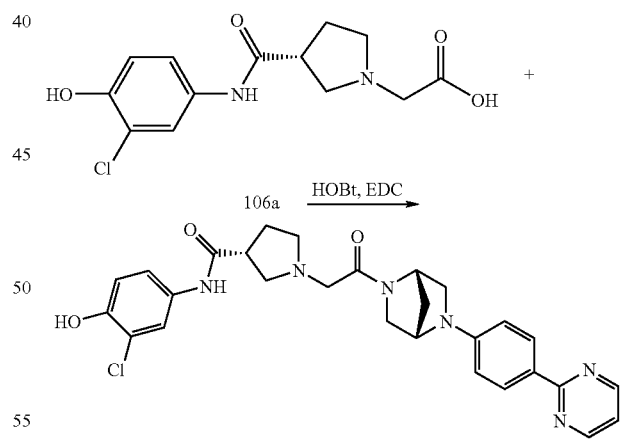

[3-(3-Chloro-4-hydroxy-phenylcarbamoyl)-pyrrolidin-1-yl]-acetic acid tert-butyl ester was dissolved in TFA/DCM (90:10) solution. After stirring at RT for 30 min, the reaction mixture was concentrated and acetonitrile/water (10 ml, 3:1) was added. After removal of solvent, the residue was purified using Prep-HPLC to give 450 mg of product.

Mass Spec ES (299.1, M+H)

PREPARATIVE EXAMPLE 42

Preparation of 1-{2-Oxo-2-[5-(4-pyrimidin-2-yl-phenyl)-2,5-diaza-bicyclo[2.2.1]hept-2-yl]-ethyl}-pyrrolidine-3-carboxylic acid (3-chloro-4-hydroxy-phenyl)-amide To a mixture of [3-(3-Chloro-4-hydroxy-phenylcarbamoyl)-pyrrolidin-1-yl]-acetic acid (10 mg, 0.034 mmol) and HOBt (6.8 mg, 0.050 mmol) in DMF (0.5 ml) at 0° C. was added EDCl (9.6 mg, 0.050 mmol). The formed reaction mixture was stirred at 0° C. for 0.5 hour and then 2-(4-Pyrimidin-2-yl-phenyl)-2,5-diaza-bicyclo[2.2.1]heptane hydrochloride salt (12.6 mg, 0.05 mmol) was added. After stirred at RT for overnight, the reaction mixture was purified using a Prep-HPLC to give titled compound (3.4 mg, 19% yield). Mass Spec ES (533.1, M+H)

PREPARATIVE EXAMPLE 43

Step 1

Preparation of 2-(tert-butyl-dimethyl-silanyloxymethyl)-acrylic acid ethyl ester

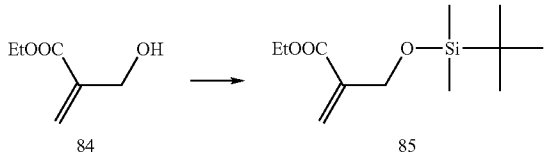

To a stirred solution of 2-hydroxymethyl-acrylic acid ethyl ester (260 mg, 2 mmol) and imidazole (163 mg, 2.4 mmol) in dry DMF (5 ml) was added tert-butyldimethylsilyl chloride (362 mg, 2.4 mmol). The reaction mixture was stirred overnight and diluted with ether, washed with water three times and dried over MgSO$_4$. Solvent was removed under reduced pressure to provide a crude product that was purified by column chromatography using a solution of ethyl acetate in hexanes (1:6) to obtain the title product (463 mg, 95%).

Step 2

Preparation of 1-benzyl-3-(tert-butyl-dimethyl-silanyloxymethyl)-pyrrolidine-3-carboxylic acid ethyl ester

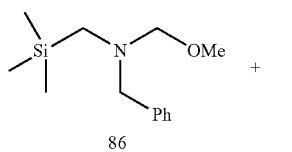

To a cold solution of 2-(tert-butyl-dimethyl-silanyloxymethyl)-acrylic acid ethyl ester (463 mg, 1.89 mmol) and N-(methoxymethyl)-N-(trimethylsilylmethyl)benzyl-amine (540 μl, 2.11 mmol) in dichloromethane (3 ml) was added at 0° C. trifluoroacetic acid (26 μl, 0.34 mmol). The resulting solution was warmed to room temperature in two hours. The crude product was purified by column chromatography on silica get eluting with a solution of ethyl acetate in hexanes (1:10, 1:5) to give the title compound (490 mg, 69%).

Step 3

Preparation of 3-(tert-butyl-dimethyl-silanyloxymethyl)-pyrrolidine-3-carboxylic acid ethyl ester

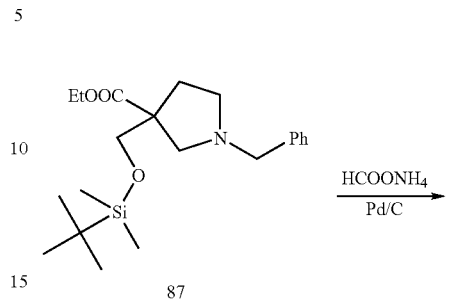

A mixture of 1-benzyl-3-(tert-butyl-dimethyl-silanyloxymethyl)-pyrrolidine-3-carboxylic acid ethyl ester (690 mg, 1.83 mmol), ammonium formate (461 mg, 7.31 mmol), 10% Pd/C (100 mg) in methanol (10 ml) and water (1 ml) was refluxed overnight. The mixture was filtered through celite, washed with ethyl acetate. The combined filtrate was concentrated and the residue was taken into ethyl acetate, washed with brine and dried over MgSO$_4$. Evaporation of solvent provided the title compound as oil (444 mg, 84%).

Step 4

Synthesis of 1-tert-butoxycarbonylmethyl-3-(tert-butyl-dimethyl-silanyloxymethyl)-pyrrolidine-3-carboxylic acid ethyl ester

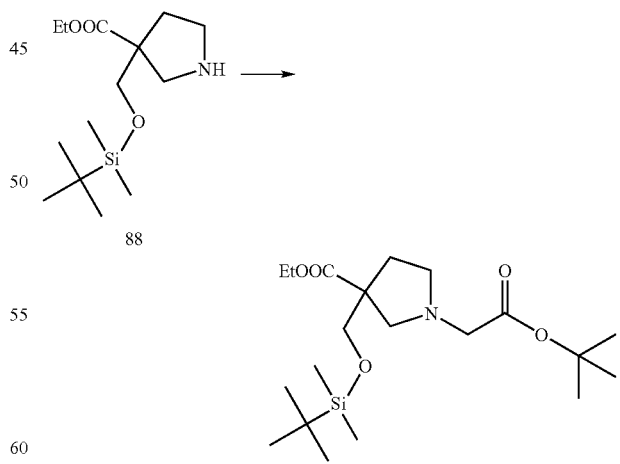

To a stirred mixture of 3-(tert-butyl-dimethyl-silanyloxymethyl)-pyrrolidine-3-carboxylic acid ethyl ester (444 mg, 1.54 mmol), triethylamine (214 μl, 1.54 mmol) and cesium carbonate (251 mg, 0.77 mmol) in acetonitrile (5 ml)

was added tert-butyl bromoacetate (351 µl, 2.38 mmol) slowly. The mixture was stirred for 1 hour, filtered and concentrated. The residue was diluted with ethyl acetate, washed with water and dried over MgSO₄. Solvent was removed under reduced pressure to give a crude product that was purified by column chromatography on silica gel. Elution with a solution of ethyl acetate in hexanes (1:4) provided 580 mg (94%) of the title compound.

Step 5

Preparation of 1-tert-butoxycarbonylmethyl-3-hydroxymethyl-pyrrolidine-3-carboxylic acid ethyl ester

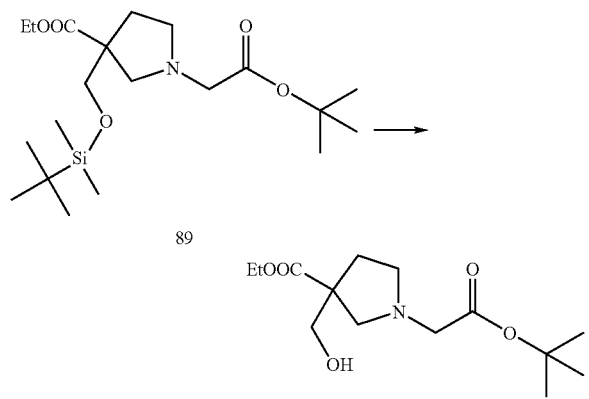

Tetrabutylammonium fluoride (1.8 ml, 1 M in THF) was added to 1-tert-butoxycarbonylmethyl-3-(tert-butyl-dimethyl-silanyloxymethyl)-pyrrolidine-3-carboxylic acid ethyl ester (726 mg, 1.8 mmol). The reaction solution was stirred for half hour and purified by column chromatography using solution of ethyl acetate in hexanes (1:1), then ethyl acetate to provide the title product (350 mg, 68%).

PREPARATIVE EXAMPLE 44

Step 1

Preparation of methyl 2-(methoxymethyl)acrylate

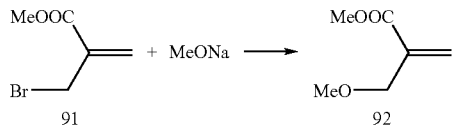

To a stirred mixture of methyl 2-(bromomethyl)acrylate (239 µl, 2 mmol) in petroleum ether (3 ml) was added potassium carbonate (276 mg, 2 mmol), followed by sodium methoxide (119 mg, 2.2 mmol) and methanol (450 µl). The resulting mixture was stirred overnight, filtered, concentrated to a residue that was purified by column chromatography eluting with 10% ether in hexanes to provide the title compound (150 mg, 58%). (Reference: J. Med. Chem.; 42; 15; 1999; 2760-2773.)

Step 2

Preparation of 1-benzyl-3-methoxymethyl-pyrrolidine-3-carboxylic acid methyl ester

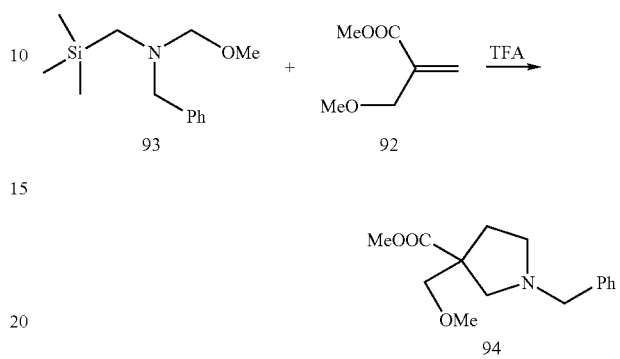

To a stirred solution of methyl 2-(methoxymethyl)acrylate (176 mg, 1.35 mmol) and N-(methoxymethyl)-N-(trimethylsilylmethyl)benzylamine (416 µl, 1.63 mmol) in dichloromethane (2 ml) was added at 0° C. trifluoroacetic acid (21 µl, 0.27 mmol). The resulting solution was warmed to room temperature and stirred overnight. The crude product was purified by column chromatography on silica, eluted with a solution of ethyl acetate in hexanes (1:3), then 5% methanol in ethyl acetate to give the title compound (293 mg, 82%).

Step 3

Preparation of 3-methoxymethyl-pyrrolidine-3-carboxylic acid methyl ester

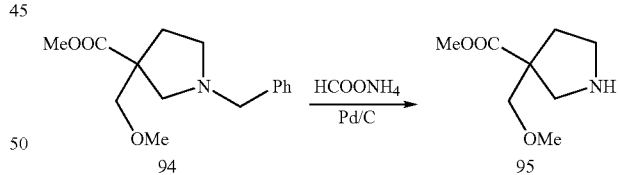

A mixture of 1-benzyl-3-methoxymethyl-pyrrolidine-3-carboxylic acid methyl ester (373 mg, 1.42 mmol), ammonium formate (358 mg, 5.68 mmol), 10% Pd/C (100 mg) and methanol (6 ml) was refluxed overnight. The mixture was filtered through Celite, washed with ethyl acetate. The combined filtrate was concentrated and the residue was taken into ethyl acetate, washed with small amount of water. Aqueous layer was isolated, extracted with dichloromethane three times. The dichloromethane extracts were combined with previous ethyl acetate extracts and dried over MgSO₄. Evaporation of solvents provided the title compound as oil (140 mg, 57%).

Step 4

Preparation of 1-tert-butoxycarbonylmethyl-3-methoxymethyl-pyrrolidine-3-carboxylic acid methyl ester

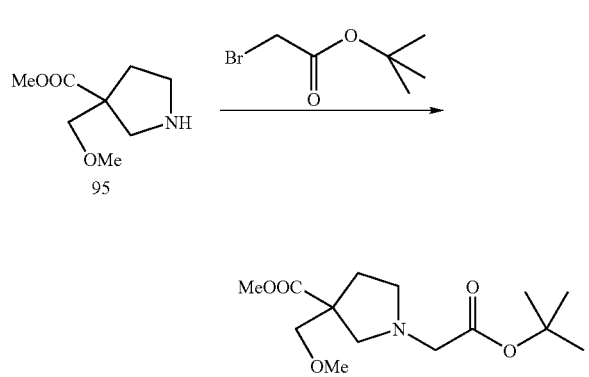

To a stirred mixture of 3-methoxymethyl-pyrrolidine-3-carboxylic acid methyl ester (140 mg, 0.81 mmol), triethylamine (112 μl, 0.82 mmol) and cesium carbonate (263 mg, 0.81 mmol) in acetonitrile (2 ml) was added tert-butyl bromoacetate (119 μl, 0.81 mmol) slowly. The mixture was stirred for 15 minutes, filtered and concentrated. The residue was purified by column chromatography on silica gel. Elution with a solution of ethyl acetate and hexanes (1:2) provided 118 mg (51%) of the title compound.

Step 5

Preparation of 1-carboxymethyl-3-methoxymethyl-pyrrolidine-3-carboxylic acid methyl ester

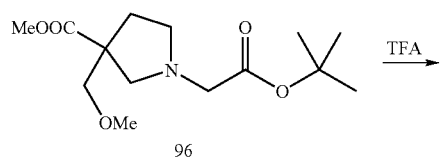

The 1-tert-butoxycarbonylmethyl-3-methoxymethyl-pyrrolidine-3-carboxylic acid methyl ester (118 mg) was treated with trifluoroacetic acid (2 ml), stirred for 20 minutes and evaporated to a residue that was exchanged with hydrochloric acid (1 ml, 4N) and lyophilized overnight to a gummy title product.

Step 6

Preparation of 3-methoxymethyl-1-{2-oxo-2-[4-(4-pyrimidin-2-yl-phenyl)-piperazin-1-yl]-ethyl}-pyrrolidine-3-carboxylic acid ethyl ester

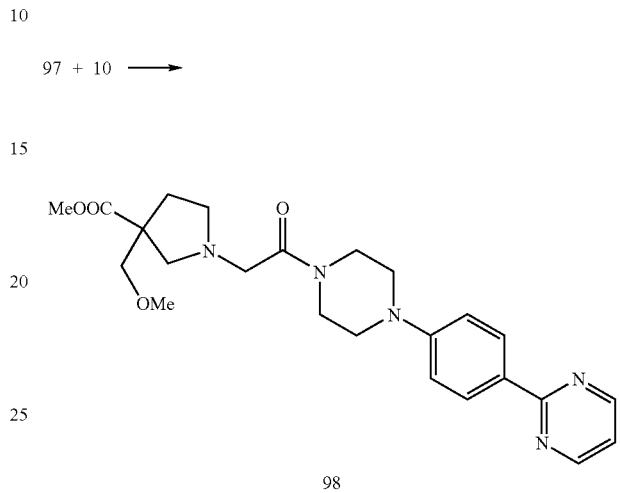

To a solution of 1-carboxymethyl-3-methoxymethyl-pyrrolidine-3-carboxylic acid methyl ester (compound 97) (0.21 mmol), 2-(4-piperazin-1-yl-phenyl)-pyrimidine (compound 10, see Example 1 Step 7) (0.21 mmol), O-(7-azabenzotriazol-1-yl-)-N,N,N',N'-tetramethyluronium hexafluorophosphate (HATU) (78 mg, 0.21 mmol) in dry DMF (2 ml) was added N,N-diisopropylethylamine (108 μl, 0.62 mmol). The reaction mixture was stirred for 4 hours, and evaporated to a residue that was partitioned in ethyl acetate and saturated sodium carbonate. Organic layer was isolated, washed with water, brine and dried over magnesium sulfate. Evaporation of solvent provided a crude product which was chromatographed with 5% methanol in dichloromethane to furnish the title compound (97 mg).

Step 7

Preparation of 3-methoxymethyl-1-{2-oxo-2-[4-(4-pyrimidin-2-yl-phenyl)-piperazin-1-yl]-ethyl}-pyrrolidine-3-carboxylic acid

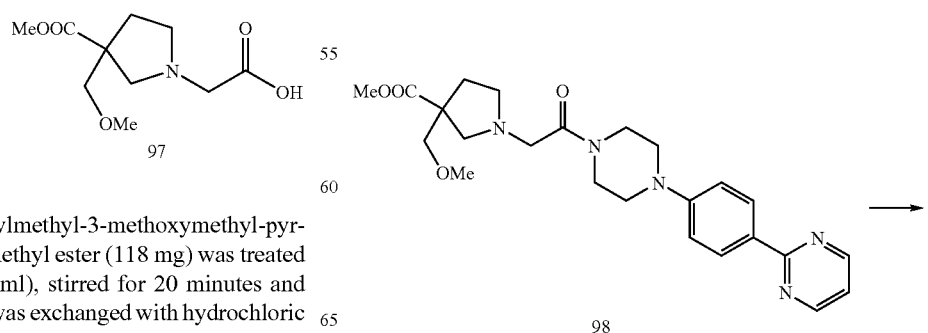

-continued

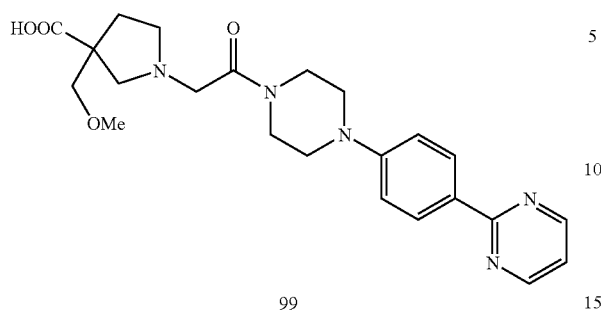

99

The 1-carboxymethyl-3-methoxymethyl-pyrrolidine-3-carboxylic acid methyl ester (97 mg, 0.21 mmol) was saponified with lithium hydroxide monohydrate (27 mg, 0.64 mmol) in tetrahydronfuran and water (2:1, 3 ml) for 2 hours. The reaction mixture was acidified with 4 N HCl and lyophilized overnight to provide the title compound which was directly used in the next step synthesis.

PREPARATIVE EXAMPLE 45

Preparation of 3-Methoxymethyl-1-{2-oxo-2-[4-(4-pyrimidin-2-yl-phenyl)-piperazin-1-yl]-ethyl}-pyrrolidine-3-carboxylic acid (4-hydroxy-3-trifluoromethyl-phenyl)-amide

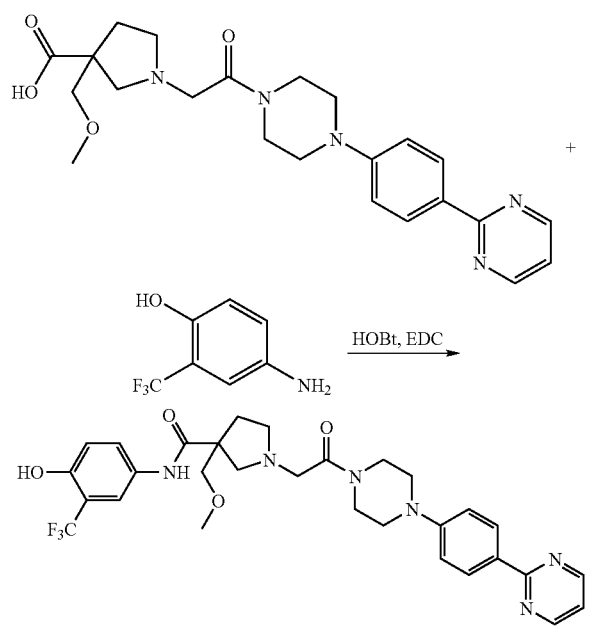

A mixture of compound 2 (0.058 mmols), HOBt (7.8 mg, 0.058 mmols), EDC (11 mg, 0.057 mmols) in DMF (1 ml) was stirred at r.t. overnight, then 55° C. overnight. The reaction mixture was directly purified by HPLC (Gilson) to provide titled compound. MS found 599.1 (M+H)

PREPARATIVE EXAMPLE 46

Step 1

Preparation of 2-fluoromethyl-acrylic acid ethyl ester

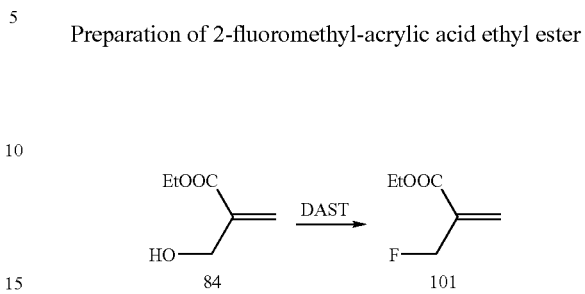

To a solution of (diethylamino)sulfur trifluoride (DAST) (363 µl, 2.76 mmol) in dichloromethane (1 ml) was slowly added at −78 C. a solution of 2-hydroxylmethyl acrylic acid ethyl ester (300 mg, 2.31 mmol) in dichloromethane (3 ml). The reaction mixture was allowed to warm to room temperature, re-chilled to −78 C. and additional DAST (100 µl, 0.76 mmol) was added to ensure complete reaction. The reaction mixture was let to warm to room temperature and quenched with saturated sodium carbonate. Organic layer was isolated, washed with water, brine and dried (MgSO$_4$). The dichloromethane solution was directly passed through a short silica gel pad, eluted with dichloromethane and the product fractions were collected. The combined fractions (ca. 12 ml) will be directly used in the next step synthesis without further concentration.

Step 2

Preparation of 1-benzyl-3-fluoromethyl-pyrrolidine-3-carboxylic acid ethyl ester

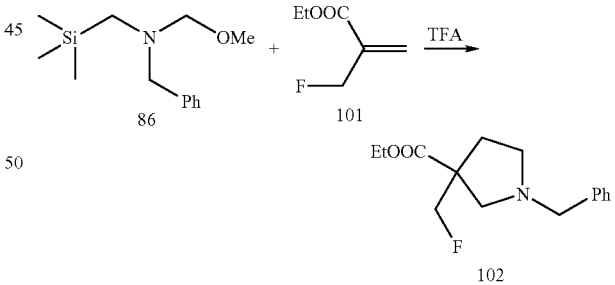

N-(methoxymethyl)-N-(trimethylsilylmethyl)benzylamine (548 µl, 2.14 mmol) was dissolved in the dichloromethane solution of the 2-fluoromethyl-acrylic acid ethyl ester from the previous reaction and chilled to 0 C. A solution of trifluoroacetic acid (67 µl, 0.87 mmol) in dichloromethane (0.5 ml) was added slowly. The reaction mixture was allowed to warm to room temperature in two hours and directly chromatographed on silica gel. Elution with solutions of ethyl acetate in hexanes (1:5, 1:4, 1:3) obtained the title product (143 mg) as oil.

PREPARATIVE EXAMPLE 47

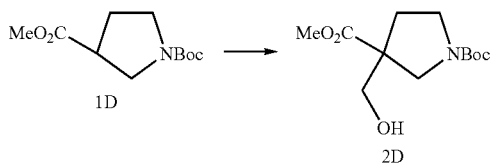

To a solution of LDA (33.5 mmol, 16.7 mL, 2 M in toluene) in 50 mL THF cooled at −78 deg C. was added a solution of 1D (5.9 g, 25.7 mmol) in 50 mL THF drop wise. The crude was stirred at −78 deg C. for 45 mins. To the crude was bubbled formaldehyde gas, freshly generated from cracking of para-formaldehyde (12 g, 400 mmol). The crude was stirred at −78 deg C. for an additional 30 mins. To the crude was added sat $NH_4Cl$ (200 mL). The crude was warmed to rt. The crude was diluted in EtOAc. The organic layer washed with brine and dried over $MgSO_4$, filtered, and conc. in vacuum. The crude was purified on Biotage using EtOAc/hexane (3:7)->EtOAc/hexane (1:1) to give 6.6 g (57%) of the product as a yellow oil.

PREPARATIVE EXAMPLE 48

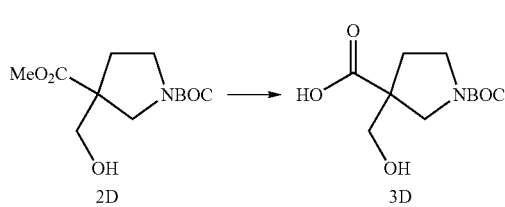

To a solution of ester 2D (2.5 g, 9.6 mmol) in MeOH (100 mL) was added 1 N NaOH (48 mL, 48.2 mmol) at rt. The crude was stirred at rt overnight. To the crude was added 1 N HCl (47.5 mL, 47.5 mmol). The crude was stirred at rt for 5 mins. PH of crude is made to 5 using PH paper. The crude was conc in vacuum and azeotropped 2× with toluene and dried under high vacuum for use the next reaction.

PREPARATIVE EXAMPLE 49

Preparation of 3-Fluoro-pyrrolidine-1,3-dicarboxylic acid 1-tert-butyl ester 3-methyl ester

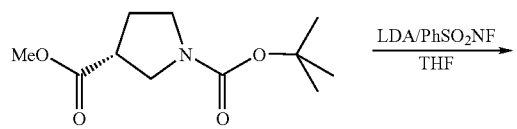

-continued

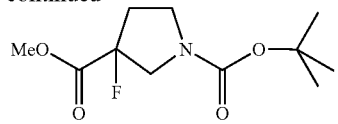

n-Butyl lithium (2.5M/Hexanes, 3.83 ml; 9.575 mmol) added dropwise to solution of diisopropylamine (1.36 ml; 9.62 mmol) at −78° C. Solution was allowed warm to room temperature and stirred for 30 minutes, then cooled to −78° C. A solution of Pyrrolidine-1,3-dicarboxylic acid 1-tert-butyl ester 3-methyl ester (2 g, 8.72 mmol) in THF (10 ml) was added dropwise, warmed to −40° C. for 1 hour, then cooled to −70° C. A solution of N-fluorobenzene-sulfonimide (3.02 g, 9.57 mmol) in THF (15 ml) was added dropwise, stirred at −78° C. for 1 hour, then stirred at room temperature overnight. Precipitated solid was filtered, washed with EtOAc (2×150 ml). Organic layer was washed with 1 N HCl (30 ml), brine (100 ml), dried ($MgSO_4$), filtered and solvent evaporated. The residue was chromatographed on silica gel eluting with 10% v/v EtOAc/hexanes yielding product as colorless oil (1.38 g:64% yield). MS (ESMS, MH 249).

PREPARATIVE EXAMPLE 50

Preparation of 3-Allyl-pyrrolidine-1,3-dicarboxylic acid 1-tert-butyl ester 3-methyl ester

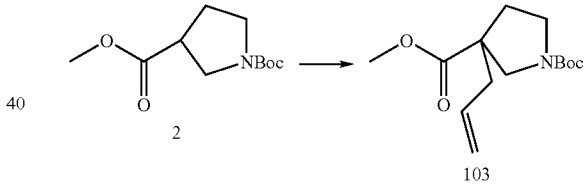

Pyrrolidine-1,3-dicarboxylic acid 1-tert-butyl ester 3-methyl ester 2 (see Example 1, Step 1) (4.58 g, 20 mmol) was dissolved in THF (100 mL) and cooled down to −78° C. in a dry ice-acetone bath. LDA (12 mL, 2.0 M, 24 mmol) was then added dropwise. The mixture was stirred at −78° C. for 1 hr. Allyl bromide (5.3 mL, 61 mmol) was added in neat. The reaction was allowed to warm to rt naturally and stirred for 24 hrs. It was then quenched with sat. $NH_4Cl$ solution, extracted with ethyl acetate 2×150 mL. The organic layer washed with brine, dried ($MgSO_4$) and concentrated. The crude was purified on silica gel column using 4:1 hexanes/ethyl acetate to get the title compound (3.6 g) as a yellow oil. MS (292, MNa).

EXAMPLES 1 TO 14

The compounds in Table 1 were prepared utilizing Scheme 8 and Preparative example 43-50 substituting the appropriate piperazine derivative for the piperazine compound 10, and appropriate pyrrolidine as described in examples 43-50.

TABLE 1

| EX | Compound | M⁺ + 1 | Retention Time (Minutes) |
|---|---|---|---|
| 1 | | | |
| 2 | | | |
| 3 | | | |
| 4 | | | |
| 5 | Preparative Example 45 | | |
| 6 | | | |
| 7 | piperazine commercially available | 519.3 | 3.41 |

TABLE 1-continued
| EX | Compound | M⁺ + 1 | Retention Time (Minutes) |
|---|---|---|---|
| 8 | 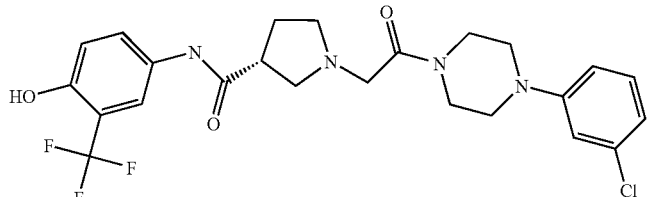 piperazine commercially available | 511.2 | 3.51 |
| 9 | 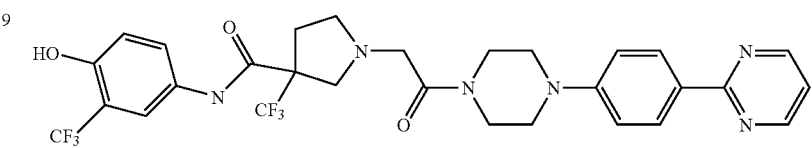 | | |
| 10 | 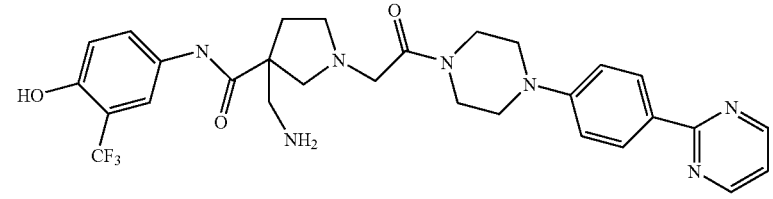 | | |
| 11 | 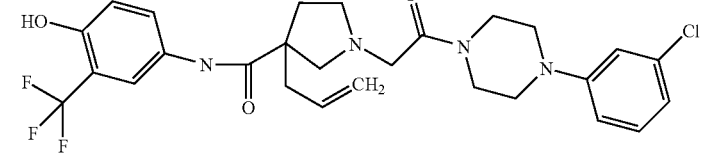 piperazine commercially available | | |
| 12 | 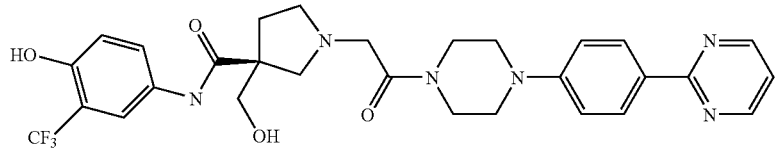 | | |
| 13 | 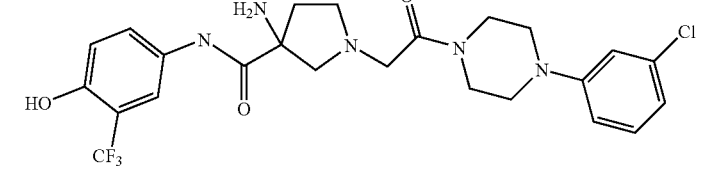 piperazine commercially available | | |

TABLE 1-continued

| EX | Compound | M+ + 1 | Retention Time (Minutes) |
|----|----------|--------|--------------------------|
| 14 | 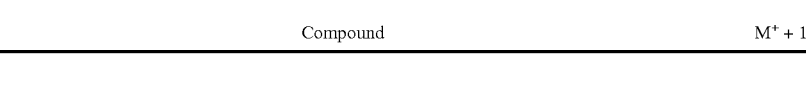 piperazine commercially available | | |

EXAMPLES 15-107, 109, 110, AND 112-117

The compounds in Table 2 were prepared utilizing Scheme 9 and Preparative example 39-42 substituting the appropriate piperazine derivative as described herein for the deprotected (de-Boc) piperazine compound 106a in preparative example 19 step 2. If the piperazine derivative is not described, it is commercially available or prepared by methods similar to procedures described herein and known in the art.

TABLE 2

| EX | Compound | M+ + 1 | Retention Time (minutes) |
|----|----------|--------|--------------------------|
| 15 | | | |
| 16 | | | |
| 17 | | | |
| 18 | | | |

TABLE 2-continued

| EX | Compound | M⁺ + 1 | Retention Time (minutes) |
|---|---|---|---|
| 19 | Preparative example 42 | 533.4 | 3.03 |
| 20 | | | |
| 21 | | | |
| 22 | | | |
| 23 | | | |
| 24 | | | |
| 25 | | | |

TABLE 2-continued

| EX | Compound | M+ + 1 | Retention Time (minutes) |
|---|---|---|---|
| 26 | | | |
| 27 | | | |
| 28 | | | |
| 29 | | | |
| 30 | | 509.3 | 3.9 |
| 31 | | | |
| 32 | | | |

TABLE 2-continued

| EX | Compound | M+ + 1 | Retention Time (minutes) |
|---|---|---|---|
| 33 | | 525.3 | 4.25 |
| 34 | | 525.3 | 4.16 |
| 35 | | | |
| 36 | | 489.2 | 3.87 |
| 37 | | | |
| 38 | | | |
| 39 | | 469.3 | 3.76 |

TABLE 2-continued

| EX | Compound | M⁺ + 1 | Retention Time (minutes) |
|---|---|---|---|
| 40 | | 501.3 | 3.42 |
| 41 | | 549.3 | 3.51 |
| 42 | | | |
| 43 | | 500.2 | 3.24 |
| 44 | | 485.3 | 3.04 |
| 45 | | 521.2 | 3.93 |
| 46 | | 553.2 | 4.54 |

TABLE 2-continued

| EX | Compound | M⁺ + 1 | Retention Time (minutes) |
|---|---|---|---|
| 47 | | | |
| 48 | | 553.2 | 4.72 |
| 49 | | 485.3 | 4.12 |
| 50 | | 477.1 | 3.52 |
| 51 | | | |
| 52 | | 482.3 | 3.14 |

TABLE 2-continued

| EX | Compound | M+ + 1 | Retention Time (minutes) |
|---|---|---|---|
| 53 | | 499.3 | 3.61 |
| 54 | | | |
| 55 | | 559.2 | 4.78 |
| 56 | | 479.3 | 3.16 |
| 57 | | 473.2 | 3.58 |
| 58 | | 545.3 | 4.69 |

TABLE 2-continued

| EX | Compound | M+ + 1 | Retention Time (minutes) |
|---|---|---|---|
| 59 | | 468.3 | 3.27 |
| 60 | | 553.3 | 4.73 |
| 61 | | 485.3 | 3.16 |
| 62 | | 510.3 | 3.14 |
| 63 | | 516.4 | 4.1 |
| 64 | | 525.3 | 4.44 |

TABLE 2-continued

| EX | Compound | M+ + 1 | Retention Time (minutes) |
|---|---|---|---|
| 65 | | 469.2 | 0.7 |
| 66 | | | |
| 67 | | 509.3 | 3.85 |
| 68 | | 527.3 | 3.91 |
| 69 | | | |
| 70 | | | |
| 71 | | | |

TABLE 2-continued

| EX | Compound | M+ + 1 | Retention Time (minutes) |
|---|---|---|---|
| 72 | | | |
| 73 | | 457.3 | 3.53 |
| 74 | | | |
| 75 | | 471.3 | 3.74 |
| 76 | | 509.3 | 3.85 |
| 77 | | | |

TABLE 2-continued

| EX | Compound | M⁺ + 1 | Retention Time (minutes) |
|---|---|---|---|
| 78 | | 458.3 | 1.98 |
| 79 | | | |
| 80 | | 489.3 | 3.85 |
| 81 | | 525.1 | 4.28 |
| 82 | | | |
| 83 | | 469.3 | 2.9 |
| 84 | | 444.7 | 1.84 |

TABLE 2-continued

| EX | Compound | M⁺ + 1 | Retention Time (minutes) |
|---|---|---|---|
| 85 | | | |
| 86 | | | |
| 87 | | | |
| 88 | | 485.2 | 2.72 |
| 89 | | | |
| 90 | | 500.3 | 2.93 |
| 91 | | 471.3 | 4.14 |

TABLE 2-continued

| EX | Compound | M⁺ + 1 | Retention Time (minutes) |
|---|---|---|---|
| 92 | | | |
| 93 | | | |
| 94 | | | |
| 95 | | 455.3 | 2.24 |
| 96 | | | |
| 97 | | 471.4 | 3.22 |
| 98 | | | |

TABLE 2-continued
| EX | Compound | M⁺ + 1 | Retention Time (minutes) |
|---|---|---|---|
| 99 | 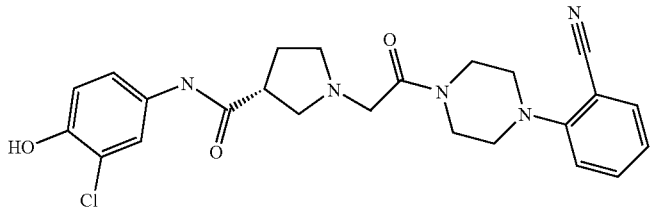 | 468.3 | 3.37 |
| 100 | 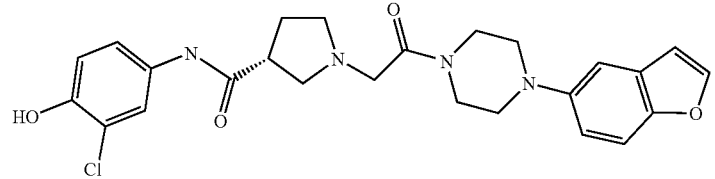 | 483.3 | 3.19 |
| 101 | 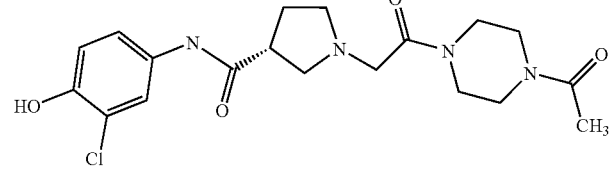 | 489.3 | 1.9 |
| 102 | 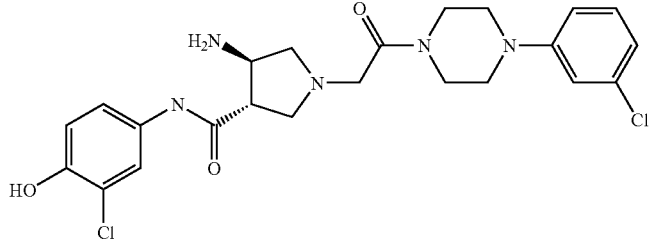 | | |
| 103 | 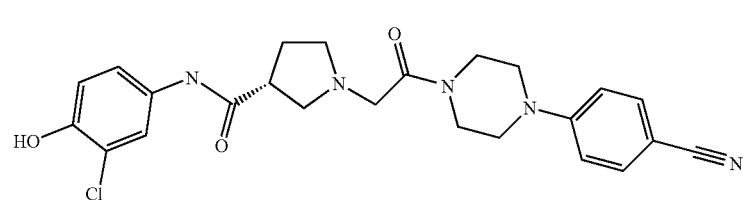 | 468.3 | 3.13 |
| 104 | 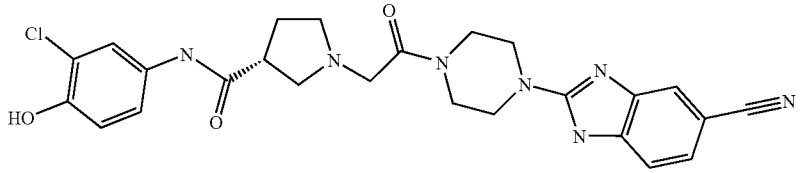 | 508.2 | 2.27 |

TABLE 2-continued

| EX | Compound | M⁺ + 1 | Retention Time (minutes) |
|---|---|---|---|
| 105 | | 559.25 | 4.8 |
| 106 | | 484.3 | 3.13 |
| 107 | | 537.4 | 2.83 |
| 109 | | 511.21 | 4.21 |
| 110 | | | |

TABLE 2-continued

| EX | Compound | M+ + 1 | Retention Time (minutes) |
|---|---|---|---|
| 112 | | | |
| 113 | | | |
| 114 | | | |
| 115 | | 483.27 | 2.24 |
| 116 | | | |

TABLE 2-continued

| EX | Compound | M+ + 1 | Retention Time (minutes) |
|---|---|---|---|
| 117 | *[structure]* | | |

EXAMPLES 118-119

The compounds in Table 3 were prepared utilizing Scheme 8 and Preparative example 33-38 substituting the appropriate piperazine derivative as described herein for the deprotected (de-Boc) piperazine compound 106a. piperazine derivative not described are either commercially available or prepared by methods similar to procedures described herein and known in the art.

TABLE 3

| EX | Compound | M+ + 1 | Retention Time (Minutes) |
|---|---|---|---|
| 118 | *[structure]* | 491.4 | 3.09 |
| 119 | *[structure]* | 527.3 | 3.26 |

EXAMPLES 120-135, 137-156, 158-163, 166-170, 172-179, 183-192, and 194

The compounds in Table 4 were prepared utilizing Scheme 8 and Preparative example 33-38 substituting 4-hydroxyaniline for 4-amino-2-cyclopropyl-phenol in preparative example 38 and substituting the appropriate piperazine derivative as described herein for the deprotected (de-Boc) piperazine compound 106a. piperazine derivative not described are either commercially available or prepared by methods similar to procedures described herein and known in the art.

TABLE 4

| Ex | Compound | M+ + 1 | Retention Time (Minutes) |
|---|---|---|---|
| 120 | | | |
| 121 | | 477.3 | 3.81 |
| 122 | | 451.1 | 2.55 |
| 123 | | 442.1 | 3.4 |
| 124 | | 443.2 | 3.16 |
| 125 | | | |

TABLE 4-continued

| Ex | Compound | M⁺ + 1 | Retention Time (Minutes) |
|---|---|---|---|
| 126 | | | |
| 127 | | | |
| 128 | | | |
| 129 | | 410.4 | 1.47 |
| 130 | | | |
| 131 | | | |
| 132 | | 457.4 | 3.7 |
| 133 | | | |

US 7,807,672 B2
TABLE 4-continued
| Ex | Compound | M+ + 1 | Retention Time (Minutes) |
|---|---|---|---|
| 134 | 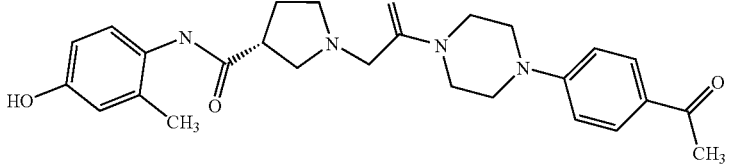 | | |
| 135 | 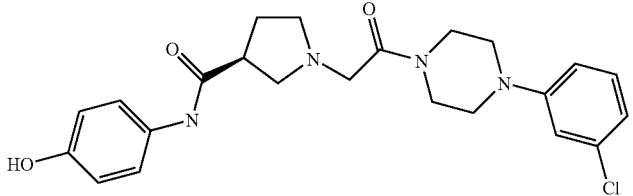 | 443.2 | 2.85 |
| 137 | 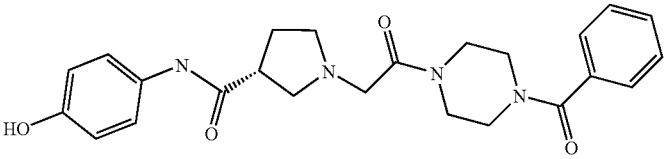 | 437.3 | 2.37 |
| 138 | 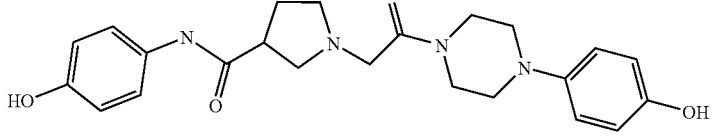 | | |
| 139 | 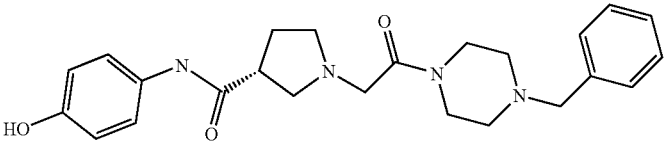 | 423.1 | 1.51 |
| 140 | 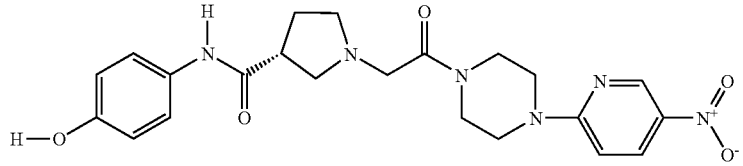 | | |
| 141 | 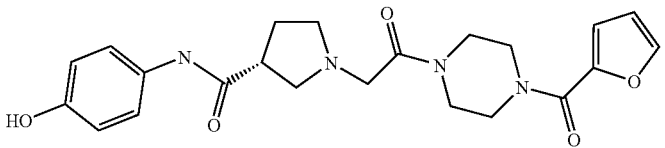 | | |
| 142 | 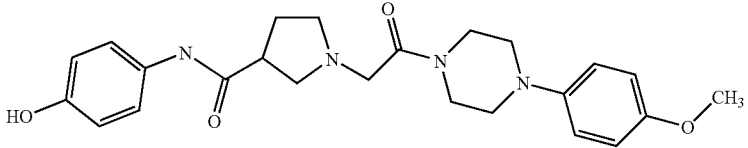 | | |

TABLE 4-continued

| Ex | Compound | M+ + 1 | Retention Time (Minutes) |
|---|---|---|---|
| 143 | | | |
| 144 | | | |
| 145 | | | |
| 146 | | | |
| 147 | | | |
| 148 | | | |
| 149 | | | |

TABLE 4-continued

| Ex | Compound | M⁺ + 1 | Retention Time (Minutes) |
|---|---|---|---|
| 150 | | | |
| 151 | | | |
| 152 | | 409.2 | 2.1 |
| 153 | | | |
| 154 | | | |
| 155 | | | |
| 156 | | | |

TABLE 4-continued

| Ex | Compound | M+ + 1 | Retention Time (Minutes) |
|---|---|---|---|
| 158 | | | |
| 159 | | 467.2 | 2.41 |
| 160 | | | |
| 161 | | | |
| 162 | | | |
| 163 | | | |
| 166 | | | |
| 167 | | | |

TABLE 4-continued

| Ex | Compound | M⁺ + 1 | Retention Time (Minutes) |
|---|---|---|---|
| 168 | | | |
| 169 | | | |
| 170 | | | |
| 172 | | | |
| 173 | | | |
| 174 | | | |
| 175 | | | |
| 176 | | | |

TABLE 4-continued
| Ex | Compound | M+ + 1 | Retention Time (Minutes) |
|---|---|---|---|
| 177 | 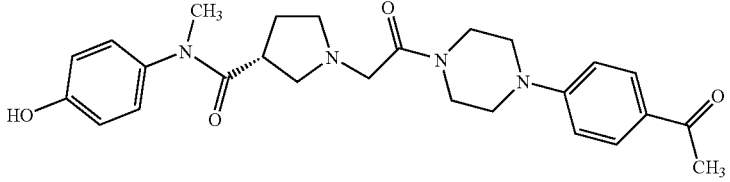 | | |
| 178 | 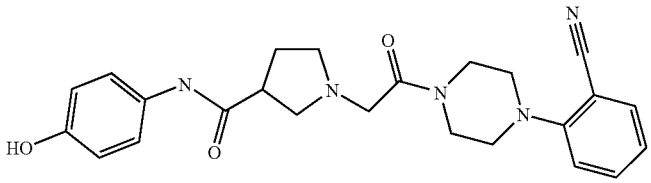 | | |
| 179 | 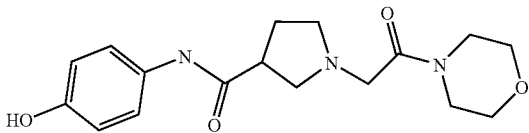 | | |
| 183 | 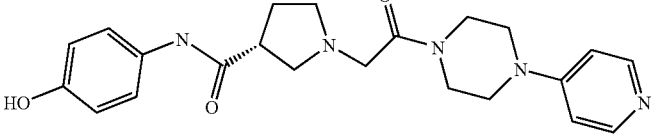 | | |
| 184 | 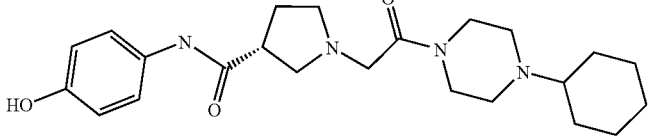 | | |
| 185 | 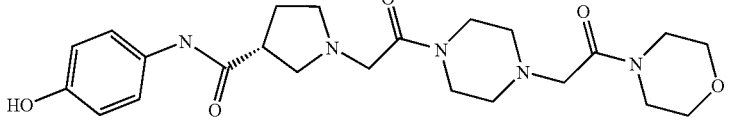 | | |
| 186 | 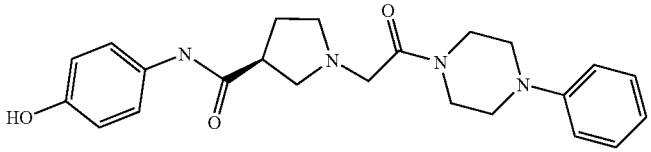 | | |
| 187 | 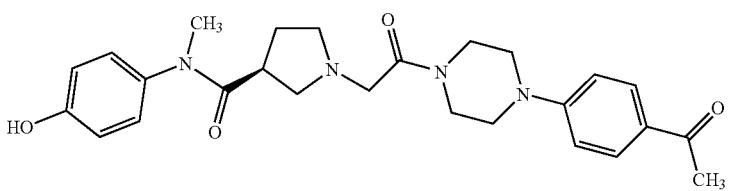 | | |

TABLE 4-continued

| Ex | Compound | M+ + 1 | Retention Time (Minutes) |
|---|---|---|---|
| 188 | | | |
| 189 | | | |
| 190 | | | |
| 191 | | | |
| 192 | | | |
| 194 | | | |

EXAMPLES 196-211

The compounds in Table 5 were prepared utilizing Scheme 8 and Preparative example 33-38 substituting 4-amino-2-isopropyl-phenol from preparative example 5 for 4-amino-2-cyclopropyl-phenol in preparative example 38 and substituting the appropriate piperazine derivative as described herein for the deprotected (de-Boc) piperazine compound 106a. piperazine derivative not described are either commercially available or prepared by methods similar to procedures described herein and known in the art.

TABLE 5

| EX | Compound | $M^+ + 1$ | Retention Time (Minutes) |
|---|---|---|---|
| 196 | | 541.34 | 3.41 |
| 197 | | 541.343 | 3.51 |
| 199 | | 529.3 | 3.51 |
| 200 | | 536.3 | |

TABLE 5-continued
| EX | Compound | M+ + 1 | Retention Time (Minutes) |
|---|---|---|---|
| 201 | 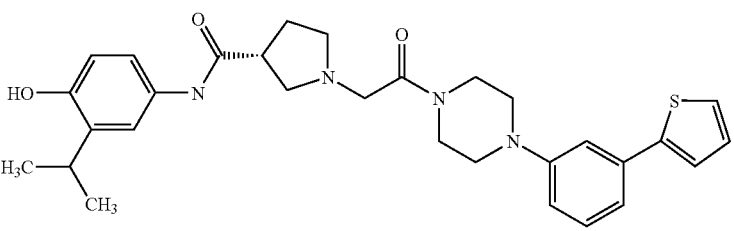 | 533.3 | 4.41 |
| 202 | 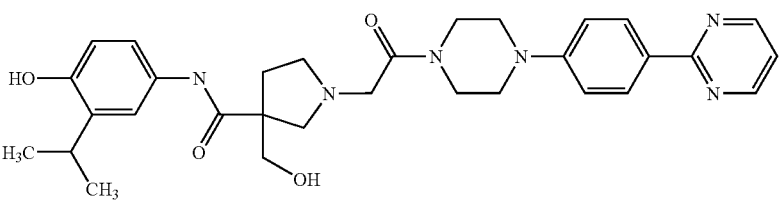 | | |
| 203 | 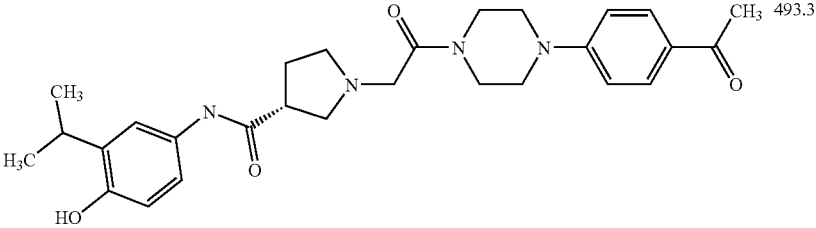 | 493.3 | 3.44 |
| 204 | 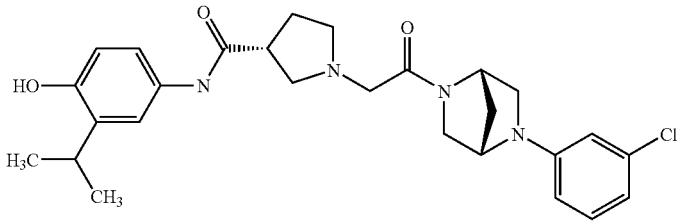 | 497.3 | 4.15 |
| 205 | 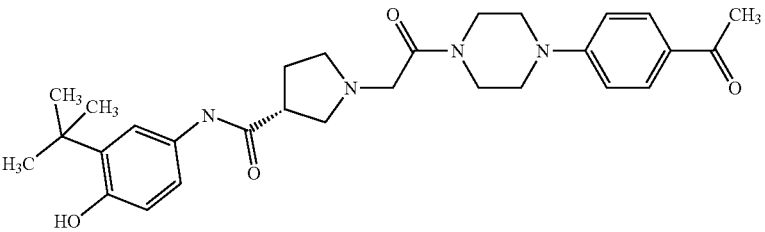 | | |
| 206 | 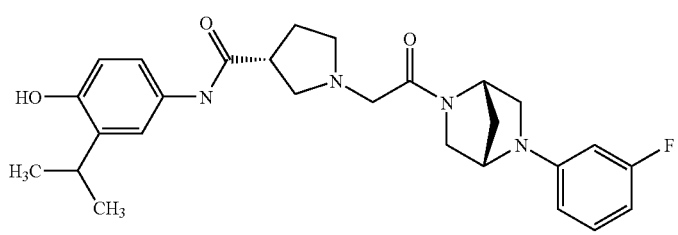 | 481.3 | 3.89 |

TABLE 5-continued
| EX | Compound | M⁺ + 1 | Retention Time (Minutes) |
|----|----------|--------|--------------------------|
| 207 | 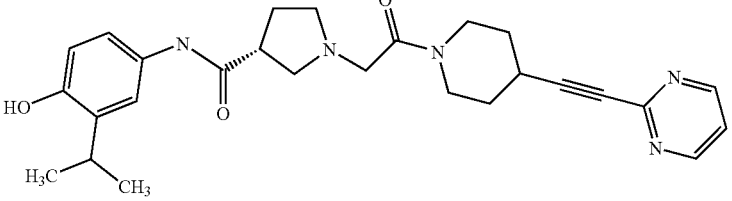 | 476.3 | 3.07 |
| 208 | 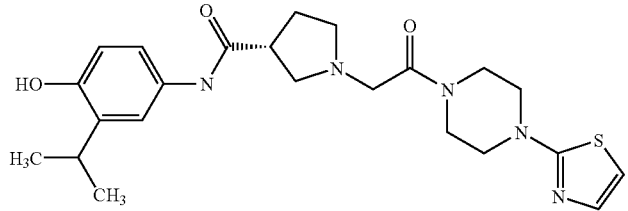 | 458.2 | 3.21 |
| 209 | 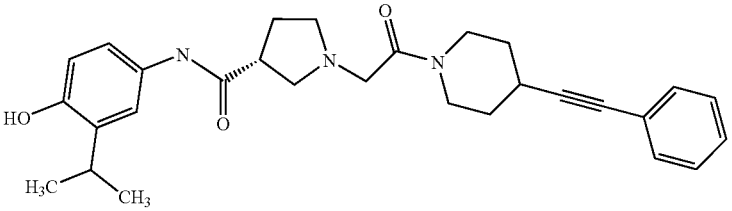 | 474.3 | 4.3 |
| 210 | 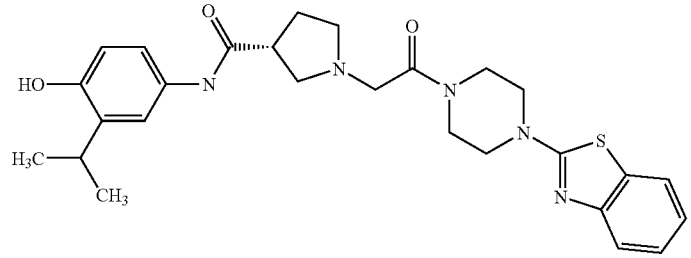 | 508.3 | 3.57 |
| 211 | 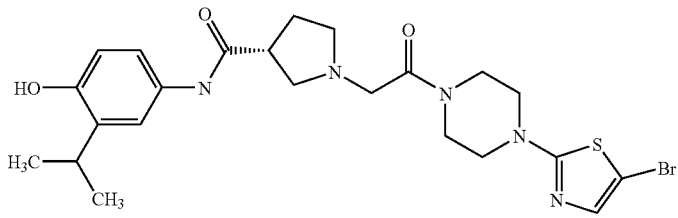 | 536 | 3.32 |

EXAMPLES 212-228

The compounds in Table 6 were prepared utilizing Scheme 8 and Preparative example 33-38 substituting the appropriate hydroxyaniline as described in preparative examples 3, 4 and 6 for 4-amino-2-cyclopropyl-phenol in preparative example 38 and substituting the appropriate piperazine derivative as described herein for the deprotected (de-Boc) piperazine compound 106a. Hydroxyanilines not described are commercially available. piperazine derivative not described are either commercially available or prepared by methods similar to procedures described herein and known in the art.

TABLE 6

| EX | Compound | M⁺ + 1 | Retention Time (Minutes) |
|---|---|---|---|
| 212 | | 581.3 | 3.51 |
| 213 | | 545.3 | 3.69 |
| 214 | | 545.3 | 3.55 |
| 215 | | 545.3 | 3.69 |
| 216 | | 527.3 | 3.57 |

TABLE 6-continued

| EX | Compound | M+ + 1 | Retention Time (Minutes) |
|---|---|---|---|
| 217 | | | |
| 218 | | 517.2 | 3.34 |
| 219 | | 481.3 | 2.47 |
| 220 | | 528.4 | 2.82 |
| 221 | | 469.1 | 2.6 |
| 222 | | 465.2 | 0.7 |
| 223 | | | |

TABLE 6-continued

| EX | Compound | M+ + 1 | Retention Time (Minutes) |
|---|---|---|---|
| 224 | 3,5-dichloro-4-hydroxyphenyl pyrrolidine carboxamide linked via CH₂-C(O)- to piperazine-(4-acetylphenyl) | | |
| 225 | 4-hydroxy-2-chlorophenyl pyrrolidine carboxamide linked via CH₂-C(O)- to piperazine-(4-acetylphenyl) | | |
| 226 | 4-hydroxy-3-carbamoylphenyl pyrrolidine carboxamide linked via CH₂-C(O)- to piperazine-(4-acetylphenyl) | | |
| 227 | 2-fluoro-4-hydroxyphenyl pyrrolidine carboxamide linked via CH₂-C(O)- to piperazine-(4-acetylphenyl) | 469.3 | 2.91 |
| 228 | 2-fluoro-4-hydroxyphenyl pyrrolidine carboxamide linked via CH₂-C(O)- to 4-phenylpiperidine | 427.2 | 2.51 |

Assays

Coupled ERK2 Assay:

Activity of compounds against inactive ERK2 was tested in a coupled MEK1/ERK2 IMAP assay as follows: Compounds were diluted to 25× final test concentration in 100% DMSO. 14 µl of kinase buffer (10 mM Tris.HCl pH 7.2, 10 mM $MgCl_2$, 0.01% Tween-20, 1 mM DTT) containing 0.4 ng unphosphorylated Mouse ERK2 protein was added to each well of a black 384-well assay plate. 1 µl of 25× compound was added to each well and incubated at room temperature for 30 minutes to allow an opportunity for the compound to bind to the inactive enzyme. DMSO concentration during initial incubation is 6.7%. ERK2 activity was determined to be insensitive to DMSO concentrations up to 20%. ERK2 was then activated and it's kinase activity measured by the addition of 10 µl kinase buffer with the following components (final concentration per reaction): 2 ng active (phosphorylated) human MEK1 protein and 4 µM (total) ERK2 IMAP substrate peptides (3.9 µM unlabeled IPTTPITTTYFFFK-$CONH_2$ and 100 nM IPTTPITTTYFFFK(5-carboxyfluorescein)-$CONH_2$) and 30 µM ATP. DMSO concentration during ERK activation was 4%. After one hour, reactions were terminated by addition of 60 µl IMAP detections beads in binding buffer (Molecular Devices). Binding was allowed to equilibrate for 30 minutes before reading the plate on an LJL Analyst Fluorescence Polarization plate reader. Compound inhibition was calculated relative to DMSO and fully inhibited standards. Active compounds were reconfirmed in an independent assay.

Active ERK2 Assay:

Activated ERK2 activity was also determined in the IMAP assay format using the procedure outlined above. 1 µl of 25× compound was added to 14 µl of kinase buffer containing 0.25 ng fully phosphorylated, active Mouse ERK2 protein. Following a 30 minute incubation, the reactions were initiated by addition of 10 µl of kinase buffer containing 1 µM ERK2 IMAP substrate peptide (0.9 µM unlabeled IPTTPITTTY-FFFK-$CONH_2$ and 100 nM IPTTPITTTYFFFK(5-carboxyfluorescein)-$CONH_2$) and 30 µM ATP. Reactions proceeded for 30 minutes before termination by addition of 60 μl IMAP detection beads in binding buffer. Plates were read as above after 30 minute binding equilibration. Active compounds were reconfirmed in an independent assay.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlaid onto growth medium solidified with 0.6% agarose containing the same concentration of ERK1 and ERK2 inhibitor as the top layer. After the top layer is solidified, plates can be incubated for 10-16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

The final compounds of Examples 1-10, 12-14, 18-65, 67-76, 78-98, 100-102, 104-105, 107, 110, 112-114, 117-128, 130-131, 133, 134-135, 138, 140, 141, 144, 147, 148, 170, 183, 188, 189, 196-223, and 225-228 had an AERK2 $IC_{50}$ in the range of 18 to >20,000 nM.

The final compounds of Examples 1-10, 14, 18-65, 67, 72-75, 78-80, 82-84, 86-95, 97, 101, 102, 104, 107, 110, 117-131, 133-135, 138, 140, 141, 144, 170, 183, 188, 189, 196-223, 225, and 228 had an AERK2 $IC_{50}$ in the range of 18 to 100,000 nM.

The AERK2 $IC_{50}$ for the final compounds of Examples 1, 19, 20, 23, 25, 119, 196, 197, and 212 were: 76 nM for Example 1, 34 nM for Example 19, 44 nM for Example 20, 57 nM for Example 23, 18 nM for Example 25, 39 nM for Example 119, 38 nM for Example 196, 40 nM for Example 197, and 53 nM for Example 212.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20th Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of formula 1.0:

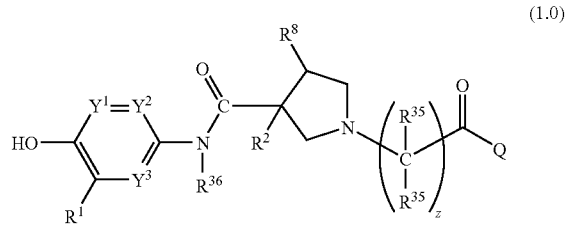

(1.0)

or the pharmaceutically acceptable salts thereof, wherein:

$Y^1$, $Y^2$, and $Y^3$ are each independently selected from the group consisting of: —CH= and —$CR^9$=;

z is 1;

Q is a substituent selected from the group consisting of:

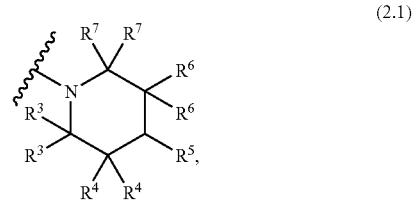

(2.1)

-continued

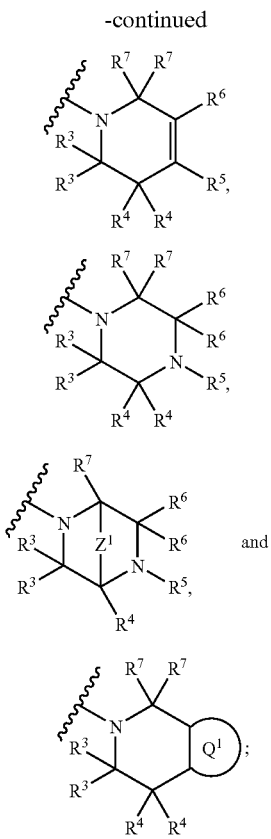

$Q^1$ is phenyl;

$Z^1$ is —$CH_2$—;

$R^1$ is selected from the group consisting of: methyl, i-propyl, t-butyl, cyclopropyl, o-F-phenyl, m-F-phenyl, p-F-phenyl, Cl, Br, F, phenyl, —$CF_3$, —$C(O)NH_2$, —$CH_2OH$, H, pyridyl, and pyrazolyl;

$R^2$ is H, ethyl, ethynyl, propynyl, —$CH_2$—$CH$=$CH_2$, —$OCH_3$, —$CH_2OCH_3$, —$CH_2OH$, —$CH_2F$, —$CF_3$, —$CH_2NH_2$, —$NH_2$, —$CH_3$, —$CH_2CN$, —$CH_2OC_2H_5$, —$(CH_2)_3OCH_3$, and —$CH_2$-triazolyl;

each $R^3$, $R^4$, $R^6$ and $R^7$ is independently selected from the group consisting of: H and $C_1$ to $C_6$ alkyl;

$R^5$ is selected from the group consisting of:

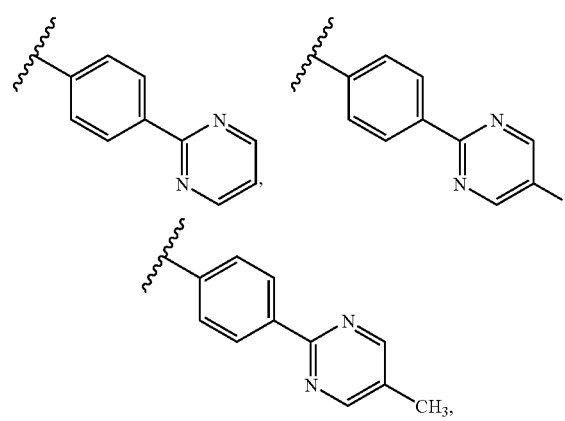

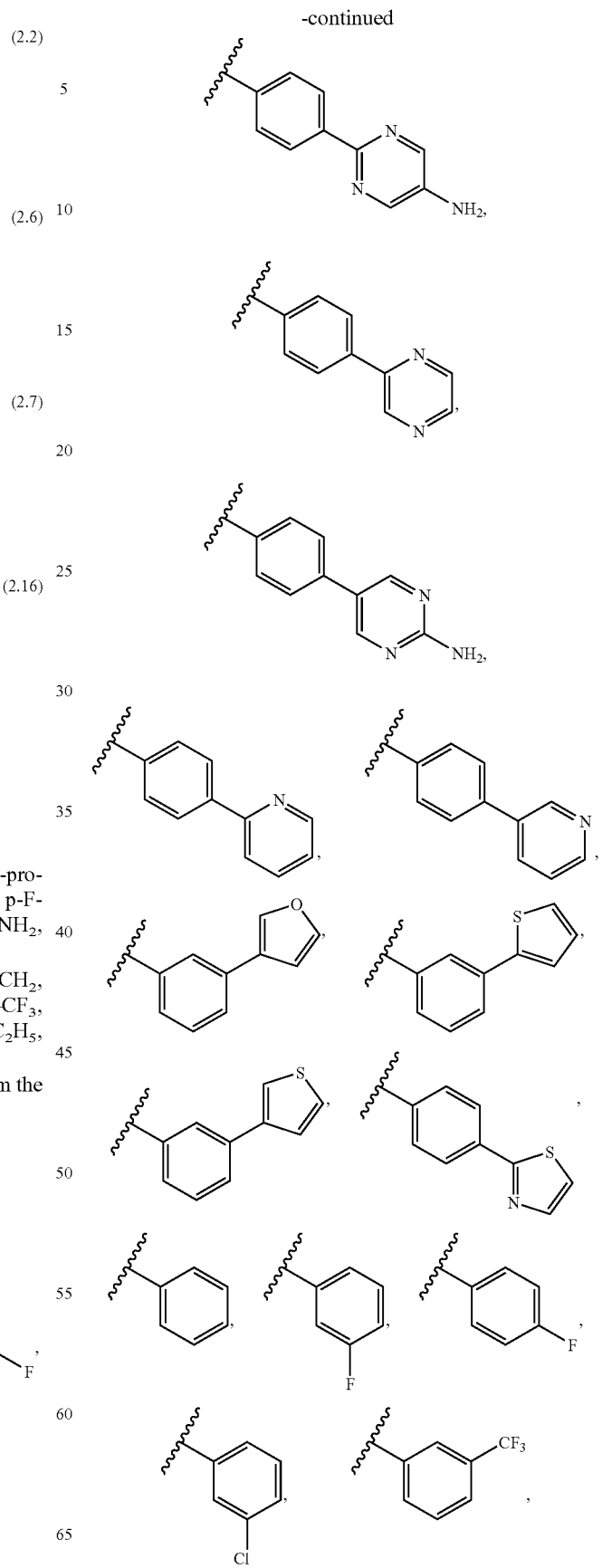

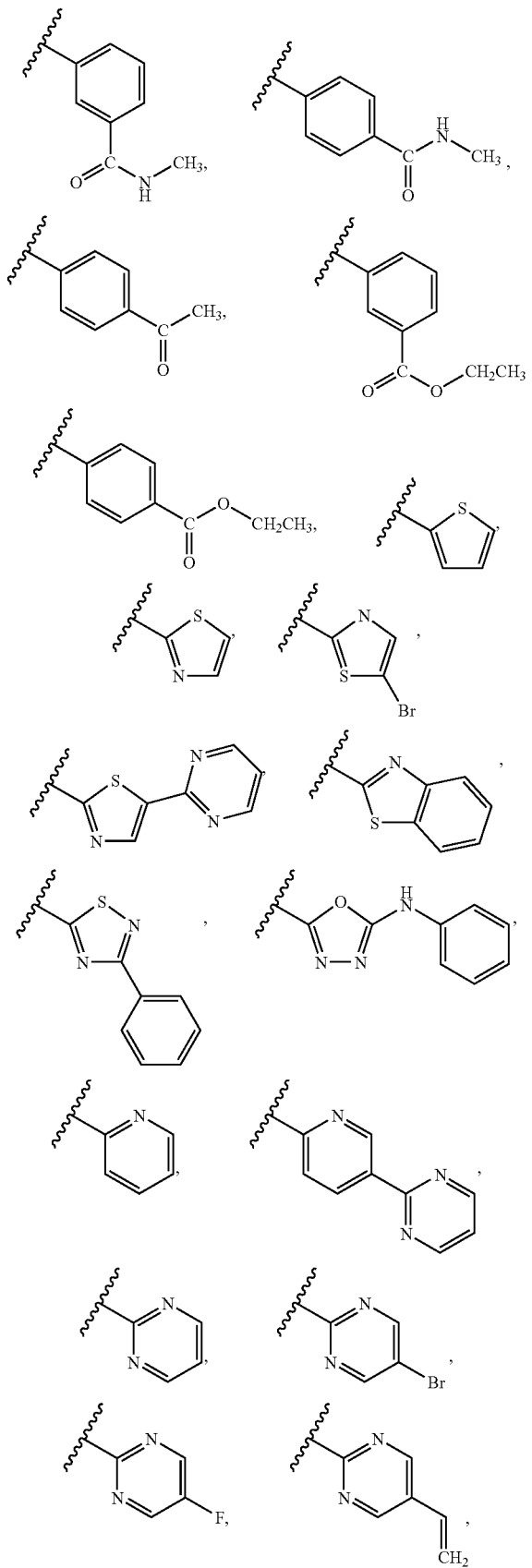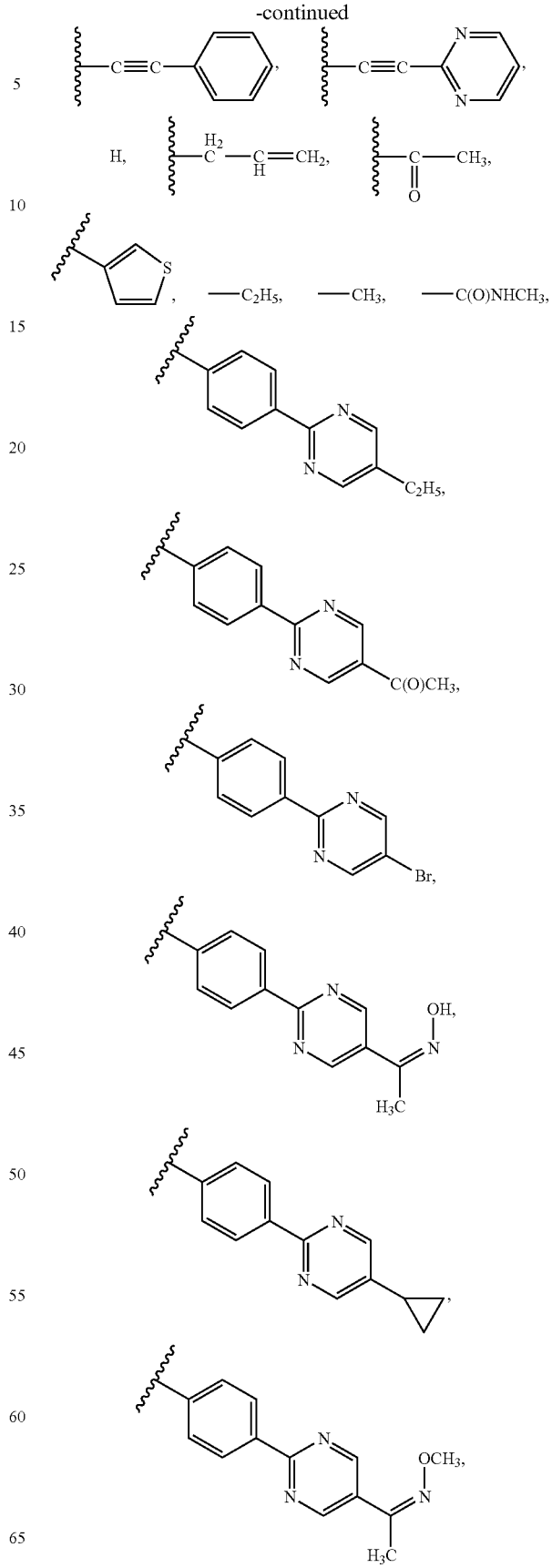

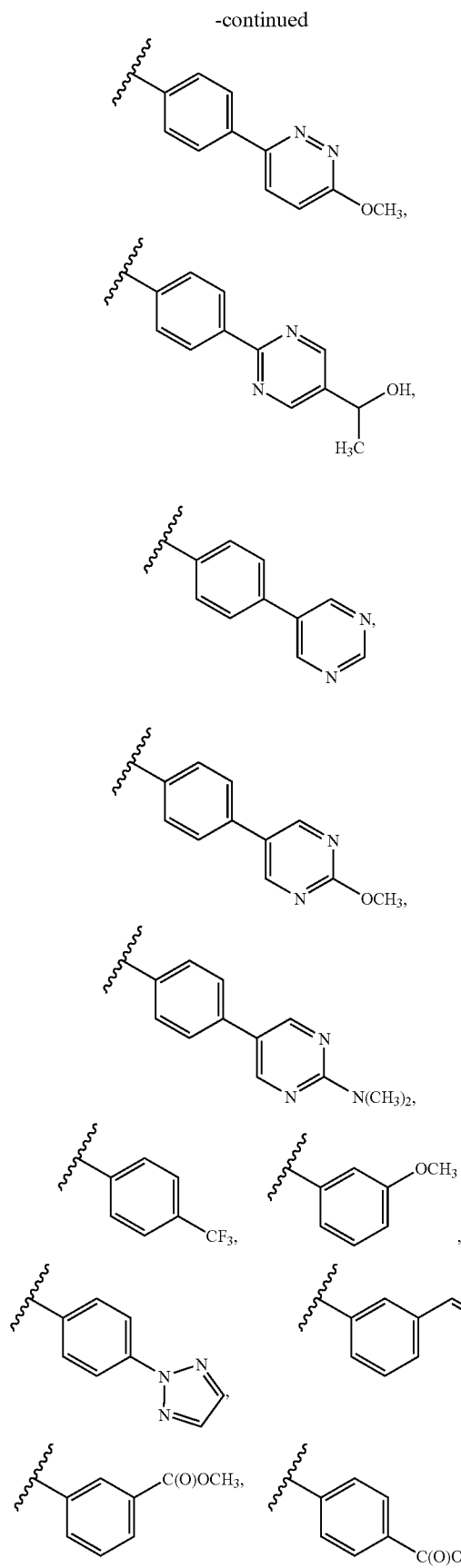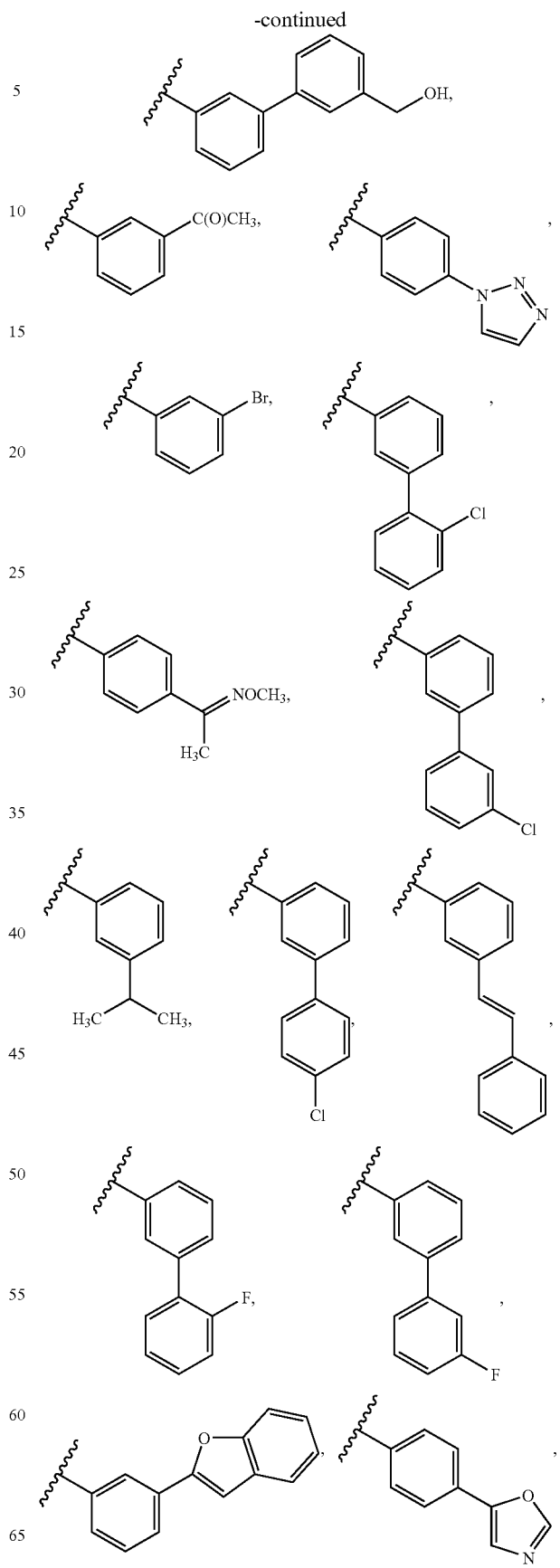

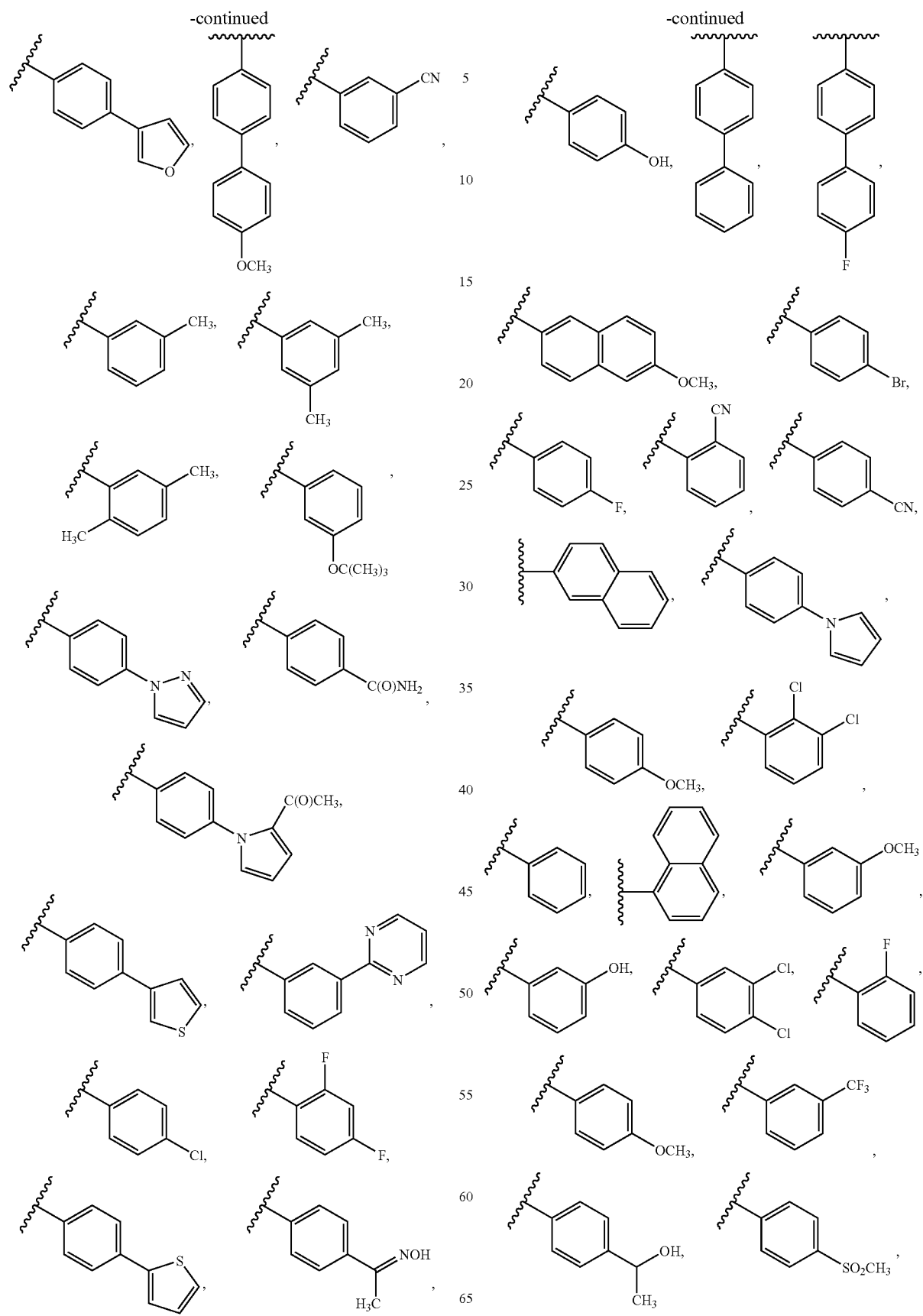

-continued
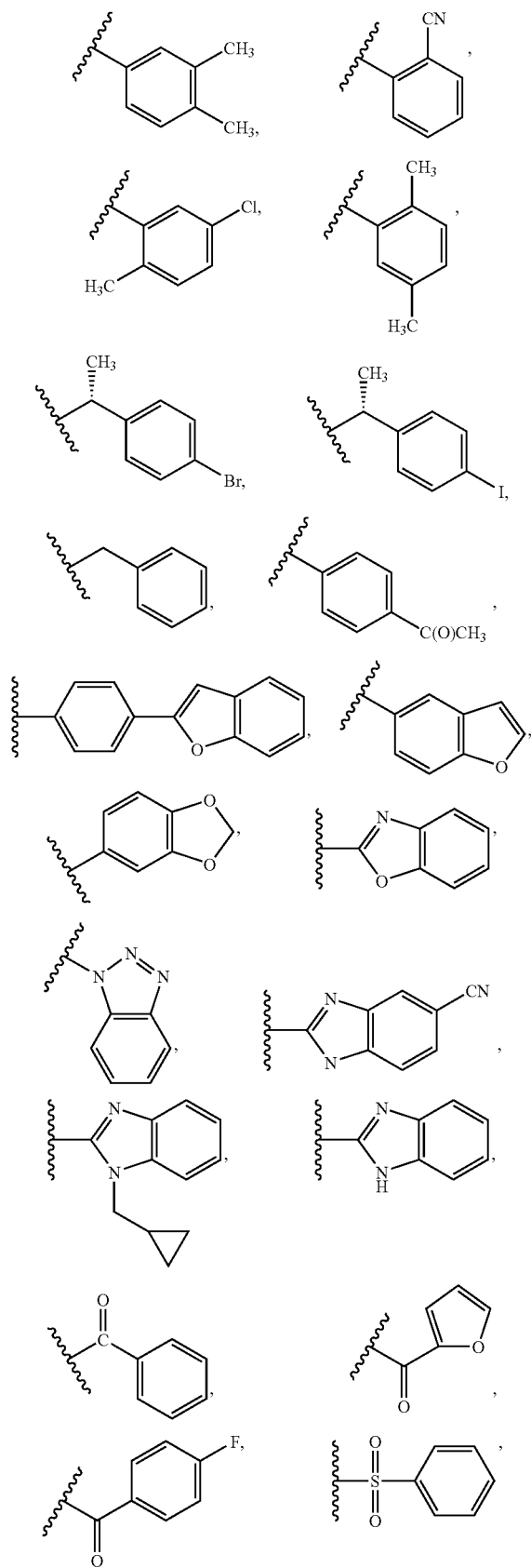
-continued
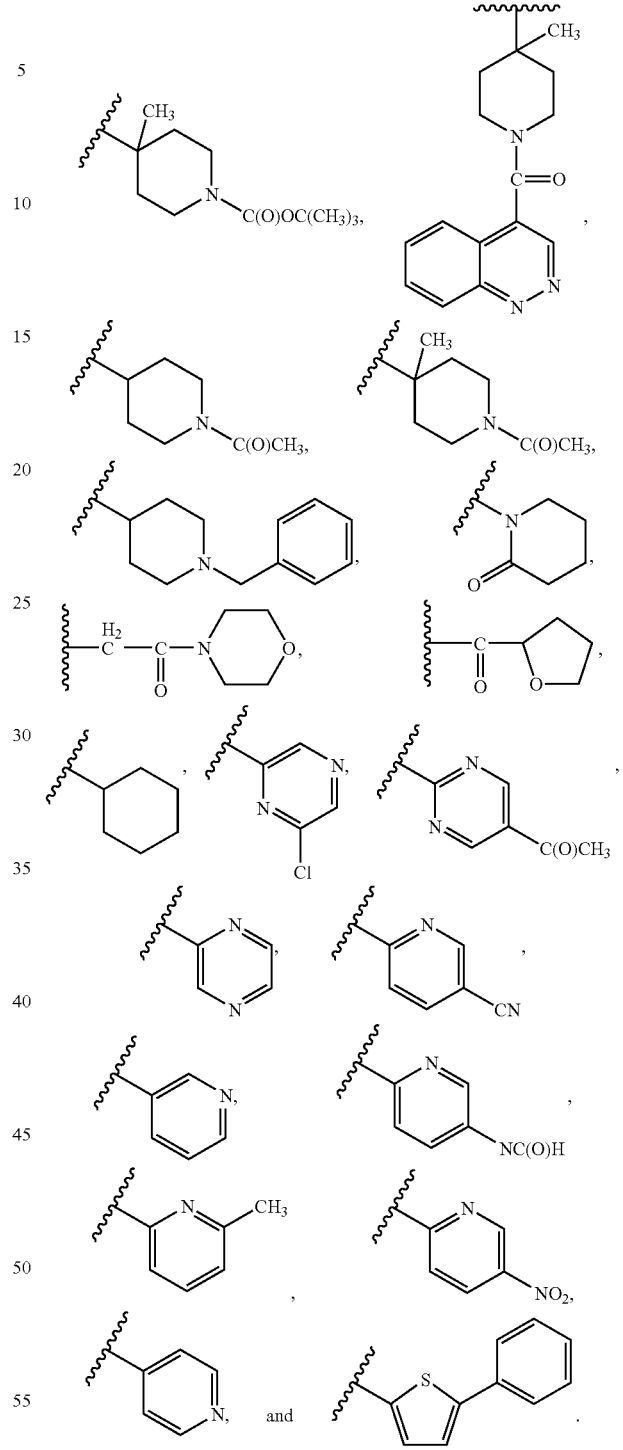
$R^8$ is H;
each $R^9$ is independently selected from the group consisting of: halogen, and $R^{10}$ wherein said $R^{10}$ is $C_1$ to $C_6$ alkyl;
each $R^{35}$ is independently selected from the group consisting of: H and $C_1$ to $C_6$ alkyl; and
$R^{36}$ is selected from the group consisting of: H and $C_1$ to $C_6$ alkyl.

2. A compound of formula 1.0:

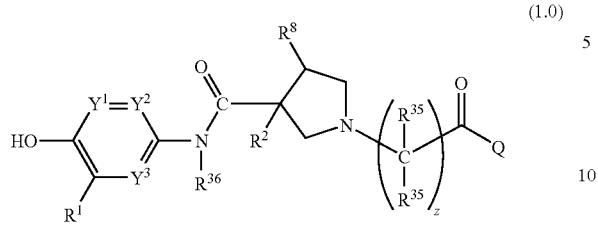
(1.0)

or the pharmaceutically acceptable salts thereof, wherein:
$Y^1$, $Y^2$, and $Y^3$ are each —CH═;
Z is 1;
Q is a substituent selected from the group consisting of:

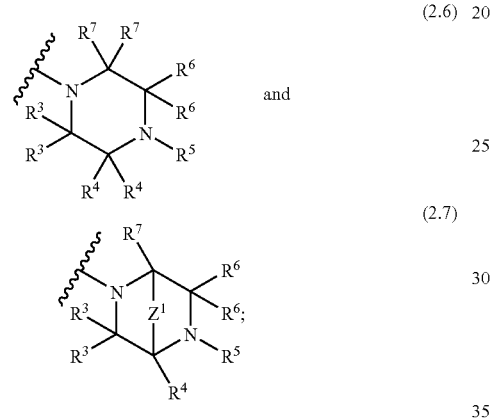

$Z^1$ is —CH$_2$—;
$R^1$ is selected from the group consisting of: methyl, i-propyl, t-butyl, cyclopropyl, o-F-phenyl, m-F-phenyl, p-F-phenyl, Cl, Br, F, phenyl, —CF$_3$, —C(O)NH$_2$, —CH$_2$OH, H, pyridyl, and pyrazolyl;
$R^2$ is H, ethyl, ethynyl, propynyl, —CH$_2$—CH═CH$_2$, —OCH$_3$, —CH$_2$OCH$_3$, —CH$_2$OH, —CH$_2$F, —CF$_3$, —CH$_2$NH$_2$, —NH$_2$, —CH$_3$, —CH$_2$CN, —CH$_2$OC$_2$H$_5$, —(CH$_2$)$_3$OCH$_3$, and —CH$_2$-triazolyl;
each $R^3$, $R^4$, $R^6$ and $R^7$ is independently selected from the group consisting of: H and $C_1$ to $C_6$ alkyl;
$R^5$ is selected from the group consisting of:

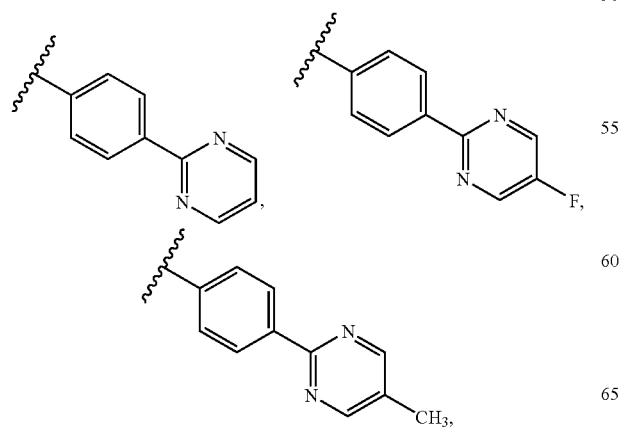

-continued

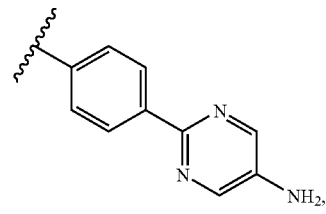

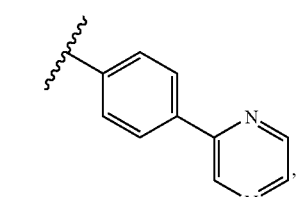

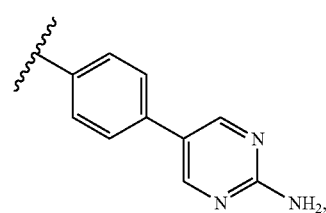

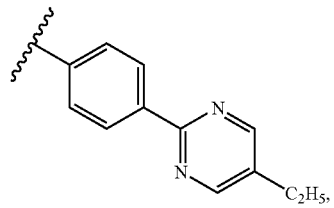

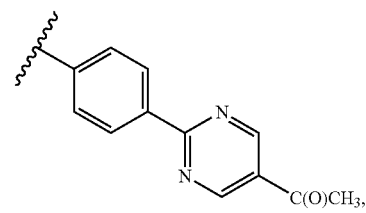

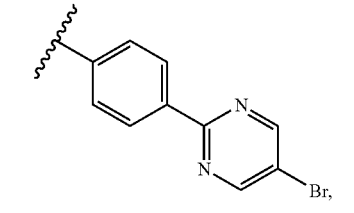

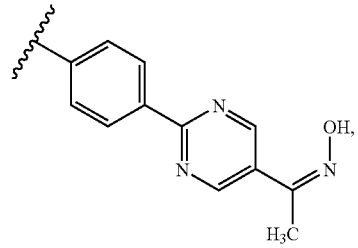

-continued

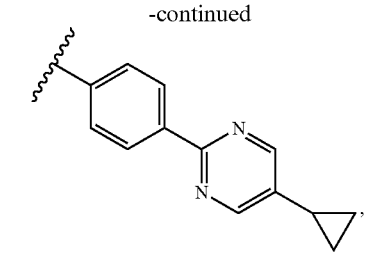

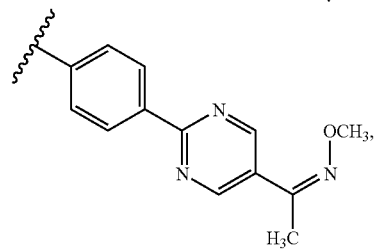

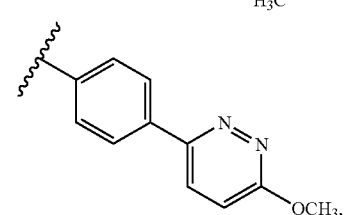

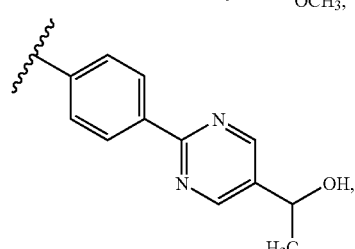

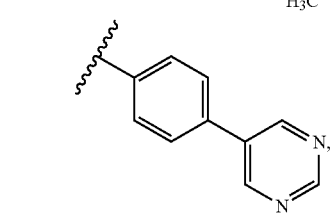

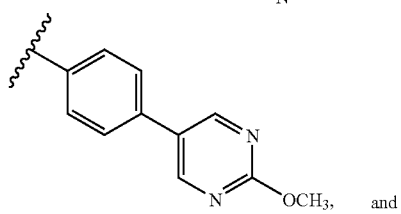

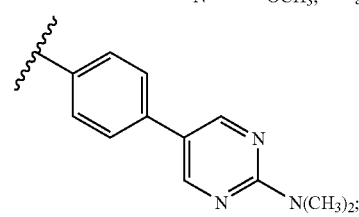

R⁸ is H;
each R³⁵ is independently selected from the group consisting of: H and $C_1$ to $C_6$ alkyl; and
R³⁶ is selected from the group consisting of: H and $C_1$ to $C_6$ alkyl.

3. The compound of claim 2 wherein Q is:

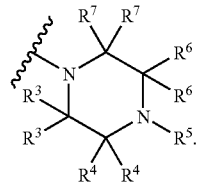
(2.6)

4. The compound of claim 3 wherein R⁵ is:

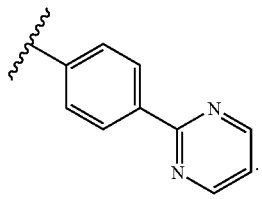

5. The compound of claim 2 wherein each R³⁵ is H.
6. The compound of claim 2 wherein each R³⁶ is H.
7. The compound of claim 2 wherein each R¹ is Cl.
8. The compound of claim 2 wherein each R¹ is —CF₃.
9. The compound of claim 2 wherein R¹ is selected from the group consisting of: o-F-phenyl, m-F-phenyl, p-F-phenyl.
10. The compound of claim 9 wherein R¹ is p-F-phenyl.
11. The compound of claim 2 wherein R¹ is cyclopropyl.
12. The compound of claim 2 wherein R² is H.
13. The compound of claim 2 wherein:
(a) Q is:

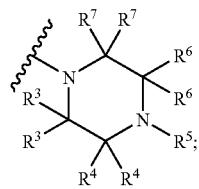
(2.6)

(b) R⁵ is:

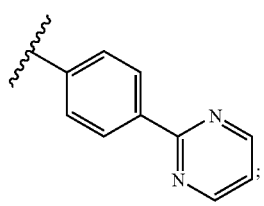

(c) each R³⁵ is H; and
(d) R³⁶ is H.
14. The compound of claim 13 wherein R² is H.
15. The compound of claim 14 wherein R¹ is Cl.
16. The compound of claim 14 wherein R¹ is —CF₃.
17. The compound of claim 14 wherein R¹ is selected from the group consisting of: o-F-phenyl, m-F-phenyl, p-F-phenyl.
18. The compound of claim 14 wherein R¹ is p-F-phenyl.
19. The compound of claim 14 wherein R¹ is cyclopropyl.
20. A pharmaceutical composition comprising at least one compound of claim 1 and a pharmaceutically acceptable carrier.
21. A pharmaceutical composition comprising at least one compound of claim 2 and a pharmaceutically acceptable carrier.

22. A compound selected from the group consisting of
| EX | Compound |
|---|---|
| 1 | 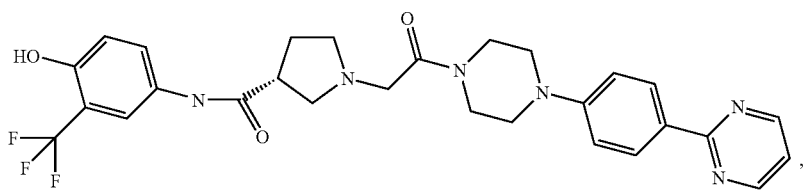 |
| 2 | 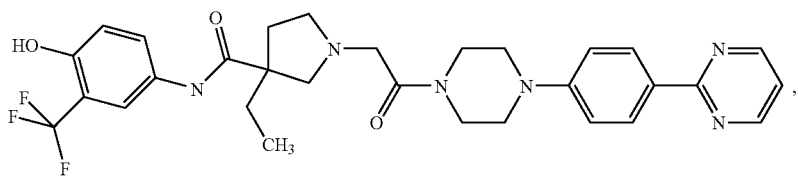 |
| 3 | 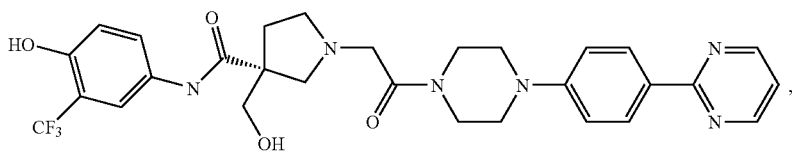 |
| 4 | 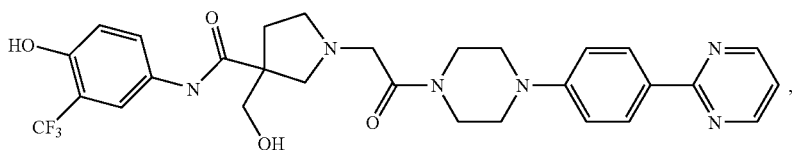 |
| 5 | 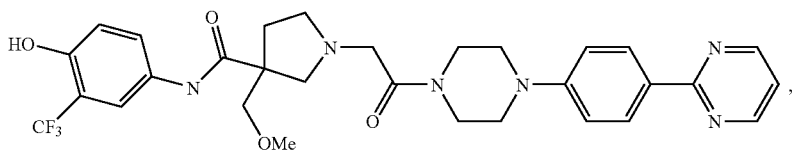 |
| 6 | 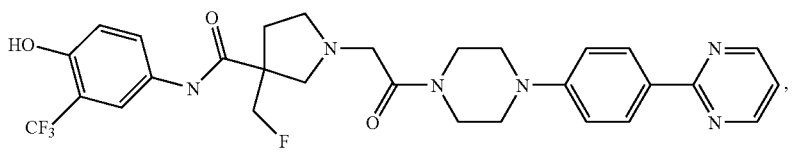 |
| 7 | 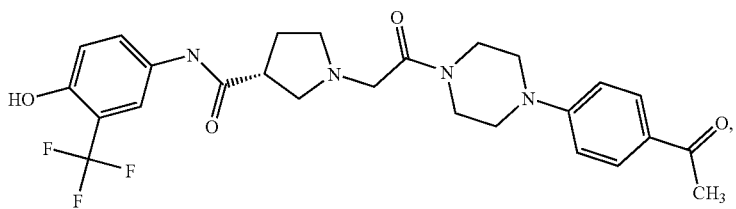 |
| 8 | 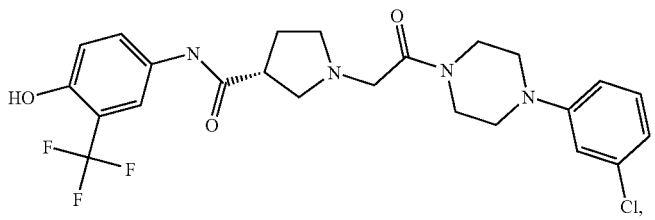 |

-continued
| EX | Compound |
|---|---|
| 9 | 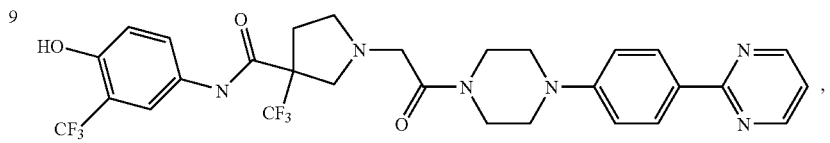 |
| 10 | 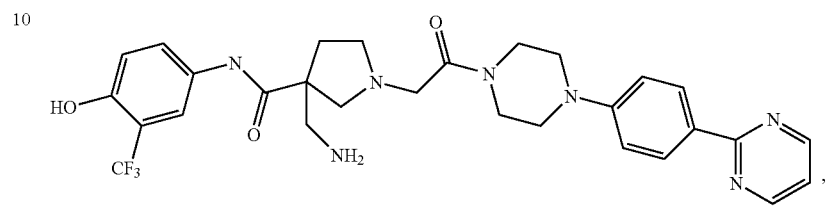 |
| 11 | 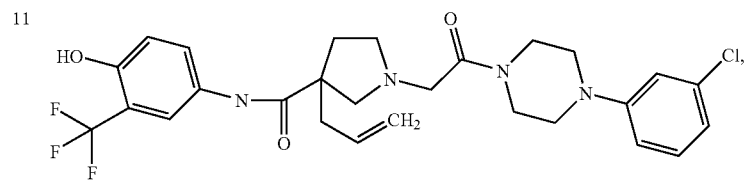 |
| 12 | 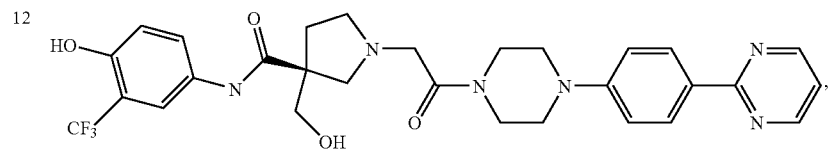 |
| 13 | 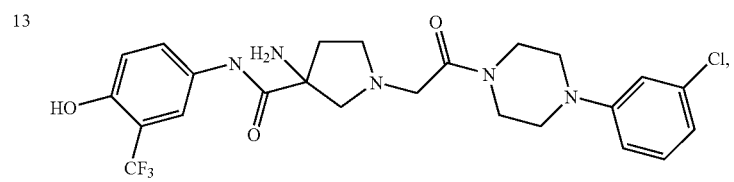 |
| 14 | 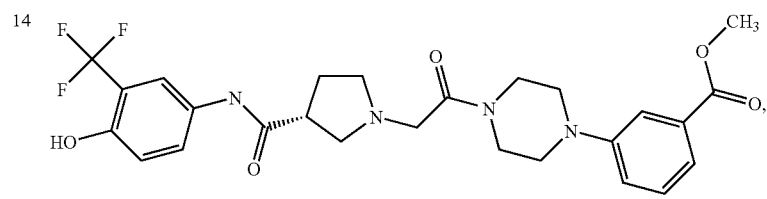 |
| 15 | 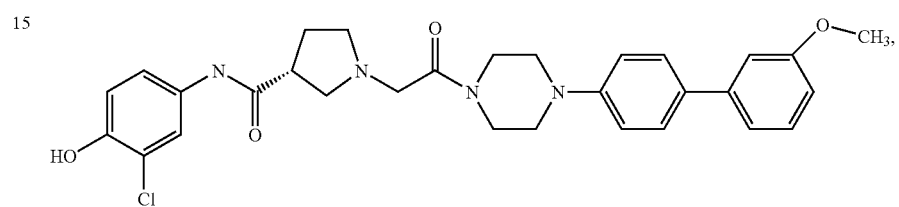 |
| 16 | 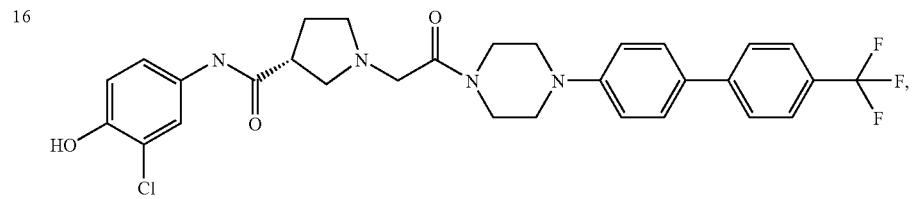 |

| EX | Compound |
|---|---|
| 17 | 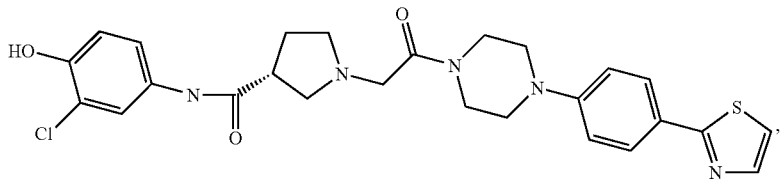 |
| 18 | 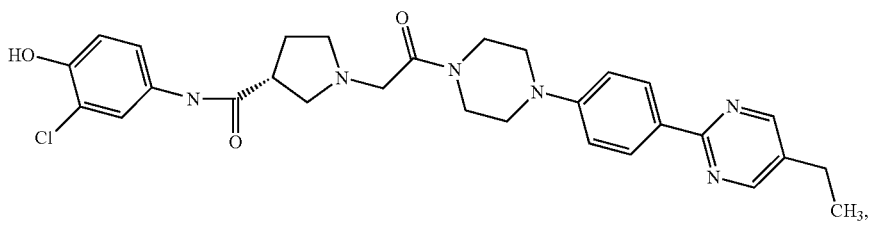 |
| 19 | 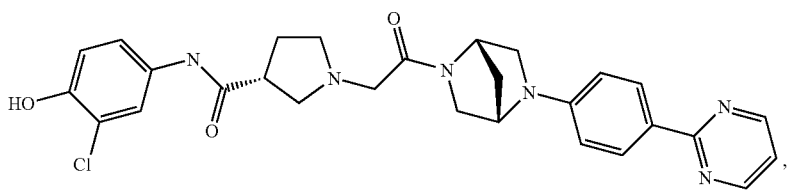 |
| 20 | 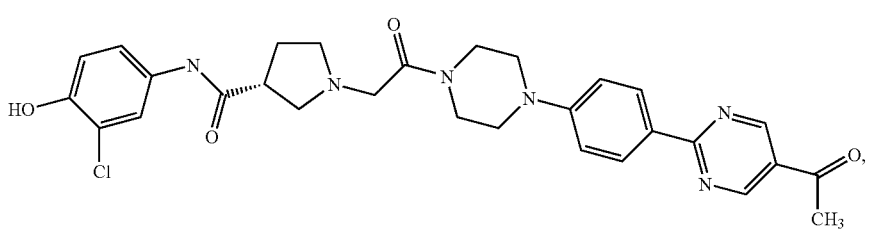 |
| 21 | 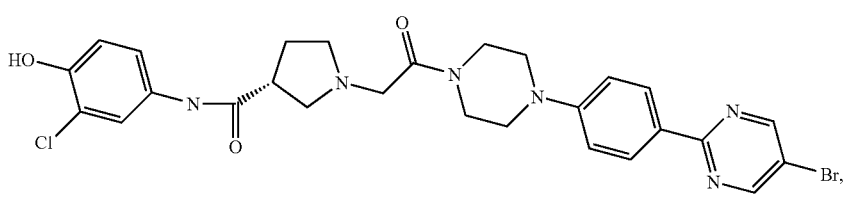 |
| 22 | 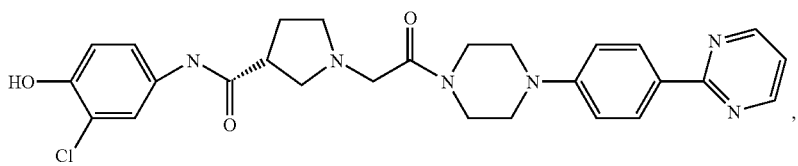 |
| 23 | 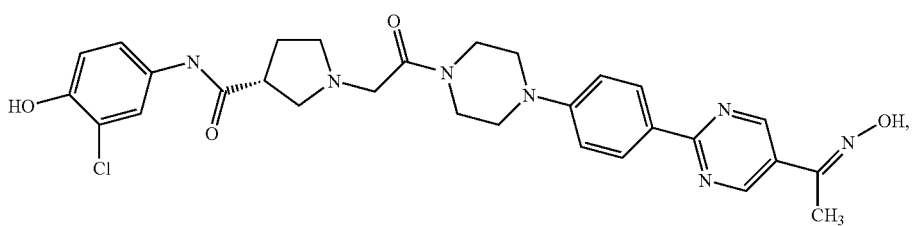 |

-continued
| EX | Compound |
|---|---|
| 24 | 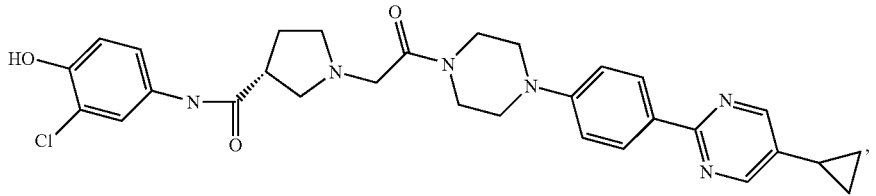 |
| 25 | 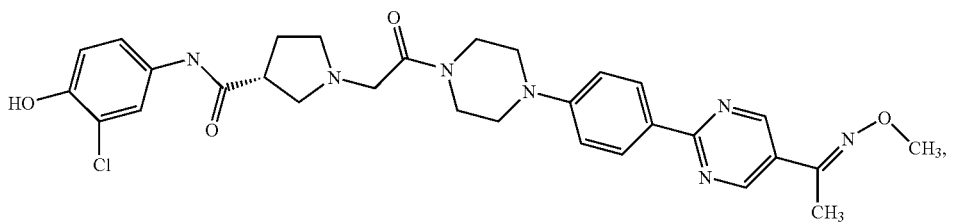 |
| 26 | 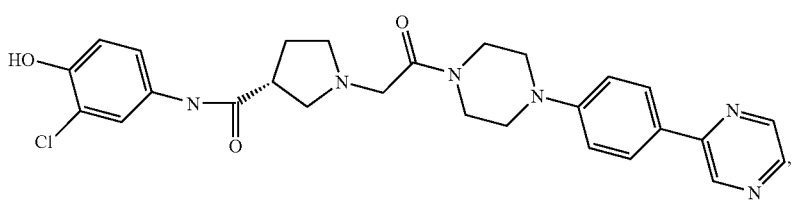 |
| 27 | 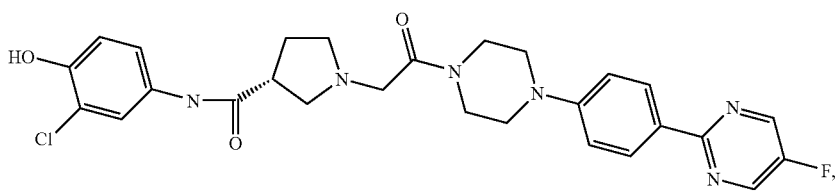 |
| 28 | 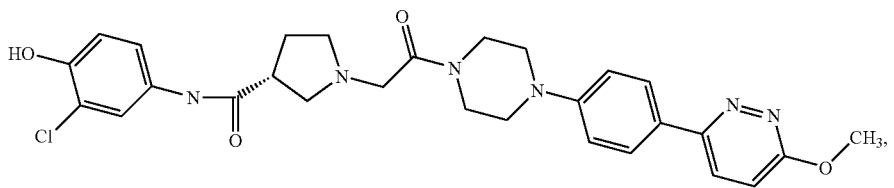 |
| 29 | 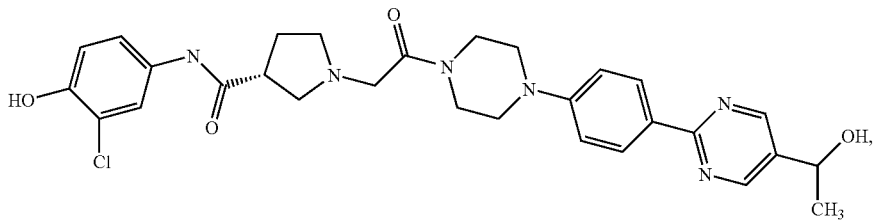 |
| 30 | 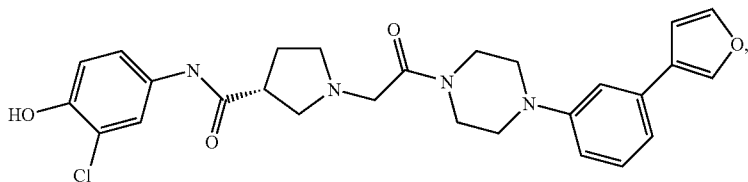 |

-continued
| EX | Compound |
|---|---|
| 31 | 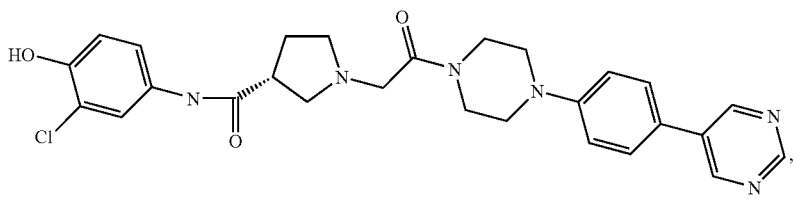 |
| 32 | 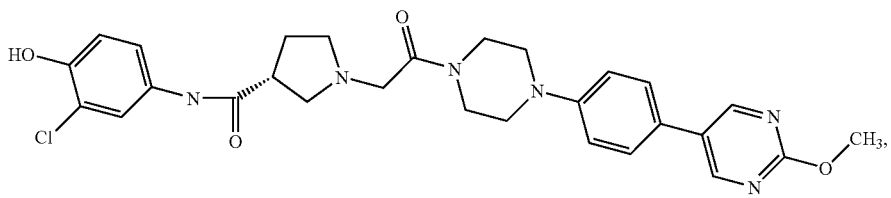 |
| 33 | 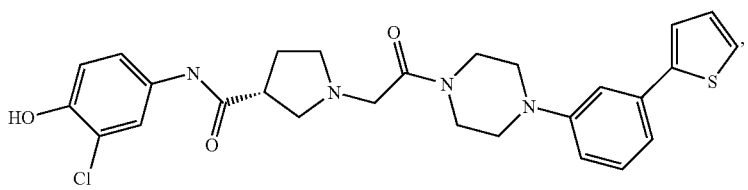 |
| 34 | 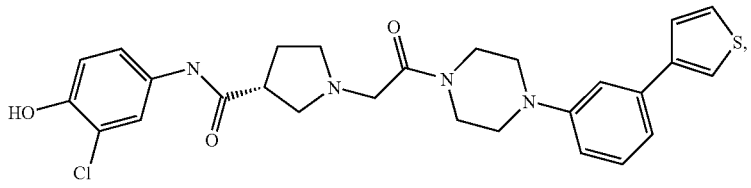 |
| 35 | 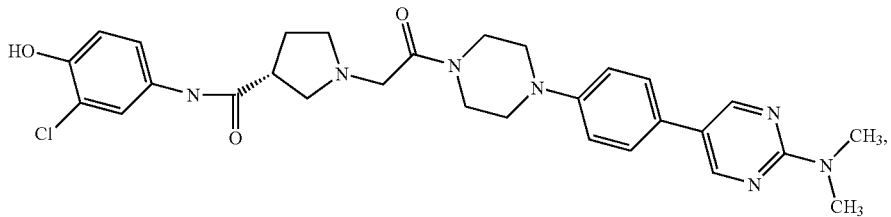 |
| 36 | 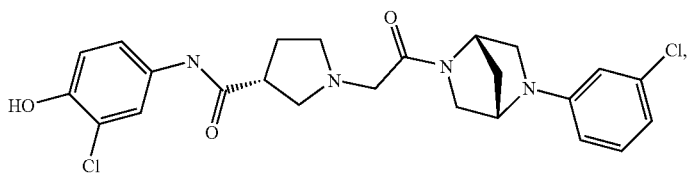 |
| 37 | 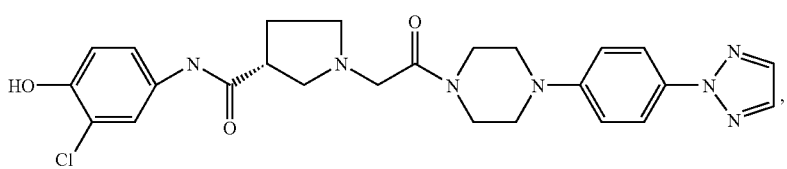 |
| 38 | 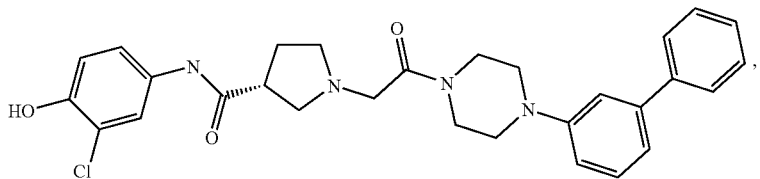 |

| EX | Compound |
|---|---|
| 39 | 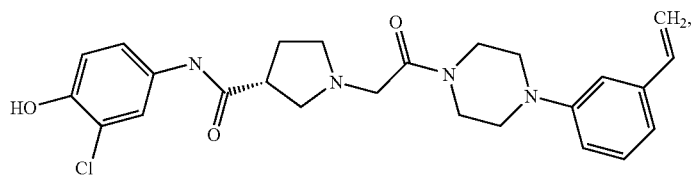 |
| 40 | 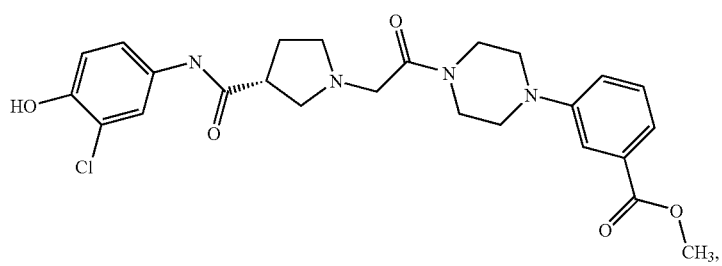 |
| 41 | 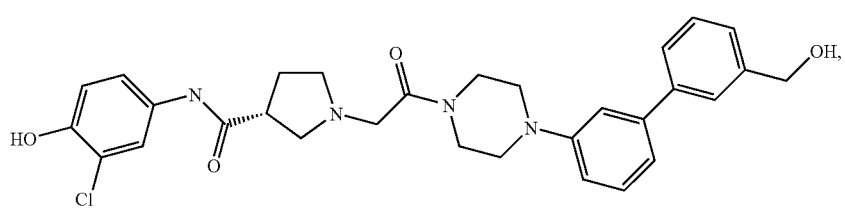 |
| 42 | 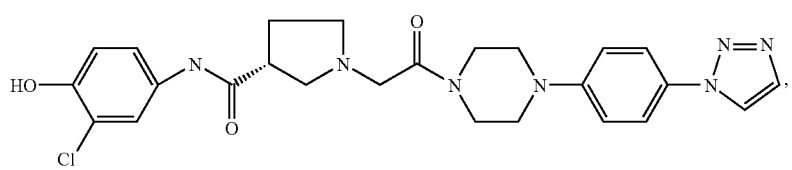 |
| 43 | 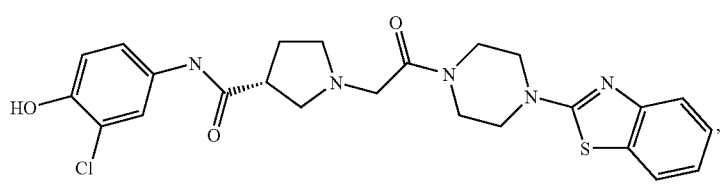 |
| 44 | 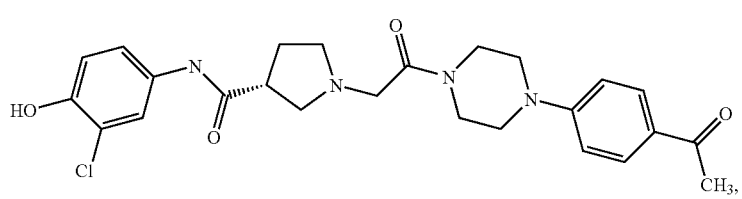 |
| 45 | 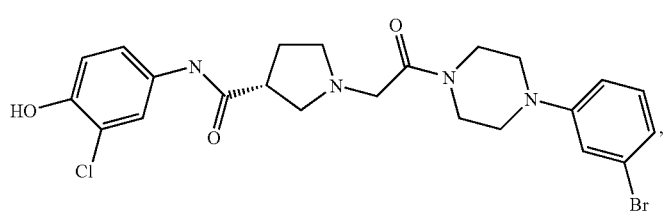 |

| EX | Compound |
|---|---|
| 46 | 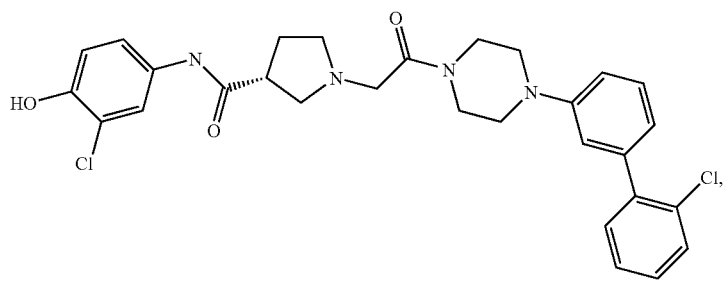 |
| 47 | 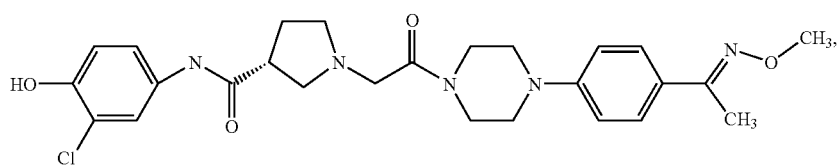 |
| 48 | 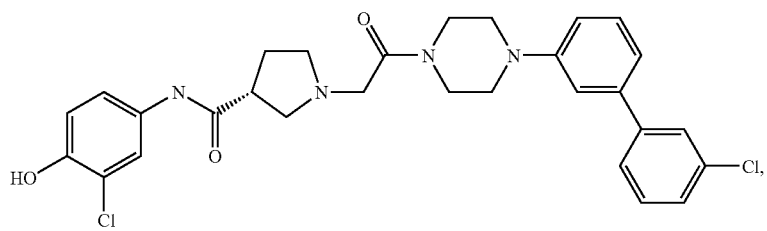 |
| 49 | 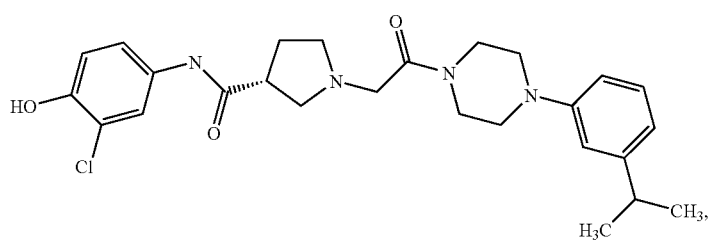 |
| 50 | 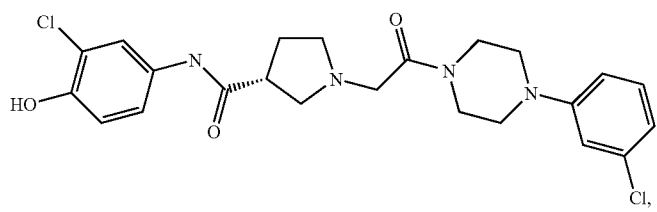 |
| 51 | 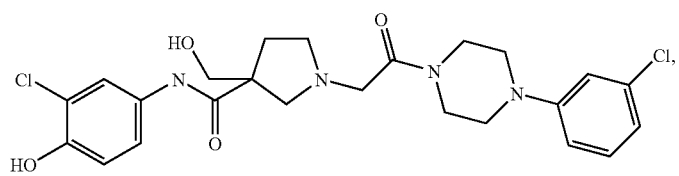 |
| 52 | 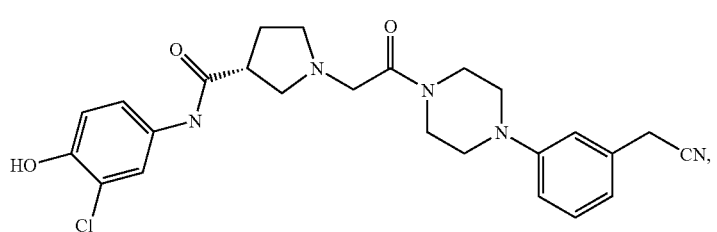 |

-continued
| EX | Compound |
|---|---|
| 53 | 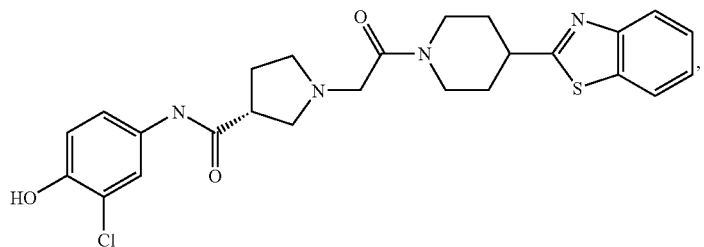 |
| 54 | 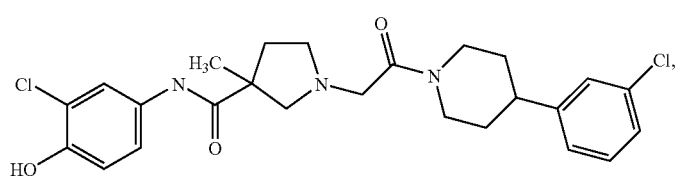 |
| 55 | 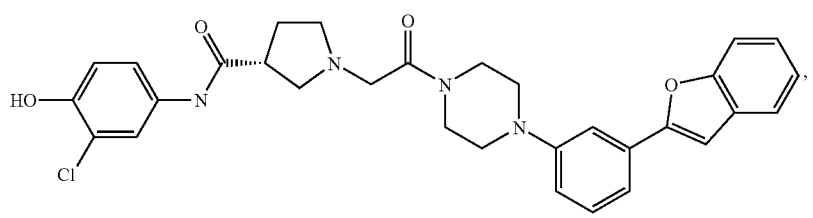 |
| 56 | 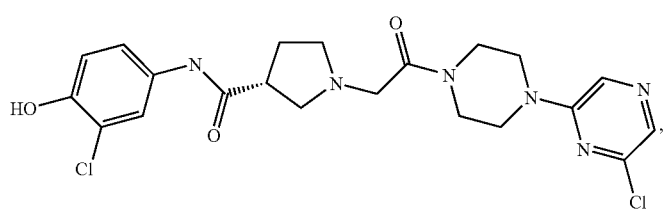 |
| 57 | 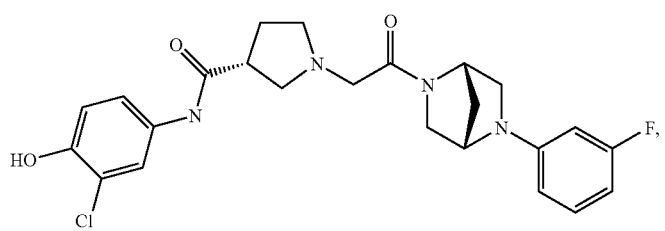 |
| 58 | 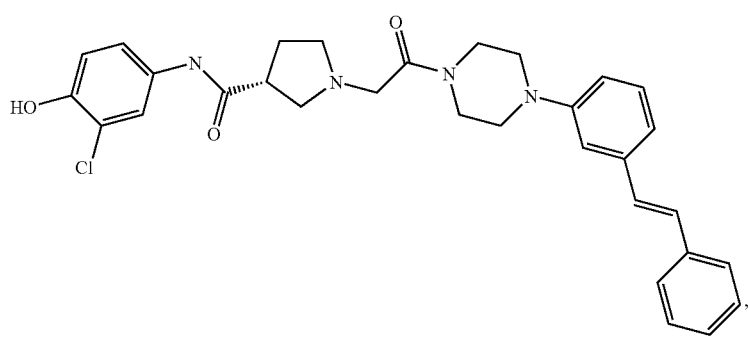 |

-continued
| EX | Compound |
|---|---|
| 59 | 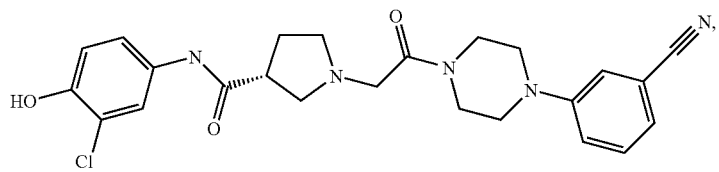 |
| 60 | 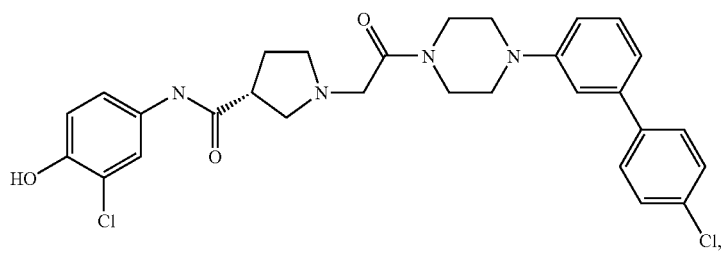 |
| 61 | 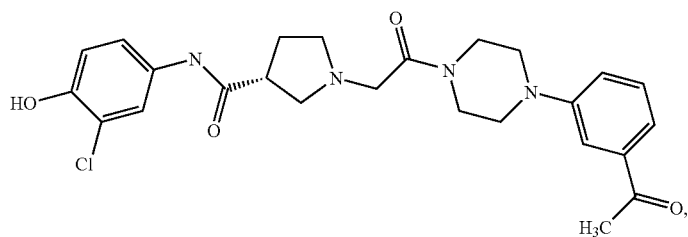 |
| 62 | 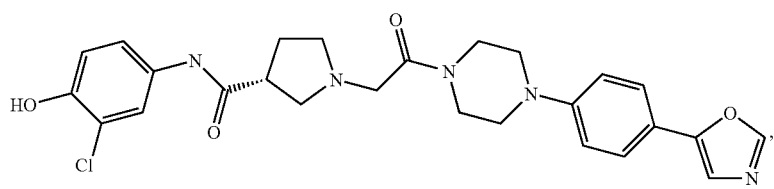 |
| 63 | 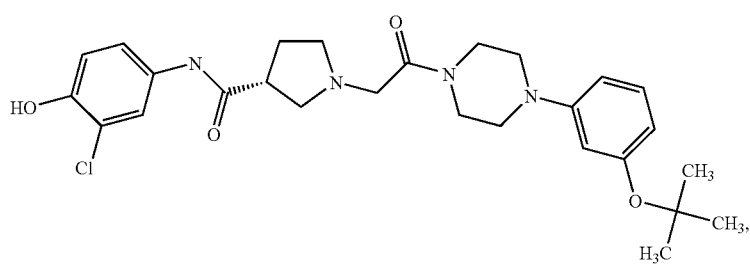 |
| 64 | 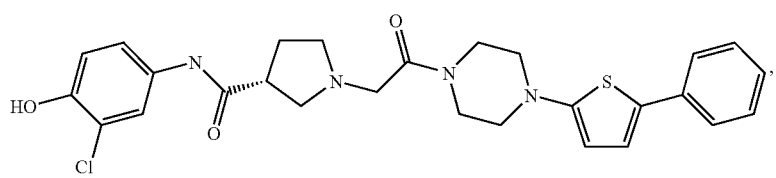 |
| 65 | 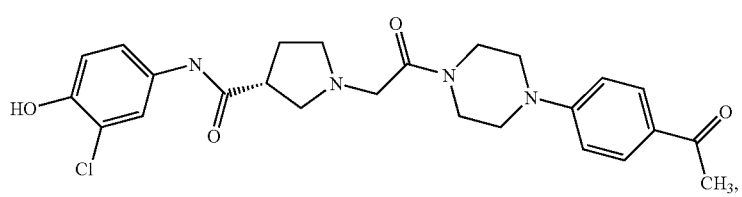 |

| EX | Compound |
|---|---|
| 66 | 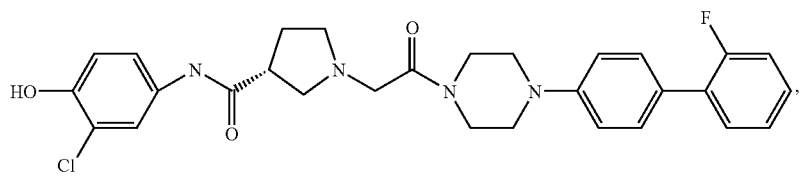 |
| 67 | 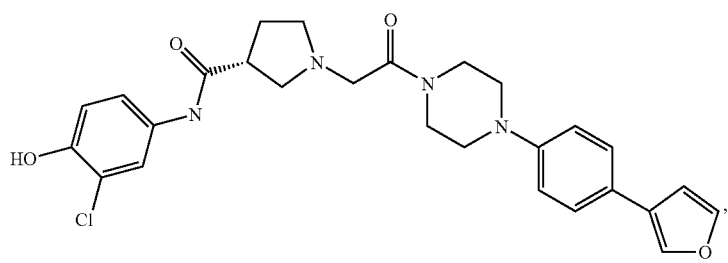 |
| 68 | 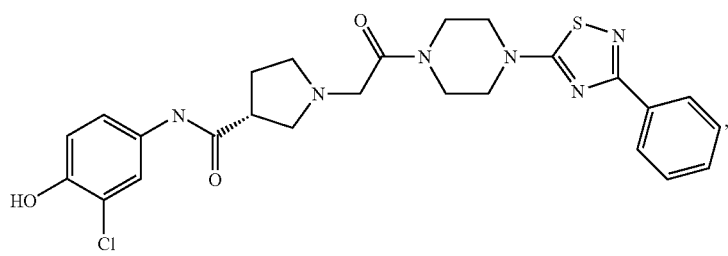 |
| 69 | 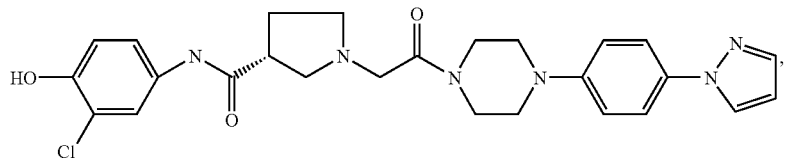 |
| 70 | 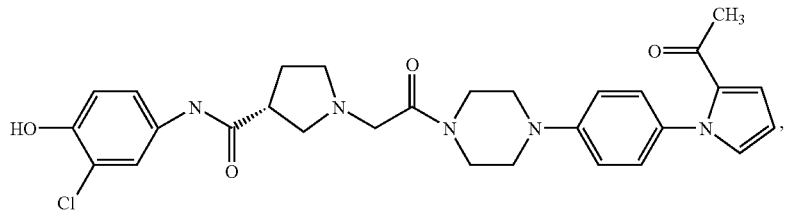 |
| 71 | 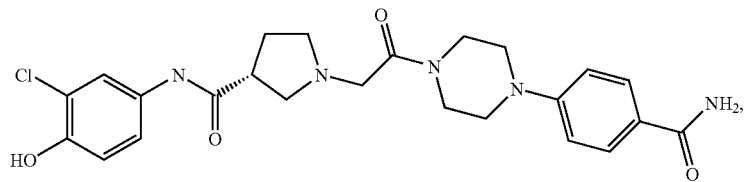 |
| 72 | 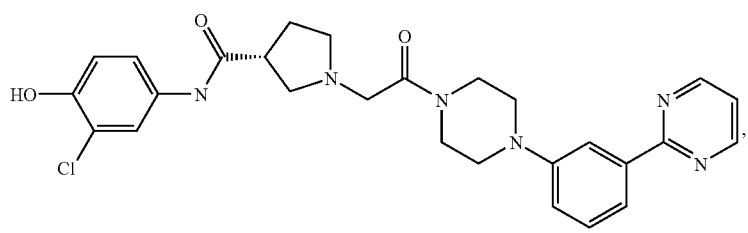 |

| EX | Compound |
|---|---|
| 73 | 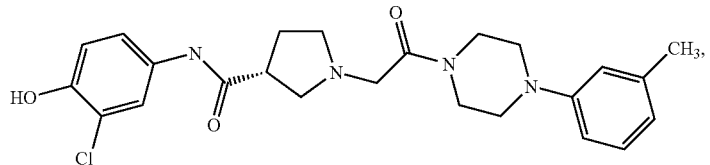 |
| 74 | 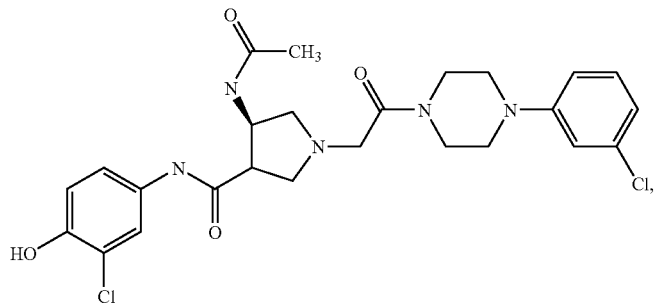 |
| 75 | 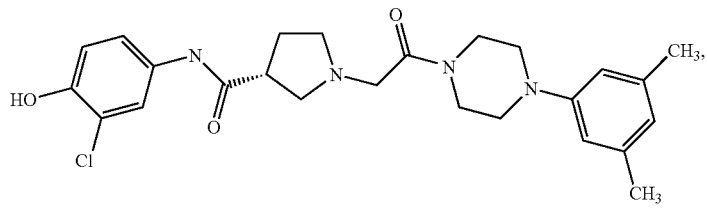 |
| 76 | 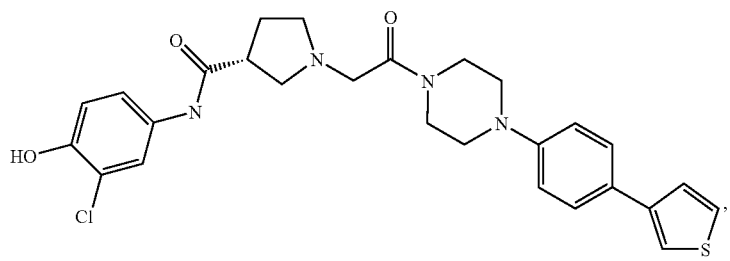 |
| 77 | 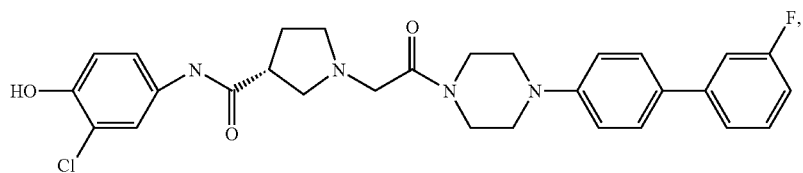 |
| 78 | 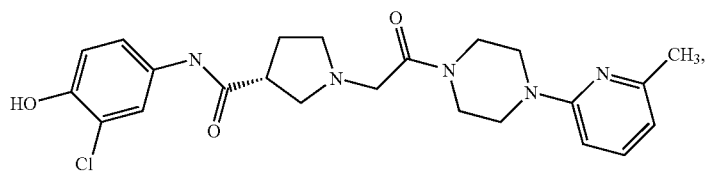 |
| 79 | 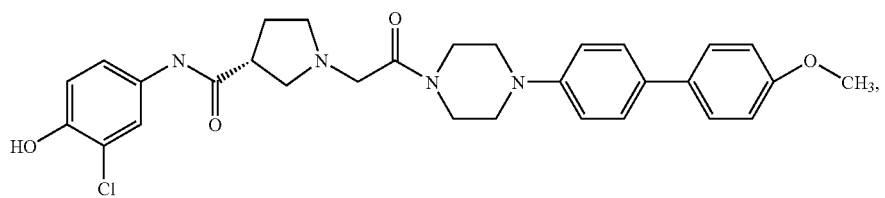 |

| EX | Compound |
|---|---|
| 80 | 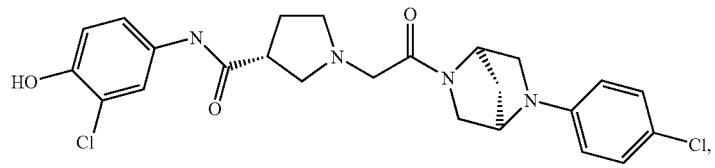 |
| 81 | 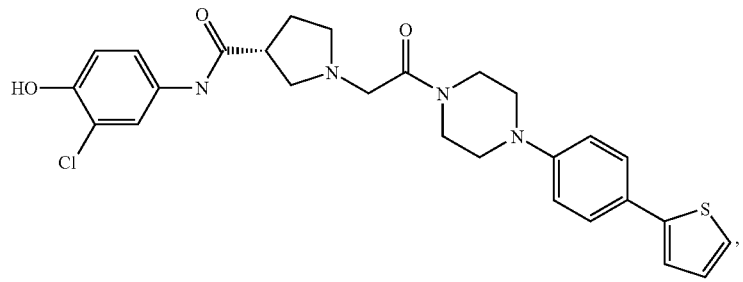 |
| 82 | 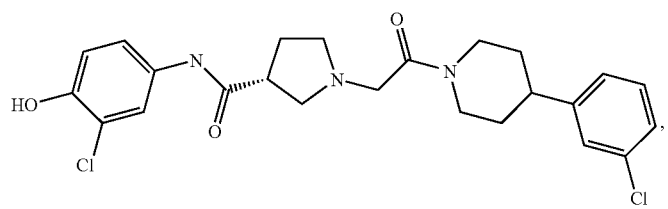 |
| 83 | 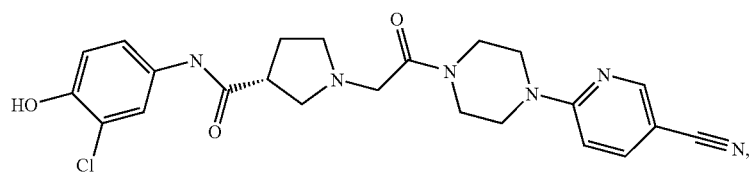 |
| 84 | 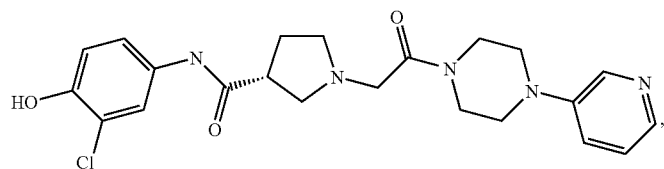 |
| 85 | 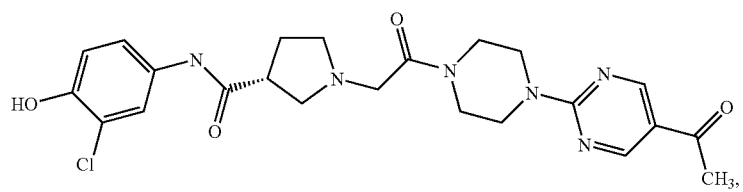 |
| 86 | 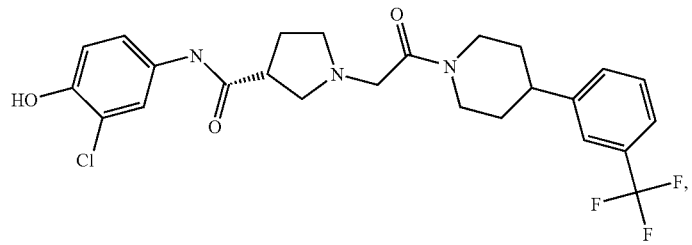 |

| EX | Compound |
|---|---|
| 87 | 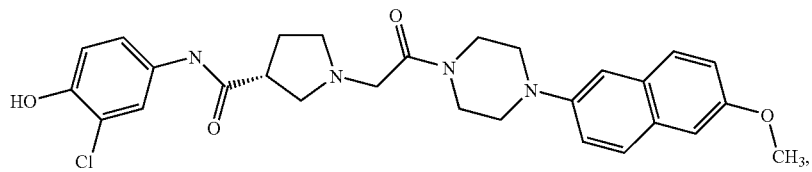 |
| 88 | 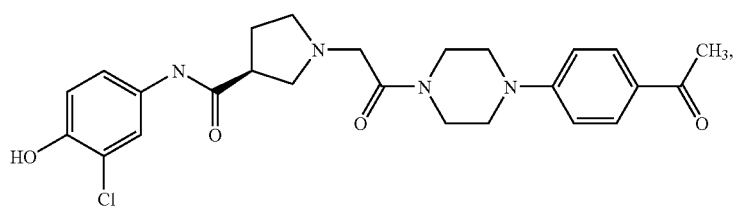 |
| 89 | 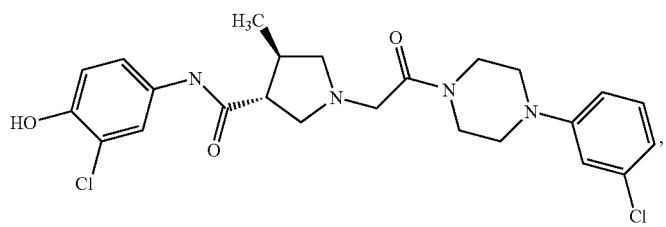 |
| 90 | 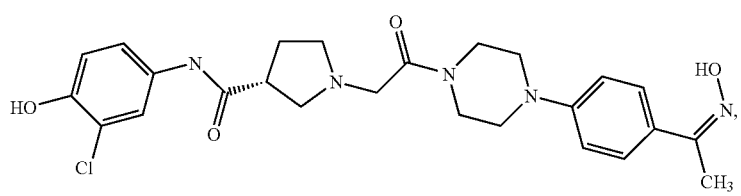 |
| 91 | 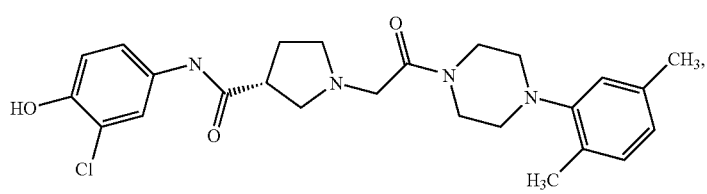 |
| 92 | 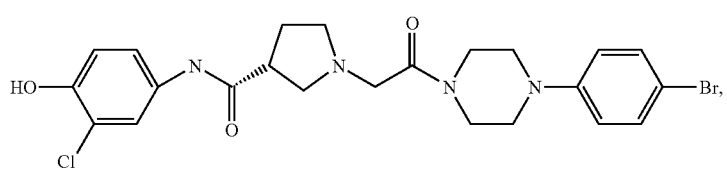 |
| 93 | 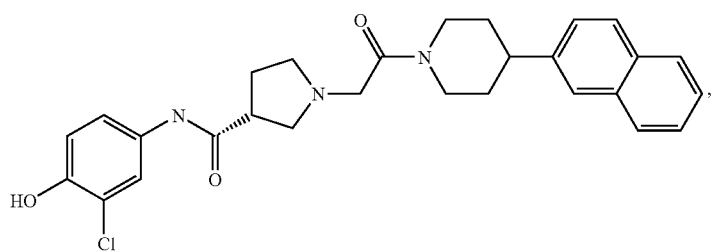 |

-continued
| EX | Compound |
|---|---|
| 94 | 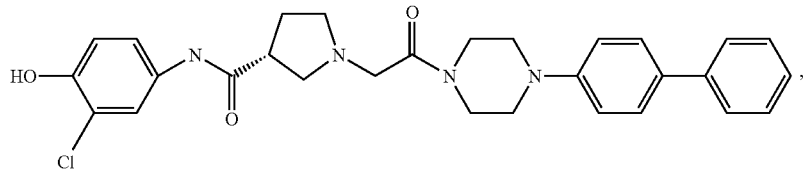 |
| 95 | 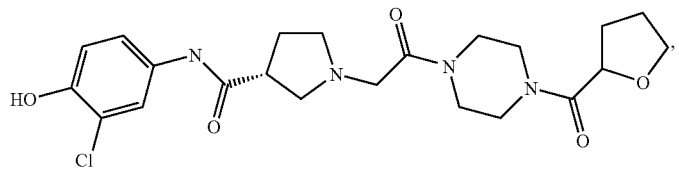 |
| 96 | 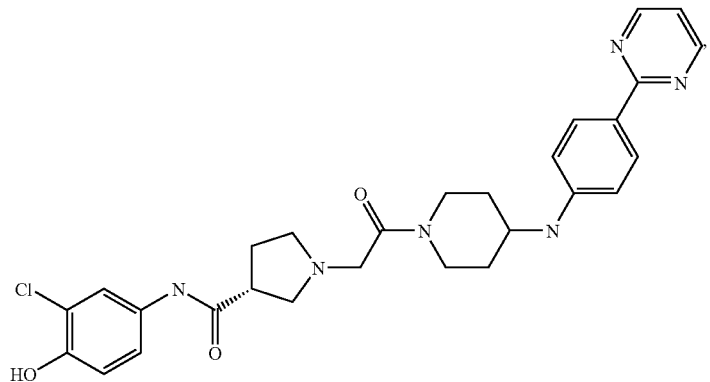 |
| 97 | 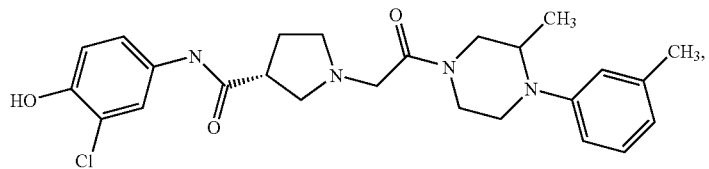 |
| 98 | 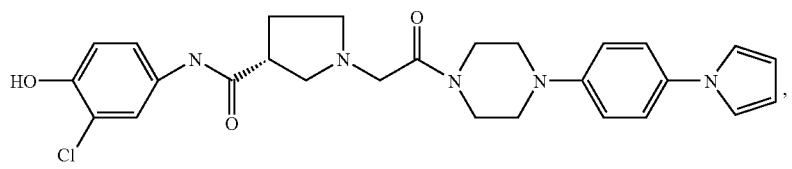 |
| 99 | 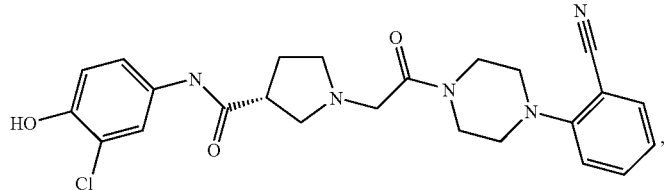 |
| 100 | 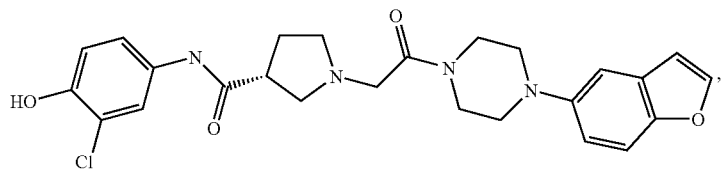 |

-continued
| EX | Compound |
|---|---|
| 101 | 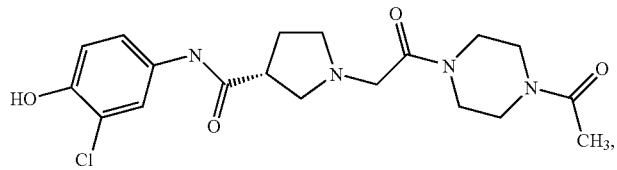 |
| 102 | 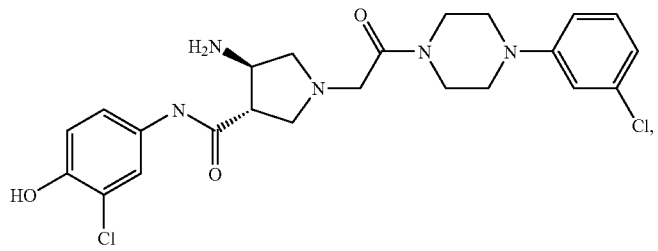 |
| 103 | 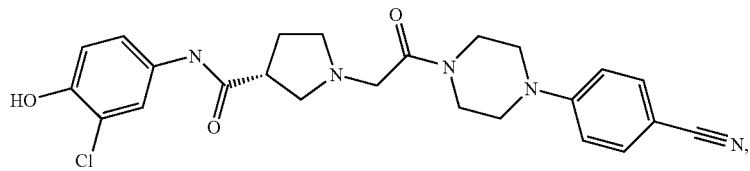 |
| 104 | 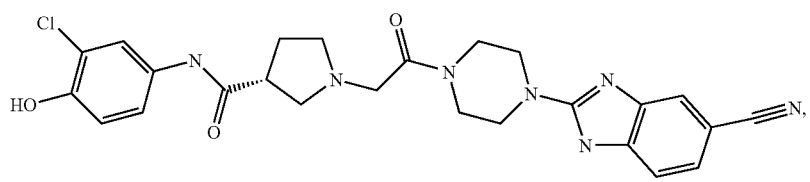 |
| 105 | 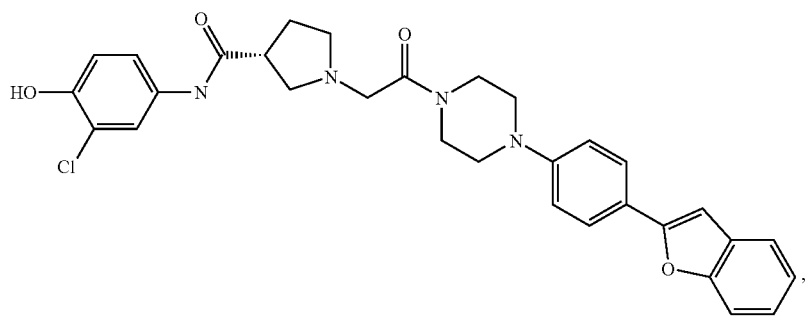 |
| 106 | 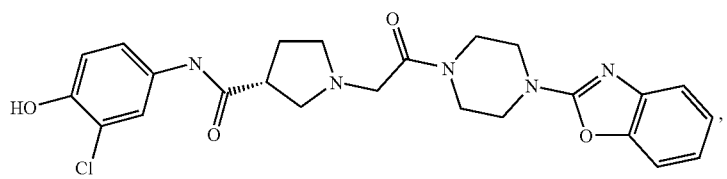 |
| 107 | 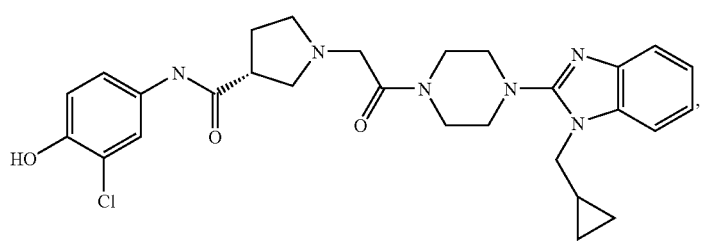 |

-continued
| EX | Compound |
|---|---|
| 109 | 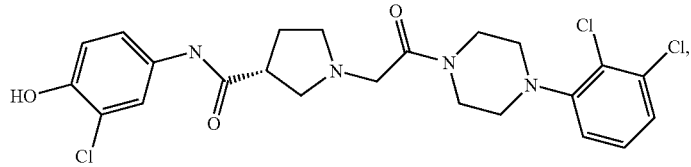 |
| 110 | 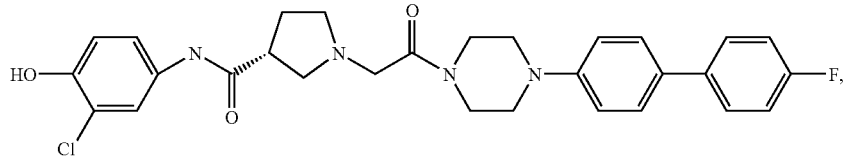 |
| 112 | 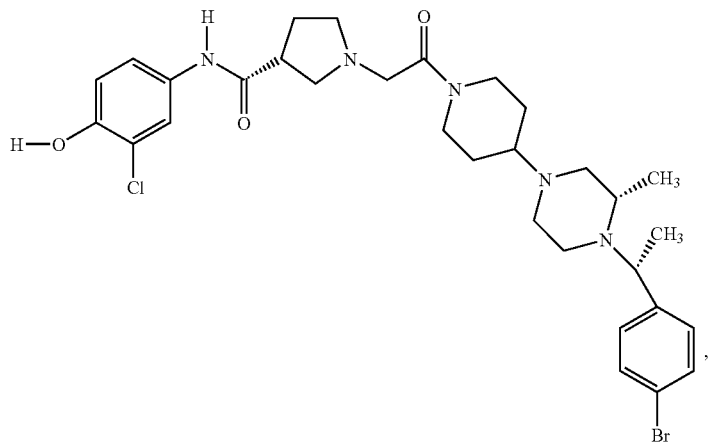 |
| 113 | 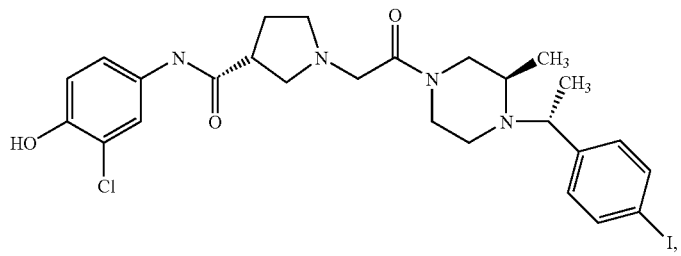 |
| 114 | 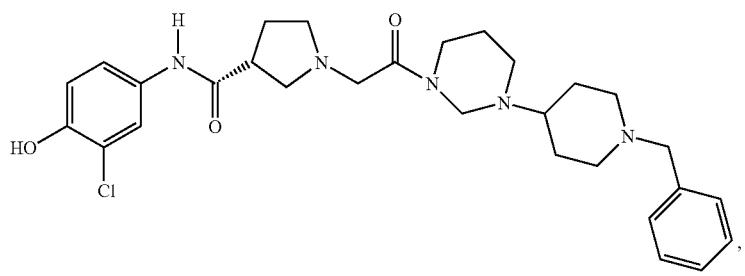 |
| 115 | 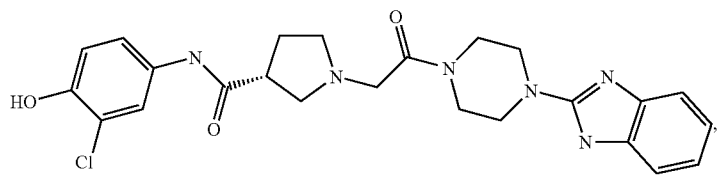 |

| EX | Compound |
|---|---|
| 116 | 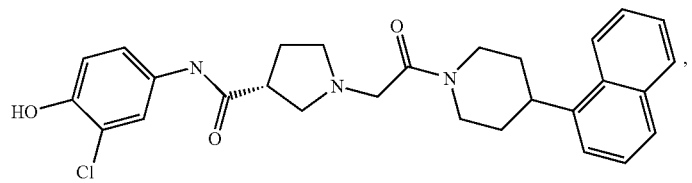 |
| 117 | 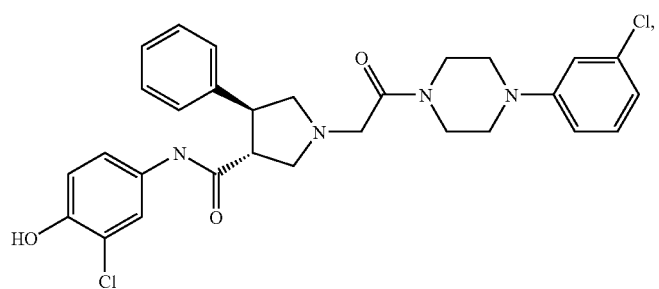 |
| 118 | 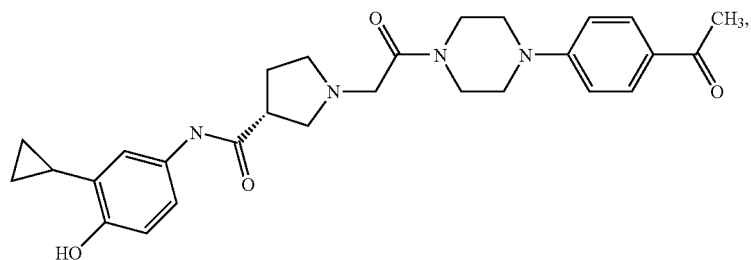 |
| 119 | 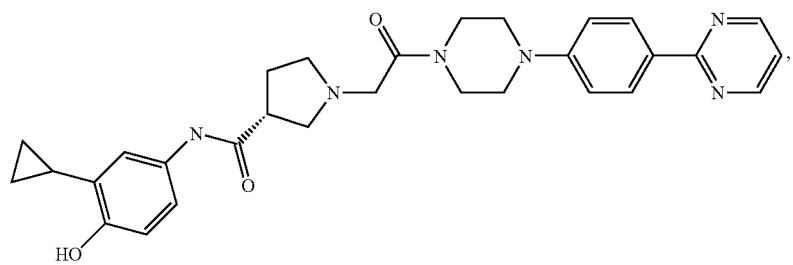 |
| 120 | 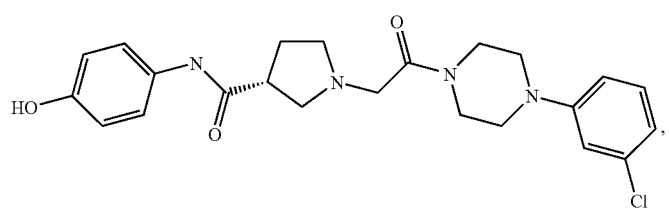 |
| 121 | 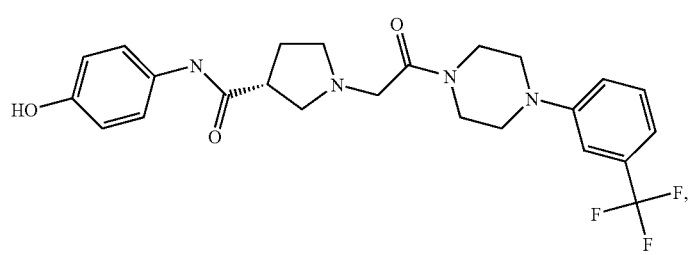 |

| EX | Compound |
|---|---|
| 122 | 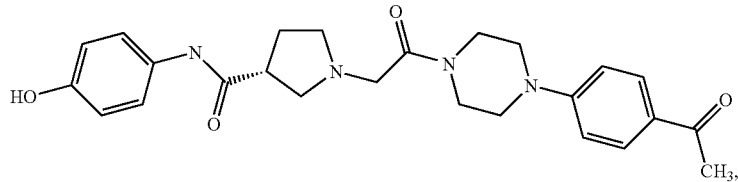 |
| 123 | 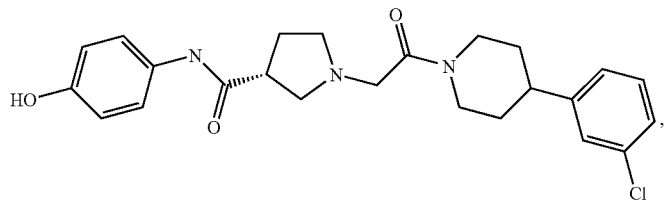 |
| 124 | 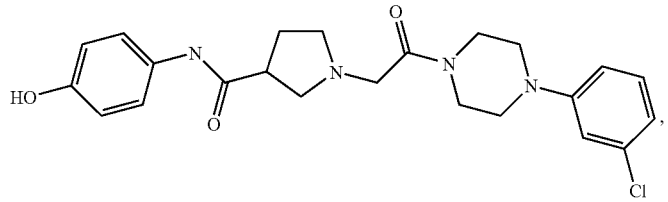 |
| 125 | 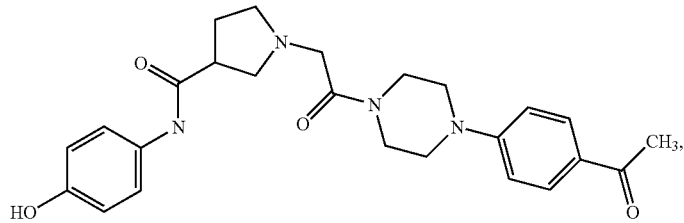 |
| 126 | 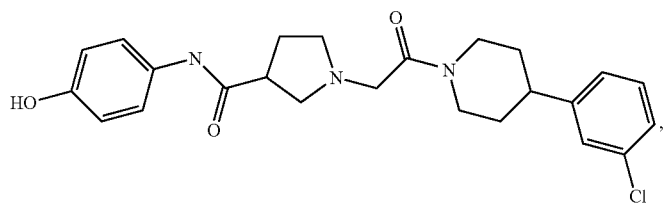 |
| 127 | 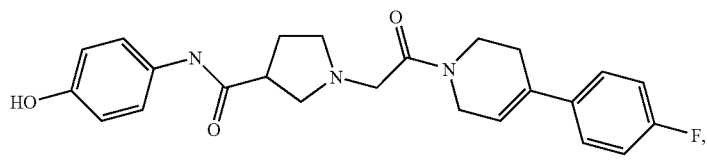 |
| 128 | 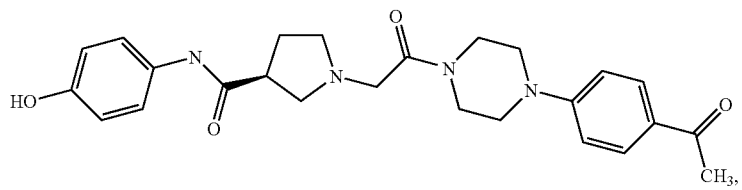 |

-continued
| EX | Compound |
|---|---|
| 129 | 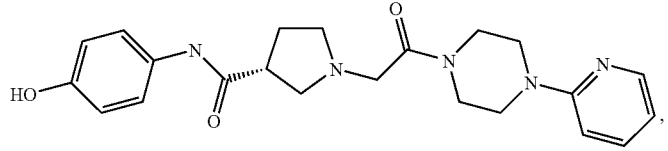 |
| 130 | 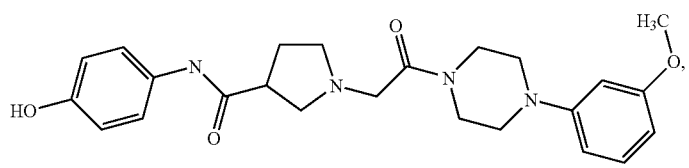 |
| 131 | 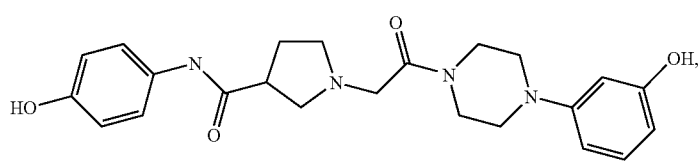 |
| 132 | 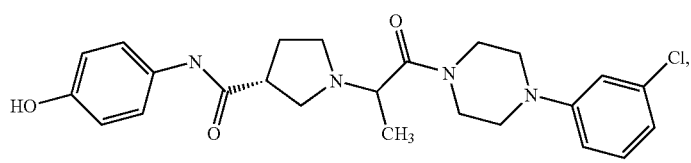 |
| 133 | 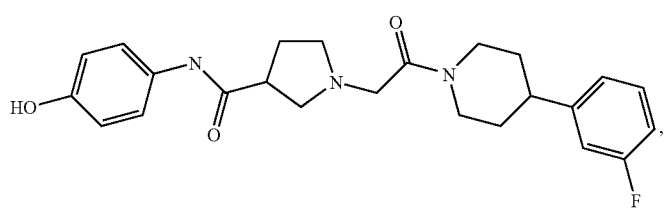 |
| 134 | 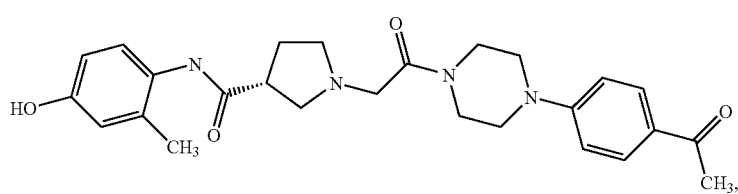 |
| 135 | 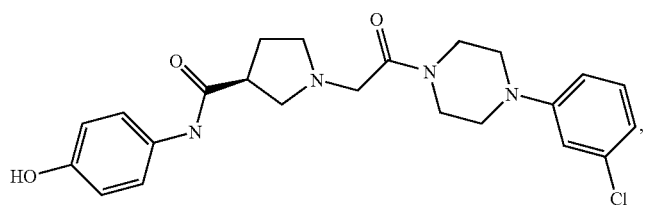 |
| 137 | 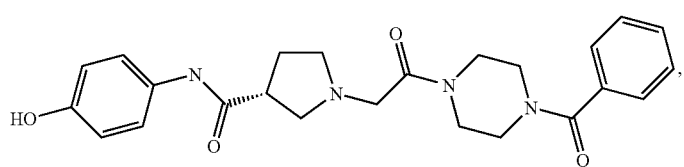 |

-continued
| EX | Compound |
|---|---|
| 138 | 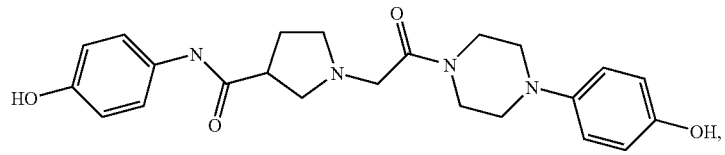 |
| 139 | 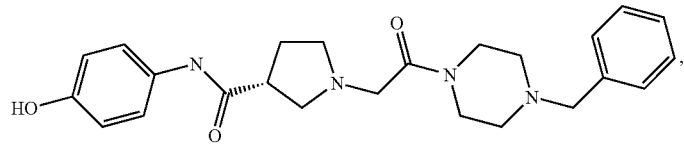 |
| 140 | 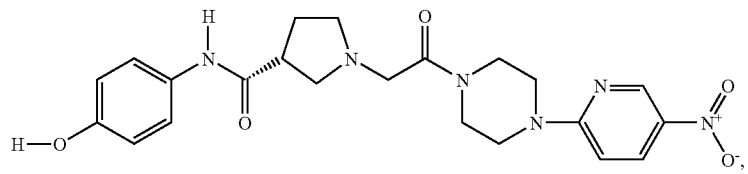 |
| 141 | 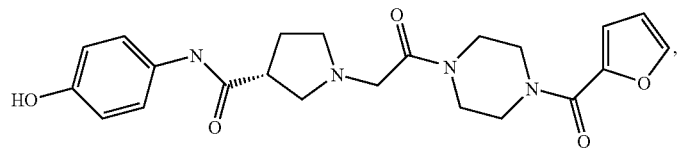 |
| 142 | 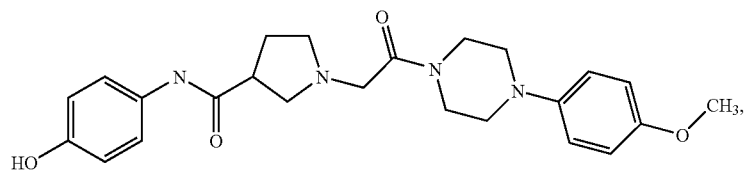 |
| 143 | 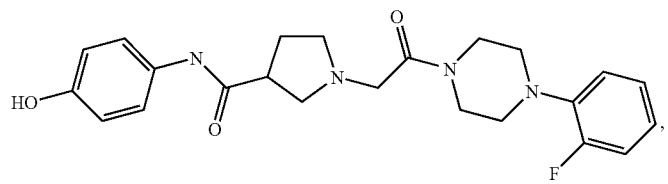 |
| 144 | 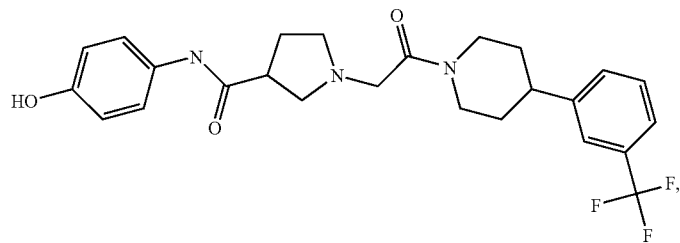 |
| 145 | 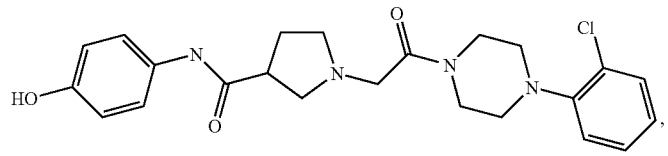 |

| EX | Compound |
|---|---|
| 146 | 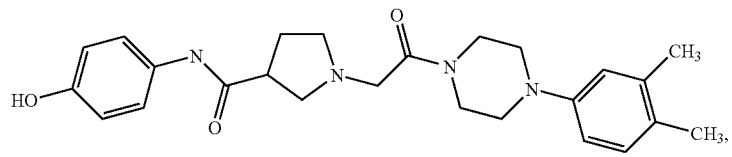 |
| 147 | 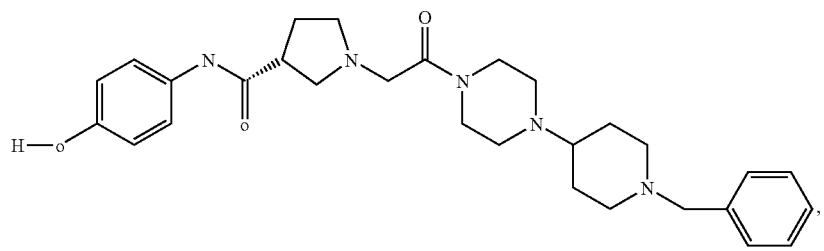 |
| 148 | 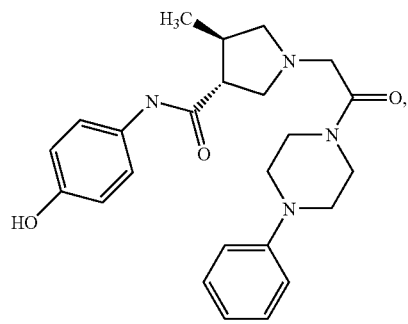 |
| 149 | 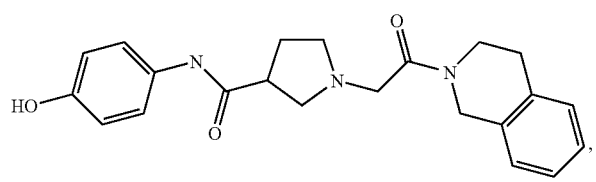 |
| 150 | 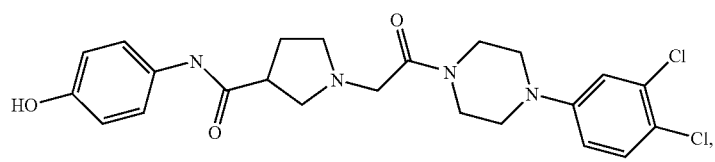 |
| 151 | 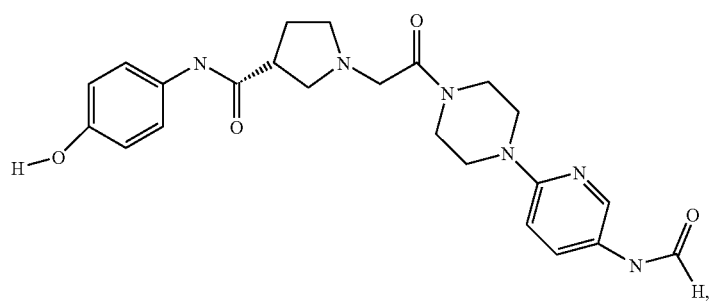 |
| 152 | 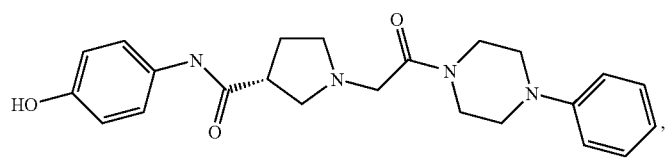 |

| EX | Compound |
|---|---|
| 153 | 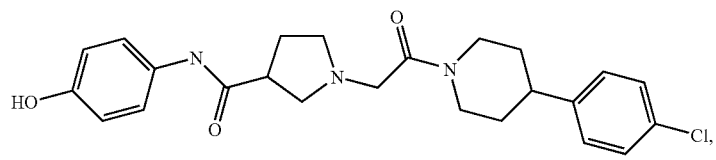 |
| 154 | 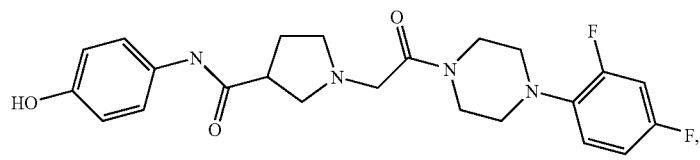 |
| 155 | 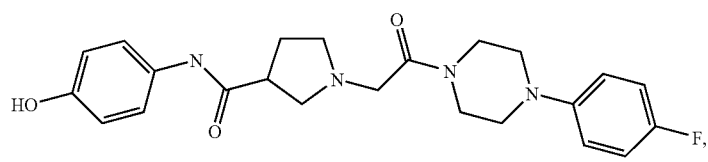 |
| 156 | 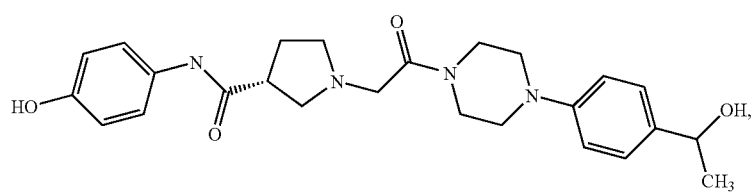 |
| 158 | 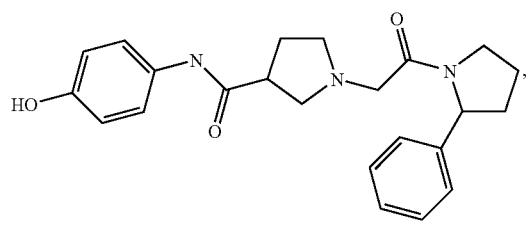 |
| 159 | 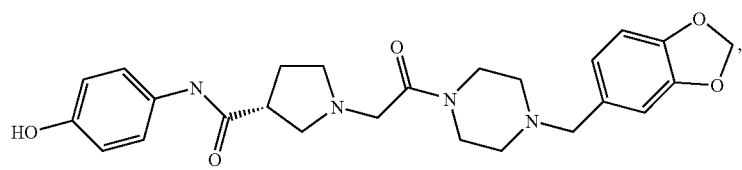 |
| 160 | 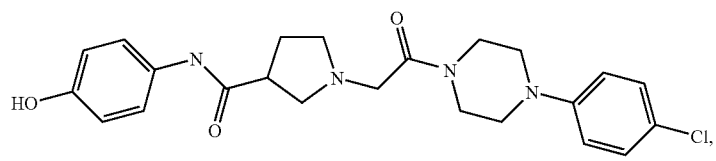 |
| 161 | 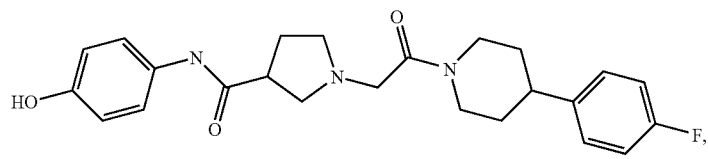 |

-continued
| EX | Compound |
|---|---|
| 162 | 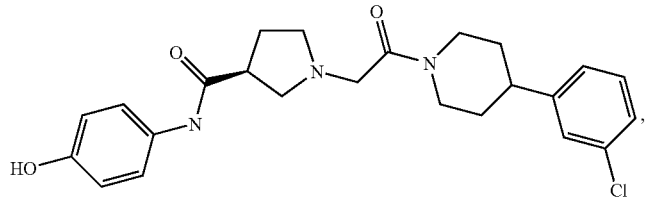 |
| 163 | 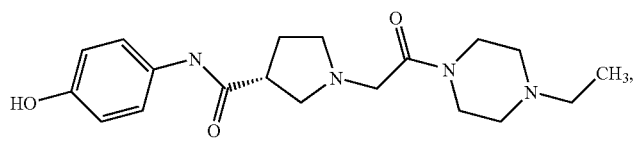 |
| 166 | 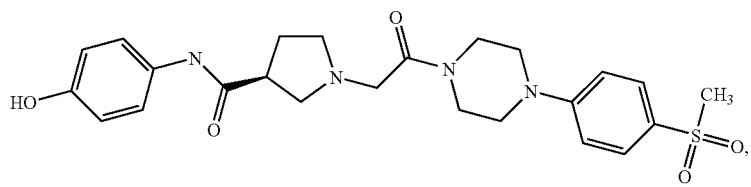 |
| 167 | 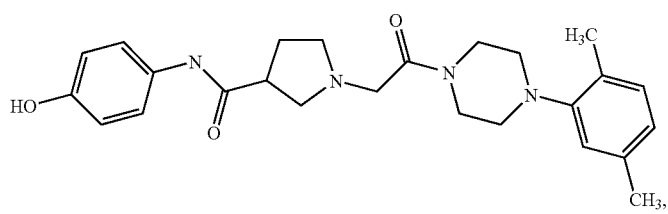 |
| 168 | 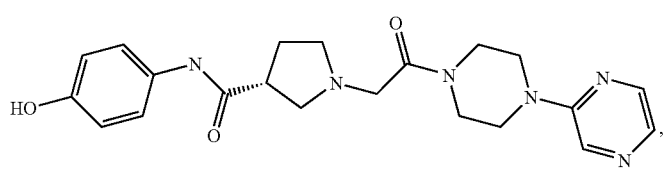 |
| 169 | 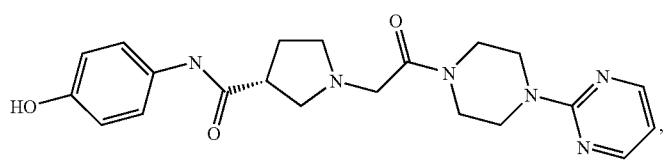 |
| 170 | 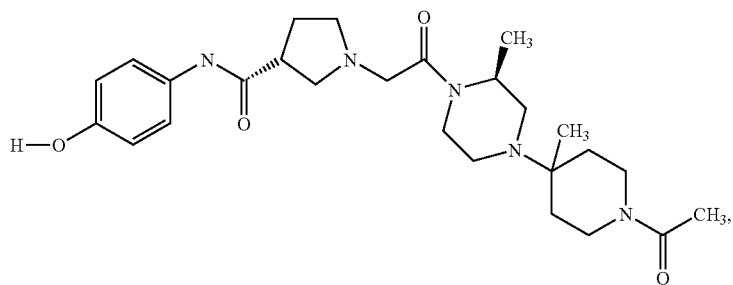 |

-continued
| EX | Compound |
|---|---|
| 172 | 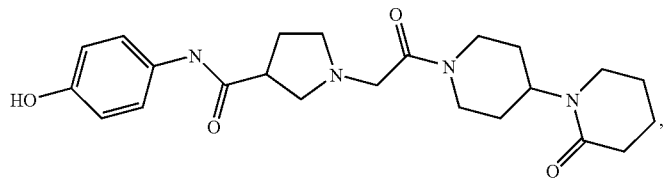 |
| 173 | 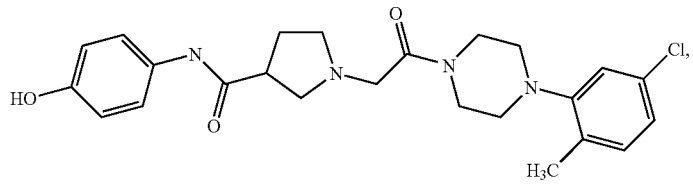 |
| 174 | 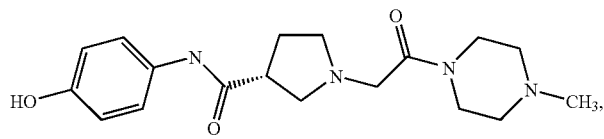 |
| 175 | 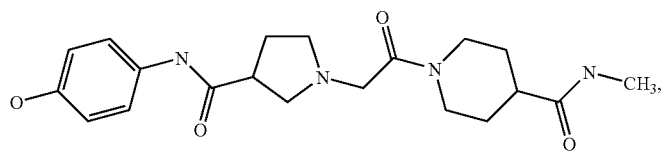 |
| 176 | 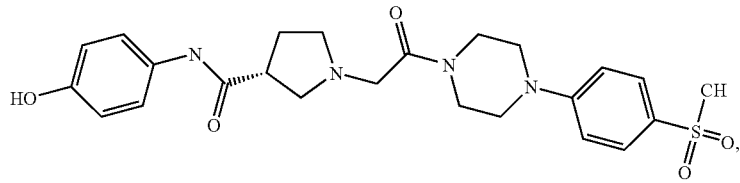 |
| 177 | 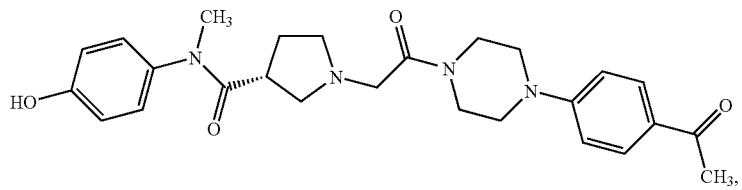 |
| 178 | 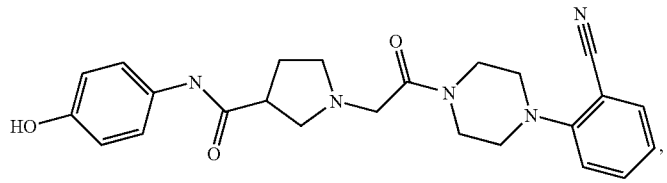 |
| 179 | 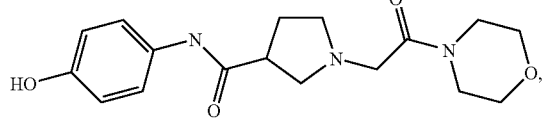 |

| EX | Compound |
|---|---|
| 183 | 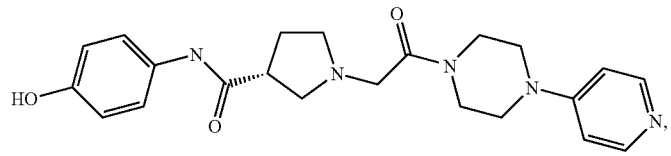 |
| 184 | 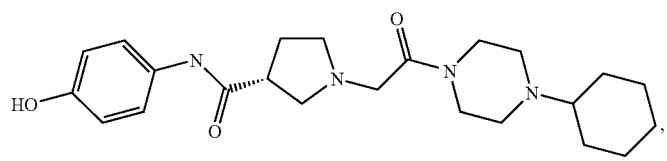 |
| 185 | 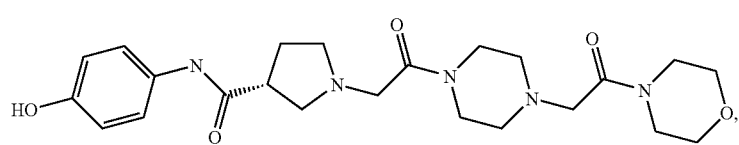 |
| 186 | 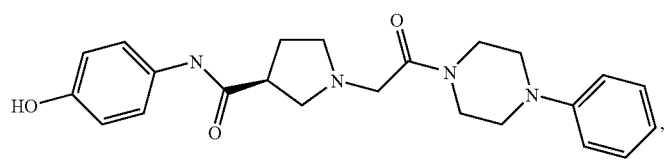 |
| 187 | 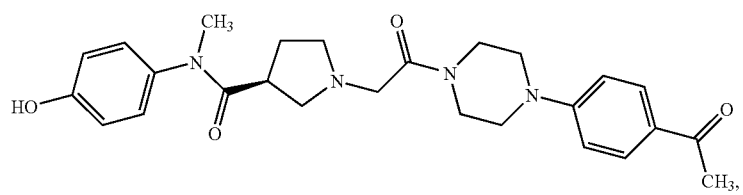 |
| 188 | 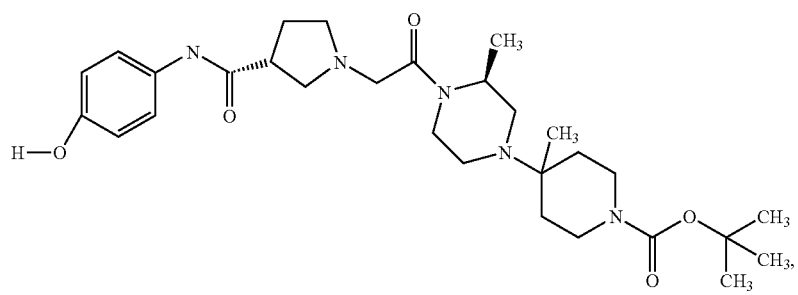 |
| 189 | 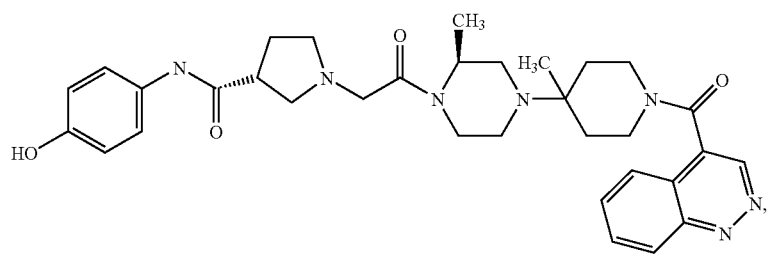 |

| EX | Compound |
|---|---|
| 190 | 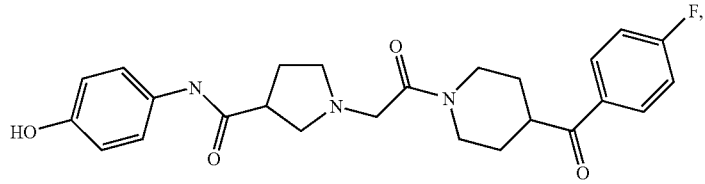 |
| 191 | 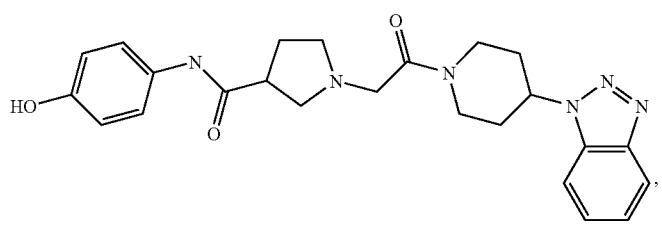 |
| 192 | 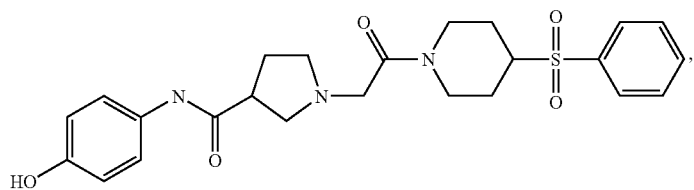 |
| 194 | 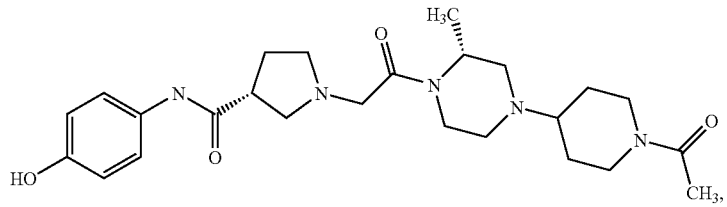 |
| 196 | 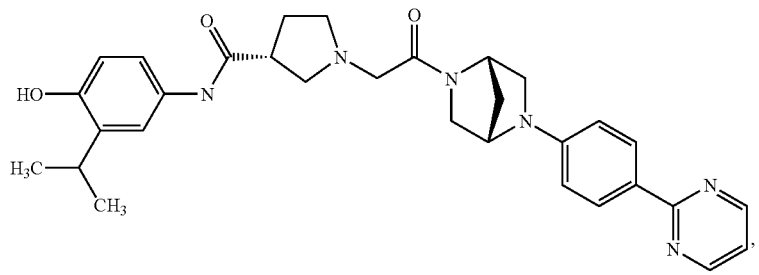 |
| 197 | 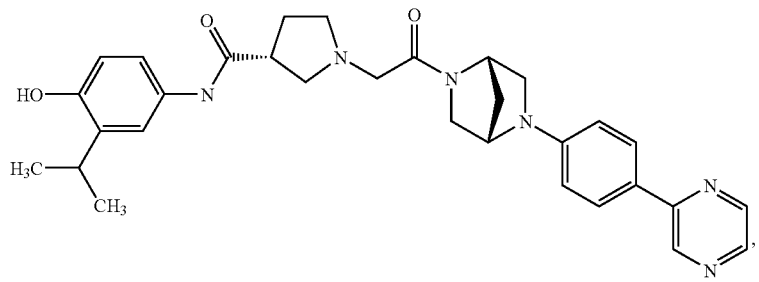 |

-continued
| EX | Compound |
|---|---|
| 199 | 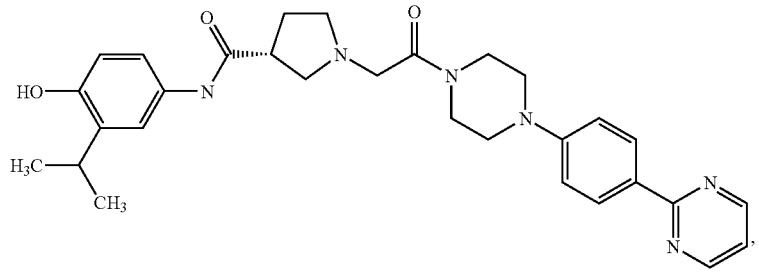 |
| 200 | 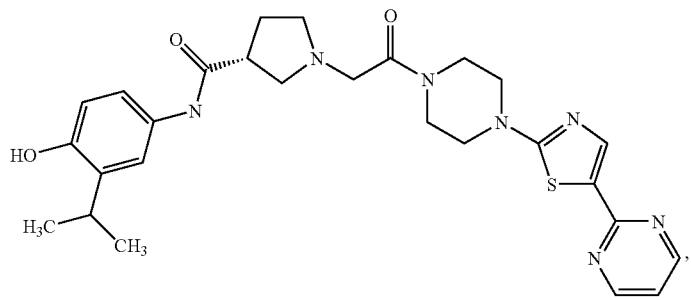 |
| 201 | 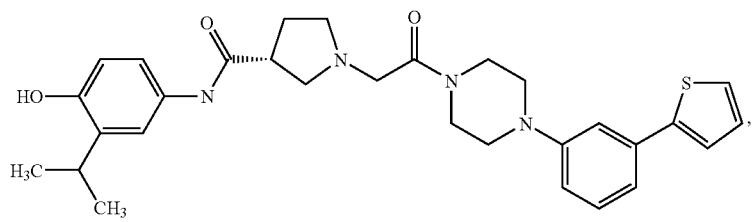 |
| 202 | 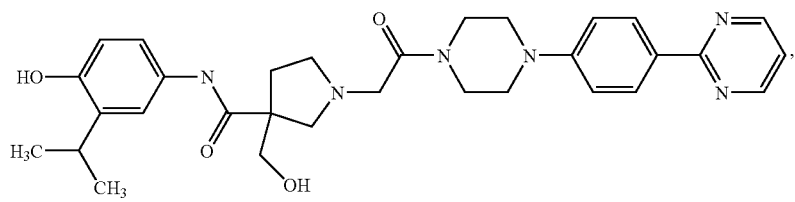 |
| 203 | 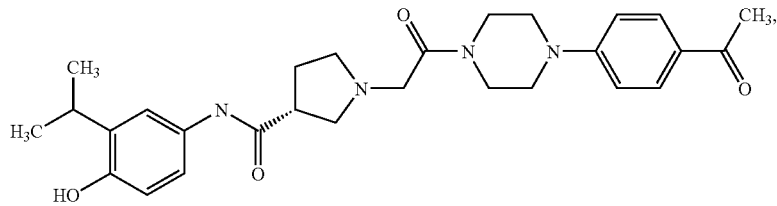 |
| 204 | 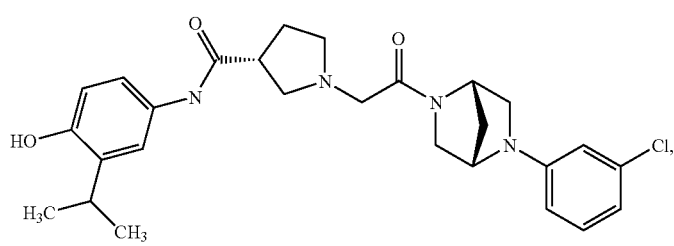 |

-continued
| EX | Compound |
|---|---|
| 205 | 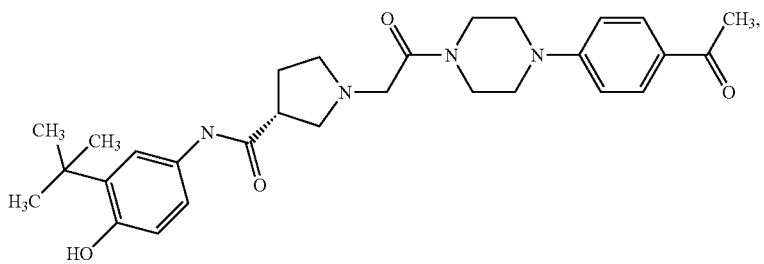 |
| 206 | 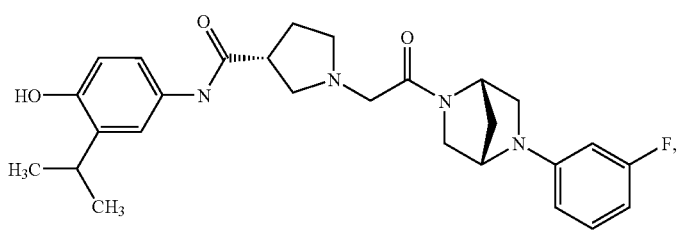 |
| 207 | 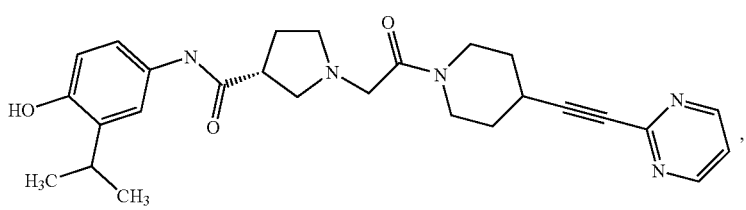 |
| 208 | 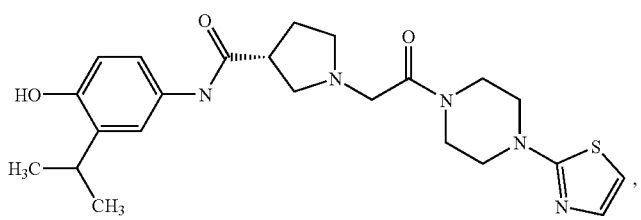 |
| 209 | 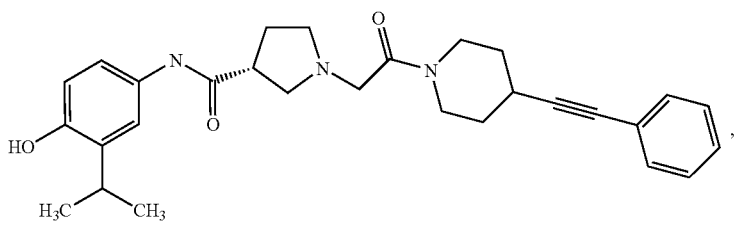 |
| 210 | 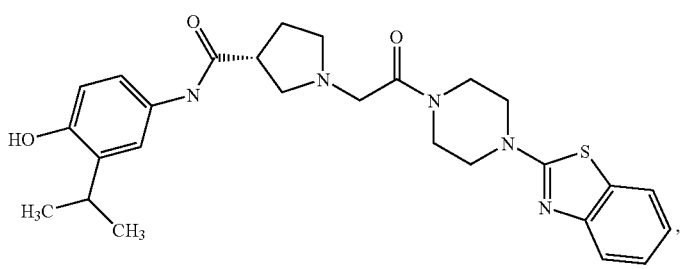 |

| EX | Compound |
|---|---|
| 211 | 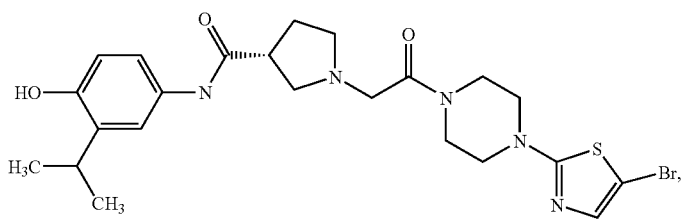 |
| 212 | 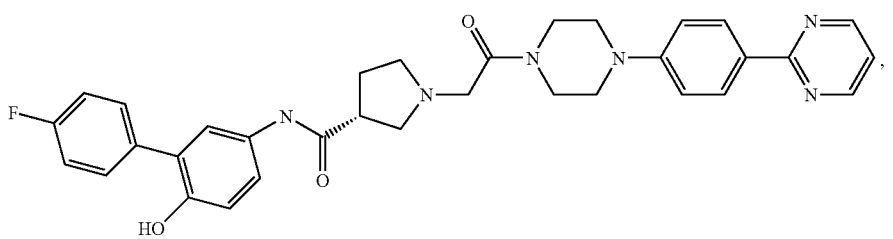 |
| 213 | 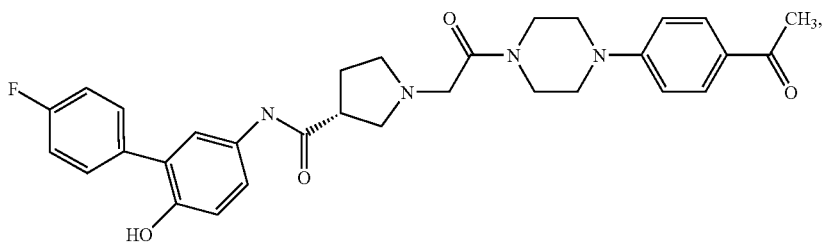 |
| 214 | 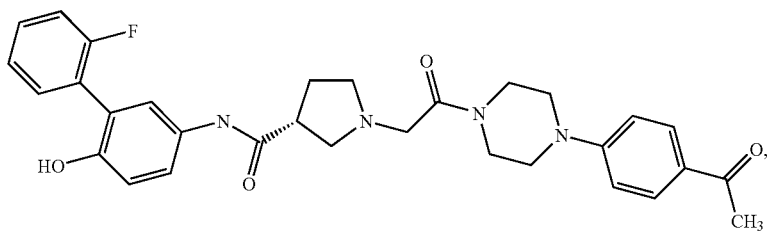 |
| 215 | 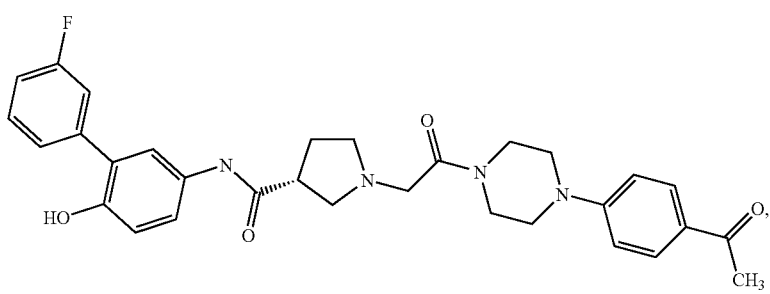 |
| 216 | 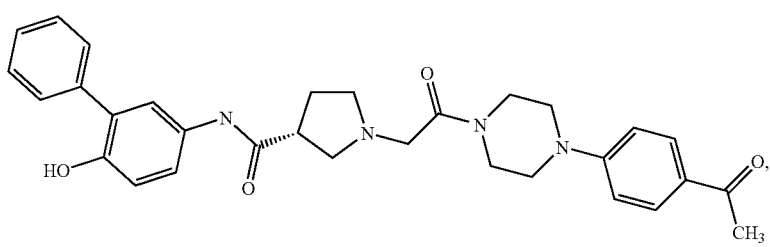 |

-continued
| EX | Compound |
|---|---|
| 217 | 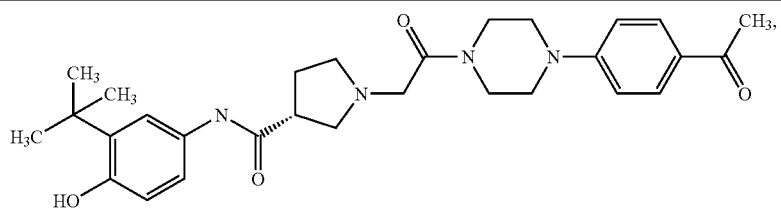 |
| 218 | 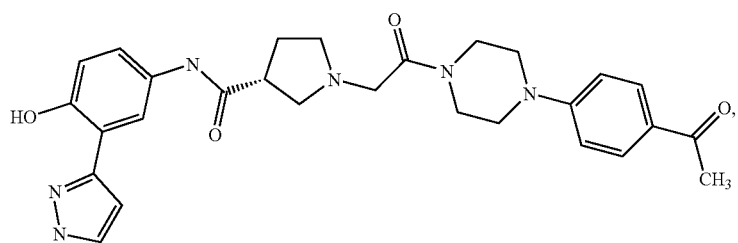 |
| 219 | 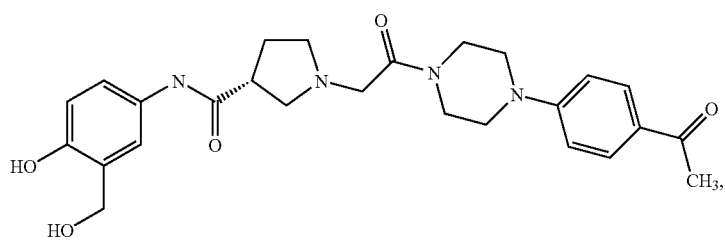 |
| 220 | 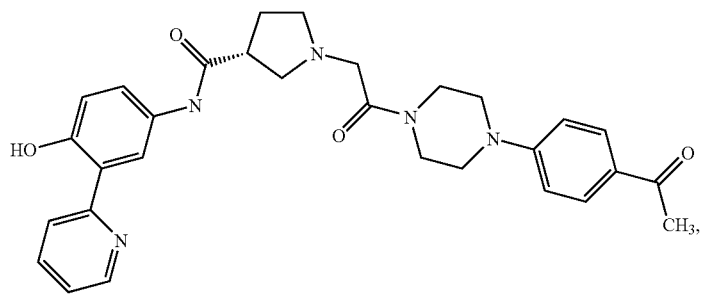 |
| 221 | 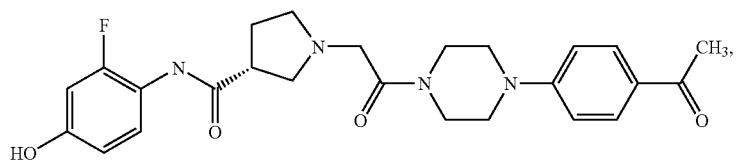 |
| 222 | 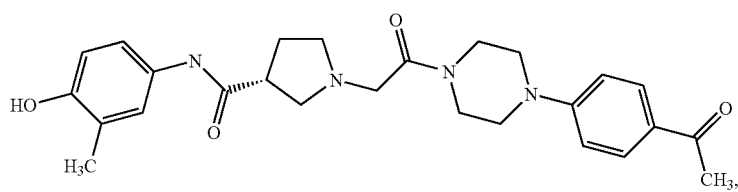 |
| 223 | 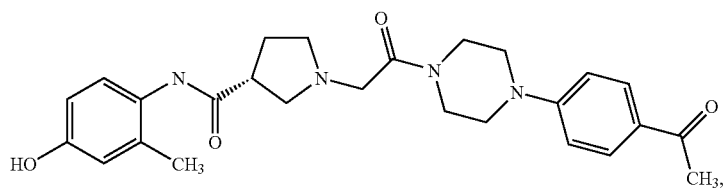 |

-continued
| EX | Compound |
|---|---|
| 224 | 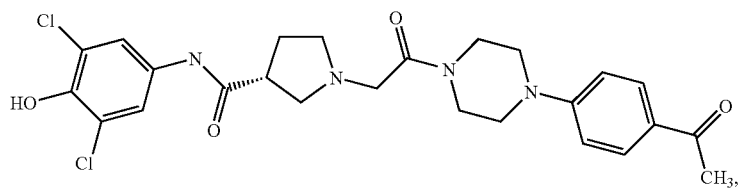 |
| 225 | 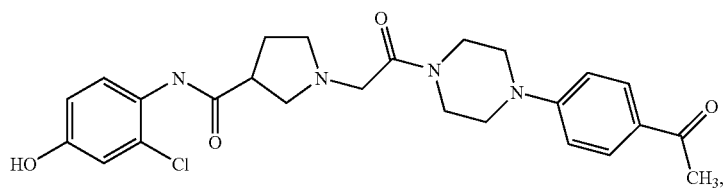 |
| 226 | 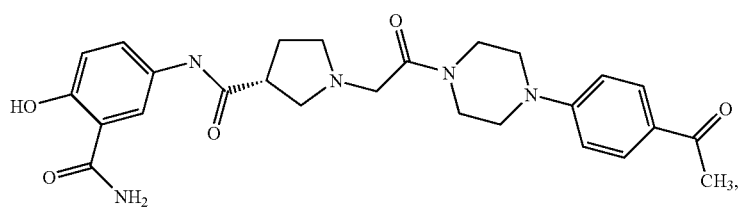 |
| 227 | 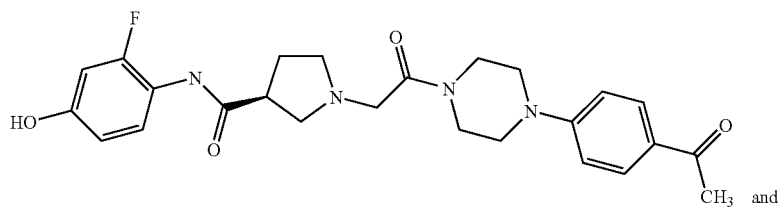 and |
| 228 | 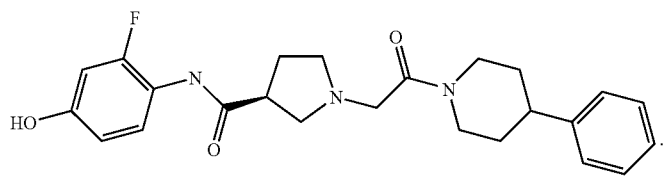 . |
23. A pharmaceutical composition comprising at least one compound of claim 22 and a pharmaceutically acceptable carrier.
* * * * *